United States Patent
Lancellotti et al.

(10) Patent No.: US 12,318,388 B2
(45) Date of Patent: Jun. 3, 2025

(54) PYRIMIDINE DERIVATIVES FOR PREVENTION AND TREATMENT OF GRAM-NEGATIVE BACTERIAL INFECTION, CONTAMINATION AND FOULING

(71) Applicant: UNIVERSITÉ DE LIÈGE, Liège (BE)

(72) Inventors: Patrizio Lancellotti, Liège (BE); Cécile Oury, Liège (BE); Bernard Pirotte, Liège (BE); Lucia Musumeci, Liège (BE); Nicolas Jacques, Liège (BE); Eric Goffin, Liège (BE)

(73) Assignee: UNIVERSITÉ DE LIÈGE, Liège (BE)

( * ) Notice: Subject to any disclaimer, the term of this patent is extended or adjusted under 35 U.S.C. 154(b) by 812 days.

(21) Appl. No.: 17/327,551

(22) Filed: May 21, 2021

(65) Prior Publication Data
US 2021/0290625 A1    Sep. 23, 2021

Related U.S. Application Data

(63) Continuation-in-part of application No. PCT/EP2020/060819, filed on Apr. 17, 2020.

(30) Foreign Application Priority Data

Apr. 18, 2019 (EP) .................................. 19170003
Jul. 26, 2019 (EP) .................................. 19188639

(51) Int. Cl.
| | |
|---|---|
| *A61K 31/52* | (2006.01) |
| *A01N 43/713* | (2006.01) |
| *A01N 43/90* | (2006.01) |
| *A61K 38/12* | (2006.01) |
| *A61K 51/04* | (2006.01) |
| *A61P 31/04* | (2006.01) |

(52) U.S. Cl.
CPC ............ *A61K 31/52* (2013.01); *A01N 43/713* (2013.01); *A01N 43/90* (2013.01); *A61K 38/12* (2013.01); *A61K 51/0459* (2013.01); *A61P 31/04* (2018.01)

(58) Field of Classification Search
None
See application file for complete search history.

(56) References Cited

U.S. PATENT DOCUMENTS

| | | | | |
|---|---|---|---|---|
| 6,555,225 | B1* | 4/2003 | Yoshioka | ............ A61L 33/0011 |
| | | | | 427/195 |
| 2005/0288503 | A1* | 12/2005 | Adams | ..................... A61P 43/00 |
| | | | | 544/280 |
| 2010/0311788 | A1* | 12/2010 | Dahne | ....................... A61P 7/02 |
| | | | | 526/287 |
| 2012/0108528 | A1* | 5/2012 | Cohen | ..................... A61P 25/00 |
| | | | | 514/331 |

FOREIGN PATENT DOCUMENTS

| | | | |
|---|---|---|---|
| WO | WO 2009/034386 A1 | 3/2009 | |
| WO | WO-2010118367 A2 * | 10/2010 | ........... C07D 239/42 |
| WO | WO-2018046174 A1 * | 3/2018 | ............ A01N 43/90 |
| WO | WO 2019/158655 A1 | 8/2019 | |

OTHER PUBLICATIONS

Thomas et al. (Platelet P2Y12 Inhibitors Reduce Systemic Inflammation and Its Prothrombotic Effects in an Experimental Human Model, Oct. 9, 2015, Arteriosclerosis, Thrombosis, and Vascular Biology, 2562-2570) (Year: 2015).*
PubChem (PubChem CID 24737634, Published Mar. 3, 2008) (Year: 2008).*
Patewski et al. (Parenteral Polymyxin B Use in Patients with Multidrug-Resistant Gram-Negative Bacteremia and Urinary Tract Infections: A Retrospective Case Series, Jul. 29, 2008, The Annals of Pharmacotherapy) (Year: 2008).*
Li et al. (Disposition and Metabolism of Ticagrelor, a Novel P2Y12 Receptor Antagonist, in Mice, Rats, and Marmosets, Jun. 13, 2011, The American Society for Pharmacology and Experimental Therapeutics) (Year: 2011).*
Miller et al. (Antibiotic Resistance and Regulation of the Gram-Negative Bacterial Outer Membrane Barrier by Host Innate Immune Molecules, Sep. 27, 2016, American Society for Microbiology, 7:5) (Year: 2016).*
Food and Drug Administration (FDA) (Center For Drug Evaluation And Research, Application No. 022433Orig1s000, Chemistry Review, Dec. 17, 2009) (Year: 2009).*
Zhan et al. (Gram-negative bacterial molecules associate with Alzheimer disease pathology, Nov. 29, 2016, American Academy of Neurology, 87:2324-2332) (Year: 2016).*

(Continued)

*Primary Examiner* — Johann R Richter
*Assistant Examiner* — Kaila A Craig
(74) *Attorney, Agent, or Firm* — Knobbe, Martens, Olson & Bear, LLP

(57) ABSTRACT

New pyrimidine derivatives together with a membrane penetrating agent, optionally with a detectable isotope and pharmaceutical composition for use in treatment or prevention of Gram-negative bacterial infection in a host mammal in need of such treatment or prevention and use as inhibitors of Gram-negative biofilm formation on a surface of biomaterial or medical device, particularly of cardiovascular device such as prosthetic heart valve or pacemakers. New pyrimidine derivatives together with a membrane penetrating agent; for use as radiotracer in diagnosing or prognosing Gram-negative bacterial infection in a host mammal.

18 Claims, 2 Drawing Sheets

(56) References Cited

OTHER PUBLICATIONS

Mueller, *Escherichia coli* Infection, 2023, National Center for Biotechnology Information (Year: 2023).*

International Search Report in International Application No. PCT/EP2020/060819, dated Jul. 2, 2020.

Ye, Hong, et al., "Carba-nucleosides as Potent Antagonists of the Adenosine 5'—Diphosphate (ADP) Purinergic Receptor ($P2Y_{12}$) on Human Platelets", ChemMedChem, 2008, 3: 732-736.

Vaara, Martti, "Polymyxin Derivatives that Sensitize Gram-Negative Bacteria to Other Antibiotics", Molecules, 2019, 24, 249 (15 Pages).

* cited by examiner

PYRIMIDINE DERIVATIVES FOR PREVENTION AND TREATMENT OF GRAM-NEGATIVE BACTERIAL INFECTION, CONTAMINATION AND FOULING

FIELD OF THE INVENTION

The present invention relates to new pyrimidine derivatives for use in prevention and treatment of Gram-negative bacterial infection and their use in inhibition of biofilm formation.

The present invention provides pyrimidine derivatives optionally with a detectable isotope for use as radiotracer in diagnosis or prognosis of Gram-negative bacterial infection.

INTRODUCTION

Infections caused by gram-negative bacteria, antibiotic-resistant bacteria and multidrug-resistant Gram-negative bacteria have dramatically increased everywhere in the world.

Antibiotic-resistance is a public health issue in regards to both Gram-positive and Gram-negative bacteria, but the problem is more serious for Gram-negative bacteria since drugs active against multidrug resistance (MDR) Gram-negative bacteria are dramatically lacking. This is partly due to the outer membrane of the Gram-negative bacteria providing an extra layer of protection without compromising a necessary exchange of molecules required for sustaining life of the bacteria. As illustrated by Jianguo Li et al (2017, Frontiers in Neuroscience, 11,73), Gram-negative bacteria differ from Gram-positive bacteria with respect to the structure of their cell wall. Indeed, as illustrated in FIG. 1 thereof (reproduced herein as FIG. 1), whereas Gram-positive bacteria (2) have an envelope constituting of a cytoplasmic or inner membrane and a peptidoglycan layer, Gram-negative bacteria (1) have an envelope consisting of 3 main layers. The Gram-negative (1) envelope comprises an outer membrane (C) containing lipopolysaccharides (LPS), a peptidoglycan cell wall (A) with peptide chains, generally cross-linked and a cytoplasmic or inner membrane (B), also called integral membrane protein. The outer membrane (C) structure comprises pores (D) called porins that allow diffusion of hydrophilic small molecules through the membrane (C).

The outer membrane (C) of the Gram-negative bacteria (1) serves as permeability barrier to toxin compounds, which include antibiotics and host innate immune molecules. It moreover results in a difference of penetration and retention of chemical agents such as antibiotics. For example, Gram-negative bacteria are naturally insensitive to vancomycin, because such antibiotic is not able to penetrate the outer membrane (C). *Klebsiella pneumoniae* exhibits an innate insensitivity towards ampicillin and *Pseudomonas aeruginosa* is naturally insensitive to sulphonamides, tetracycline, chloramphenicol and trimethoprim. Apart from innate resistance, Gram-negative bacteria can also become resistant to antibiotics through genomic mutations.

According to the World Health Organization the most critical bacteria for which new antibiotics are urgently needed are gram-negative bacteria, namely carbapenem-resistant *Acinetobacter* baumannil, carbapenem-resistant *Pseudomonas aeruginosa*, and 3$^{rd}$ generation cephalosporin-resistant Enterobacteriaceae (*Klebsiella pneumonia, Escherichia coli, Enterobacter* spp, *Serratia* spp, *Proteus* spp, Providentia spp, and *Morganella* spp).

Clinical isolates where only two, or fewer, unrelated antibiotics are active against the bacterium are commonly referred to as multidrug-resistant (MDR) bacteria. Several multiresistant isolates have been observed in hospitals. They include *Acinetobacter baumannii* susceptible to two or fewer of meropenem or imipenem, third-generation cephalosporins, piperacillin/tazobactam, (tigecycline), aminoglycosides, quinolones, trimethoprim, colistin, *Klebsiella* spp., *Enterobacter* spp., *Serratia* spp. and *Citrobacter* spp. that are susceptible to two or fewer of carbapenems, third-generation cephalosporins, including with β-lactamase inhibitors, piperacillin/tazobactam, temocillin, tigecycline, aminoglycosides, quinolones, trimethoprim or colistin; *Proteus* spp., *Morganella* spp. and *Providencia* spp. that are resistant to third-generation cephalosporin, piperacillin/tazobactam, and aminoglycosides and susceptible only to carbapenems, and the new BL/BLI combinations (ceftolozane/tazobactam or ceftazidime/avibactam). These Proteeae are inherently resistant to tigecycline and colistin.

There is therefore an urgent need in the art for a new Gram-negative antibacterial therapy.

SUMMARY OF THE INVENTION

We have surprisingly found pyrimidine derivatives that possess antibacterial activity against Gram-negative bacteria when administered together with a membrane penetrating agent and can be used in the treatment or prevention of bacterial infection in a host mammal and in the treatment and/or prevention of bacterial contamination and fouling.

The pyrimidine derivatives, optionally with a detectable isotope, can also be used as radiotracer in diagnosis or prognosis of bacterial infection.

It is also found that such pyrimidine derivatives can be used in a method for controlling Gram-negative bacterial growth in biofilm formation at early stage such as step 1 or 2 or for killing bacteria at all steps of biofilm formation including the last step 3 wherein the biofilm has reached its maturation stage of matrix formation and the bacteria start detachment from the surface with a consequent spreading of the bacteria into other locations. In preferred embodiments of this use, the pyrimidine derivatives of the invention are used in combination with a membrane penetrating agent.

In one aspect, the invention provides pyrimidine derivatives represented by formula (I)

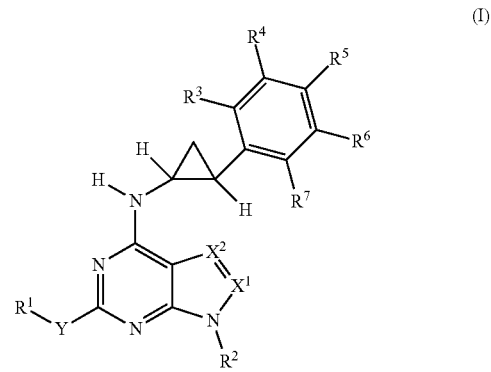

or isomers, racemic mixtures thereof, pharmaceutically acceptable acid addition salts, pharmaceutically acceptable metal salts, or alkylated ammonium salts or prodrug thereof;

for use together with a membrane penetrating agent in a treatment or prevention of Gram-negative bacterial infection in a host mammal in need of such treatment or prevention, wherein:
X¹ and X² are independently N, CH, CR⁸ wherein R⁸ is C$_{1-6}$ alkyl, C$_{2-6}$ alkenyl or C$_{2-6}$ alkynyl; with the exception that if one of X¹ or X² is equal to N, then the remaining of X¹ or X² are selected from CH, CR⁸;
—Y— is —O— or —S—;
R¹ and R² are independently C$_{1-6}$-alkyl, C$_{2-6}$-alkenyl, C$_{2-6}$-alkynyl, C$_{3-6}$-cycloalkyl, aryl, aryl-C$_{1-6}$-alkyl wherein the alkyl or cycloalkyl moiety is optionally mono or polysubstituted with OH or an halogen and the aryl moiety is optionally mono or polysubstituted with an halogen, —C$_{1-6}$ alkyl, —C$_{1-6}$alkoxy, —OH, —NO$_2$, —CN, —NH$_2$, —NHR⁸, —N(R⁸)$_2$—COOH, —COOR⁸, —CONH$_2$, —CONHR⁸, —CON(R⁸)$_2$, —SO$_2$NH$_2$, —SO$_2$NHR⁸, or —SO$_2$N(R⁸)$_2$;
R³, R⁴, R⁵, R⁶ and R⁷ are independently H, an halogen, a C$_{1-6}$alkyl, C$_{1-6}$alkoxy, —OH, —NO$_2$, —CN, —NH$_2$, —NHR⁸, —N(R⁸)$_2$—COOH, —COOR⁸, —CONH$_2$, —CONHR⁸, —CON(R⁸)$_2$, —SO$_2$NH$_2$, —SO$_2$NHR⁸, or —SO$_2$N(R⁸)$_2$.

In particular embodiments, R³ and R⁷ are hydrogen and R⁴ and R⁵ are independently an halogen.

In particular embodiments, X¹ is CH or CR⁸ and X² is N.
In particular embodiments, the pyrimidine derivative comprises a N-(2-phenylcyclopropyl)-9H-purin-6-amine scaffold represented by formula (V)

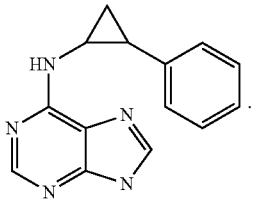

(V)

In particular embodiments, the pyrimidine derivative is selected from:
N-((1R,2S)-2-(3,4-difluorophenyl)cyclopropyl)-9-methyl-2-(propylthio)-9H-purin-6-amine (1c);
9-methyl-N-((1R,2S)-2-phenylcyclopropyl)-2-(propylthio)-9H-purin-6-amine (2c);
N-((1R,2S)-2-(3,4-difluorophenyl)cyclopropyl)-9-ethyl-2-(propylthio)-9H-purin-6-amine (3c);
N-((1R,2S)-2-(3,4-difluorophenyl)cyclopropyl)-9-propyl-2-(propylthio)-9H-purin-6-amine (4c);
N-((1R,2S)-2-(3,4-difluorophenyl)cyclopropyl)-9-isopropyl-2-(propylthio)-9H-purin-6-amine (5c);
9-cyclopropyl-N-((1R,2S)-2-(3,4-difluorophenyl)cyclopropyl)-2-(propylthio)-9H-purin-6-amine (6c);
9-butyl-N-((1R,2S)-2-(3,4-difluorophenyl)cyclopropyl)-2-(propylthio)-9H-purin-6-amine (7c);
9-(sec-butyl)-N-((1R,2S)-2-(3,4-difluorophenyl)cyclopropyl)-2-(propylthio)-9H-purin-6-amine (8c);
9-(tert-butyl)-N-((1R,2S)-2-(3,4-difluorophenyl)cyclopropyl)-2-(propylthio)-9H-purin-6-amine (9c);
9-cyclobutyl-N-((1R,2S)-2-(3,4-difluorophenyl)cyclopropyl)-2-(propylthio)-9H-purin-6-amine (10c);
N-((1R,2S)-2-(3,4-difluorophenyl)cyclopropyl)-9-pentyl-2-(propylthio)-9H-purin-6-amine (11c);
9-cyclopentyl-N-((1R,2S)-2-(3,4-difluorophenyl)cyclopropyl)-2-(propylthio)-9H-purin-6-amine (12c);
N-((1R,2S)-2-(3,4-difluorophenyl)cyclopropyl)-9-hexyl-2-(propylthio)-9H-purin-6-amine (13c);
9-cyclohexyl-N-((1R,2S)-2-(3,4-difluorophenyl)cyclopropyl)-2-(propylthio)-9H-purin-6-amine (14c);
9-allyl-N-((1R,2S)-2-(3,4-difluorophenyl)cyclopropyl)-2-(propylthio)-9H-purin-6-amine (15c);
2-(6-(((1R,2S)-2-(3,4-difluorophenyl)cyclopropyl)amino)-2-(propylthio)-9H-purin-9-yl)ethanol (16c);
N-((1R,2S)-2-(3,4-difluorophenyl)cyclopropyl)-9-(prop-2-yn-1-yl)-2-(propylthio)-9H-purin-6-amine (17c);
N-((1R,2S)-2-(3,4-difluorophenyl)cyclopropyl)-2-(propylthio)-9-(2,2,2-trifluoroethyl)-9H-purin-6-amine (18c);
(1S,2R,3S,4R)-4-(6-(((1R,2S)-2-(3,4-difluorophenyl)cyclopropyl)amino)-2-(propylthio)-9H-purin-9-yl)cyclopentane-1,2,3-triol (19d);
N-((1R,2S)-2-(3,4-difluorophenyl)cyclopropyl)-2-(ethylthio)-9-methyl-9H-purin-6-amine (20c);
N-((1R,2S)-2-(3,4-difluorophenyl)cyclopropyl)-9-ethyl-2-(ethylthio)-9H-purin-6-amine (21c);
N-((1R,2S)-2-(3,4-difluorophenyl)cyclopropyl)-9-methyl-2-(methylthio)-9H-purin-6-amine (22c);
N-((1R,2S)-2-(3,4-difluorophenyl)cyclopropyl)-9-methyl-2-propoxy-9H-purin-6-amine hydrochloride (23t·HCl);
N-((1R,2S)-2-(3,4-difluorophenyl)cyclopropyl)-9-ethyl-2-(methylthio)-9H-purin-6-amine (24c);
2-(butylthio)-N-((1R,2S)-2-(3,4-difluorophenyl)cyclopropyl)-9-methyl-9H-purin-6-amine (25c);
2-(butylthio)-N-((1R,2S)-2-(3,4-difluorophenyl)cyclopropyl)-9-ethyl-9H-purin-6-amine (26c);
or isomers, racemic mixtures thereof, pharmaceutically acceptable acid addition salts, pharmaceutically acceptable metal salts, or alkylated ammonium salts or prodrug thereof.

In particular embodiments, the pyrimidine derivatives are selected from:
N-((1R,2S)-2-(3,4-difluorophenyl)cyclopropyl)-9-methyl-2-(propylthio)-9H-purin-6-amine (1c);
N-((1R,2S)-2-(3,4-difluorophenyl)cyclopropyl)-9-ethyl-2-(propylthio)-9H-purin-6-amine (3c);
9-allyl-N-((1R,2S)-2-(3,4-difluorophenyl)cyclopropyl)-2-(propylthio)-9H-purin-6-amine (15c);
N-((1R,2S)-2-(3,4-difluorophenyl)cyclopropyl)-9-(prop-2-yn-1-yl)-2-(propylthio)-9H-purin-6-amine (17c);
(1S,2R,3S,4R)-4-(6-(((1R,2S)-2-(3,4-difluorophenyl)cyclopropyl)amino)-2-(propylthio)-9H-purin-9-yl)cyclopentane-1,2,3-triol (19d);
N-((1R,2S)-2-(3,4-difluorophenyl)cyclopropyl)-9-methyl-2-(methylthio)-9H-purin-6-amine (22c);
N-((1R,2S)-2-(3,4-difluorophenyl)cyclopropyl)-9-ethyl-2-(methylthio)-9H-purin-6-amine (24c);
N-((1R,2S)-2-(3,4-difluorophenyl)cyclopropyl)-2-(ethylthio)-9-methyl-9H-purin-6-amine (20c);
N-((1R,2S)-2-(3,4-difluorophenyl)cyclopropyl)-9-ethyl-2-(ethylthio)-9H-purin-6-amine (21c);
2-(butylthio)-N-((1R,2S)-2-(3,4-difluorophenyl)cyclopropyl)-9-methyl-9H-purin-6-amine (25c);
or isomers, racemic mixtures thereof, pharmaceutically acceptable acid addition salts, pharmaceutically acceptable metal salts, or alkylated ammonium salts or prodrug thereof.

In particular embodiments, the pyrimidine derivative is N-((1R,2S)-2-(3,4-difluorophenyl)cyclopropyl)-9-methyl-2-(propylthio)-9H-purin-6-amine (1c); or
an isomer, a racemic mixture thereof, a pharmaceutically acceptable acid addition salt, pharmaceutically acceptable metal salt, or alkylated ammonium salt or prodrug thereof.

In particular embodiments, the pyrimidine derivatives are selected from

N-((1R,2S)-2-(3,4-difluorophenyl)cyclopropyl)-9-methyl-2-(propylthio)-9H-purin-6-amine (1c); 9-allyl-N-((1R,2S)-2-(3,4-difluorophenyl)cyclopropyl)-2-(propylthio)-9H-purin-6-amine (15c);

N-((1R,2S)-2-(3,4-difluorophenyl)cyclopropyl)-9-(prop-2-yn-1-yl)-2-(propylthio)-9H-purin-6-amine (17c); or (1S,2R,3S,4R)-4-(6-(((1R,2S)-2-(3,4-difluorophenyl)cyclopropyl)amino)-2-(propylthio)-9H-purin-9-yl)cyclopentane-1,2,3-triol (19d).

In particular embodiments, $X^1$ is N and $X^2$ is CH or $CR^8$.

In particular embodiments, the pyrimidine derivative is selected from:

N-((1R,2S)-2-(3,4-difluorophenyl)cyclopropyl)-1-methyl-6-(methylthio)-1H-pyrazolo[3,4-d]pyrimidin-4-amine (27k);

N-((1R,2S)-2-(3,4-difluorophenyl)cyclopropyl)-6-(ethylthio)-1-methyl-1H-pyrazolo[3,4-d]pyrimidin-4-amine hydrochloride (28x·HCl);

N-((1R,2S)-2-(3,4-difluorophenyl)cyclopropyl)-6-(propylthio)-1-methyl-1H-pyrazolo[3,4-d]pyrimidin-4-amine hydrochloride (29x·HCl);

N-((1R,2S)-2-(3,4-difluorophenyl)cyclopropyl)-1-ethyl-6-(methylthio)-1H-pyrazolo[3,4-d]pyrimidin-4-amine (30k);

N-((1R,2S)-2-(3,4-difluorophenyl)cyclopropyl)-1-ethyl-6-(ethylthio)-1H-pyrazolo[3,4-d]pyrimidin-4-amine hydrochloride (31x·HCl);

N-((1R,2S)-2-(3,4-difluorophenyl)cyclopropyl)-1-ethyl-6-(propylthio)-1H-pyrazolo[3,4-d]pyrimidin-4-amine hydrochloride (32x·HCl);

N-((1R,2S)-2-(3,4-difluorophenyl)cyclopropyl)-1-isopropyl-6-(methylthio)-1H-pyrazolo[3,4-d]pyrimidin-4-amine hydrochloride (33k·HCl);

N-((1R,2S)-2-(3,4-difluorophenyl)cyclopropyl)-6-(methylthio)-1-propyl-1H-pyrazolo[3,4-d]pyrimidin-4-amine hydrochloride (34k·HCl);

or isomers, racemic mixtures thereof, pharmaceutically acceptable acid addition salts, pharmaceutically acceptable metal salts, or alkylated ammonium salts or prodrug thereof.

In particular embodiments, the pyrimidine derivative is selected from:

N-((1R,2S)-2-(3,4-difluorophenyl)cyclopropyl)-1-methyl-6-(methylthio)-1H-pyrazolo[3,4-d]pyrimidin-4-amine (27k);

N-((1R,2S)-2-(3,4-difluorophenyl)cyclopropyl)-1-ethyl-6-(methylthio)-1H-pyrazolo[3,4-d]pyrimidin-4-amine (30k);

N-((1R,2S)-2-(3,4-difluorophenyl)cyclopropyl)-6-(ethylthio)-1-methyl-1H-pyrazolo[3,4-d]pyrimidin-4-amine hydrochloride (28x·HCl);

N-((1R,2S)-2-(3,4-difluorophenyl)cyclopropyl)-1-isopropyl-6-(methylthio)-1H-pyrazolo[3,4-d]pyrimidin-4-amine hydrochloride (33k·HCl);

or isomers, racemic mixtures thereof, pharmaceutically acceptable acid addition salts, pharmaceutically acceptable metal salts, or alkylated ammonium salts or prodrug thereof.

In particular embodiments, $X^1$ and $X^2$ are CH or $CR^8$.

In particular embodiments, the pyrimidine derivative is:

N-((1R,2S)-2-(3,4-difluorophenyl)cyclopropyl)-7-ethyl-2-(methylthio)-7H-pyrrolo[2,3-d]pyrimidin-4-amine hydrochloride (35p·HCl);

or an isomer, racemic mixture thereof, pharmaceutically acceptable acid addition salt, pharmaceutically acceptable metal salt, or alkylated ammonium salt or prodrug thereof.

In particular embodiments, $R^3$ and $R^7$ are H and $R^4$, $R^5$ is a fluorine.

The invention further relates to the use of pyrimidine derivative represented by formula (I)

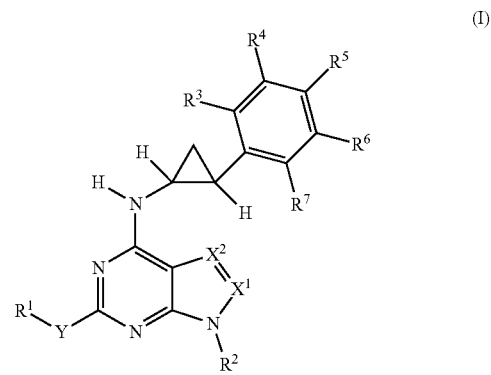

(I)

wherein:

$X^1$ and $X^2$ are independently N, CH, $CR^8$ wherein $R^8$ is $C_{1-6}$ alkyl, $C_{2-6}$ alkenyl or $C_{2-6}$ alkynyl; with the exception that if one of $X^1$ or $X^2$ is equal to N, then the remaining of $X^1$ or $X^2$ are selected from CH, $CR^8$;

—Y— is —O— or —S—;

$R^1$ and $R^2$ are independently $C_{1-6}$-alkyl, $C_{2-6}$-alkenyl, $C_{2-6}$-alkynyl, $C_{3-6}$-cycloalkyl, aryl, aryl-$C_{1-6}$-alkyl wherein the alkyl or cycloalkyl moiety is optionally mono or polysubstituted with OH or an halogen and the aryl moiety is optionally mono or polysubstituted with an halogen, —$C_{1-6}$ alkyl, —$C_{1-6}$alkoxy, —OH, —$NO_2$, —CN, —$NH_2$, —$NHR^8$, —$N(R^8)_2$—COOH, —$COOR^8$, —$CONH_2$, —$CONHR^8$, —$CON(R^8)_2$, —$SO_2NH_2$, —$SO_2NHR^8$, or —$SO_2N(R^8)_2$;

$R^3$, $R^4$, $R^5$, $R^6$ and $R^7$ are independently H, an halogen, a $C_{1-6}$ alkyl, $C_{1-6}$alkoxy, —OH, —$NO_2$, —CN, —$NH_2$, —$NHR^8$, —$N(R^8)_2$—COOH, —$COOR^8$, —$CONH_2$, —$CONHR^8$, —$CON(R^8)_2$, —$SO_2NH_2$, —$SO_2NHR^8$, or —$SO_2N(R^8)_2$;

together with a membrane penetrating agent ex vivo as inhibitor of Gram-negative bacterial growth in biofilm formation on a surface of a medical device.

The invention further relates to a method for killing or preventing Gram-negative bacterial growth in biofilm formation comprising applying on a surface of a medical device, an effective amount of pyrimidine derivatives represented by formula (I) together with a membrane penetrating agent

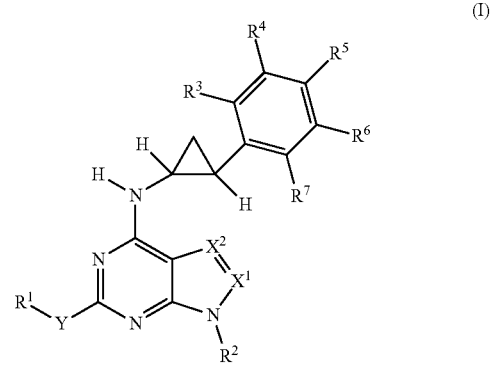

(I)

wherein:
X¹ and X² are independently N, CH, CR⁸ wherein R⁸ is $C_{1-6}$ alkyl, $C_{2-6}$ alkenyl or $C_{2-6}$ alkynyl; with the exception that if one of X¹ or X² is equal to N, then the remaining of X¹ or X² are selected from CH, CR⁸;
—Y— is —O— or —S—;
R¹ and R² are independently $C_{1-6}$-alkyl, $C_{2-6}$-alkenyl, $C_{2-6}$-alkynyl, $C_{3-6}$-cycloalkyl, aryl, aryl-$C_{1-6}$-alkyl wherein the alkyl or cycloalkyl moiety is optionally mono or polysubstituted with OH or an halogen and the aryl moiety is optionally mono or polysubstituted with an halogen, —$C_{1-6}$ alkyl, —$C_{1-6}$alkoxy, —OH, —NO₂, —CN, —NH₂, —NHR⁸, —N(R⁸)₂—COOH, —COOR⁸, —CONH₂, —CONHR⁸, —CON(R⁸)₂, —SO₂NH₂, —SO₂NHR⁸, or —SO₂N(R⁸)₂;
R³, R⁴, R⁵, R⁶ and R⁷ are independently H, an halogen, a $C_{1-6}$ alkyl, $C_{1-6}$alkoxy, —OH, —NO₂, —CN, —NH₂, —NHR⁸, —N(R⁸)₂—COOH, —COOR⁸, —CONH₂, —CONHR⁸, —CON(R⁸)₂, —SO₂NH₂, —SO₂NHR⁸, or —SO₂N(R⁸)₂, wherein said method is not a method of treatment of the human or animal body.

In particular embodiments, the medical device is a cardiovascular device.

The invention further relates to the pyrimidine derivative represented by formula (I)

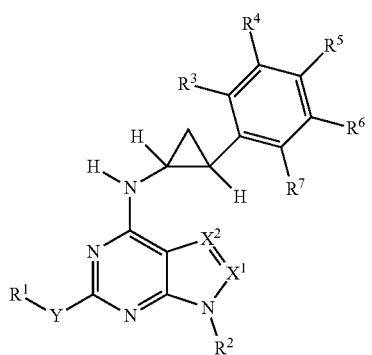

(I)

wherein:
X¹ and X² are independently N, CH, CR⁸ wherein R⁸ is $C_{1-6}$ alkyl, $C_{2-6}$ alkenyl or $C_{2-6}$ alkynyl; with the exception that if one of X¹ or X² is equal to N, then the remaining of X¹ or X² are selected from CH, CR⁸;
—Y— is —O— or —S—;
R¹ and R² are independently $C_{1-6}$-alkyl, $C_{2-6}$-alkenyl, $C_{2-6}$-alkynyl, $C_{3-6}$-cycloalkyl, aryl, aryl-$C_{1-6}$-alkyl wherein the alkyl or cycloalkyl moiety is optionally mono or polysubstituted with OH or an halogen and the aryl moiety is optionally mono or polysubstituted with an halogen, —$C_{1-6}$ alkyl, —$C_{1-6}$alkoxy, —OH, —NO₂, —CN, —NH₂, —NHR⁸, —N(R⁸)₂—COOH, —COOR⁸, —CONH₂, —CONHR⁸, —CON(R⁸)₂, —SO₂NH₂, —SO₂NHR⁸, or —SO₂N(R⁸)₂;
R³, R⁴, R⁵, R⁶ and R⁷ are independently H, an halogen, a $C_{1-6}$ alkyl, $C_{1-6}$alkoxy, —OH, —NO₂, —CN, —NH₂, —NHR⁸, —N(R⁸)₂—COOH, —COOR⁸, —CONH₂, —CONHR⁸, —CON(R⁸)₂, —SO₂NH₂, —SO₂NHR⁸, or —SO₂N(R⁸)₂. comprising a marker for use together with a membrane penetrating agent in diagnosing or prognosing Gram-negative bacterial infection.

In particular embodiments of the compositions, uses and methods described herein, the membrane penetrating agent is polymyxin B nonapeptide.

The invention further relates to pharmaceutical compositions comprising a pyrimidine derivative of formula (I) or isomars, racemic mixtures thereof, pharmaceutically acceptable acid addition salts thereof as provided herein for use in the prevention or treatment of gram-negative bacterial infections. In particular embodiments, the pharmaceutical composition further comprises a membrane-penetrating agent.

DETAILED DESCRIPTION

In a first aspect, the invention provides new pyrimidine derivatives represented by formula (I)

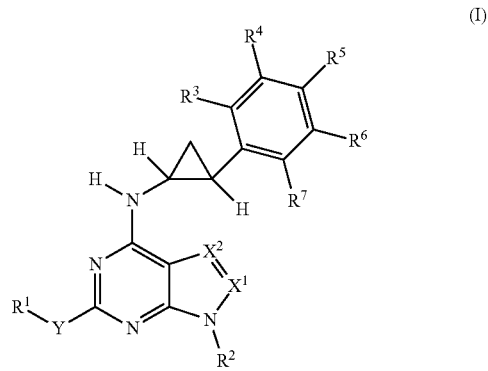

(I)

or isomers, racemic mixtures thereof, pharmaceutically acceptable acid addition salts, pharmaceutically acceptable metal salts, or alkylated ammonium salts or prodrug thereof; for use in the treatment or prevention of Gram-negative bacterial infection in a host mammal in need of such treatment or prevention;
wherein:
X¹ and X² are independently N, CH, CR⁸ wherein R⁸ is $C_{1-6}$ alkyl, $C_{2-6}$ alkenyl or $C_{2-6}$ alkynyl; with the exception that if one of X¹ or X² is equal to N, then the remaining X¹ or X² are selected from CH, CR⁸;
—Y— is —O— or —S—;
R¹ and R² are independently $C_{1-6}$-alkyl, $C_{2-6}$-alkenyl, $C_{2-6}$-alkynyl, $C_{3-6}$-cycloalkyl, aryl, aryl-$C_{1-6}$-alkyl wherein the alkyl or cycloalkyl moiety is optionally mono or polysubstituted with OH or an halogen and the aryl moiety is optionally mono or polysubstituted with an halogen, —$C_{1-6}$ alkyl, —$C_{1-6}$alkoxy, —OH, —NO₂, —CN, —NH₂, —NHR⁸, —N(R⁸)₂—COOH, —COOR⁸, —CONH₂, —CONHR⁸, —CON(R⁸)₂, —SO₂NH₂, —SO₂NHR⁸, or —SO₂N(R⁸)₂;
R³, R⁴, R⁵, R⁶ and R⁷ are independently H, an halogen, a $C_{1-6}$ alkyl, $C_{1-6}$alkoxy, —OH, —NO₂, —CN, —NH₂, —NHR⁸, —N(R⁸)₂—COOH, —COOR⁸, —CONH₂, —CONHR⁸, —CON(R⁸)₂, —SO₂NH₂, —SO₂NHR⁸, or —SO₂N(R⁸)₂.

In particular embodiments said use is together with a membrane penetrating agent.

Within its scope, the invention includes all optical isomers of pyrimidine derivatives of formula (I), some of which are optically active, and also their mixtures including racemic mixtures thereof, but also their polymorphic forms.

The term "$C_{1-6}$-alkyl" as used herein, alone or in combination, refers to a straight or branched, saturated hydrocarbon chain having 1 to 6 carbon atoms such as for example methyl, ethyl, n-propyl, isopropyl, n-butyl, sec-butyl, isobutyl, tert-butyl, n-pentyl, 2-methylbutyl, 3-methylbutyl, n-hexyl, 4-methylpentyl, neopentyl, n-hexyl, 1,2-dimethylpropyl, 2,2-dimethylpropyl, 1,2,2-trimethylpropyl, and the like.

The term "$C_{2-6}$-alkenyl" as used herein, alone or in combination, refers to a straight or branched, unsaturated hydrocarbon chain having 2 to 6 carbon atoms with at least one carbon-carbon double bond such as for example vinyl, allyl, 1-butenyl, 2-butenyl, isobutenyl, 1-pentenyl, 2-pentenyl, 3-methyl-1-butenyl, 1-methyl-2-butenyl, 2,3-dimethyl-2-butenyl, 1-hexenyl, 2-hexenyl, 3-hexenyl and the like.

The term "$C_{2-6}$-alkynyl" as used herein, alone or in combination, refers to a straight or branched, unsaturated hydrocarbon chain having 2 to 6 carbon atoms with at least one carbon-carbon triple bond such as for example acetylenyl, propynyl, 1-butynyl, 2-butynyl, 1-pentynyl, 2-pentynyl, 3-methyl-1-butynyl, 1-hexynyl, 2-hexynyl, 3-hexenyl and the like.

The term "$C_{3-6}$-cycloalkyl" as used herein, alone or in combination refers to a radical of a saturated cyclic hydrocarbon with 3 to 6 carbon atoms such as cyclopropyl, cyclobutyl, cyclopentyl or cyclohexyl.

The term "aryl" as used herein, alone or in combination refers to a monocyclic or polycyclic aromatic ring having 6 to 20 carbon atoms, such as phenyl, anthracenyl, naphthyl and the like.

The term "$C_{1-6}$-alkoxy" as used herein, refers to a straight or branched monovalent substituent comprising a $C_{1-6}$-alkyl group linked through an ether oxygen having its free valence bond from the ether oxygen and having 1 to 6 carbon atoms e.g. methoxy, ethoxy, propoxy, isopropoxy, butoxy, pentoxy.

The term "—CN" as used herein refers to a carbon-nitrogen triple bond.

The term halogen as used herein refers to fluorine, chlorine, bromine or iodine.

The acceptable salts include pharmaceutically acceptable acid addition salts, pharmaceutically acceptable metal salts, or optionally alkylated ammonium salts, such as hydrochloric, hydrobromic, hydroiodic, phosphoric, sulfuric, trifluoroacetic, trichloroacetic, oxalic, maleic, pyruvic, malonic, succinic, citric, tartaric, fumaric, mandelic, benzoic, cinnamic, methanesulfonic, ethanesulfonic, picric acid and the like, and include acids related to the pharmaceutically acceptable salts listed in Journal of Pharmaceutical Science, 66, 2 (1977) and incorporated herein by reference, or lithium, sodium, potassium, magnesium and the like.

The term prodrug has been defined in Burger's Medicinal Chemistry and Drug discovery ($5^{th}$ edition 1995) as compounds, which undergo biotransformation prior to exhibiting their pharmacological effects. The term prodrug as used herein refers therefore to an analogue or a derivative of a compound of general formula (I) that comprises biohydrolysable moieties such as biohydrolysable ester functions, biohydrolysable carbamate functions, biohydrolysable ureides and the like obtained under biological conditions. Prodrugs can be prepared using well-known methods such as those described in Burgers medicinal chemistry and drug discovery (1995) 172-178, 949-982 (Manfred E. Wolff).

The term "membrane penetrating agent" as used herein refers to a molecule able to penetrate through the outer membrane of a Gram-negative bacteria. It is for example a small hydrophilic molecule such as a β-lactam that use the pores formed by porins to gain access inside to the bacteria or a hydrophobic molecule that diffuse across the outer membrane layer.

Preferred membrane penetrating agents include but are not limited to polymyxin, polymyxin derivatives, aminoglycosides, dibasic macrolides, oligo-acyl-lysyls (OAKs) or cationic peptides such as for example dilipid ultrashort cationic lipopeptides.

Polymyxins are for example Polymyxin B (PMB) and Polymyxin E (also called colistin). Polymyxins are cyclic lipodecapeptide and have five free amino groups (di-aminobutyric acid residues) and a $C_8$-$C_9$ fatty acid side chain as illustrated in formula (VII). Polymyxins are therefore both cationic and lipophilic.

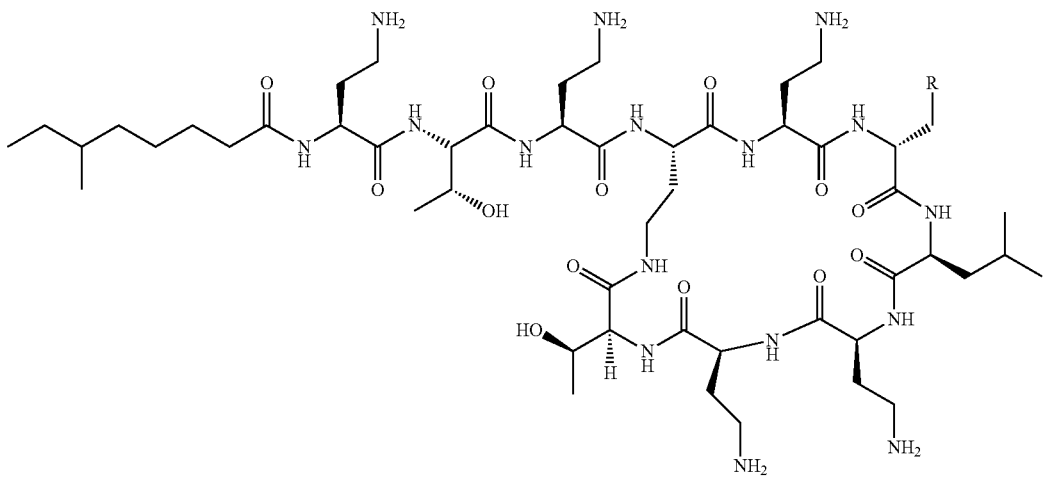

(VI)

R - Ph, polymyxin B (1)
R = CH(CH₃)₂, polymyxin E (2)

Polymyxin derivatives are for example polymyxin B nonapeptide (PMBN) wherein the fatty acyl tail and N-terminal diaminobutyryl (Dab) residue of polymyxin B are lacking, as illustrated in formula (VII):

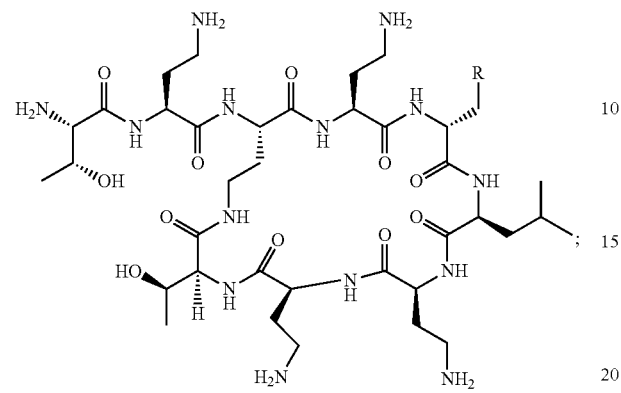

(VII)

wherein R is Ph or polymyxin B derivatives wherein a DAB residue (di-aminobutyryl residue) of the linear chain of polymyxin has been replaced by an aminobutyric acid or serine as illustrated in formula (VIII) and formula (IX) respectively:

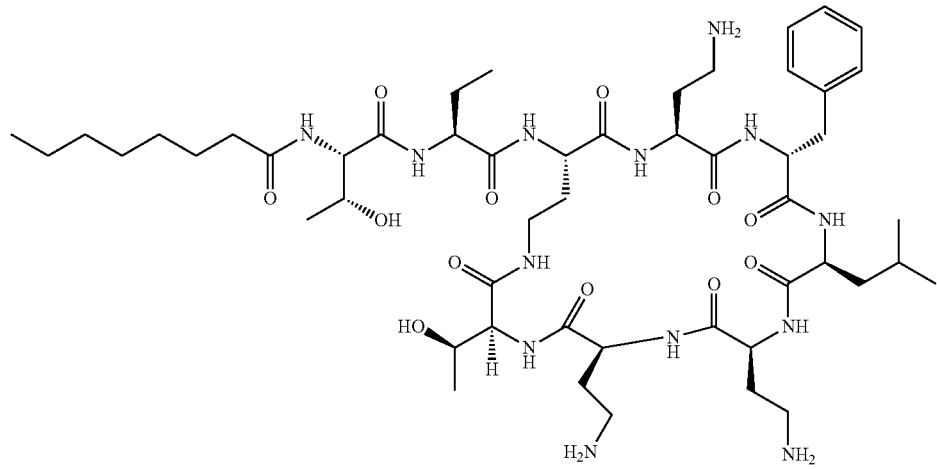

(VIII)

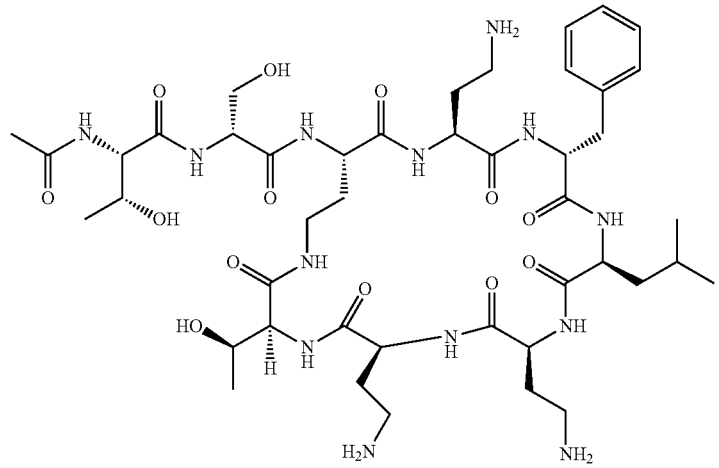

(IX)

Polymyxin derivatives corresponding to formula (VIII) and (IX) are also respectively called SPR7061 and SPR741 in the art.

Aminoglycosides are amino-modified glycosides. Aminoglycosides have between 2 and 5 glycosides substituted by an amino group. Aminoglycosides are for example streptomycin, kanamycin, tobramycin, gentamycin and the like.

Dibasic macrolides are for example Azithromycine, Dirithromycine and the like.

Oligo-acyl-lysyls (OAKs) are peptides with acyl chains alternating with cationic amino acids, such as lysine, histidine and arginine; as illustrated in formula (X).

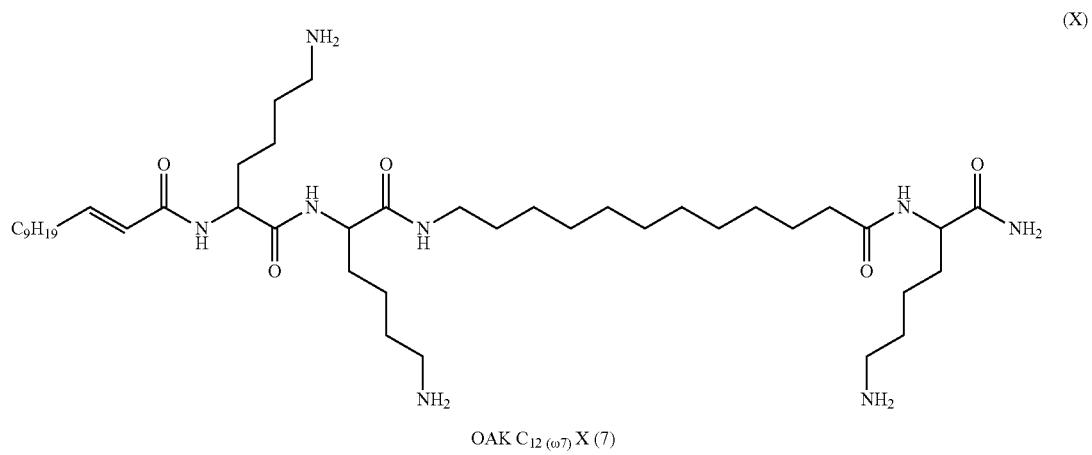

OAK $C_{12\,(\omega 7)}$ X (7)

Preferred oligo-acyl-lysyl is $C_{12}K\text{-}7\alpha_8$ wherein a represents aminooctanoyllysyls as illustrated in formula (XI) wherein n is 7:

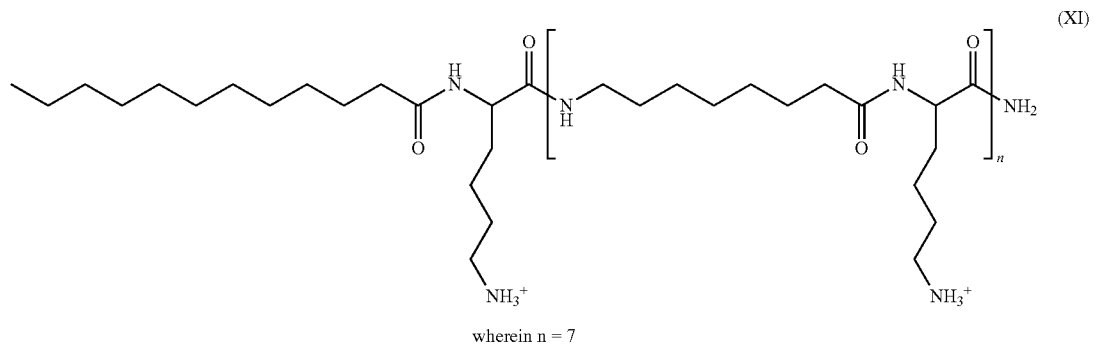

wherein n = 7

Dilipid ultrashort cationic lipopeptides are cationic peptides of only four amino acids with varying aliphatic dilipids that may range from seven ($C_7$) to fourteen ($C_{14}$) carbons long.

Preferred ultrashort dilipid cationic lipoptides have a short sequence KKKK and KKGK and are acethylated with an aliphatic dilipid of 9 carbons-long as illustrated in formulae (XII) and (XIII).

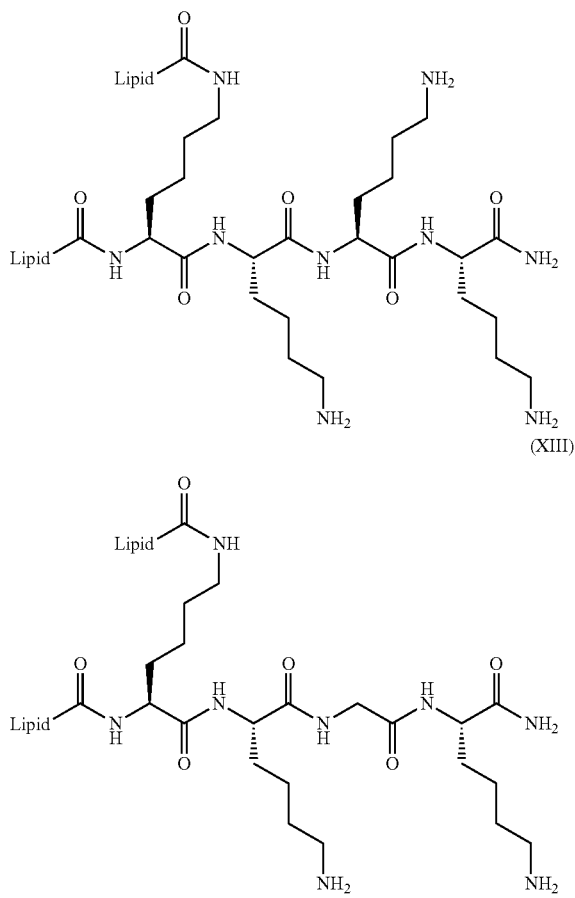

(XII)

(XIII)

Most preferred penetrating agent is polymyxin B nonapeptide.

The term "bacterial infection" as used herein generally refers to the presence of undesirable Gram-negative bacteria. In particular embodiments said undesired infection is an invasion of a body, body tissues or cells by bacteria. However, It is used herein to also refer to bacterial fouling (which typically refers to unwanted contamination on surfaces, such as on bio-sensors, cardiovascular implants, catheters, contact lenses, and surgical tools) or other types of contamination (as in food, feed and other fluid products).

In the context of the present invention, a bacterial infection in a human and animal refers to a Gram-negative bacterial infection such as for example pneumonia, septicemia, endocarditis, meningitis, urinary tract, gastroenteritis, skin and soft tissue infections.

The source of bacterial infection can be diverse, and it can be caused for example by the use of biomaterial implants.

By biomaterials, or biomaterial implant, reference is made to all implantable foreign material for clinical use in host mammals such as for prosthetic joints, pacemakers, implantable cardioverter-defibrillators, intravascular or urinary catheters, stent including coronary stent, prosthetic heart valves, bioprostheses, intraocular lens, dental implants, breast implants, endotracheal tubes, gastrostomy tubes and the like.

By host mammal, it is intended to refer preferably to a human, but also an animal in need of treatment or prevention of bacterial treatment.

By prevention of bacterial infection, it is intended to refer to a reduction in risk of acquiring infection, or reduction or inhibition of recurrence of infection. For example, the pyrimidine derivatives may be administered together with a membrane penetrating agent as prevention before a surgical treatment to prevent infection.

The term "Gram-negative bacteria" as used herein corresponds to the term in as known in the art, i.e. bacteria characterized by an envelope consisting of 3 main layers, i.e. an outer membrane containing lipopolysaccharides (LPS), a peptidoglycan cell wall with peptide chains that are generally cross-linked and a cytoplasmic or inner membrane, also called integral membrane protein. In particular embodiments, the gram-negative bacteria is for example *Adnetobacter* spp., such as *Adnetobacter baumannii*, *Bordetella pertussis*, *Campylobacter* spp.; Enterobacteriaceae such as *Citrobacter* spp., *Enterobacter* spp., *Escherichia coli*, *Klebsiella* spp., *Salmonella* spp., *Serratia marcescens*, *Shigella* spp., *Yersinia* spp.; *Haemophilus influenza*, *Helocobacter pylorilegionella pneumophila*, *Neisseria* spp., *Pseudomonas aeruginosa*, *Vibrio cholera* and the like.

In particular embodiments, the "Gram-negative bacteria" are resistant to one or more commonly used antibiotics including quinolones (such as ciprofloxacin), colistins (polymyxins), carbapenems (such as imipenem, meropenem), cephalosporins (such as cefotaxime, ceftazidime), and other β-lactam antibiotics and the like.

Besides humans, companion animals, such as cats, dogs, and horses, can also be colonized and infected by Gram-negative bacteria, without host adaptation, and therefore may act as reservoirs for human infections. Bacteria can also develop distinct resistance when hosted by animals. Antibiotic use in agriculture (for example inappropriate uses of antibiotics in food animals and other aspects of agriculture and aquaculture) contributes to the emergence of resistant bacteria and their spread to humans.

In particular embodiments, the invention relates to pyrimidine derivatives comprising an imidazolo group and that are represented by formula (I) wherein $X^1$ is CH or $CR^8$ and $X^2$ is N; or an acceptable salt or prodrug thereof; said pyrimidine derivatives comprising an imidazolo group may also be called purine derivatives.

It is surprisingly found that said pyrimidine derivatives comprising an imidazolo group exhibit antibacterial activity against Gram-negative bacteria. In preferred embodiments, the pyrimidine derivatives are administered together with a membrane penetrating agent.

Preferred pyrimidine derivatives comprising an imidazolo group comprise a phenylcyclopropyl group as illustrated in formula (IV)

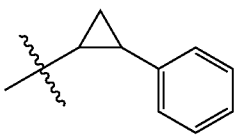

(IV)

such as for example 9-methyl-N-((1R,2S)-2-phenylcyclopropyl)-2-(propylthio)-9H-purin-6-amine (2c); or isomers, racemic mixtures thereof, pharmaceutically acceptable acid addition salts, pharmaceutically acceptable metal salts, or alkylated ammonium salts or prodrug thereof.

More preferred pyrimidine derivatives with an imidazolo group comprises a 3,4-difluorophenylcyclopropyl group as illustrated in formula II

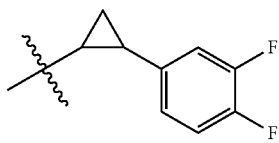
(II)

Most preferred pyrimidine derivatives with an imidazolo group are substituted by a 3,4-difluorophenylcyclopropylamino group as illustrated for example in formula (III)

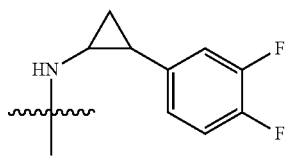
(III)

and are for example:
N-((1R,2S)-2-(3,4-difluorophenyl)cyclopropyl)-9-methyl-2-(propylthio)-9H-purin-6-amine (1c);
9-methyl-N-((1R,2S)-2-phenylcyclopropyl)-2-(propylthio)-9H-purin-6-amine (2c);
N-((1R,2S)-2-(3,4-difluorophenyl)cyclopropyl)-9-ethyl-2-(propylthio)-9H-purin-6-amine (3c);
N-((1R,2S)-2-(3,4-difluorophenyl)cyclopropyl)-9-propyl-2-(propylthio)-9H-purin-6-amine (4c);
N-((1R,2S)-2-(3,4-difluorophenyl)cyclopropyl)-9-isopropyl-2-(propylthio)-9H-purin-6-amine (5c);
9-cyclopropyl-N-((1R,2S)-2-(3,4-difluorophenyl)cyclopropyl)-2-(propylthio)-9H-purin-6-amine (6c);
9-butyl-N-((1R,2S)-2-(3,4-difluorophenyl)cyclopropyl)-2-(propylthio)-9H-purin-6-amine (7c);
9-(sec-butyl)-N-((1R,2S)-2-(3,4-difluorophenyl)cyclopropyl)-2-(propylthio)-9H-purin-6-amine (8c);
9-(tert-butyl)-N-((1R,2S)-2-(3,4-difluorophenyl)cyclopropyl)-2-(propylthio)-9H-purin-6-amine (9c);
9-cyclobutyl-N-((1R,2S)-2-(3,4-difluorophenyl)cyclopropyl)-2-(propylthio)-9H-purin-6-amine (10c);
N-((1R,2S)-2-(3,4-difluorophenyl)cyclopropyl)-9-pentyl-2-(propylthio)-9H-purin-6-amine (11c);
9-cyclopentyl-N-((1R,2S)-2-(3,4-difluorophenyl)cyclopropyl)-2-(propylthio)-9H-purin-6-amine (12c);
N-((1R,2S)-2-(3,4-difluorophenyl)cyclopropyl)-9-hexyl-2-(propylthio)-9H-purin-6-amine (13c);
9-cyclohexyl-N-((1R,2S)-2-(3,4-difluorophenyl)cyclopropyl)-2-(propylthio)-9H-purin-6-amine (14c);
9-allyl-N-((1R,2S)-2-(3,4-difluorophenyl)cyclopropyl)-2-(propylthio)-9H-purin-6-amine (15c);
2-(6-(((1R,2S)-2-(3,4-difluorophenyl)cyclopropyl)amino)-2-(propylthio)-9H-purin-9-yl)ethanol (16c);
N-((1R,2S)-2-(3,4-difluorophenyl)cyclopropyl)-9-(prop-2-yn-1-yl)-2-(propylthio)-9H-purin-6-amine (17c.);
N-((1R,2S)-2-(3,4-difluorophenyl)cyclopropyl)-2-(propylthio)-9-(2,2,2-trifluoroethyl)-9H-purin-6-amine (18c);
(1S,2R,3S,4R)-4-(6-(((1R,2S)-2-(3,4-difluorophenyl)cyclopropyl)amino)-2-(propylthio)-9H-purin-9-yl)cyclopentane-1,2,3-triol (19d);
N-((1R,2S)-2-(3,4-difluorophenyl)cyclopropyl)-2-(ethylthio)-9-methyl-9H-purin-6-amine (20c);
N-((1R,2S)-2-(3,4-difluorophenyl)cyclopropyl)-9-ethyl-2-(ethylthio)-9H-purin-6-amine (21c);
N-((1R,2S)-2-(3,4-difluorophenyl)cyclopropyl)-9-methyl-2-(methylthio)-9H-purin-6-amine (22c);
N-((1R,2S)-2-(3,4-difluorophenyl)cyclopropyl)-9-methyl-2-propoxy-9H-purin-6-amine hydrochloride (23t·HCl);
N-((1R,2S)-2-(3,4-difluorophenyl)cyclopropyl)-9-ethyl-2-(methylthio)-9H-purin-6-amine (24c);
2-(butylthio)-N-((1R,2S)-2-(3,4-difluorophenyl)cyclopropyl)-9-methyl-9H-purin-6-amine (25c);
2-(butylthio)-N-((1R,2S)-2-(3,4-difluorophenyl)cyclopropyl)-9-ethyl-9H-purin-6-amine (26c);
or isomers, racemic mixtures thereof, pharmaceutically acceptable acid addition salts, pharmaceutically acceptable metal salts, or alkylated ammonium salts or prodrug thereof.

The most preferred pyrimidine derivatives comprising an imidazolo group are:
N-((1R,2S)-2-(3,4-difluorophenyl)cyclopropyl)-9-methyl-2-(propylthio)-9H-purin-6-amine (1c);
N-((1R,2S)-2-(3,4-difluorophenyl)cyclopropyl)-9-ethyl-2-(propylthio)-9H-purin-6-amine (3c);
9-allyl-N-((1R,2S)-2-(3,4-difluorophenyl)cyclopropyl)-2-(propylthio)-9H-purin-6-amine (15c);
N-((1R,2S)-2-(3,4-difluorophenyl)cyclopropyl)-9-(prop-2-yn-1-yl)-2-(propylthio)-9H-purin-6-amine (17c);
(1S,2R,3S,4R)-4-(6-(((1R,2S)-2-(3,4-difluorophenyl)cyclopropyl)amino)-2-(propylthio)-9H-purin-9-yl)cyclopentane-1,2,3-triol (19d);
N-((1R,2S)-2-(3,4-difluorophenyl)cyclopropyl)-9-methyl-2-(methylthio)-9H-purin-6-amine (22c);
N-((1R,2S)-2-(3,4-difluorophenyl)cyclopropyl)-9-ethyl-2-(methylthio)-9H-purin-6-amine (24c);
N-((1R,2S)-2-(3,4-difluorophenyl)cyclopropyl)-2-(ethylthio)-9-methyl-9H-purin-6-amine (20c);
N-((1R,2S)-2-(3,4-difluorophenyl)cyclopropyl)-9-ethyl-2-(ethylthio)-9H-purin-6-amine (21c);
2-(butylthio)-N-((1R,2S)-2-(3,4-difluorophenyl)cyclopropyl)-9-methyl-9H-purin-6-amine (25c);
or isomers, racemic mixtures thereof, pharmaceutically acceptable acid addition salts, pharmaceutically acceptable metal salts, or alkylated ammonium salts or prodrug thereof.

In particular embodiments, the invention relates to pyrimidine derivatives comprising a pyrazolo group and are represented by formula (I) wherein $X^1$ is N and $X^2$ is CH or $CR^8$; or isomers, racemic mixtures thereof, pharmaceutically acceptable acid addition salts, pharmaceutically acceptable metal salts, or alkylated ammonium salts or prodrug thereof.

The inventors have surprisingly found that said pyrimidine derivatives comprising a pyrazolo group exhibit Gram-negative antibacterial activity. In particular embodiments, the pyrimidine derivatives are administered together with a membrane penetrating agent.

Preferred pyrimidine derivatives comprising a pyrazolo group are substituted by a 3,4-difluorophenylcyclopropyl group, most preferred pyrimidine derivatives comprising a pyrazolo group are substituted by a 3,4-difluorophenylcyclopropylamino group as for example:
N-((1R,2S)-2-(3,4-difluorophenyl)cyclopropyl)-1-methyl-6-(methylthio)-1H-pyrazolo[3,4-d]pyrimidin-4-amine (27k);
N-((1R,2S)-2-(3,4-difluorophenyl)cyclopropyl)-6-(ethylthio)-1-methyl-1H-pyrazolo[3,4-d]pyrimidin-4-amine hydrochloride (28x·HCl);
N-((1R,2S)-2-(3,4-difluorophenyl)cyclopropyl)-6-(propylthio)-1-methyl-1H-pyrazolo[3,4-d]pyrimidin-4-amine hydrochloride (29x·HCl);

N-((1R,2S)-2-(3,4-difluorophenyl)cyclopropyl)-1-ethyl-6-(methylthio)-1H-pyrazolo[3,4-d]pyrimidin-4-amine (30k);

N-((1R,2S)-2-(3,4-difluorophenyl)cyclopropyl)-1-ethyl-6-(ethylthio)-1H-pyrazolo[3,4-d]pyrimidin-4-amine hydrochloride (31x·HCl);

N-((1R,2S)-2-(3,4-difluorophenyl)cyclopropyl)-1-ethyl-6-(propylthio)-1H-pyrazolo[3,4-d]pyrimidin-4-amine hydrochloride (32x·HCl);

N-((1R,2S)-2-(3,4-difluorophenyl)cyclopropyl)-1-isopropyl-6-(methylthio)-1H-pyrazolo[3,4-d]pyrimidin-4-amine hydrochloride (33k·HCl);

N-((1R,2S)-2-(3,4-difluorophenyl)cyclopropyl)-6-(methylthio)-1-propyl-1H-pyrazolo[3,4-d]pyrimidin-4-amine hydrochloride (34k·HCl);

or isomers, racemic mixtures thereof, pharmaceutically acceptable acid addition salts, pharmaceutically acceptable metal salts, or alkylated ammonium salts or prodrug thereof.

The most preferred pyrimidine derivatives comprising a pyrazolo group are:

N-((1R,2S)-2-(3,4-difluorophenyl)cyclopropyl)-1-methyl-6-(methylthio)-1H-pyrazolo[3,4-d]pyrimidin-4-amine (27k);

N-((1R,2S)-2-(3,4-difluorophenyl)cyclopropyl)-1-ethyl-6-(methylthio)-1H-pyrazolo[3,4-d]pyrimidin-4-amine (30k);

N-((1R,2S)-2-(3,4-difluorophenyl)cyclopropyl)-6-(ethylthio)-1-methyl-1H-pyrazolo[3,4-d]pyrimidin-4-amine hydrochloride (28xHCl);

N-((1R,2S)-2-(3,4-difluorophenyl)cyclopropyl)-1-isopropyl-6-(methylthio)-1H-pyrazolo[3,4-d]pyrimidin-4-amine hydrochloride (33kHCl);

or isomers, racemic mixtures thereof, pharmaceutically acceptable acid addition salts, pharmaceutically acceptable metal salts, or alkylated ammonium salts or prodrug thereof.

In particular embodiments, the invention relates to pyrimidine derivatives comprising a pyrrolo group and are represented by formula (I) wherein $X^1$ and $X^2$ are CH or $CR^8$ or isomers, racemic mixtures thereof, pharmaceutically acceptable acid addition salts, pharmaceutically acceptable metal salts, or alkylated ammonium salts or prodrug thereof.

It is surprisingly found that said pyrimidine derivatives comprising a pyrrolo group exhibit antibiotic activity. In particular embodiments, the pyrimidine derivatives are administered together with a membrane penetrating agent.

Preferred pyrimidine derivatives comprising a pyrrolo group, comprise a 3,4-difluorophenylcyclopropyl group. Most preferred pyrimidine derivatives comprising a pyrrolo group, comprise a 3,4-difluorophenylcyclopropylamino group.

The most preferred pyrimidine derivatives comprising a pyrrolo group is

N-((1R,2S)-2-(3,4-difluorophenyl)cyclopropyl)-7-ethyl-2-(methylthio)-7H-pyrrolo[2,3-d]pyrimidin-4-amine hydrochloride (35p·HCl);

or isomers, racemic mixtures thereof, pharmaceutically acceptable acid addition salts, pharmaceutically acceptable metal salts, or alkylated ammonium salts or prodrug thereof.

Further preferred pyrimidine derivatives according to formula (I) comprise at least one detectable isotope selected from $^3H$, $^{18}F$, $^{19}F$, $^{11}C$, $^{13}C$, $^{14}C$, $^{75}Br$, $^{76}Br$, $^{120}I$, $^{123}I$, $^{125}I$, $^{131}I$, $^{15}O$, and $^{13}N$.

Further preferred pyrimidine derivatives according to formula (I) comprise a detectable isotope selected from $^3H$, $^{18}F$, $^{19}F$, $^{11}C$, $^{14}C$ and $^{123}I$.

Particularly preferred pyrimidine derivatives according to formula (I) comprise a detectable isotope selected from $^{18}F$ and $^{11}C$.

Particularly preferred pyrimidine derivatives according to formula (I) or a salt thereof comprise the detectable isotope $^{18}F$.

Preferred pyrimidine derivative or isomers, racemic mixtures thereof, pharmaceutically acceptable acid addition salts, pharmaceutically acceptable metal salts, or alkylated ammonium salts comprising at least one detectable isotope also comprise a phenylcyclopropyl group (IV),

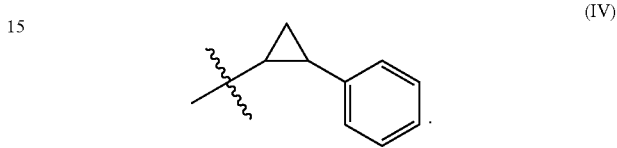

(IV)

Particularly preferred pyrimidine derivatives comprising at least one detectable isotope also comprises a 3,4-difluorophenylcyclopropyl group.

In particular embodiments, the bacterial infection is an infection caused by Enterobacteriaceae, more particularly *E. coli*.

In another particular embodiment, the bacterial infection is an infection caused by *Pseudomonas aeruginosa*.

In particular embodiments, the membrane penetrating agent is a drug. In further particular embodiments, the membrane penetrating agent is polymyxin B nonapeptide as illustrated in formula (VI)

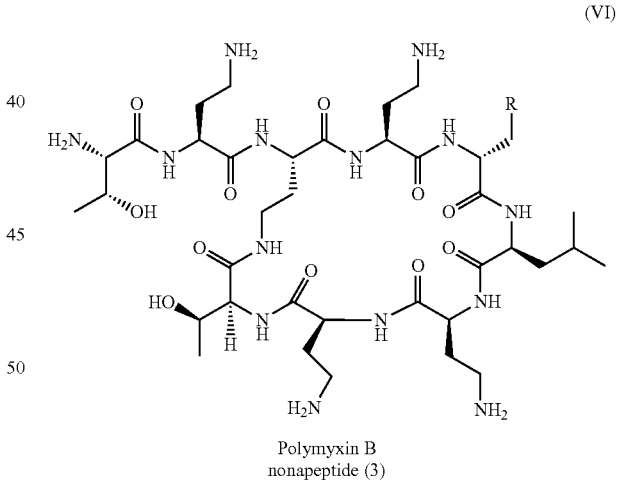

(VI)

Polymyxin B
nonapeptide (3)

In other particular embodiments, the membrane penetrating agent is a dilipid ultrashort cationic lipopeptide of less than 10 amino acids, preferably of 7 amino acids linked to aliphatic lipids ranged from 7 ($C_7$) to 14 ($C_{1-4}$) carbons-long.

In still other particular embodiments, the membrane penetrating agent is an oligo-acyl-lysyl with acyl chains comprising between 8 to 15 carbons, preferably 12 carbons long alternating with cationic amino acids such as for example lysyl-lysyl-aminododecanoyl-lysyl-amide sequence. Preferred oligo-acyl-lysyl is $C_{1-2}$ K-7 as illustrated in formula (XI) wherein n equal 7:

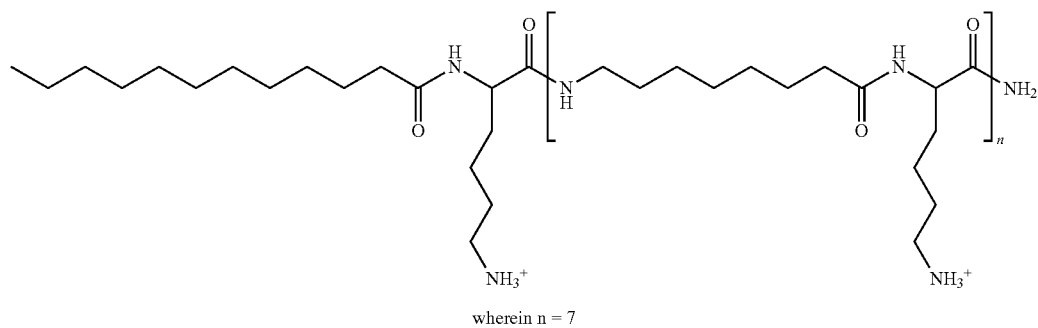

wherein n = 7

The pyrimidine derivatives and acceptable salts thereof are prepared according to the following chemical pathways:

In particular embodiments, the pyrimidine derivatives according to formula (I) or acceptable salts thereof, and comprising an imidazolo group or corresponding to purine derivatives are made according to a general common chemical pathway that comprises first: a preparation of a starting product, a 2-substituted-4,6-dihalogenopyrimidin-5-amine (Xh) such as for example a 2-substituted-4,6-dichloropyrimidin-5-amine according to scheme 1, and further reacting the starting product with reagents according to the following steps ib to iiib in scheme 2. The general chemical pathway is common for pyrimidine derivative with imidazolo group having —Y— equal to —S— or —O—. Formation of 3 intermediates Xa, Xb, Xc wherein $R^1, R^2, R^3, R^4, R^5, R^6$ and $R^7$ as defined in formula (I), are successively provided along the 3 steps ib to iiib.

Finally, pyrimidine derivative with an imidazolo group and having —Y═—O— is differentiated by an additional chemical pathway that allows conversion of the thioether (wherein Y is S) pyrimidine derivative into a corresponding ether (Y═O) pyrimidine derivative (scheme 3).

1 Preparation of the Starting Product: 2-substituted 4,6-dihalogenopynmidin-5-amines Such as for Example 2-substituted 4,6-dichloropyrimidin-5-amines According to the Following Chemical Pathway:

A 2-substituted 4,6-dihalogeno-5-nitropyrimidine Xg such as for example 2-substituted 4,6-dichloro-5-nitropyrimidine is obtained by reacting thiobarbituric acid with the halide $R^1$hal in aqueous alkaline medium such as KOH (step ia) at a temperature between 20° C. to 100° C., followed by a nitration reaction using nitric acid in the presence of another acid such as acetic acid at low temperature varying from −20° C. to room temperature (step iia) and an aromatic nucleophilic substitution at a varying temperature from −20° C. to 100° C. using an organic base such as for example diethylamine, 2,6 lutidine or the like, with a phosphoryl halide such as phosphoryl chloride (step iiia).

The 2-substituted 4,6-dihalogeno-5-nitropyrimidine Xg is then reduced at room temperature by iron in acidic medium such as for example acetic acid to obtain the corresponding 2-substituted 4,6-dihalogenopyrimidin-5-amine Xh such as for example 2-substituted 4,6-dichloropyrimidin-5-amine (step iva).

Scheme 1

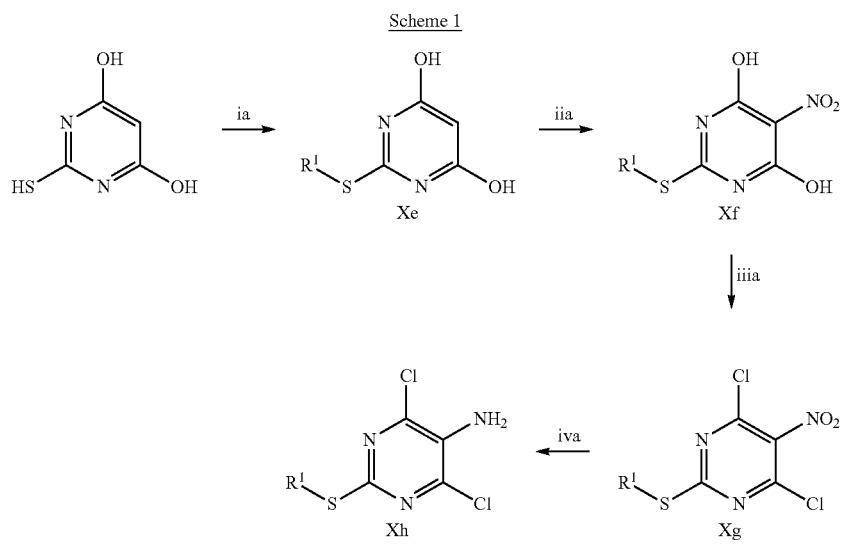

wherein $R^1$ is defined as above in formula (I).

2° Reaction of Starting Product with Reagents According to the Following Steps Ib to Ivb

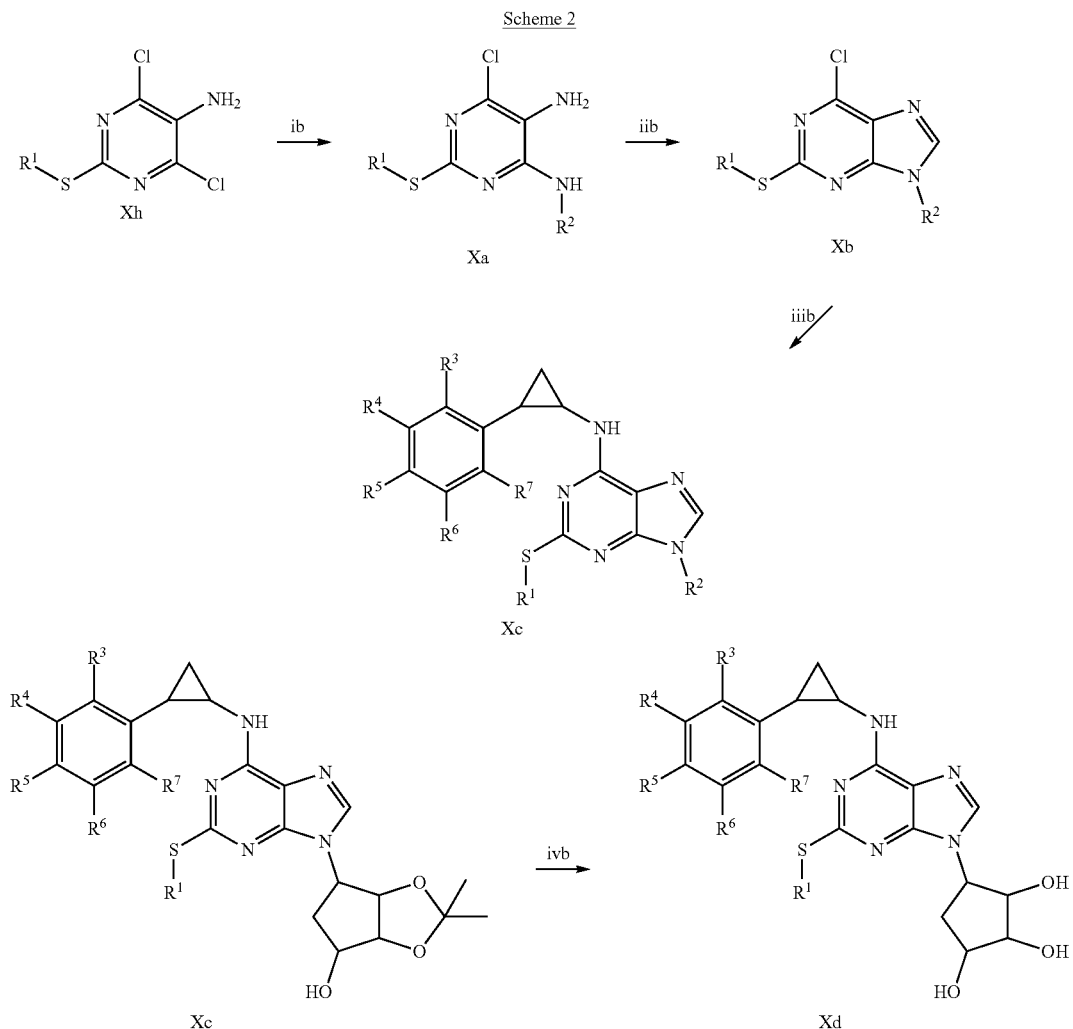

Scheme 2

In a first step (ib), $N^4$,2-disubstituted 6-halogenopyrimidine-4,5-diamines (Xa) such as for example $N^4$,2-disubstituted 6-chloropyrimidine-4,5-diamines is obtained by reaction of $R^2NH_2$ with the 2-substituted 4,6-dihalogenopyrimidin-5-amine (Xh) such as for example 2-substituted 4,6-dichloropyrimidin-5-amine and is carried out in an alcohol such as methanol at a temperature of for example 100° C.

The first step is followed by a ring closure reaction of the intermediate Xa by means of a trialkyl orthoformate such as triethyl orthoformate carried out at a temperature of for example 130° C., in the presence of an acid such as for example acetic acid (step iib) to obtain the corresponding intermediates 2,9-disubstituted 6-halogeno-9H-purines (Xb) such as for example 2,9-disubstituted 6-chloro-9H-purines.

In step iiib, 2,9-disubstituted N—(($R^3$-$R^7$)-substituted phenyl)cyclopropyl-9H-purin-6-amines (Xc) are obtained by nucleophilic substitution of the halogen atom preferably a chlorine atom of intermediate Xb by a ($R^3$-$R^7$)-substituted phenylcyclopropylamine at a temperature of for example 90° C.

In case of an acetonide of a pentane-1,2,3-triol intermediate, deprotection occurred in acidic hydroalcoholic conditions to provide a pentane-1,2,3-triol Xd (step ivb). The reaction is carried out at a room temperature.

3° Conversion of the Thioether (Y=S) Pyrimidine Derivative into a Corresponding Ether (Y=O) Pyrimidine Derivative:

Scheme 3

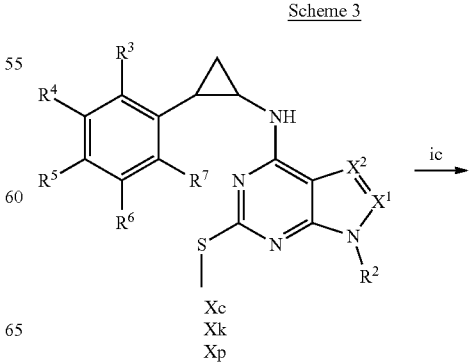

Xc
Xk
Xp

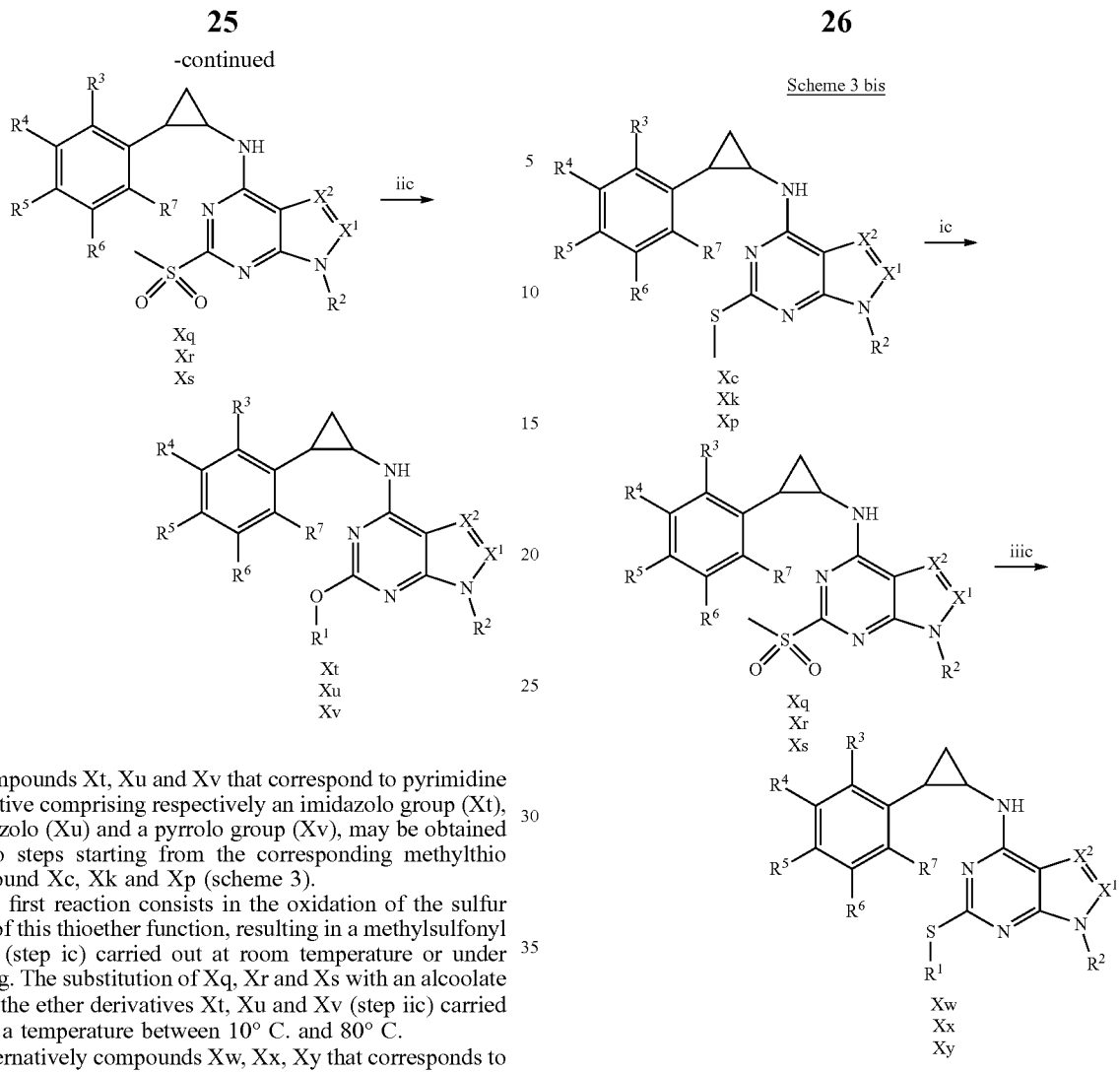

Compounds Xt, Xu and Xv that correspond to pyrimidine derivative comprising respectively an imidazolo group (Xt), a pyrazolo (Xu) and a pyrrolo group (Xv), may be obtained in two steps starting from the corresponding methylthio compound Xc, Xk and Xp (scheme 3).

The first reaction consists in the oxidation of the sulfur atom of this thioether function, resulting in a methylsulfonyl group (step ic) carried out at room temperature or under heating. The substitution of Xq, Xr and Xs with an alcoolate led to the ether derivatives Xt, Xu and Xv (step iic) carried out at a temperature between 10° C. and 80° C.

Alternatively compounds Xw, Xx, Xy that corresponds to pyrimidine derivatives of formula (I) comprising respectively an imidazolo, a pyrazolo or a pyrrolo group and wherein Y is equal to S and $R^1$ is different from —$CH_3$, may be obtained according to scheme 3bis. It corresponds to a conversion of methylsulfanyl-substituted pyrimidine derivative wherein Y is S and $R^1$ is a methyl group into other corresponding alkylsulfanyl-substituted pyrimidine derivatives wherein Y is S and $R^1$ is different from a methyl group. The conversion is carried out in two steps. A first step starting from a corresponding methylthio compound Xc, Xk, Xp is an oxidation reaction of the sulphur atom of the thioether function resulting in a methylsulfonyl group (step ic) carried out at room temperature or under heating as in scheme 3.

The second step (iiic in scheme 3bis) is a substitution reaction of the methylsulfonyl group in Xq, Xr, Xs with an alkylthiol leading to the alkylsulfanyl-substituted derivatives Xw, Xx, Xy wherein $R^1$ is different from —$CH_3$. The substitution reaction is carried out at a temperature between 10° C. and 100° C.

In the second embodiment, the preparation of the pyrimidine derivative comprising a pyrazolo group and represented by formula (I) wherein $X^1$ is N and $X^2$ is CH or $CR^8$; or an acceptable salt thereof are generally made according to the following chemical pathway:

Scheme 4

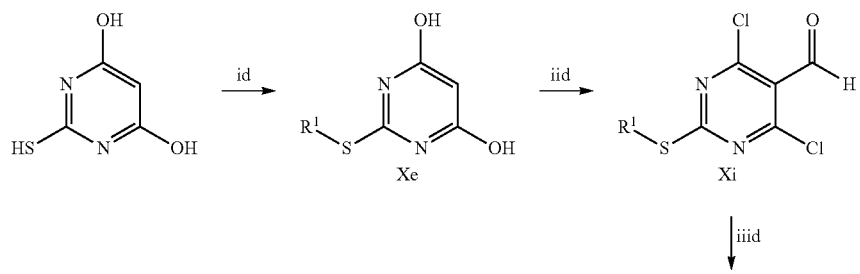

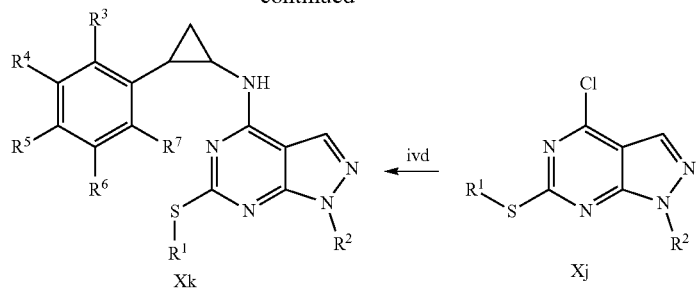

wherein $R^1$, $R^2$, $R^3$, $R^4$, $R^5$, $R^6$ and $R^7$ are defined in the general formula (I).

After reaction between thiobarbituric acid and $R^1$-halide at a temperature of for example 80° C. (step id), the 2-substituted pyrimidine 4,6-diol Xe is reacted with phosphoryl halide such as for example phosphoryl chloride in presence of DMF at a temperature between 0° C. and 110° C. to obtain the corresponding 2-substituted 4,6-dichloro-pyrimidine-5-carbaldehyde Xi (step iid).

The ring closure reaction of Xi by means of a substituted hydrazine provided the corresponding 1H-pyrazolo[3,4-d]pyrimidine Xj at a temperature between –80° C. and 20° C. (step iiid).

Further conversion of the thioether (Y=S) pyrimidine derivative into a corresponding ether (Y=O) pyrimidine derivative (Xu) can be made according to scheme 3 as described above.

Alternatively the pyrimidine derivatives of formula (I) comprising a pyrazolo group may be prepared according to scheme 4bis wherein step (id) and (iid) are identical to scheme 4 but the ring closure of Xi is carried out in step (vd) by a non-substituted hydrazine to provide a non-alkylated 1H-pyrazolo[3,4-d]pyrimidine Xi' at a temperature between –80° C. and 20° C. (step vd), followed in step vid by a N-alkylation to provide Xj at a temperature between 0° C. and 80° C.

Scheme 4bis

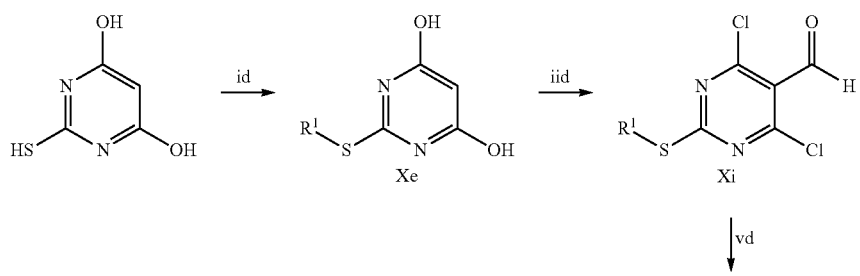

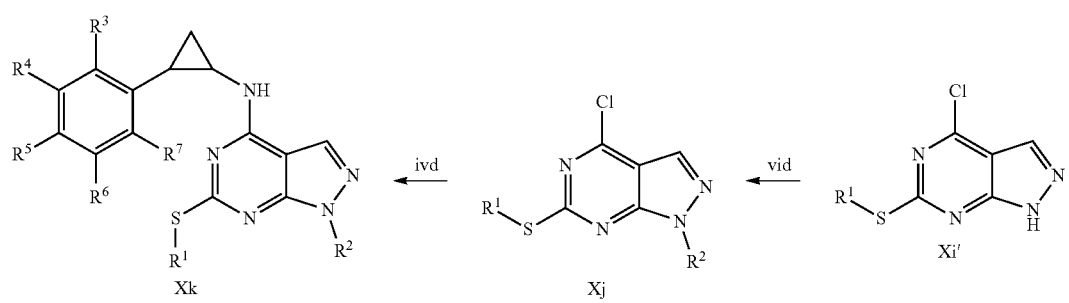

In the third embodiment, the preparation of the pyrimidine derivatives comprising a pyrrolo group and represented by formula (I) wherein $X^1$ and $X^2$ are CH or $CR^8$ or an acceptable salt thereof are generally made according to the following chemical pathway:

Scheme 5

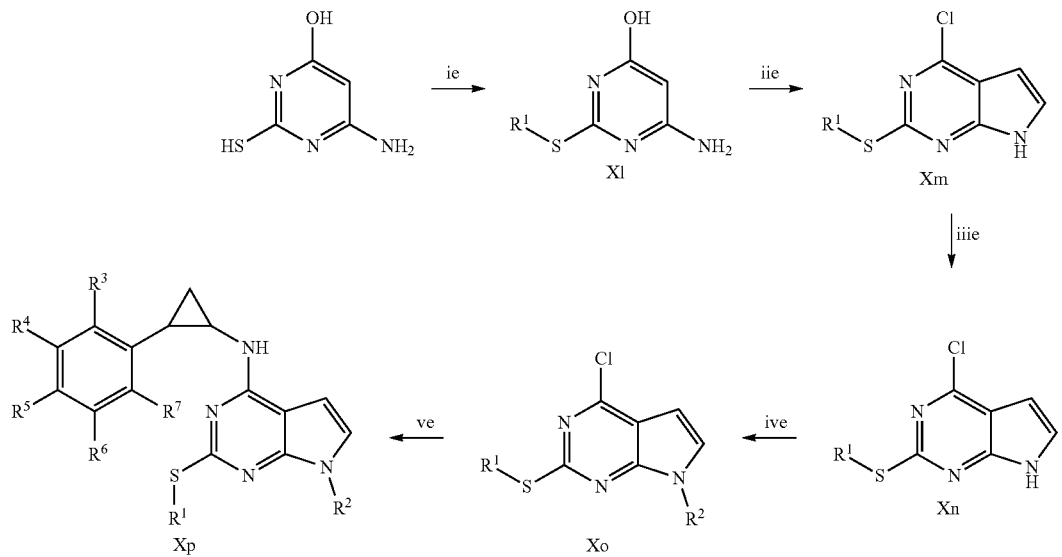

wherein $R^1$, $R^2$, $R^3$, $R^4$, $R^5$, $R^6$ and $R^7$ are defined as defined in formula (I).

The 2-substituted 6-amino-4-hydroxypyrimidine Xl is obtained by reacting 6-amino-2-mercaptopyrimidine-4-ol with the $R^1$-halide in alkaline medium a temperature between 70° C. and 110° C. (step ie).

Xl is converted into the corresponding 7H-pyrrolo[2,3-d]pyrimidine Xm by means of an halogenoacetaldehyde such as chloroacetaldehyde at a temperature between 60° C. and 100° C. (step iie).

An aromatic nucleophilic substitution using phosphoryl halide such as for example phosphoryl chloride at a temperature between 0° C. and 110° C. is then achieved to give Xn (step iiie), followed by a N-alkylation to give Xo (step ive) at a temperature between 0° C. and 100° C.

2,7-disubstituted N—(($R^3$-$R^7$)-substituted phenyl)cyclopropyl-7H-pyrrolo[2,3-d]pyrimidin-4-amines (Xp) are obtained by nucleophilic substitution of the chlorine atom of Xo by the appropriate phenylcyclopropylamine at a temperature between 40° C. and 90° C. (step ve).

Alternatively, the pyrimidine derivative comprising a pyrrolo group and represented by formula (I) wherein $X^1$ and $X^2$ are CH or $CR^8$ may be provided according to scheme 5bis, wherein step ie to iiie are identical to scheme 5 but the nucleophilic substitution of the halogen atom such as for example the chlorine atom in Xn is carried out with a ($R^3$-$R^7$)-substituted phenylcyclopropylamine at a temperature between 40° C. and 90° C. (step vie) to provide Xo', followed by the N-alkylation with a $R^2$-halide at a temperature between 0° C. and 100° C. (step viie) to provide Xp Scheme 5bis

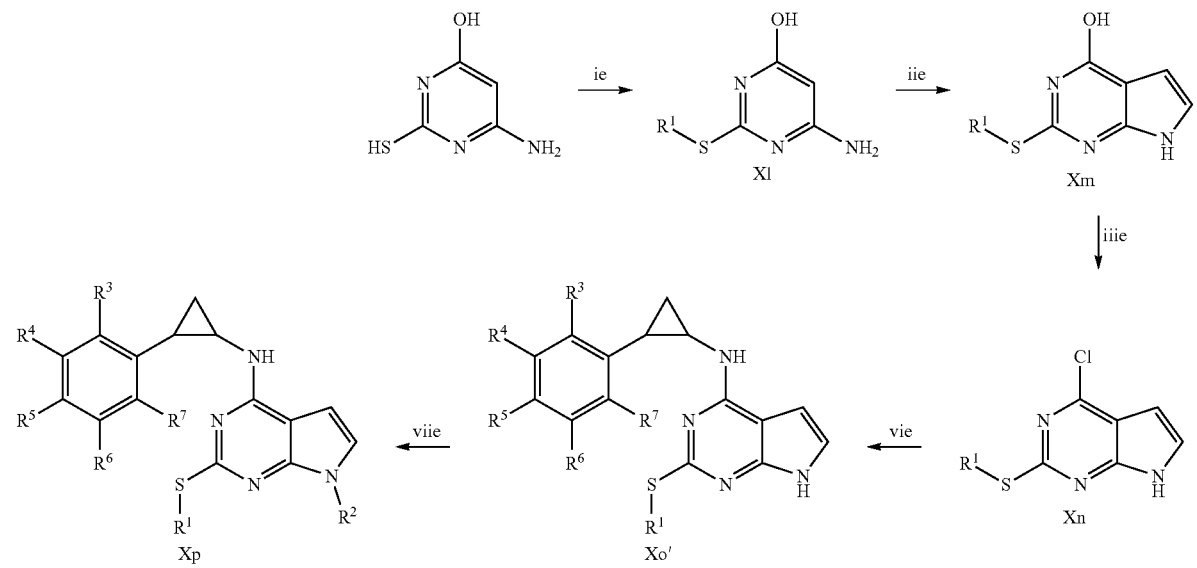

Further conversion of the thioether (Y=S) pyrimidine derivative into a corresponding ether (Y=O) pyrimidine derivative (Xv) can be made according to scheme 3 described above.

The same reactions are used for the preparation of pyrimidine derivatives represented by formula (I) or an acceptable salt thereof comprising at least one detectable isotope, with incorporation of the detectable isotope as the last step. Such incorporation of the detectable isotope or labelling step is well known to the one skilled in the art and is described in the art for example in Lanström et al Acta. Chem. Scand 1999, 53,651.

In particular embodiments, in the therapeutic uses of the present invention, the pyrimidine derivatives according to the invention are administered to the patient over several days (especially in case of prevention). The pyrimidine derivatives may be administered on their own or as a pharmaceutical composition, with non-toxic doses being inferior to 3 g per day.

A further preferred aspect of the invention is a pharmaceutical composition comprising a pyrimidine derivative of formula (I) or isomers, racemic mixtures thereof, pharmaceutically acceptable acid addition salts, pharmaceutically acceptable metal salts, or alkylated ammonium salts or prodrug thereof as described herein for use in the prevention or treatment of Gram-negative bacterial infection.

The pharmaceutical composition may be in the form of a dry powder or a liquid composition having physiological compatibility. In particular embodiments, the composition further comprises a membrane penetrating agent. In further embodiments, the compositions include, in addition to pyrimidine derivative and the membrane penetrating agent, auxiliary substances, preservatives, solvents and/or viscosity modulating agents. By solvent, one means for example water, saline or any other physiological solution, ethanol, glycerol, oil such as vegetable oil or a mixture thereof. By viscosity modulating agent reference is made for example to carboxymethylcellulose.

The pyrimidine derivatives optionally with a membrane penetrating agent exhibit their effects through oral, intravenous, intravascular, intramuscular, parenteral, or topical administration, and can be additionally used into a composition for parenteral administration, particularly an injection composition or in a composition for topical administration. They may also be loaded in nanoparticles for nanomedicine applications or PEGylated to improve its bioavailability, particularly when used in an aerosol composition. An aerosol composition is for example a solution, a suspension, a micronised powder mixture and the like. The composition can be administered by using a nebulizer, a metered dose inhaler or a dry powder inhaler or any device designed for such an administration.

Examples of galenic compositions include tablets, capsules, powders, pills, syrups, chewing, granules, and the like. These may be produced through well known technique and with use of typical additives such as excipients, lubricants, and binders.

Suitable auxiliary substances and pharmaceutical compositions are described in Remington's Pharmaceutical Sciences, 16th ed., 1980, Mack Publishing Co., edited by Oslo et al. Typically, an appropriate amount of a pharmaceutically-acceptable salt is used in the composition to render the composition isotonic. Examples of pharmaceutically acceptable substances include saline, Ringer's solution and dextrose solution. pH of the solution is preferably from about 5 to about 8, and more preferably from about 7 to about 7.5.

A still further aspect of the invention is a method of treatment or prevention of Gram-negative bacterial infection in a host mammal in need of such treatment or prevention. The method comprises administering to the host an effective amount of pyrimidine derivative as defined in formula (I) or isomers, racemic mixtures thereof, pharmaceutically acceptable acid addition salts, pharmaceutically acceptable metal salts, or alkylated ammonium salts or prodrug thereof In particular embodiments, the pyrimidine derivative of the invention is administered together with a membrane penetrating agent. In particular embodiments, the pyrimidine derivative is substituted with a difluorophenylcyclopropyl group; such as for example the ones selected in the first aspect of the invention; and most preferably a pyrimidine derivative selected from the group:

N-((1R,2S)-2-(3,4-difluorophenyl)cyclopropyl)-9-methyl-2-(propylthio)-9H-purin-6-amine (1c);

9-allyl-N-((1R,2S)-2-(3,4-difluorophenyl)cyclopropyl)-2-(propylthio)-9H-purin-6-amine (15c);

N-((1R,2S)-2-(3,4-difluorophenyl)cyclopropyl)-9-(prop-2-yn-1-yl)-2-(propylthio)-9H-purin-6-amine (17c);

(1S,2R,3S,4R)-4-(6-(((1R,2S)-2-(3,4-difluorophenyl)cyclopropyl)amino)-2-(propylthio)-9H-purin-9-yl)cyclopentane-1,2,3-triol (19d);

N-((1R,2S)-2-(3,4-difluorophenyl)cyclopropyl)-9-methyl-2-(methylthio)-9H-purin-6-amine (22c);

N-((1R,2S)-2-(3,4-difluorophenyl)cyclopropyl)-9-ethyl-2-(methylthio)-9H-purin-6-amine (24c);

N-((1R,2S)-2-(3,4-difluorophenyl)cyclopropyl)-2-(ethylthio)-9-methyl-9H-purin-6-amine (20c);

N-((1R,2S)-2-(3,4-difluorophenyl)cyclopropyl)-9-ethyl-2-(ethylthio)-9H-purin-6-amine (21c);

2-(butylthio)-N-((1R,2S)-2-(3,4-difluorophenyl)cyclopropyl)-9-methyl-9H-purin-6-amine (25c);

N-((1R,2S)-2-(3,4-difluorophenyl)cyclopropyl)-1-methyl-6-(methylthio)-1H-pyrazolo[3,4-d]pyrimidin-4-amine (27k);

N-((1R,2S)-2-(3,4-difluorophenyl)cyclopropyl)-1-ethyl-6-(methylthio)-1H-pyrazolo[3,4-d]pyrimidin-4-amine (30k);

N-((1R,2S)-2-(3,4-difluorophenyl)cyclopropyl)-6-(ethylthio)-1-methyl-1H-pyrazolo[3,4-d]pyrimidin-4-amine hydrochloride (28x·HCl);

N-((1R,2S)-2-(3,4-difluorophenyl)cyclopropyl)-1-isopropyl-6-(methylthio)-1H-pyrazolo[3,4-d]pyrimidin-4-amine hydrochloride (33k·HCl);

N-((1R,2S)-2-(3,4-difluorophenyl)cyclopropyl)-7-ethyl-2-(methylthio)-7H-pyrrolo[2,3-d]pyrimidin-4-amine hydrochloride (35p·HCl);

or isomers, racemic mixtures thereof, pharmaceutically acceptable acid addition salts, pharmaceutically acceptable metal salts, or alkylated ammonium salts or prodrug thereof.

The compounds according to the invention may be administered as the sole active ingredient or together, i.e. in a fixed or free combination, with a membrane penetrating agent.

The compounds according to the invention and a membrane penetrating agent may be administered together or separately and, when administered separately, administration may occur simultaneously or sequentially, in any order. The amounts of the compounds according to the invention and membrane penetrating agent, and the relative timings of administration will be selected in order to achieve the desired combined therapeutic effect. The administration in combination of a pyrimidine derivative of formula (I) or isomers, racemic mixtures thereof, pharmaceutically acceptable acid addition salts, pharmaceutically acceptable metal salts, or alkylated ammonium salts or prodrug thereof, with a membrane penetrating agent may be in combination by administration concomitantly in: (1) a unitary pharmaceutical composition including both compounds; or (2) separate pharmaceutical compositions each including one of the compounds. Alternatively, the combination may be administered separately in a sequential manner wherein one treatment agent is administered first and the other second or vice versa. Such sequential administration may be close in time or remote in time.

Administration together with a membrane-penetrating agent as used herein includes administration in one pharmaceutical composition, simultaneous administration of separate compositions and separate administration, for example sequential administration as described herein, provided it ensures in the body the presence of both the pyrimidine derivative and the membrane-penetrating agent.

In still a further aspect, the invention provides the use of pyrimidine derivatives of formula (I) or isomers, racemic mixtures thereof, pharmaceutically acceptable acid addition salts, pharmaceutically acceptable metal salts, or alkylated ammonium salts or prodrug thereof as inhibitor of Gram-negative biofilm formation on a surface of a biomaterial implant in a host mammal.

More particularly, the invention provides derivatives of formula (I) or isomers, racemic mixtures thereof, pharmaceutically acceptable acid addition salts, pharmaceutically acceptable metal salts, or alkylated ammonium salts or prodrug thereof; for use in the prevention of a Gram-negative bacterial infection or contamination, wherein said pyrimidine derivative is applied to the surface of a biomaterial implant. In particular embodiments, the pyrimidine derivative is applied together with a membrane penetrating agent. In particular embodiments, the infection or contamination is an implant-related infection or contamination (i.e. caused by the presence of the implant). Similarly, the invention provides for the use of the derivatives of the invention as described herein for the prevention and treatment of bacterial contamination or fouling, such as of an implant. It will be understood that throughout the description, the use of the derivatives is envisaged for these different in vivo, ex vivo and in vitro aspects.

Biomaterial implants such as for example pacemakers and implantable cardioverter-defibrillators [ICDs]) can become infected, with a rate of infections ranging from 0.8 to 5.7 percent.

The infection can involve a subcutaneous pocket containing the biomaterial implant or subcutaneous segment of the leads. Deeper infections can also occur which involve the transvenous portion of the lead, usually with associated bacteremia and/or endovascular infection. This implies that patients that have such implants suffer from diseases related thereto.

The implant and/or pocket itself can be source of infection, usually due to contamination at the time of implantation, or the infection can be secondary to bacteremia from a different source.

Perioperative contamination of the pacemaker pocket with skin flora appears to be the most common source of subcutaneous infection.

For instance, Cardiac implant-related infective endocarditis (CDRIE) is a life-threatening condition, with increasing incidence due to growing number of implantations (81,000 pacemaker implantation per year in Europe).

Successful treatment of an infected biomaterial implant, regardless of the involved component, generally requires removal of the implant and administration of antibiotics targeting the causative bacteria. Importantly, medical therapy alone is associated with high mortality and risk of recurrence.

Prosthetic valve endocarditis (PVE) is a serious infection with potentially fatal consequences.

Bacteria can reach the valve prosthesis by direct contamination intraoperatively or via hematogenous spread during the initial days and weeks after surgery. The bacteria have direct access to the prosthesis-annulus interface and to perivalvular tissue along suture pathways because the valve sewing ring, cardiac annulus, and anchoring sutures are not endothelialized early after valve implantation. The valve's structures are coated with host proteins, such as fibronectin and fibrinogen, to which bacteria can adhere and initiate infection.

The most frequently encountered bacteria in PVE are *S. aureus* (23%) and coagulase-negative staphylococci (16.9%), but *Escherichia Coli* is also reported at 1.3%.

Periprosthetic joint infection (PJI) is another pathogenesis that occurs in 1 to 2 percent of joint replacement surgeries and is a leading cause of arthroplasty failure.

Biofilms play an important role in the pathogenesis of PJIs. Bacteria within biofilm become resistant to therapy; as a result, antibacterial therapy is often unsuccessful unless the biofilm is physically disrupted or removed by surgical debridement.

Prosthetic joint infections have the following characteristics. Early-onset infections are usually acquired during implantation and are often due to virulent bacteria, or mixed infections. Delayed-onset infections are also usually acquired during implantation. Consistent with the indolent presentation, delayed infections are usually caused by less virulent bacteria.

The present invention allows to inhibit Periprosthetic joint infection (PJIs) without surgery. In particular embodiments, the implant is treated with the pyrimidine derivatives of the invention prior to implantation. Additionally or alternatively, the patient is administered the pyrimidine derivatives of the invention before or after receiving the implant to prevent or treat the infection.

In further aspects the invention provides the use of pyrimidine derivatives of formula (I) or salts thereof as inhibitor of Gram-negative biofilm formation on a surface, suh as on a surface of a medical device.

The term medical device as used herein particularly refers to any instrument, tool device like for example surgical device, needle, tube, gloves and the like relating to medicine or the practice of human or veterinary medicine, or intended for use to heal or treat or prevent a disease, such as for example an oxygenator, peristaltic pump chambers, kidney membranes and the like; medical product such as wound dressing, soft tissue fillers, root canal fillers, contact lens, blood bag; but also biomaterials that need to be sterile to be introduced in the mammal host, Preferably pyrimidine derivatives of formula (I) or an acceptable salt or prodrug thereof is bearing difluorophenylcyclopropyl group;

and are most preferably (N-((1R,2S)-2-(3,4-difluorophenyl)cyclopropyl)-9-methyl-2-(propylthio)-9H-purin-6-amine (1c);

9-allyl-N-((1R,2S)-2-(3,4-difluorophenyl)cyclopropyl)-2-(propylthio)-9H-purin-6-amine (15c);

N-((1R,2S)-2-(3,4-difluorophenyl)cyclopropyl)-9-(prop-2-yn-1-yl)-2-(propylthio)-9H-purin-6-amine (17c);

(1S,2R,3S,4R)-4-(6-(((1R,2S)-2-(3,4-difluorophenyl)cyclopropyl)amino)-2-(propylthio)-9H-purin-9-yl)cyclopentane-1,2,3-triol (19d);

N-((1R,2S)-2-(3,4-difluorophenyl)cyclopropyl)-9-methyl-2-(methylthio)-9H-purin-6-amine (22c);
N-((1R,2S)-2-(3,4-difluorophenyl)cyclopropyl)-9-ethyl-2-(methylthio)-9H-purin-6-amine (24c);
N-((1R,2S)-2-(3,4-difluorophenyl)cyclopropyl)-2-(ethylthio)-9-methyl-9H-purin-6-amine (20c);
N-((1R,2S)-2-(3,4-difluorophenyl)cyclopropyl)-9-ethyl-2-(ethylthio)-9H-purin-6-amine (21c);
2-(butylthio)-N-((1R,2S)-2-(3,4-difluorophenyl)cyclopropyl)-9-methyl-9H-purin-6-amine (25c);
N-((1R,2S)-2-(3,4-difluorophenyl)cyclopropyl)-1-methyl-6-(methylthio)-1H-pyrazolo[3,4-d]pyrimidin-4-amine (27k);
N-((1R,2S)-2-(3,4-difluorophenyl)cyclopropyl)-1-ethyl-6-(methylthio)-1H-pyrazolo[3,4-d]pyrimidin-4-amine (30k);
N-((1R,2S)-2-(3,4-difluorophenyl)cyclopropyl)-6-(ethylthio)-1-methyl-1H-pyrazolo[3,4-d]pyrimidin-4-amine hydrochloride (28x·HCl);
N-((1R,2S)-2-(3,4-difluorophenyl)cyclopropyl)-1-isopropyl-6-(methylthio)-1H-pyrazolo[3,4-d]pyrimidin-4-amine hydrochloride (33k·HCl);
N-((1R,2S)-2-(3,4-difluorophenyl)cyclopropyl)-7-ethyl-2-(methylthio)-7H-pyrrolo[2,3-d]pyrimidin-4-amine hydrochloride (35p·HCl);
or isomers, racemic mixtures thereof, pharmaceutically acceptable acid addition salts, pharmaceutically acceptable metal salts, or alkylated ammonium salts or prodrug thereof.

The most preferred inhibitor of Gram-negative biofilm on a surface is N-((1R,2S)-2-(3,4-difluorophenyl)cyclopropyl)-9-methyl-2-(propylthio)-9H-purin-6-amine (1c) as illustrated:

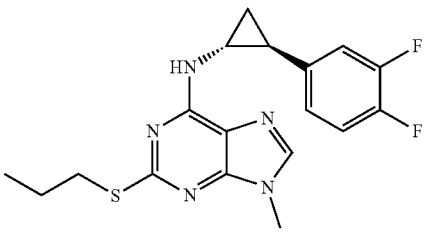 [SMILES: CCCSc1nc(N[C@@H]2C[C@H]2c2ccc(F)c(F)c2)c2ncn(C)c2n1]

or isomers, racemic mixtures thereof, pharmaceutically acceptable acid addition salts, pharmaceutically acceptable metal salts, or alkylated ammonium salts or prodrug thereof.

Medical devices and biomaterial implants are susceptible to bacterial colonization and may respectively become infected by a bacterial biofilm formation, either when they are used outside of the human or animal body or inside of the human or animal body.

To avoid having to remove the infected biomaterial implant from the host or to avoid a further administration to the host of a high dose of antibiotics to inhibit bacterial infection, it has surprisingly been found that applying pyrimidine derivative of formula (I) or acceptable salts thereof, directly on the surface of the medical device or of the biomaterial implant, prevents bacterial contamination.

Such application may be carried out, by various techniques well-known in the art, such as for example dipping the surface to be coated or spraying the surface with either pyrimidine derivatives of formula (I) or salts thereof or with a pharmaceutical composition comprising pyrimidine derivatives of formula (I) or isomers, racemic mixtures thereof, pharmaceutically acceptable acid addition salts, pharmaceutically acceptable metal salts, or alkylated ammonium salts thereof.

By surface one means any type of surface such as rubber or plastic surface as for example surface made of polyethylene, polypropylene, polyurethane, polyvinyl chloride, polyvinylpyrrolidone, polytetrafluoroethylene, silicone or the like, or copolymers but also and preferably metallic surface such as stainless steel, silver, gold, titanium, metallic alloys pyrolytic carbon, and the like. It can also be used on bioabsorbable or biomaterial surface such as biological prosthesis or devices which are made of biological material such as for example porcine heart valve or bovine pericardium.

By inhibition of biofilm on a surface one means inhibition of the bacterial biofilm formation at all stages of its formation starting from the prevention or inhibition of adherence of bacteria on the surface at step 1 but also and mainly an inhibition in bacteria growth, multiplication, and formation of microcolonies on the surface at step 2. By inhibition of biofilm one also means inhibition of the matrix at the maturation step 3 and inhibition of bacteria dispersion from the matrix in a colonisation step. By inhibition of biofilm, one also means killing bacteria at all steps of the biofilm formation.

A further aspect according to the invention, is a method for killing or preventing Gram-negative bacterial growth during biofilm formation on a surface.

The method comprises applying pyrimidine derivative of formula (I) or isomers, racemic mixtures thereof, pharmaceutically acceptable acid addition salts, pharmaceutically acceptable metal salts, or alkylated ammonium salts thereof on a surface either at a prevention step, reducing bacteria adherence and survival on the substrate or at a stage where the biofilm is already present, or even at a maturation step with a matrix formation wherein a more complex architecture of biofilm is established protecting bacteria as a barrier to conventional antibacterial agent. In particular embodiments, the methods comprise applying the pyrimidine derivative together with a membraned penetrating agent. Application together with a membrane-penetrating agent as used herein includes application as one combined composition, simultaneous application of separate compositions and separate application provided it ensures the presence of both the pyrimidine derivative and the membrane-penetrating agent on the surface for a given amount of time.

Factors that make bacteria especially adept at surviving on various biomaterials or medical devices include adherence and production of a biofilm.

An initial stage of biofilm formation is the attachment/adherence to surface, which is stronger in shear stress conditions. A protein mainly responsible for this adhesion is the polysaccharide intercellular adhesin (PIA), which allows bacteria to bind to each other, as well as to surfaces, creating the biofilm. The second stage of biofilm formation is the development of a community structure and ecosystem, which gives rise to a mature biofilm. The final stage is the detachment from the surface with consequent spreading into other locations. In all stages of biofilm formation a quorum sensing (QS) system, mediating cell-to-cell communication, is involved.

Bacteria in the biofilm produce extracellular polymeric substances (EPS) consisting mainly of polysaccharides, nucleic acids (extracellular DNA) and proteins, that protect them from external threats, including immune system components and antimicrobials. Moreover, bacteria in the biofilm have a decreased metabolism, making them less susceptible to antibiotics; this is due to the fact that most antimicrobials require a certain degree of cellular activity in order to be effective. Another factor reinforcing such resistance is the impaired diffusion of the antibiotics throughout the biofilm because of the presence of the EPS matrix barrier.

It was also well-known that in the biofilm there is higher rate of plasmid exchange increasing the chances of developing naturally occurring and antimicrobial-induced resistance.

Strategies that have been developed to eliminate biofilms target 3 different steps in the biofilm formation: inhibition of the initial stage, i.e. the adhesion of bacteria to surfaces; disrupting the biofilm architecture during the maturation process or step 2; inhibiting the QS system or step 3.

Because of a high resistance of these biofilms to antibiotics, there is an increasing need of control and prevention of microbial growth and biofilm formation at stage 2 to avoid removal of the biomaterial implant from the host together with a long treatment with antibiotics.

The method of killing bacteria or prevention of bacterial growth on a surface is generally applied to biomaterial implant or any medical devices, implantable or not.

The biomaterial implants or medical devices are preferably implantable foreign material for clinical use in host mammals such as prosthetic devices, pacemakers, implantable cardioverter-defibrillators, intravascular catheters, coronary stent, heart valves, intraocular lens and the like but include other non-implantable medical devices that needs to be sterile such as for example wound dressings, soft tissue fillers containing local anaesthetics, root canal fillers with ancillary medicinal substances and the like.

The method of killing bacteria or prevention of bacterial growth could also be applied to the surface of an experimental or surgical device in need of such antibacterial treatment. Practically the method may be applied and is not limited to any device, tool, instrument, relating to medicine or the practice of human or veterinary medicine, or intended for use to heal or treat or prevent a disease.

In a still further aspect, the present invention provides new pyrimidine derivatives of formula (I) or salt thereof, optionally comprising a detectable marker, for use in diagnosing or prognosing bacterial infection in a host mammal.

The term "detectable marker" as used herein refers to any type of tag which is detectable, linked to or incorporated into the pyrimidine derivative and thus allows the determination of the presence of the pyrimidine derivative. In particular embodiments, the marker is an isotope, such as a radioisotope which allows the use of the pyrimidine derivative as a radiotracer. Methods for incorporating markers such as isotopes into compounds are known in the art. The presence of the marker allows the use of the pyrimidine derivatives of the invention in diagnosis or prognosis.

In particular embodiments, the pyrimidine derivative comprising a marker is used together with a membrane-penetrating agent.

The present invention also provides a pharmaceutical composition comprising the pyrimidine derivatives of formula (I) or salt thereof, optionally comprising a detectable marker, for use in diagnosing or prognosing bacterial infection in a host mammal. In particular embodiments, the composition further comprises a membrane-penetrating agent.

The inventors have surprisingly found that pyrimidine derivatives of formula (I) or a composition thereof, optionally comprising a detectable isotope atom may be used to detect a bacterial infection in a host mammal; such as for example for the diagnosing of endocarditis, a disease developed after a prosthetic valve surgery. Indeed the pyrimidine derivatives according to the invention or compositions thereof comprising a detectable label can identify a Gram-negative bacterial infection in the host and can be absorbed by a bacterial cell. Preferably, their use is in the presence of a membrane-penetrating agent. Pyrimidine derivatives or compositions thereof may therefore for instance be used as radiotracer for in vivo-imaging.

Generally, the detection method used in the diagnosis will depend on the nature of the marker. For instance, for the purpose of in-vivo imaging the pyrimidine derivative will comprise a radiotracer, and the type of detection instrument will depend of the radiotracer. For example, the pyrimidin derivative comprising optionally at least one detectable isotope according to the invention, can be detected using beta, gamma, positron or x-ray imaging wherein, for example beta or gamma irradiation is provided by the relevant isotope and is detected at an appropriate wavelength.

The pyrimidine derivative comprising optionally a detectable isotope may be used for example with X-Ray imaging, magnetic resonance spectroscopy (MRS) or imaging (MRI), ultrasonography, positron emission tomography (PET) and single emission computed tomography (SPECT).

The detectable pyrimidine derivative may be detected through isotope $^{19}F$ or $^{13}C$ or a combination thereof for MRS/MRI by well know organic chemistry techniques.

Other detectable pyrimidine derivative may also comprise an isotope selected from $^{19}F$, $^{11}C$, $^{75}Br$, $^{76}Br$ or $^{120}I$ or a combination thereof for PET techniques.

Other detectable pyrimidine derivatives comprise an isotope selected from $^{18}F$ or $^{11}C$ or a combination thereof for PET in-vivo imaging as described in Bengt Langström in Acta Chemica Scandinavia, 53:651-669 (1999) or the journal of Nuclear Medicine 58(7): 1094-1099 (2017) A. M. J. Paans in https://cds.cern.ch/record/1005065/files/p363.pdf Pyrimidine derivative may also comprise $^{123}I$ and $^{131}I$ for SPECT as described by Kulkarni, Int. J. Rad. Appl.& Inst (part B) 18:647 (1991).

Pyrimidine derivative may also be detectable with technetium-99m ($^{99m}Tc$). Modification of Pyrimidin derivative to introduce a ligand that binds to such metal ions can be carried out by a man skilled in the art. Preparing detectable derivatives of $^{99m}Tc$ is well known in the art (Zhuang in Nuclear Medicine & Biology 26(2):217-24 (1999).

A preferred pyrimidine derivative of formula (I) or isomers, racemic mixtures thereof, pharmaceutically acceptable acid addition salts, pharmaceutically acceptable metal salts, or alkylated ammonium salts thereof; for use as radiotracer, such as in diagnosing or prognosing bacterial infection, comprises a phenylcyclopropyl group as illustrated in formula (IV)

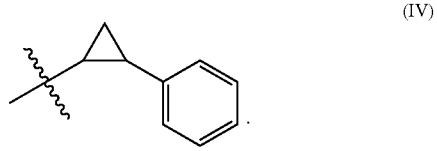 [SMILES: *C1CC1c1ccccc1]

(IV)

Most preferred pyrimidine derivatives of formula (I) or isomers, racemic mixtures thereof, pharmaceutically acceptable acid addition salts, pharmaceutically acceptable metal salts, or alkylated ammonium salts thereof, such as for use as radiotracer comprise a difluorophenylcyclopropyl group.

The most preferred pyrimidine derivatives of formula (I) or isomers, racemic mixtures thereof, pharmaceutically acceptable acid addition salts, pharmaceutically acceptable metal salts, or alkylated ammonium salts thereof; for use as a radiotracer comprise a 3,4 difluorophenylcyclopropyl group as illustrated in formula (II).

By radiotracer one means a pyrimidine derivative wherein one or more atoms are replaced by a radionuclide or isotope to be used as tracer to explore cells, tissues or fluids from a host mammal and identify the presence and importance of a bacterial infection in the host for example at the surface of a prosthetic valve.

By radionuclide or isotope, one means for example $^3H$, $^{18}F$, $^{19}F$, $^{11}C$, $^{13}C$, $^{14}C$, $^{75}Br$, $^{76}Br$, $^{120}I$, $^{123}I$, $^{125}I$, $^{131}I$, $^{15}O$, $^{13}N$.

By radiotracer, one also means pyrimidine derivative associated with a contrast agent such as for example a MRI contrast agent or MR tracers for Magnetic Resonance Imaging (MRI); or contrast agent used in contrast-enhanced ultrasound imaging.

The pyrimidine derivative or composition thereof used as radiotracer is administered locally or systemically by inhalation, ingestion or injection or via an implanted reservoir in the mammal host at a dose that is relevant to a selected imaging device. The administration may be orally, parenterally, topically, rectally, nasally, vaginally.

By parenterally, one means subcutaneously, intravenously, intraarterially, intraperitoneally, intrathecally, intraventricularly and the like.

In particular embodiments, the pyrimidine derivative is administered together with a membrane-penetrating agent. Administration together with a membrane-penetrating agent as used herein may be by administration concomitantly in: (1) a unitary pharmaceutical composition including both compounds; or (2) separate pharmaceutical compositions each including one of the compounds provided it ensures in the body the presence of both the pyrimidine derivative and the membrane-penetrating agent. Alternatively, the combination may be administered separately in a sequential manner wherein one treatment agent is administered first and the other second or vice versa. Such sequential administration may be close in time or remote in time provided it ensures in the body the presence of both the pyrimidine derivative and the membrane-penetrating agent.

Dose levels of administration to the host are depending upon his age, weight, general health, sex, time of administration, form of administration and the like and is well known by the one skilled in the art. They may vary between 0.001 µg/kg/day and 10,000 mg/kg/day according to the imaging technique selected.

A resulting in-vivo image of the bacterial infection of the host mammal is provided, for example at the prosthetic valve position.

Further applications of the pyrimidine derivatives of the present invention include monitoring bacterial contamination in samples such as in biological samples. Typical samples where this is of interest are water, blood, meat etc.

Figure 1:
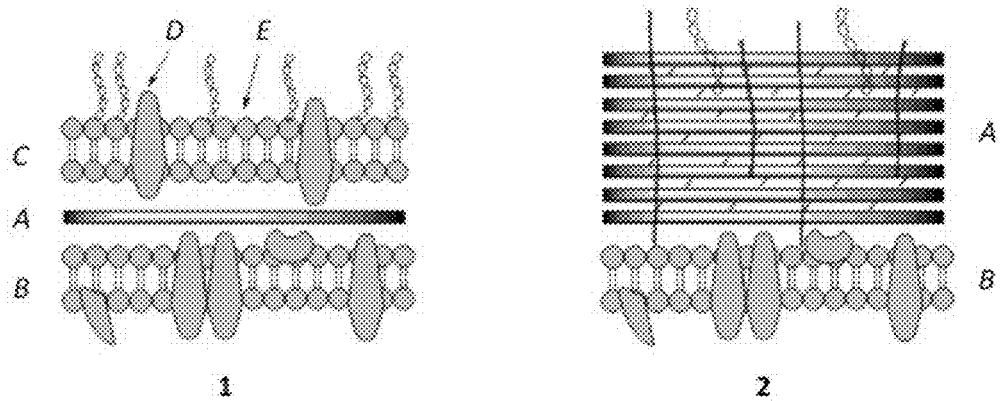
FIG. 1 illustrates a cell wall structure comparison between Gram-negative bacteria (1) and Gram-positive bacteria (2) envelope with a similar inner cytoplasmic membrane (B) made of porins (D) and a peptidoglycan cell wall (A) made of peptide chains generally crosslinked for both class of bacteria. The Gram-negative bacterium (1) differs from the Gram-positive bacterium (2) by an additional outer membrane (C) made of lipids (E), lipopolysaccharides (LPS) and porins (D).

The invention is illustrated hereafter by the following non limiting examples.

1. Preparation of New Pyrimidine Derivatives

Example 1: synthesis of N-((1R,2S)-2-(3,4-difluorophenyl)cyclopropyl)-9-methyl-2-(propylthio)-9H-purin-6-amine (1c)

6-Chloro-$N^4$-methyl-2-(propylthio)pyrimidine-4,5-diamine (1a)

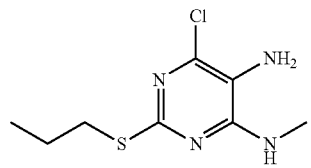

4,6-Dichloro-2-(propylthio)pyrimidin-5-amine (0.5 g, 2.1 mmol) was dissolved in methanol (2 mL) and supplemented with a solution of methylamine 33% w/w in methanol (0.76 mL, 6.3 mmol).

The reaction mixture was introduced in a sealed vessel and heated at 100° C. for 1 h. After concentration of the reaction mixture to dryness under vacuum, the residue was purified by silica gel column chromatography.

Yield: 96%.

Melting point: 119-121° C.

$^1H$ NMR (DMSO-$d_6$) δ0.95 (t, J=7.4 Hz, 3H, $SCH_2CH_2CH_3$), 1.64 (h, J=7.3 Hz, 2H, $SCH_2CH_2CH_3$), 2.87 (d, J=4.5 Hz, 3H, $NHCH_3$), 2.96 (t, J=7.2 Hz, 2H, $SCH_2CH_2CH_3$), 4.71 (s, 2H, $NH_2$), 7.01 (q, J=4.4 Hz, 1H, $NHCH_3$).

$^{13}C$ NMR (DMSO-$d_6$) δ 13.3 ($SCH_2CH_2CH_3$), 22.6 ($SCH_2CH_2CH_3$), 27.8 ($NHCH_3$), 32.1 ($SCH_2CH_2CH_3$), 120.0 (C-5), 137.1 (C-6), 153.2 (C-4), 155.4 (C-2).

6-Chloro-9-methyl-2-(propylthio)-9H-purine (1b)

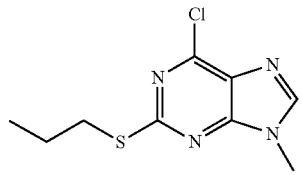

A solution of (1a) (233.0 mg, 1 mmol) in acetic acid (2.5 mL) and triethyl orthoformate (2.5 mL, 15 mmol) was heated at a temperature of 130° C. under reflux for 1 h. After distillation of the acetic acid and triethyl orthoformate under vacuum, the residue was purified by silica gel column chromatography.

Yield: 77%.

Melting point: 75-78° C.

$^1$H NMR (DMSO-$d_6$) δ 1.01 (t, J=7.4 Hz, 3H, SCH$_2$CH$_2$CH$_3$), 1.74 (h, J=7.3 Hz, 2H, SCH$_2$CH$_2$CH$_3$), 3.18 (t, J=7.2 Hz, 2H, SCH$_2$CH$_2$CH$_3$), 3.79 (s, 3H, NCH$_3$), 8.48 (s, 1H, 8-H).

$^{13}$C NMR (DMSO-$d_6$) δ 13.2 (SCH$_2$CH$_2$CH$_3$), 22.0 (SCH$_2$CH$_2$CH$_3$), 29.9 (NCH$_3$), 32.6 (SCH$_2$CH$_2$CH$_3$), 127.9 (C-5), 147.0 (C-8), 148.7 (C-6), 153.2 (C-4), 163.9 (C-2).

N-((1R,2S)-2-(3,4-Difluorophenyl)cyclopropyl)-9-methyl-2-(propylthio)-9H-purin-6-amine (1c)

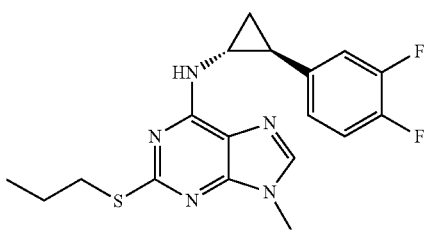 [SMILES: CCCSc1nc(N[C@@H]2C[C@H]2c2ccc(F)c(F)c2)c2ncn(C)c2n1]

A solution of (1b) (122.0 mg, 0.5 mmol) in acetonitrile (2.5 mL) was supplemented with (1R,2S)-2-(3,4-difluorophenyl)cyclopropanamine (93.0 mg, 0.55 mmol) and triethylamine (0.13 mL) and then heated at 90° C. under reflux for 1 h. After distillation of acetonitrile and triethylamine under vacuum, the residue was purified by silica gel column chromatography.

Yield: 42%.

Melting point: 94-96° C.

$^1$H NMR (CDCl$_3$) δ 0.93 (t, J=7.4 Hz, 3H, SCH$_2$CH$_2$CH$_3$), 1.32 (m, 2H, NHCH(CH$_2$)CHPh), 1.65 (h, J=7.3 Hz, 2H, SCH$_2$CH$_2$CH$_3$), 2.09 (m, 1H, NHCH(CH$_2$) CHPh), 3.02 (m, 2H, SCH$_2$CH$_2$CH$_3$), 3.12 (bs, 1H, NHCH (CH$_2$)CHPh), 3.76 (s, 3H, NCH$_3$), 5.98 (bs, 1H, NH), 6.97 (m, 1H, 6'-H), 7.07 (m, 2H, 2'-H/5'-H), 7.59 (s, 1H, 8-H).

$^{13}$C NMR (CDCl$_3$) S 13.4 (SCH$_2$CH$_2$CH$_3$), 16.2 (NHCH (CH$_2$)CHPh), 22.8 (SCH$_2$CH$_2$CH$_3$), 25.2 (NHCH(CH$_2$) CHPh), 29.7 (NCH$_3$), 33.2 (SCH$_2$CH$_2$CH$_3$), 33.4 (NHCH (CH$_2$)CHPh), 115.5 (d, J=17 Hz, C-2'), 116.9 (d, J=17 Hz, C-5'), 117.4 (C-5), 122.6 (C-6'), 137.9 (C-1'), 139.5 (C-8), 147.9-149.9 (dd, 246 Hz/13 Hz, C-4'), 149.2-151.2 (dd, 247 Hz/13 Hz, C-3'), 150.8 (C-4), 154.5 (C-6), 165.6 (C-2).

Example 2: synthesis of 9-methyl-N-((1R,2S)-2-phenylcyclopropyl)-2-(propylthio)-9H-purin-6-amine (2c)

9-Methyl-N-((1R,2S)-2-phenylcyclopropyl)-2-(propylthio)-9H-purin-6-amine (2c)

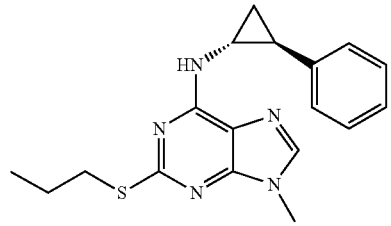 [SMILES: CCCSc1nc(N[C@@H]2C[C@H]2c2ccccc2)c2ncn(C)c2n1]

A solution of (1b) (122.0 mg, 0.5 mmol) in acetonitrile (2.5 mL) was supplemented with (1R,2S)-2-phenylcyclopropanamine (56.0 mg, 1.1 mmol) and triethylamine (0.13 mL) and then heated at 90° C. under reflux for 4 h. After distillation of the solvents under vacuum, the residue was purified by silica gel column chromatography.

Yield: 27%.

Melting point: 171-172.5° C.

$^1$H NMR (CDCl$_3$) δ0.88 (t, J=7.4 Hz, 3H, SCH$_2$CH$_2$CH$_3$), 1.33 (m, 2H, NHCH(CH$_2$)CHPh), 1.60 (h, J=7.3 Hz, 2H, SCH$_2$CH$_2$CH$_3$), 2.13 (m, 1H, NHCH(CH$_2$) CHPh), 2.92 (m, 1H, SCH$_2$CH$_2$CH$_3$), 3.06 (m, 1H, SCH$_2$CH$_2$CH$_3$), 3.22 (bs, 1H, NHCH(CH$_2$)CHPh), 3.75 (s, 3H, NCH$_3$), 5.97 (bs, 1H, NH), 7.19 (m, 3H, 2'-H/4'-H/6'-H), 7.30 (m, 2H, 3'-H/5'-H), 7.58 (s, 1H, 8-H).

$^{13}$C NMR (CDCl$_3$) S 13.3 (SCH$_2$CH$_2$CH$_3$), 16.8 (NHCH (CH$_2$)CHPh), 22.8 (SCH$_2$CH$_2$CH$_3$), 25.7 (NHCH(CH$_2$) CHPh), 29.7 (NCH$_3$), 33.3 (SCH$_2$CH$_2$CH$_3$), 33.5 (NHCH (CH$_2$)CHPh), 117.4 (C-5), 126.0 (C-4'), 126.2 (C-2'/C-6'), 128.3 (C-3'/C-5'), 139.5 (C-8), 140.9 (C-1'), 150.8 (C-4), 154.6 (C-6), 165.6 (C-2).

Example 3: synthesis of N-((1R,2S)-2-(3,4-difluorophenyl)cyclopropyl)-9-ethyl-2-(propylthio)-9H-purin-6-amine (3c)

6-Chloro-N$^4$-ethyl-2-(propylthio)pyrimidine-4,5-diamine (3a)

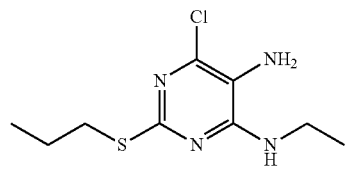

4,6-Dichloro-2-(propylthio)pyrimidin-5-amine (0.5 g, 2.1 mmol) was dissolved in a solution of ethylamine 2.0 M in methanol (3.2 mL, 6.4 mmol). The reaction mixture was introduced in a sealed vessel and heated at 100° C. for 1 h. After concentration of the reaction mixture to dryness under vacuum, the residue was purified by silica gel column chromatography.

Yield: 77%.

Melting point: 96-98° C.

$^1$H NMR (DMSO-d$_6$) δ 0.95 (t, J=7.4 Hz, 3H, SCH$_2$CH$_2$CH$_3$), 1.16 (t, J=7.2 Hz, 3H, NHCH$_2$CH$_3$), 1.63 (h, J=7.3 Hz, 2H, SCH$_2$CH$_2$CH$_3$), 2.94 (t, J=7.2 Hz, 2H, SCH$_2$CH$_2$CH$_3$), 3.37 (m, 2H, NHCH$_2$CH$_3$), 4.75 (s, 2H, NH$_2$), 6.95 (t, J=4.8 Hz, 1H, NHCH$_2$CH$_3$).

$^{13}$C NMR (DMSO-d$_6$) δ 13.3 (SCH$_2$CH$_2$CH$_3$), 14.3 (NHCH$_2$CH$_3$), 22.7 (SCH$_2$CH$_2$CH$_3$), 32.1 (SCH$_2$CH$_2$CH$_3$), 35.7 (NHCH$_2$CH$_3$), 119.8 (C-5), 137.3 (C-6), 152.5 (C-4), 155.3 (C-2).

6-Chloro-9-ethyl-2-(propylthio)-9H-purine (3b)

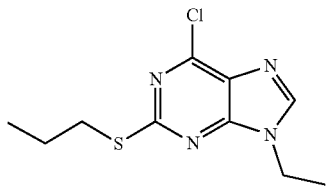 [SMILES: CCCSc1nc(Cl)c2ncn(CC)c2n1]

A solution of (3a) (247.0 mg, 1 mmol) in acetic acid (2.5 mL) and triethyl orthoformate (2.5 mL, 15 mmol) was heated at a temperature of 130° C. under reflux for 1 h. After distillation of the acetic acid and triethyl orthoformate under vacuum, the residue was purified by silica gel column chromatography.

Yield: 77%.

Melting point: 96-97.5° C.

$^1$H NMR (DMSO-d$_6$) δ 1.01 (t, J=7.4 Hz, 3H, SCH$_2$CH$_2$CH$_3$), 1.44 (t, J=7.3 Hz, 3H, NCH$_2$CH$_3$), 1.74 (h, J=7.3 Hz, 2H, SCH$_2$CH$_2$CH$_3$), 3.17 (t, J=7.2 Hz, 2H, SCH$_2$CH$_2$CH$_3$), 4.24 (q, J=7.3 Hz, 2H, NCH$_2$CH$_3$), 8.56 (s, 1H, 8-H).

$^{13}$C NMR (DMSO-d$_6$) δ13.2 (SCH$_2$CH$_2$CH$_3$), 14.6 (NCH$_2$CH$_3$), 22.0 (SCH$_2$CH$_2$CH$_3$), 32.6 (SCH$_2$CH$_2$CH$_3$), 39.9 (NCH$_2$CH$_3$), 128.1 (C-5), 146.0 (C-8), 148.8 (C-6), 152.7 (C-4), 163.8 (C-2).

N-((1R,2S)-2-(3,4-Difluorophenyl)cyclopropyl)-9-ethyl-2-(propylthio)-9H-purin-6-amine (3c)

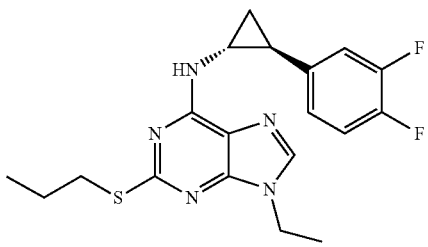 [SMILES: CCCSc1nc(N[C@@H]2C[C@H]2c2ccc(F)c(F)c2)c2ncn(CC)c2n1]

A solution of (3b) (129.0 mg, 0.5 mmol) in acetonitrile (2.5 mL) was supplemented with (1R,2S)-2-(3,4-difluorophenyl)cyclopropanamine (93.0 mg, 0.55 mmol) and triethylamine (0.13 mL) and then heated at 90° C. under reflux for 1 h. After distillation of acetonitrile and triethylamine under vacuum, the residue was purified by silica gel column chromatography.

Yield: 43%.

Melting point: 109.5-111.5° C.

$^1$H NMR (CDCl$_3$) δ0.94 (t, J=7.4 Hz, 3H, SCH$_2$CH$_2$CH$_3$), 1.32 (m, 2H, NHCH(CH$_2$)CHPh), 1.50 (t, J=7.3 Hz, 3H, NCH$_2$CH$_3$), 1.67 (h, J=7.3 Hz, 2H, SCH$_2$CH$_2$CH$_3$), 2.09 (m, 1H, NHCH(CH$_2$)CHPh), 3.03 (m, 2H, SCH$_2$CH$_2$CH$_3$), 3.12 (bs, 1H, NHCH(CH$_2$)CHPh), 4.18 (q, J=7.3 Hz, 2H, NCH$_2$CH$_3$), 5.90 (bs, 1H, NH), 6.99 (m, 1H, 6'-H), 7.08 (m, 2H, 2'-H/5'-H), 7.63 (s, 1H, 8-H).

$^{13}$C NMR (CDCl$_3$) δ 13.4 (SCH$_2$CH$_2$CH$_3$), 15.5 (NCH$_2$CH$_3$), 16.1 (NHCH(CH$_2$)CHPh), 22.9 (SCH$_2$CH$_2$CH$_3$), 25.2 (NHCH(CH$_2$)CHPh), 33.2 (SCH$_2$CH$_2$CH$_3$), 33.3 (NHCH(CH$_2$)CHPh), 38.7 (NCH$_2$CH$_3$), 115.6 (d, J=17 Hz, C-2'), 116.9 (d, J=17 Hz, C-5'), 117.6 (C-5), 122.7 (C-6'), 137.9 (C-1'), 138.5 (C-8), 147.9-149.9 (dd, 246 Hz/13 Hz, C-4'), 149.2-151.2 (dd, 247 Hz/13 Hz, C-3'), 150.3 (C-4), 154.5 (C-6), 165.4 (C-2).

Example 4: synthesis of N-((1R,2S)-2-(3,4-difluorophenyl)cyclopropyl)-9-propyl-2-(propylthio)-9H-purin-6-amine (4c)

6-Chloro-N$^4$-propyl-2-(propylthio)pyrimidine-4,5-diamine (4a)

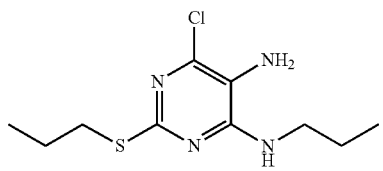 [SMILES: CCCNc1nc(SCCC)nc(Cl)c1N]

4,6-Dichloro-2-(propylthio)pyrimidin-5-amine (0.5 g, 2.1 mmol) was dissolved in methanol (2 mL) and supplemented with n-propylamine (370.0 mg, 6.3 mmol). The reaction mixture was introduced in a sealed vessel and heated at 100° C. for 30 min. After concentration of the reaction mixture to dryness under vacuum, the residue was purified by silica gel column chromatography.

Yield: 91%.

Melting point: 100-102° C.

$^1$H NMR (DMSO-d$_6$) δ 0.91 (t, J=7.4 Hz, 3H, NHCH$_2$CH$_2$CH$_3$), 0.95 (t, J=7.3 Hz, 3H, SCH$_2$CH$_2$CH$_3$), 1.56 (h, J=7.3 Hz, 2H, NHCH$_2$CH$_2$CH$_3$), 1.64 (h, J=7.3 Hz, 2H, SCH$_2$CH$_2$CH$_3$), 2.93 (t, J=7.2 Hz, 2H, SCH$_2$CH$_2$CH$_3$), 3.32 (m, 2H, NHCH$_2$CH$_2$CH$_3$), 4.76 (s, 2H, NH$_2$), 6.96 (t, J=4.8 Hz, 1H, NHCH$_2$CH$_2$CH$_3$).

$^{13}$C NMR (DMSO-d$_6$) δ 11.5 (NHCH$_2$CH$_2$CH$_3$), 13.3 (SCH$_2$CH$_2$CH$_3$), 21.9 (NHCH$_2$CH$_2$CH$_3$), 22.8 (SCH$_2$CH$_2$CH$_3$), 32.1 (SCH$_2$CH$_2$CH$_3$), 42.7 (NHCH$_2$CH$_2$CH$_3$), 119.8 (C-5), 137.3 (C-6), 152.6 (C-4), 155.2 (C-2).

6-Chloro-9-propyl-2-(propylthio)-9H-purine (4b)

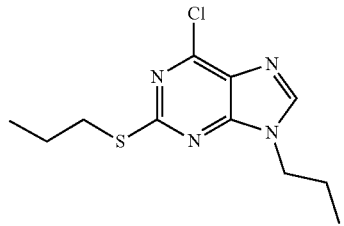 [SMILES: CCCSc1nc(Cl)c2ncn(CCC)c2n1]

A solution of (4a) (261.0 mg, 1 mmol) in acetic acid (2.5 mL) and triethyl orthoformate (2.5 mL, 15 mmol) was heated at a temperature of 130° C. under reflux for 1 h. After distillation of the acetic acid and triethyl orthoformate under vacuum, the residue was purified by silica gel column chromatography.

Yield: 94%.

Melting point: liquid.

$^1$H NMR (DMSO-$d_6$) δ0.85 (t, J=7.4 Hz, 3H, NCH$_2$CH$_2$CH$_3$), 1.01 (t, J=7.4 Hz, 3H, SCH$_2$CH$_2$CH$_3$), 1.74 (h, J=7.3 Hz, 2H, SCH$_2$CH$_2$CH$_3$), 1.86 (h, J=7.3 Hz, 2H, NCH$_2$CH$_2$CH$_3$), 3.17 (t, J=7.2 Hz, 2H, SCH$_2$CH$_2$CH$_3$), 4.18 (t, J=7.0 Hz, 2H, NCH$_2$CH$_2$CH$_3$), 8.55 (s, 1H, 8-H).

$^{13}$C NMR (DMSO-$d_6$) δ 10.9 (NCH$_2$CH$_2$CH$_3$), 13.2 (SCH$_2$CH$_2$CH$_3$), 22.1 (SCH$_2$CH$_2$CH$_3$), 22.3 (NCH$_2$CH$_2$CH$_3$), 32.6 (SCH$_2$CH$_2$CH$_3$), 45.3 (NCH$_2$CH$_2$CH$_3$), 128.0 (C-5), 146.4 (C-8), 148.9 (C-6), 152.9 (C-4), 163.8 (C-2).

N-((1R,2S)-2-(3,4-Difluorophenyl)cyclopropyl)-9-propyl-2-(propylthio)-9H-purin-6-amine (4c)

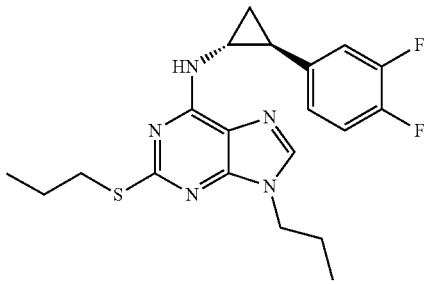 [SMILES: CCCSc1nc(N[C@@H]2C[C@H]2c2ccc(F)c(F)c2)c2ncn(CCC)c2n1]

A solution of (4b) (136.0 mg, 0.5 mmol) in acetonitrile (2.5 mL) was supplemented with (1R,2S)-2-(3,4-difluorophenyl)cyclopropanamine (93.0 mg, 0.55 mmol) and triethylamine (0.13 mL) and then heated at 90° C. under reflux for 1 h. After distillation of acetonitrile and triethylamine under vacuum, the residue was purified by silica gel column chromatography.

Yield: 45%.

Melting point: 97-99° C.

$^1$H NMR (CDCl$_3$) δ 0.94 (t, J=7.4 Hz, 6H, NCH$_2$CH$_2$CH$_3$/SCH$_2$CH$_2$CH$_3$), 1.32 (m, 2H, NHCH(CH$_2$)CHPh), 1.67 (h, J=7.3 Hz, 2H, SCH$_2$CH$_2$CH$_3$), 1.90 (h, J=7.4 Hz, 2H, NCH$_2$CH$_2$CH$_3$), 2.09 (m, 1H, NHCH(CH$_2$)CHPh), 3.03 (m, 2H, SCH$_2$CH$_2$CH$_3$), 3.11 (bs, 1H, NHCH(CH$_2$)CHPh), 4.09 (t, J=7.1 Hz, 2H, NCH$_2$CH$_2$CH$_3$), 5.86 (bs, 1H, NH), 7.00 (m, 1H, 6'-H), 7.09 (m, 2H, 2'-H/5'-H), 7.61 (s, 1H, 8-H).

$^{13}$C NMR (CDCl$_3$) S 11.2 (NCH$_2$CH$_2$CH$_3$), 13.4 (SCH$_2$CH$_2$CH$_3$), 15.7 (NHCH(CH$_2$)CHPh), 22.9 (SCH$_2$CH$_2$CH$_3$), 23.3 (NCH$_2$CH$_2$CH$_3$), 25.2 (NHCH(CH$_2$)CHPh), 33.2 (SCH$_2$CH$_2$CH$_3$), 33.3 (NHCH(CH$_2$)CHPh), 45.3 (NCH$_2$CH$_2$CH$_3$), 115.6 (d, J=17 Hz, C-2'), 116.9 (d, J=17 Hz, C-5'), 117.6 (C-5), 122.7 (C-6'), 137.9 (C-1'), 139.0 (C-8), 147.9-149.9 (dd, 246 Hz/13 Hz, C-4'), 149.2-151.2 (dd, 247 Hz/13 Hz, C-3'), 150.5 (C-4), 154.5 (C-6), 165.4 (C-2).

Example 5: synthesis of N-((1R,2S)-2-(3,4-difluorophenyl)cyclopropyl)-9-isopropyl-2-(propylthio)-9H-purin-6-amine (5c)

6-Chloro-N$^4$-isopropyl-2-(propylthio)pyrimidine-4,5-diamine (5a)

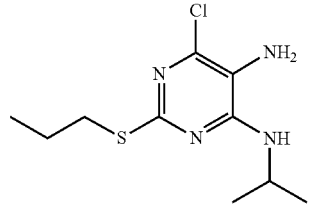 [SMILES: CCCSc1nc(Cl)c(N)c(NC(C)C)n1]

4,6-Dichloro-2-(propylthio)pyrimidin-5-amine (0.5 g, 2.1 mmol) was dissolved in methanol (2 mL) and supplemented with isopropylamine (370.0 mg, 6.3 mmol). The reaction mixture was introduced in a sealed vessel and heated at 100° C. for 90 min. After concentration of the reaction mixture to dryness under vacuum, the residue was purified by silica gel column chromatography.

Yield: 95%.

Melting point: 81-83° C.

$^1$H NMR (DMSO-$d_6$) δ0.95 (t, J=7.3 Hz, 3H, SCH$_2$CH$_2$CH$_3$), 1.19 (d, J=6.5 Hz, 6H, NHCH(CH$_3$)$_2$), 1.63 (h, J=7.3 Hz, 2H, SCH$_2$CH$_2$CH$_3$), 2.93 (t, J=7.2 Hz, 2H, SCH$_2$CH$_2$CH$_3$), 4.16 (m, 1H, NHCH(CH$_3$)$_2$), 4.81 (s, 2H, NH$_2$), 6.69 (d, J=6.9 Hz, 1H, NHCH(CH$_3$)$_2$).

$^{13}$C NMR (DMSO-$d_6$) δ 13.3 (SCH$_2$CH$_2$CH$_3$), 22.2 (NHCH(CH$_3$)$_2$), 22.8 (SCH$_2$CH$_2$CH$_3$), 32.1 (SCH$_2$CH$_2$CH$_3$), 42.6 (NHCH(CH$_3$)$_2$), 119.7 (C-5), 137.3 (C-6), 151.7 (C-4), 155.1 (C-2).

6-Chloro-9-isopropyl-2-(propylthio)-9H-purine (5b)

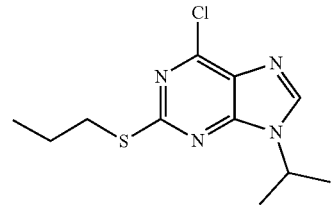 [SMILES: CCCSc1nc(Cl)c2ncn(C(C)C)c2n1]

A solution of (5a) (261.0 mg, 1 mmol) in acetic acid (2.5 mL) and triethyl orthoformate (2.5 mL, 15 mmol) was heated at a temperature of 130° C. under reflux for 1 h. After distillation of the acetic acid and triethyl orthoformate under vacuum, the residue was purified by silica gel column chromatography.

Yield: 37%.

Melting point: 121-122.5° C.

$^1$H NMR (DMSO-$d_6$) δ 1.01 (t, J=7.4 Hz, 3H, SCH$_2$CH$_2$CH$_3$), 1.56 (d, J=6.8 Hz, 6H, NCH(CH$_3$)$_2$), 1.74 (h, J=7.3 Hz, 2H, SCH$_2$CH$_2$CH$_3$), 3.16 (t, J=7.2 Hz, 2H, SCH$_2$CH$_2$CH$_3$), 4.80 (hept, J=6.8 Hz, 1H, NCH(CH$_3$)$_2$), 8.62 (s, 1H, 8-H).

$^{13}$C NMR (DMSO-d$_6$) δ 13.3 (SCH$_2$CH$_2$CH$_3$), 21.7 (NCH(CH$_3$)$_2$), 22.1 (SCH$_2$CH$_2$CH$_3$), 32.6 (SCH$_2$CH$_2$CH$_3$), 47.9 (NCH(CH$_3$)$_2$), 128.4 (C-5), 144.7 (C-8), 148.9 (C-6), 152.3 (C-4), 163.5 (C-2).

N-((1R,2S)-2-(3,4-Difluorophenyl)cyclopropyl)-9-isopropyl-2-(propylthio)-9H-purin-6-amine (5c)

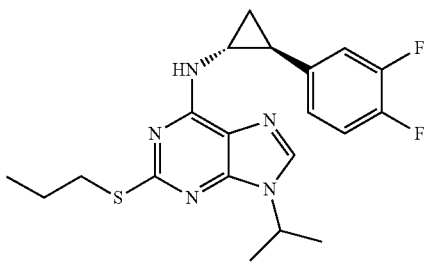 [SMILES: CCCSc1nc(N[C@@H]2C[C@H]2c2ccc(F)c(F)c2)c2ncn(C(C)C)c2n1]

A solution of (5b) (136.0 mg, 0.5 mmol) in acetonitrile (2.5 mL) was supplemented with (1R,2S)-2-(3,4-difluorophenyl)cyclopropanamine (93.0 mg, 0.55 mmol) and triethylamine (0.13 mL) and then heated at 90° C. under reflux for 1 h. After distillation of acetonitrile and triethylamine under vacuum, the residue was purified by silica gel column chromatography.

Yield: 47%.

Melting point: 98.5-100.5° C.

$^1$H NMR (CDCl$_3$) δ 0.95 (t, J=7.4 Hz, 3H, SCH$_2$CH$_2$CH$_3$), 1.31 (m, 2H, NHCH(CH$_2$)CHPh), 1.58 (dd, J=6.8 Hz/1.6 Hz, 6H, NCH(CH$_3$)$_2$), 1.68 (h, J=7.3 Hz, 2H, SCH$_2$CH$_2$CH$_3$), 2.08 (m, 1H, NHCH(CH$_2$)CHPh), 3.04 (m, 2H, SCH$_2$CH$_2$CH$_3$), 3.10 (bs, 1H, NHCH(CH$_2$)CHPh), 4.77 (hept, J=6.8 Hz, 1H, NCH(CH$_3$)$_2$), 5.95 (bs, 1H, NH), 7.00 (m, 1H, 6'-H), 7.09 (m, 2H, 2'-H/5'-H), 7.68 (s, 1H, 8-H).

$^{13}$C NMR (CDCl$_3$) δ 13.5 (SCH$_2$CH$_2$CH$_3$), 16.0 (NHCH(CH$_2$)CHPh), 22.6 (NCH(CH$_3$)$_2$), 22.9 (SCH$_2$CH$_2$CH$_3$), 25.2 (NHCH(CH$_2$)CHPh), 33.2 (SCH$_2$CH$_2$CH$_3$), 33.3 (NHCH(CH$_2$)CHPh), 47.0 (NCH(CH$_3$)$_2$), 115.7 (d, J=17 Hz, C-2'), 116.9 (d, J=17 Hz, C-5'), 117.9 (C-5), 122.8 (C-6'), 136.7 (C-8), 137.9 (C-1'), 147.9-149.9 (dd, 246 Hz/13 Hz, C-4'), 149.2-151.2 (dd, 247 Hz/13 Hz, C-3'), 150.0 (C-4), 154.6 (C-6), 165.1 (C-2).

Example 6: synthesis of 9-cyclopropyl-N-((1R,2S)-2-(3,4-difluorophenyl)cyclopropyl)-2-(propylthio)-9H-purin-6-amine (6c)

6-Chloro-N$^4$-cyclopropyl-2-(propylthio)pyrimidine-4,5-diamine (6a)

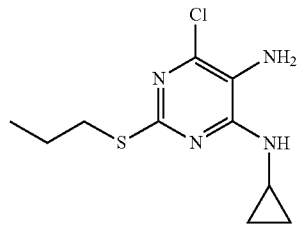 [SMILES: CCCSc1nc(Cl)c(N)c(NC2CC2)n1]

4,6-Dichloro-2-(propylthio)pyrimidin-5-amine (0.5 g, 2.1 mmol) was dissolved in methanol (2 mL) and supplemented with cyclopropylamine (360.0 mg, 6.3 mmol). The reaction mixture was introduced in a sealed vessel and heated at 100° C. for 30 min. After concentration of the reaction mixture to dryness under vacuum, the residue was purified by silica gel column chromatography.

Yield: 92%.

Melting point: 96-98° C.

$^1$H NMR (DMSO-d$_6$) δ 0.49 (s, 2H, NHCH(CH$_2$)$_2$), 0.73 (d, J=5.7 Hz, 2H, NHCH(CH$_2$)$_2$), 0.95 (t, J=7.1 Hz, 3H, SCH$_2$CH$_2$CH$_3$), 1.66 (h, J=7.0 Hz, 2H, SCH$_2$CH$_2$CH$_3$), 2.80 (m, 1H, NHCH(CH$_2$)$_2$), 2.97 (t, J=6.9 Hz, 2H, SCH$_2$CH$_2$CH$_3$), 4.74 (s, 2H, NH$_2$), 7.09 (s, 1H, NHCH(CH$_2$)$_2$).

$^{13}$C NMR (DMSO-d$_6$) δ 6.2 (NHCH(CH$_2$)$_2$), 13.3 (SCH$_2$CH$_2$CH$_3$), 22.8 (SCH$_2$CH$_2$CH$_3$), 24.1 (NHCH(CH$_2$)$_2$), 32.2 (SCH$_2$CH$_2$CH$_3$), 120.0 (C-5), 137.3 (C-6), 153.4 (C-4), 155.2 (C-2).

6-Chloro-9-cyclopropyl-2-(propylthio)-9H-purine (6b)

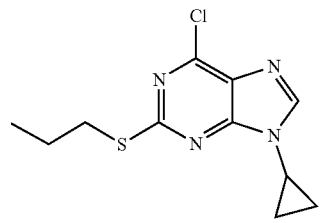 [SMILES: CCCSc1nc(Cl)c2ncn(C3CC3)c2n1]

A solution of (6a) (259.0 mg, 1 mmol) in acetic acid (2.5 mL) and triethyl orthoformate (2.5 mL, 15 mmol) was heated at a temperature of 130° C. under reflux for 1 h. After distillation of the acetic acid and triethyl orthoformate under vacuum, the residue was purified by silica gel column chromatography.

Yield: 58%.

Melting point: 128.5-130° C.

$^1$H NMR (DMSO-d$_6$) δ 1.02 (t, J=7.4 Hz, 3H, SCH$_2$CH$_2$CH$_3$), 1.09 (m, 2H, NCH(CH$_2$)$_2$), 1.16 (m, 2H, NCH(CH$_2$)$_2$), 1.75 (h, J=7.3 Hz, 2H, SCH$_2$CH$_2$CH$_3$), 3.17 (t, J=7.2 Hz, 2H, SCH$_2$CH$_2$CH$_3$), 3.55 (m, 1H, NCH(CH$_2$)$_2$), 8.52 (s, 1H, 8-H).

$^{13}$C NMR (DMSO-d$_6$) δ 5.4 (NCH(CH$_2$)$_2$), 13.3 (SCH$_2$CH$_2$CH$_3$), 22.1 (SCH$_2$CH$_2$CH$_3$), 25.6 (NCH(CH$_2$)$_2$), 32.7 (SCH$_2$CH$_2$CH$_3$), 128.2 (C-5), 146.7 (C-8), 148.8 (C-6), 153.9 (C-4), 163.9 (C-2).

9-Cyclopropyl-N-((1R,2S)-2-(3,4-difluorophenyl)cyclopropyl)-2-(propylthio)-9H-purin-6-amine (6c)

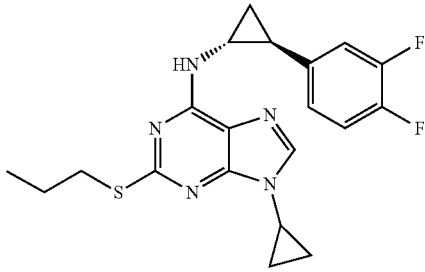 [SMILES: CCCSc1nc(N[C@@H]2C[C@H]2c2ccc(F)c(F)c2)c2ncn(C3CC3)c2n1]

A solution of (6b) (135.0 mg, 0.5 mmol) in acetonitrile (2.5 mL) was supplemented with (1R,2S)-2-(3,4-difluorophenyl)cyclopropanamine (93.0 mg, 0.55 mmol) and triethylamine (0.13 mL) and then heated at 90° C. under reflux for 1 h. After distillation of acetonitrile and triethylamine under vacuum, the residue was purified by silica gel column chromatography.

Yield: 40%.

Melting point: 137-139° C.

$^1$H NMR (CDCl$_3$) δ 0.95 (t, J=7.4 Hz, 3H, SCH$_2$CH$_2$CH$_3$), 1.10 (m, 2H, NCH(CH$_2$)$_2$), 1.13 (m, 2H, NCH(CH$_2$)$_2$), 1.31 (m, 2H, NHCH(CH$_2$)CHPh), 1.68 (h, J=7.3 Hz, 2H, SCH$_2$CH$_2$CH$_3$), 2.08 (m, 1H, NHCH(CH$_2$)CHPh), 3.03 (m, 2H, SCH$_2$CH$_2$CH$_3$), 3.10 (bs, 1H, NHCH(CH$_2$)CHPh), 3.38 (tt, J=7.1 Hz/3.9 Hz, 1H, NCH(CH$_2$)$_2$), 5.88 (bs, 1H, NH), 6.99 (m, 1H, 6'-H), 7.08 (m, 2H, 2'-H/5'-H), 7.61 (s, 1H, 8-H).

$^{13}$C NMR (CDCl$_3$) δ 5.9 (NCH(CH$_2$)$_2$), 13.5 (SCH$_2$CH$_2$CH$_3$), 16.1 (NHCH(CH$_2$)CHPh), 22.9 (SCH$_2$CH$_2$CH$_3$), 25.2 (NHCH(CH$_2$)CHPh), 25.3 (NCH(CH$_2$)$_2$), 33.2 (SCH$_2$CH$_2$CH$_3$), 33.3 (NHCH(CH$_2$)CHPh), 115.6 (d, J=17 Hz, C-2'), 116.9 (d, J=17 Hz, C-5'), 117.4 (C-5), 122.7 (C-6'), 137.9 (C-1'), 139.4 (C-8), 147.9-149.9 (dd, 246 Hz/13 Hz, C-4'), 149.2-151.2 (dd, 247 Hz/13 Hz, C-3'), 151.6 (C-4), 154.4 (C-6), 165.6 (C-2).

Example 7: synthesis of 9-butyl-N-((1R,2S)-2-(3,4-difluorophenyl)cyclopropyl)-2-(propylthio)-9H-purin-6-amine (7c)

N$^4$-Butyl-6-chloro-2-(propylthio)pyrimidine-4,5-diamine (7a)

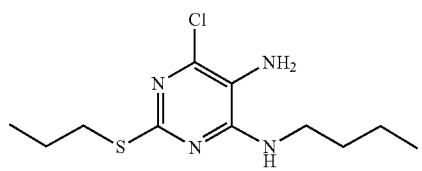 [SMILES: CCCCNc1nc(SCCC)nc(Cl)c1N]

4,6-Dichloro-2-(propylthio)pyrimidin-5-amine (0.5 g, 2.1 mmol) was dissolved in methanol (2 mL) and supplemented with n-butylamine (460.0 mg, 6.3 mmol). The reaction mixture was introduced in a sealed vessel and heated at 100° C. for 30 min. After concentration of the reaction mixture to dryness under vacuum, the residue was purified by silica gel column chromatography.

Yield: 95%.

Melting point: liquid.

$^1$H NMR (DMSO-d$_6$) δ0.91 (t, J=7.4 Hz, 3H, NHCH$_2$CH$_2$CH$_2$CH$_3$), 0.95 (t, J=7.4 Hz, 3H, SCH$_2$CH$_2$CH$_3$), 1.35 (h, J=7.4 Hz, 2H, NHCH$_2$CH$_2$CH$_2$CH$_3$), 1.55 (p, J=7.5 Hz, 2H, NHCH$_2$CH$_2$CH$_2$CH$_3$), 1.64 (h, J=7.4 Hz, 2H, SCH$_2$CH$_2$CH$_3$), 2.95 (t, J=7.3 Hz, 2H, SCH$_2$CH$_2$CH$_3$), 3.37 (m, 2H, NHCH$_2$CH$_2$CH$_2$CH$_3$), 4.76 (s, 2H, NH$_2$), 6.94 (t, J=5.2 Hz, 1H, NHCH$_2$CH$_2$CH$_2$CH$_3$).

$^{13}$C NMR (DMSO-d$_6$) δ13.3 (SCH$_2$CH$_2$CH$_3$), 13.7 (NHCH$_2$CH$_2$CH$_2$CH$_3$), 19.6 (NHCH$_2$CH$_2$CH$_2$CH$_3$), 22.8 (SCH$_2$CH$_2$CH$_3$), 30.8 (NHCH$_2$CH$_2$CH$_2$CH$_3$), 32.1 (SCH$_2$CH$_2$CH$_3$), 40.6 (NHCH$_2$CH$_2$CH$_2$CH$_3$), 119.8 (C-5), 137.3 (C-6), 152.6 (C-4), 155.2 (C-2).

9-Butyl-6-chloro-2-(propylthio)-9H-purine (7b)

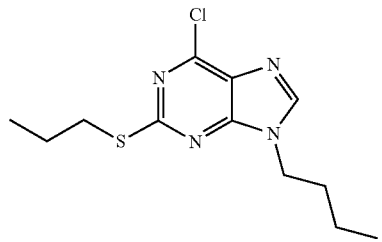 [SMILES: CCCCn1cnc2c(Cl)nc(SCCC)nc21]

A solution of (7a) (275.0 mg, 1 mmol) in acetic acid (2.5 mL) and triethyl orthoformate (2.5 mL, 15 mmol) was heated at a temperature of 130° C. under reflux for 1 h. After distillation of the acetic acid and triethyl orthoformate under vacuum, the residue was purified by silica gel column chromatography.

Yield: 72%.

Melting point: liquid.

$^1$H NMR (DMSO-d$_6$) δ 0.90 (t, J=7.4 Hz, 3H, NCH$_2$CH$_2$CH$_2$CH$_3$), 1.01 (t, J=7.4 Hz, 3H, SCH$_2$CH$_2$CH$_3$), 1.26 (h, J=7.4 Hz, 2H, NCH$_2$CH$_2$CH$_2$CH$_3$), 1.74 (h, J=7.3 Hz, 2H, SCH$_2$CH$_2$CH$_3$), 1.83 (p, J=7.2 Hz, 2H, NCH$_2$CH$_2$CH$_2$CH$_3$), 3.16 (t, J=7.2 Hz, 2H, SCH$_2$CH$_2$CH$_3$), 4.22 (t, J=7.1 Hz, 2H, NCH$_2$CH$_2$CH$_2$CH$_3$), 8.56 (s, 1H, 8-H).

$^{13}$C NMR (DMSO-d$_6$) δ 13.2 (SCH$_2$CH$_2$CH$_3$), 13.3 (NCH$_2$CH$_2$CH$_2$CH$_3$), 19.2 (NCH$_2$CH$_2$CH$_2$CH$_3$), 22.1 (SCH$_2$CH$_2$CH$_3$), 30.9 (NCH$_2$CH$_2$CH$_2$CH$_3$), 32.6 (SCH$_2$CH$_2$CH$_3$), 43.3 (NCH$_2$CH$_2$CH$_2$CH$_3$), 127.9 (C-5), 146.3 (C-8), 148.9 (C-6), 152.8 (C-4), 163.8 (C-2).

9-Butyl-N-((1R,2S)-2-(3,4-difluorophenyl)cyclopropyl)-2-(propylthio)-9H-purin-6-amine (7c)

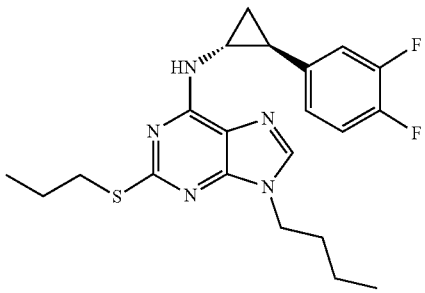 [SMILES: CCCCn1cnc2c(N[C@@H]3C[C@H]3c3ccc(F)c(F)c3)nc(SCCC)nc21]

A solution of (7b) (143.0 mg, 0.5 mmol) in acetonitrile (2.5 mL) was supplemented with (1R,2S)-2-(3,4-difluorophenyl)cyclopropanamine (93.0 mg, 0.55 mmol) and triethylamine (0.13 mL) and then heated at 90° C. under reflux for 1 h. After distillation of acetonitrile and triethylamine under vacuum, the residue was purified by silica gel column chromatography.

Yield: 61%.

Melting point: 85-87° C.

$^1$H NMR (CDCl$_3$) δ 0.95 (m, 6H, NCH$_2$CH$_2$CH$_2$CH$_3$/SCH$_2$CH$_2$CH$_3$), 1.33 (m, 4H, NCH$_2$CH$_2$CH$_2$CH$_3$/NHCH(CH$_2$)CHPh), 1.68 (h, J=7.3 Hz, 2H, SCH$_2$CH$_2$CH$_3$), 1.86 (p, J=7.3 Hz, 2H, NCH$_2$CH$_2$CH$_2$CH$_3$), 2.10 (m, 1H, NHCH(CH$_2$)CHPh), 3.03 (m, 2H, SCH$_2$CH$_2$CH$_3$), 3.13 (bs, 1H,

NHCH(CH₂)CHPh), 4.14 (t, J=7.1 Hz, 2H, NCH₂CH₂CH₂CH₃), 6.19 (bs, 1H, NH), 6.99 (m, 1H, 6'-H), 7.08 (m, 2H, 2'-H/5'-H), 7.64 (s, 1H, 8-H).

$^{13}$C NMR (CDCl₃) S 13.5 (SCH₂CH₂CH₃/NCH₂CH₂CH₂CH₃), 16.0 (NHCH(CH₂)CHPh), 19.8 (NCH₂CH₂CH₂CH₃), 22.9 (SCH₂CH₂CH₃), 25.2 (NHCH(CH₂)CHPh), 31.9 (NCH₂CH₂CH₂CH₃), 33.2 (SCH₂CH₂CH₃), 33.4 (NHCH(CH₂)CHPh), 43.5 (NCH₂CH₂CH₂CH₃), 115.7 (d, J=17 Hz, C-2'), 116.9 (d, J=17 Hz, C-5'), 117.5 (C-5), 122.7 (C-6'), 136.5 (C-8), 137.9 (C-1'), 147.9-149.9 (dd, 246 Hz/13 Hz, C-4'), 149.2-151.2 (dd, 247 Hz/13 Hz, C-3'), 150.4 (C-4), 154.3 (C-6), 165.8 (C-2).

Example 8: synthesis of 9-(sec-butyl)-N-((1R,2S)-2-(3,4-difluorophenyl)cyclopropyl)-2-(propylthio)-9H-purin-6-amine (8c)

N⁴-(sec-Butyl)-6-chloro-2-(propylthio)pyrimidine-4,5-diamine (8a)

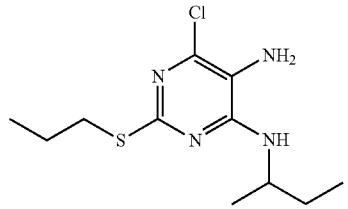 [SMILES: CCCSc1nc(Cl)c(N)c(NC(C)CC)n1]

4,6-Dichloro-2-(propylthio)pyrimidin-5-amine (0.5 g, 2.1 mmol) was dissolved in methanol (2 mL) and supplemented with sec-butylamine (460.0 mg, 6.3 mmol). The reaction mixture was introduced in a sealed vessel and heated at 100° C. for 90 min. After concentration of the reaction mixture to dryness under vacuum, the residue was purified by silica gel column chromatography.

Yield: 81%.
Melting point: liquid.

$^1$H NMR (DMSO-d₆) δ 0.87 (t, J=7.4 Hz, 3H, NHCH(CH₃)CH₂CH₃), 0.95 (t, J=7.3 Hz, 3H, SCH₂CH₂CH₃), 1.15 (d, J=6.6 Hz, 3H, NHCH(CH₃)CH₂CH₃), 1.53 (m, 2H, NHCH(CH₃)CH₂CH₃), 1.64 (h, J=7.3 Hz, 2H, SCH₂CH₂CH₃), 2.93 (t, J=7.2 Hz, 2H, SCH₂CH₂CH₃), 4.01 (hept, J=6.6 Hz, 1H, NHCH(CH₃)CH₂CH₃), 4.81 (s, 2H, NH₂), 6.64 (d, J=7.5 Hz, 1H, NHCH(CH₃)CH₂CH₃).

$^{13}$C NMR (DMSO-d₆) δ 10.5 (NHCH(CH₃)CH₂CH₃), 13.3 (SCH₂CH₂CH₃), 19.8 (NHCH(CH₃)CH₂CH₃), 22.8 (SCH₂CH₂CH₃), 28.6 (NHCH(CH₃)CH₂CH₃), 32.1 (SCH₂CH₂CH₃), 47.9 (NHCH(CH₃)CH₂CH₃), 119.7 (C-5), 137.3 (C-6), 152.0 (C-4), 155.0 (C-2).

9-(sec-Butyl)-6-chloro-2-(propylthio)-9H-purine (8b)

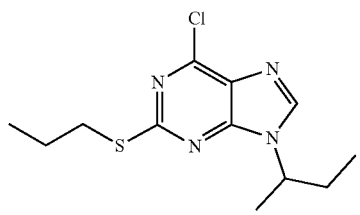 [SMILES: CCCSc1nc(Cl)c2ncn(C(C)CC)c2n1]

A solution of (8a) (275.0 mg, 1 mmol) in acetic acid (2.5 mL) and triethyl orthoformate (2.5 mL, 15 mmol) was heated at a temperature of 130° C. under reflux for 4 h. After distillation of the acetic acid and triethyl orthoformate under vacuum, the residue was purified by silica gel column chromatography.

Yield: 39%.
Melting point: 64-66° C.

$^1$H NMR (DMSO-d₆) δ 0.74 (t, J=7.4 Hz, 3H, NCH(CH₃)CH₂CH₃), 1.01 (t, J=7.4 Hz, 3H, SCH₂CH₂CH₃), 1.57 (d, J=6.9 Hz, 3H, NCH(CH₃)CH₂CH₃), 1.74 (h, J=7.3 Hz, 2H, SCH₂CH₂CH₃), 1.95 (m, 2H, NCH(CH₃)CH₂CH₃), 3.15 (m, 2H, SCH₂CH₂CH₃), 4.57 (m, 1H, NCH(CH₃)CH₂CH₃), 8.63 (s, 1H, 8-H).

$^{13}$C NMR (DMSO-d₆) δ 10.5 (NCH(CH₃)CH₂CH₃), 13.3 (SCH₂CH₂CH₃), 19.8 (NCH(CH₃)CH₂CH₃), 22.1 (SCH₂CH₂CH₃), 28.3 (NCH(CH₃)CH₂CH₃), 32.6 (SCH₂CH₂CH₃), 53.6 (NCH(CH₃)CH₂CH₃), 128.2 (C-5), 145.1 (C-8), 149.0 (C-6), 152.5 (C-4), 163.6 (C-2).

9-(sec-Butyl)-N-((1R,2S)-2-(3,4-difluorophenyl)cyclopropyl)-2-(propylthio)-9H-purin-6-amine (8c)

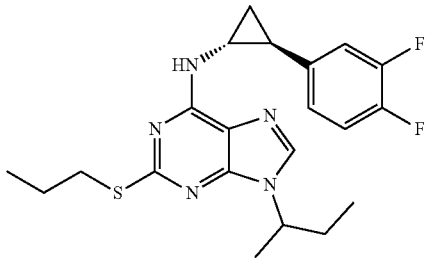 [SMILES: CCCSc1nc(N[C@@H]2C[C@H]2c2ccc(F)c(F)c2)c2ncn(C(C)CC)c2n1]

A solution of (8b) (143.0 mg, 0.5 mmol) in acetonitrile (2.5 mL) was supplemented with (1R,2S)-2-(3,4-difluorophenyl)cyclopropanamine (93.0 mg, 0.55 mmol) and triethylamine (0.13 mL) and then heated at 90° C. under reflux for 4 h. After distillation of acetonitrile and triethylamine under vacuum, the residue was purified by silica gel column chromatography.

Yield: 66%.
Melting point: 68-71° C.

$^1$H NMR (CDCl₃) δ 0.85 (td, J=7.4 Hz/1.6 Hz, 3H, NCH(CH₃)CH₂CH₃), 0.96 (t, J=7.3 Hz, 3H, SCH₂CH₂CH₃), 1.33 (m, 2H, NHCH(CH₂)CHPh), 1.57 (d, J=6.9 Hz, 3H, NCH(CH₃)CH₂CH₃), 1.69 (h, J=7.3 Hz, 2H, SCH₂CH₂CH₃), 1.95 (m, 2H, NCH(CH₃)CH₂CH₃), 2.10 (m, 1H, NHCH(CH₂)CHPh), 3.03 (m, 2H, SCH₂CH₂CH₃), 3.11 (bs, 1H, NHCH(CH₂)CHPh), 4.52 (m, 1H, NCH(CH₃)CH₂CH₃), 6.12 (bs, 1H, NH), 7.00 (m, 1H, 6'-H), 7.10 (m, 2H, 2'-H/5'-H), 7.67 (s, 1H, 8-H).

$^{13}$C NMR (CDCl₃) S 10.7 (NCH(CH₃)CH₂CH₃), 13.5 (SCH₂CH₂CH₃), 15.9 (NHCH(CH₂)CHPh), 20.6 (NCH(CH₃)CH₂CH₃), 22.9 (SCH₂CH₂CH₃), 25.2 (NHCH(CH₂)CHPh), 29.5 (NCH(CH₃)CH₂CH₃), 33.2 (SCH₂CH₂CH₃), 33.3 (NHCH(CH₂)CHPh), 53.0 (NCH(CH₃)CH₂CH₃), 115.8 (d, J=17 Hz, C-2'), 116.9 (d, J=17 Hz, C-5'), 117.3 (C-5), 122.8 (C-6'), 137.0 (C-8), 137.9 (C-1'), 147.9-149.9 (dd, 246 Hz/13 Hz, C-4'), 149.2-151.2 (dd, 247 Hz/13 Hz, C-3'), 150.3 (C-4), 154.4 (C-6), 165.1 (C-2).

Example 9: synthesis of 9-(tert-butyl)-N-((1R,2S)-2-(3,4-difluorophenyl)cyclopropyl)-2-(propylthio)-9H-purin-6-amine (9c)

N⁴-(tert-Butyl)-6-chloro-2-(propylthio)pyrimidine-4,5-diamine (9a)

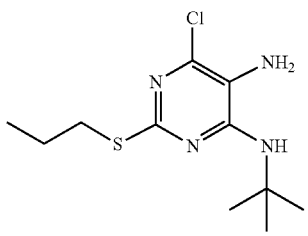 [SMILES: CCCSc1nc(Cl)c(N)c(NC(C)(C)C)n1]

4,6-Dichloro-2-(propylthio)pyrimidin-5-amine (0.5 g, 2.1 mmol) was dissolved in methanol (2 mL) and supplemented with tert-butylamine (460.0 mg, 6.3 mmol). The reaction mixture was introduced in a sealed vessel and heated at 100° C. for 24 h. After concentration of the reaction mixture to dryness under vacuum, the residue was purified by silica gel column chromatography.

Yield: 88%.

Melting point: 88-89° C.

$^1$H NMR (DMSO-$d_6$) δ 0.95 (t, J=7.3 Hz, 3H, SCH$_2$CH$_2$CH$_3$), 1.43 (s, 9H, NHC(CH$_3$)$_3$), 1.62 (h, J=7.3 Hz, 2H, SCH$_2$CH$_2$CH$_3$), 2.95 (t, J=7.3 Hz, 2H, SCH$_2$CH$_2$CH$_3$), 4.91 (bs, 2H, NH$_2$), 6.19 (s, 1H, NHC(CH$_3$)$_3$).

$^{13}$C NMR (DMSO-$d_6$) δ 13.3 (SCH$_2$CH$_2$CH$_3$), 22.9 (SCH$_2$CH$_2$CH$_3$), 28.5 (NHC(CH$_3$)$_3$), 31.9 (SCH$_2$CH$_2$CH$_3$), 51.9 (NHC(CH$_3$)$_3$), 120.3 (C-5), 137.6 (C-6), 152.1 (C-4), 154.5 (C-2).

9-(tert-Butyl)-6-chloro-2-(propylthio)-9H-purine (9b)

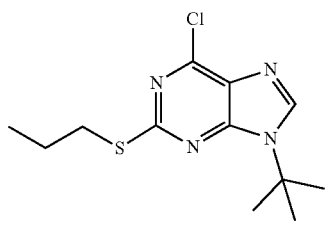 [SMILES: CCCSc1nc(Cl)c2ncn(C(C)(C)C)c2n1]

A solution of (9a) (275.0 mg, 1 mmol) in acetic acid (2.5 mL) and triethyl orthoformate (2.5 mL, 15 mmol) was heated at a temperature of 130° C. under reflux for 10 h. After distillation of the acetic acid and triethyl orthoformate under vacuum, the residue was purified by silica gel column chromatography.

Yield: 41%.

Melting point: 116-117° C.

$^1$H NMR (DMSO-$d_6$) δ 1.02 (t, J=7.4 Hz, 3H, SCH$_2$CH$_2$CH$_3$), 1.74 (m, 11H, SCH$_2$CH$_2$CH$_3$/NC(CH$_3$)$_3$), 3.14 (t, J=7.2 Hz, 2H, SCH$_2$CH$_2$CH$_3$), 8.54 (s, 1H, 8-H).

$^{13}$C NMR (DMSO-$d_6$) δ 13.3 (SCH$_2$CH$_2$CH$_3$), 22.1 (SCH$_2$CH$_2$CH$_3$), 28.3 (NC(CH$_3$)$_3$), 32.7 (SCH$_2$CH$_2$CH$_3$), 58.0 (NC(CH$_3$)$_3$), 129.0 (C-5), 144.2 (C-8), 149.3 (C-6), 152.6 (C-4), 162.9 (C-2).

9-(tert-Butyl)-N-((1R,2S)-2-(3,4-difluorophenyl)cyclopropyl)-2-(propylthio)-9H-purin-6-amine (9c)

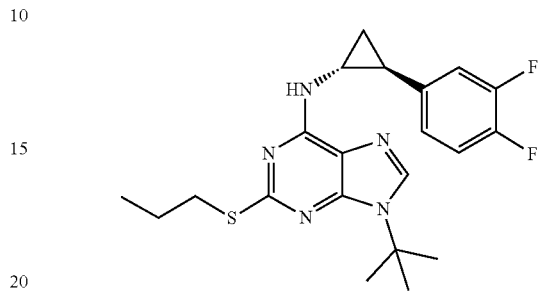

A solution of (9b) (143.0 mg, 0.5 mmol) in acetonitrile (2.5 mL) was supplemented with (1R,2S)-2-(3,4-difluorophenyl)cyclopropanamine (93.0 mg, 0.55 mmol) and triethylamine (0.13 mL) and then heated at 90° C. under reflux for 2 h. After distillation of acetonitrile and triethylamine under vacuum, the residue was purified by silica gel column chromatography.

Yield: 56%.

Melting point: 125-128° C.

$^1$H NMR (CDCl$_3$) δ 1.01 (t, J=7.4 Hz, 3H, SCH$_2$CH$_2$CH$_3$), 1.29 (m, 2H, NHCH(CH$_2$)CHPh), 1.77 (m, 11H, SCH$_2$CH$_2$CH$_3$/NC(CH$_3$)$_3$), 2.08 (m, 1H, NHCH(CH$_2$)CHPh), 3.06 (m, 3H, SCH$_2$CH$_2$CH$_3$/NHCH(CH$_2$)CHPh), 5.95 (bs, 1H, NH), 7.08 (m, 2H, 5'-H/6'-H), 7.17 (m, 1H, 2'-H), 7.70 (s, 1H, 8-H).

$^{13}$C NMR (CDCl$_3$) δ 13.6 (SCH$_2$CH$_2$CH$_3$), 15.6 (NHCH(CH$_2$)CHPh), 23.1 (SCH$_2$CH$_2$CH$_3$), 25.2 (NHCH(CH$_2$)CHPh), 29.0 (NC(CH$_3$)$_3$), 33.0 (NHCH(CH$_2$)CHPh), 33.2 (SCH$_2$CH$_2$CH$_3$), 57.1 (NC(CH$_3$)$_3$), 116.2 (d, J=17 Hz, C-2'), 116.9 (d, J=17 Hz, C-5'), 118.9 (C-5), 123.1 (C-6'), 136.5 (C-8), 137.8 (C-1'), 147.9-149.9 (dd, 246 Hz/13 Hz, C-4'), 149.2-151.2 (dd, 247 Hz/13 Hz, C-3'), 150.7 (C-4), 154.9 (C-6), 164.3 (C-2).

Example 10: synthesis of 9-cyclobutyl-N-((1R,2S)-2-(3,4-difluorophenyl)cyclopropyl)-2-(propylthio)-9H-purin-6-amine (10c)

6-Chloro-N⁴-cyclobutyl-2-(propylthio)pyrimidine-4,5-diamine (10a)

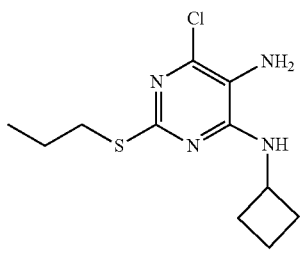 [SMILES: CCCSc1nc(Cl)c(N)c(NC2CCC2)n1]

4,6-Dichloro-2-(propylthio)pyrimidin-5-amine (0.5 g, 2.1 mmol) was dissolved in methanol (2 mL) and supplemented with cyclobutylamine (440.0 mg, 6.3 mmol). The reaction mixture was introduced in a sealed vessel and heated at 100° C. for 1 h. After concentration of the reaction mixture to dryness under vacuum, the residue was purified by silica gel column chromatography.

Yield: 96%.

Melting point: 73-75.5° C.

$^1$H NMR (DMSO-d$_6$) δ 0.96 (t, J=7.4 Hz, 3H, SCH$_2$CH$_2$CH$_3$), 1.63 (h, J=7.3 Hz, 2H, SCH$_2$CH$_2$CH$_3$), 1.72 (m, 2H, NHCH(CH$_2$)$_3$), 1.95 (m, 2H, NHCH(CH$_2$)$_3$), 2.29 (m, 2H, NHCH(CH$_2$)$_3$), 2.94 (t, J=7.2 Hz, 2H, SCH$_2$CH$_2$CH$_3$), 4.38 (h, J=8.0 Hz, 1H, NHCH(CH$_2$)$_3$), 4.80 (s, 2H, NH$_2$), 7.11 (d, J=6.3 Hz, 1H, NHCH(CH$_2$)$_3$).

$^{13}$C NMR (DMSO-d$_6$) δ 13.3 (SCH$_2$CH$_2$CH$_3$), 14.9 (NHCH(CH$_2$)$_3$), 22.7 (SCH$_2$CH$_2$CH$_3$), 30.2 (NHCH(CH$_2$)$_3$), 32.1 (SCH$_2$CH$_2$CH$_3$), 46.3 (NHCH(CH$_2$)$_3$), 119.7 (C-5), 137.4 (C-6), 151.5 (C-4), 155.1 (C-2).

6-Chloro-9-cyclobutyl-2-(propylthio)-9H-purine (10b)

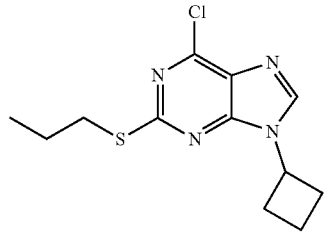 [SMILES: CCCSc1nc(Cl)c2ncn(C3CCC3)c2n1]

A solution of (10a) (273.0 mg, 1 mmol) in acetic acid (2.5 mL) and triethyl orthoformate (2.5 mL, 15 mmol) was heated at a temperature of 130° C. under reflux for 1 h. After distillation of the acetic acid and triethyl orthoformate under vacuum, the residue was purified by silica gel column chromatography.

Yield: 62%.

Melting point: 89-91.5° C.

$^1$H NMR (DMSO-d$_6$) δ 1.02 (t, J=7.3 Hz, 3H, SCH$_2$CH$_2$CH$_3$), 1.75 (h, J=7.3 Hz, 2H, SCH$_2$CH$_2$CH$_3$), 1.90 (m, 2H, NCH(CH$_2$)$_3$), 2.47 (m, 2H, NCH(CH$_2$)$_3$), 2.73 (m, 2H, NCH(CH$_2$)$_3$), 3.17 (t, J=7.2 Hz, 2H, SCH$_2$CH$_2$CH$_3$), 5.03 (p, J=8.6 Hz, 1H, NCH(CH$_2$)$_3$), 8.66 (s, 1H, 8-H).

$^{13}$C NMR (DMSO-d$_6$) δ 13.3 (SCH$_2$CH$_2$CH$_3$), 14.8 (NCH(CH$_2$)$_3$), 22.1 (SCH$_2$CH$_2$CH$_3$), 29.2 (NCH(CH$_2$)$_3$), 32.7 (SCH$_2$CH$_2$CH$_3$), 48.8 (NCH(CH$_2$)$_3$), 128.3 (C-5), 145.1 (C-8), 148.9 (C-6), 152.5 (C-4), 163.7 (C-2).

9-Cyclobutyl-N-((1R,2S)-2-(3,4-difluorophenyl)cyclopropyl)-2-(propylthio)-9H-purin-6-amine (10c)

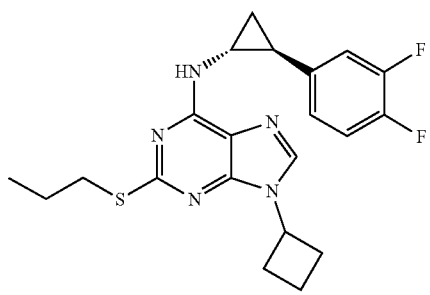 [SMILES: CCCSc1nc(N[C@@H]2C[C@H]2c2ccc(F)c(F)c2)c2ncn(C3CCC3)c2n1]

A solution of (10b) (142.0 mg, 0.5 mmol) in acetonitrile (2.5 mL) was supplemented with (1R,2S)-2-(3,4-difluorophenyl)cyclopropanamine (93.0 mg, 0.55 mmol) and triethylamine (0.13 mL) and then heated at 90° C. under reflux for 2 h. After distillation of acetonitrile and triethylamine under vacuum, the residue was purified by silica gel column chromatography.

Yield: 76%.

Melting point: 143-145° C.

$^1$H NMR (CDCl$_3$) δ 0.96 (t, J=7.4 Hz, 3H, SCH$_2$CH$_2$CH$_3$), 1.32 (m, 2H, NHCH(CH$_2$)CHPh), 1.70 (h, J=7.3 Hz, 2H, SCH$_2$CH$_2$CH$_3$), 1.95 (m, 2H, NCH(CH$_2$)$_3$), 2.09 (m, 1H, NHCH(CH$_2$)CHPh), 2.56 (m, 2H, NCH(CH$_2$)$_3$), 2.64 (m, 2H, NCH(CH$_2$)$_3$), 3.04 (m, 2H, SCH$_2$CH$_2$CH$_3$), 3.10 (bs, 1H, NHCH(CH$_2$)CHPh), 4.95 (p, J=8.6 Hz, 1H, NCH(CH$_2$)$_3$), 6.06 (bs, 1H, NH), 7.00 (m, 1H, 6'-H), 7.09 (m, 2H, 2'-H/5'-H), 7.74 (s, 1H, 8-H).

$^{13}$C NMR (CDCl$_3$) δ 13.5 (SCH$_2$CH$_2$CH$_3$), 15.3 (NCH(CH$_2$)$_3$), 16.0 (NHCH(CH$_2$)CHPh), 22.9 (SCH$_2$CH$_2$CH$_3$), 25.2 (NHCH(CH$_2$)CHPh), 30.5 (NCH(CH$_2$)$_3$), 33.2 (SCH$_2$CH$_2$CH$_3$), 33.3 (NHCH(CH$_2$)CHPh), 48.8 (NCH(CH$_2$)$_3$), 115.8 (d, J=17 Hz, C-2'), 116.9 (d, J=17 Hz, C-5'), 117.5 (C-5), 122.8 (C-6'), 137.3 (C-8), 137.8 (C-1'), 147.9-149.9 (dd, 246 Hz/13 Hz, C-4'), 149.2-151.2 (dd, 247 Hz/13 Hz, C-3'), 150.4 (C-4), 154.5 (C-6), 165.2 (C-2).

Example 11: synthesis of N-((1R,2S)-2-(3,4-difluorophenyl)cyclopropyl)-9-pentyl-2-(propylthio)-9H-purin-6-amine (11c)

6-Chloro-N$^4$-pentyl-2-(propylthio)pyrimidine-4,5-diamine (11a)

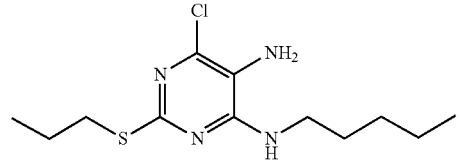 [SMILES: CCCCCNc1nc(SCCC)nc(Cl)c1N]

4,6-Dichloro-2-(propylthio)pyrimidin-5-amine (0.5 g, 2.1 mmol) was dissolved in methanol (2 mL) and supplemented with n-pentylamine (550.0 mg, 6.3 mmol). The reaction mixture was introduced in a sealed vessel and heated at 100° C. for 30 min. After concentration of the reaction mixture to dryness under vacuum, the residue was purified by silica gel column chromatography.

Yield: 96%.

Melting point: 68-69° C.

$^1$H NMR (DMSO-d$_6$) δ 0.87 (t, J=7.0 Hz, 3H, NHCH$_2$CH$_2$CH$_2$CH$_2$CH$_3$), 0.95 (t, J=7.4 Hz, 3H, SCH$_2$CH$_2$CH$_3$), 1.30 (m, 4H, NHCH$_2$CH$_2$CH$_2$CH$_2$CH$_3$), 1.55 (p, J=7.3 Hz, 2H, NHCH$_2$CH$_2$CH$_2$CH$_2$CH$_3$), 1.63 (h, J=7.3 Hz, 2H, SCH$_2$CH$_2$CH$_3$), 2.94 (t, J=7.2 Hz, 2H, SCH$_2$CH$_2$CH$_3$), 3.34 (m, 2H, NHCH$_2$CH$_2$CH$_2$CH$_2$CH$_3$), 4.75 (s, 2H, NH$_2$), 6.95 (t, J=5.2 Hz, 1H, NHCH$_2$CH$_2$CH$_2$CH$_2$CH$_3$).

$^{13}$C NMR (DMSO-d$_6$) δ 13.3 (SCH$_2$CH$_2$CH$_3$), 13.9 (NHCH$_2$CH$_2$CH$_2$CH$_2$CH$_3$), 21.9 (NHCH$_2$CH$_2$CH$_2$CH$_2$CH$_3$), 22.8 (SCH$_2$CH$_2$CH$_3$), 28.3 (NHCH$_2$CH$_2$CH$_2$CH$_2$CH$_3$), 28.7 (NHCH$_2$CH$_2$CH$_2$CH$_2$CH$_3$), 32.1 (SCH$_2$CH$_2$CH$_3$), 40.8 (NHCH$_2$CH$_2$CH$_2$CH$_2$CH$_3$), 119.8 (C-5), 137.3 (C-6), 152.6 (C-4), 155.2 (C-2).

6-Chloro-9-pentyl-2-(propylthio)-9H-purine (11b)

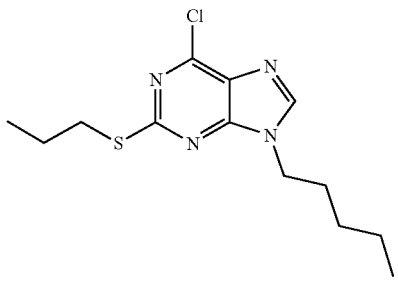 [SMILES: CCCCCn1cnc2c(Cl)nc(SCCC)nc21]

A solution of (11a) (289.0 mg, 1 mmol) in acetic acid (2.5 mL) and triethyl orthoformate (2.5 mL, 15 mmol) was heated at a temperature of 130° C. under reflux for 1 h. After distillation of the acetic acid and triethyl orthoformate under vacuum, the residue was purified by silica gel column chromatography.

Yield: 87%.

Melting point: liquid.

$^1$H NMR (DMSO-d$_6$) δ 0.85 (t, J=7.3 Hz, 3H, NCH$_2$CH$_2$CH$_2$CH$_2$CH$_3$), 1.02 (t, J=7.4 Hz, 3H, SCH$_2$CH$_2$CH$_3$), 1.23 (m, 2H, NCH$_2$CH$_2$CH$_2$CH$_2$CH$_3$), 1.31 (m, 2H, NCH$_2$CH$_2$CH$_2$CH$_2$CH$_3$), 1.75 (h, J=7.3 Hz, 2H, SCH$_2$CH$_2$CH$_3$), 1.86 (p, J=7.2 Hz, 2H, NCH$_2$CH$_2$CH$_2$CH$_2$CH$_3$), 3.17 (t, J=7.2 Hz, 2H, SCH$_2$CH$_2$CH$_3$), 4.22 (t, J=7.1 Hz, 2H, NCH$_2$CH$_2$CH$_2$CH$_2$CH$_3$), 8.56 (s, 1H, 8-H).

$^{13}$C NMR (DMSO-d$_6$) δ 13.3 (SCH$_2$CH$_2$CH$_3$), 13.7 (NCH$_2$CH$_2$CH$_2$CH$_2$CH$_3$), 21.5 (NCH$_2$CH$_2$CH$_2$CH$_2$CH$_3$), 22.1 (SCH$_2$CH$_2$CH$_3$), 28.1 (NCH$_2$CH$_2$CH$_2$CH$_2$CH$_3$), 28.5 (NCH$_2$CH$_2$CH$_2$CH$_2$CH$_3$), 32.6 (SCH$_2$CH$_2$CH$_3$), 43.6 (NCH$_2$CH$_2$CH$_2$CH$_2$CH$_3$), 127.9 (C-5), 146.3 (C-8), 148.9 (C-6), 152.8 (C-4), 163.8 (C-2).

N-((1R,2S)-2-(3,4-Difluorophenyl)cyclopropyl)-9-pentyl-2-(propylthio)-9H-purin-6-amine (11c)

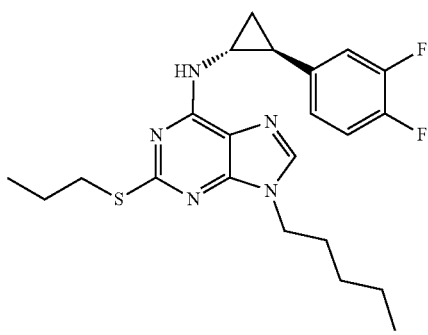 [SMILES: CCCCCn1cnc2c(N[C@@H]3C[C@H]3c3ccc(F)c(F)c3)nc(SCCC)nc21]

A solution of (11b) (150.0 mg, 0.5 mmol) in acetonitrile (2.5 mL) was supplemented with (1R,2S)-2-(3,4-difluorophenyl)cyclopropanamine (93.0 mg, 0.55 mmol) and triethylamine (0.13 mL) and then heated at 90° C. under reflux for 3 h. After distillation of acetonitrile and triethylamine under vacuum, the residue was purified by silica gel column chromatography.

Yield: 83%.

Melting point: 98-100.5° C.

$^1$H NMR (CDCl$_3$) δ 0.89 (t, J=7.2 Hz, 3H, NCH$_2$CH$_2$CH$_2$CH$_2$CH$_3$), 0.95 (t, J=7.4 Hz, 3H, SCH$_2$CH$_2$CH$_3$), 1.32 (m, 6H, NCH$_2$CH$_2$CH$_2$CH$_2$CH$_3$/NHCH(CH$_2$)CHPh), 1.68 (h, J=7.3 Hz, 2H, SCH$_2$CH$_2$CH$_3$), 1.87 (p, J=7.3 Hz, 2H, NCH$_2$CH$_2$CH$_2$CH$_2$CH$_3$), 2.09 (m, 1H, NHCH(CH$_2$)CHPh), 3.04 (m, 2H, SCH$_2$CH$_2$CH$_3$), 3.10 (bs, 1H, NHCH(CH$_2$)CHPh), 4.12 (t, J=7.2 Hz, 2H, NCH$_2$CH$_2$CH$_2$CH$_2$CH$_3$), 5.97 (bs, 1H, NH), 7.00 (m, 1H, 6'-H), 7.09 (m, 2H, 2'-H/5'-H), 7.60 (s, 1H, 8-H).

$^{13}$C NMR (CDCl$_3$) δ 13.5 (SCH$_2$CH$_2$CH$_3$), 13.9 (NCH$_2$CH$_2$CH$_2$CH$_2$CH$_3$), 16.0 (NHCH(CH$_2$)CHPh), 22.2 (NCH$_2$CH$_2$CH$_2$CH$_2$CH$_3$), 22.9 (SCH$_2$CH$_2$CH$_3$), 25.2 (NHCH(CH$_2$)CHPh), 28.7 (NCH$_2$CH$_2$CH$_2$CH$_2$CH$_3$), 29.7 (NCH$_2$CH$_2$CH$_2$CH$_2$CH$_3$), 33.2 (SCH$_2$CH$_2$CH$_3$), 33.3 (NHCH(CH$_2$)CHPh), 43.7 (NCH$_2$CH$_2$CH$_2$CH$_2$CH$_3$), 115.7 (d, J=17 Hz, C-2'), 116.9 (d, J=17 Hz, C-5'), 117.5 (C-5), 122.7 (C-6'), 137.9 (C-1'), 139.0 (C-8), 147.9-149.9 (dd, 246 Hz/13 Hz, C-4'), 149.2-151.2 (dd, 247 Hz/13 Hz, C-3'), 150.5 (C-4), 154.6 (C-6), 165.4 (C-2).

Example 12: synthesis of 9-cyclopentyl-N-((1R,2S)-2-(3,4-difluorophenyl)cyclopropyl)-2-(propylthio)-9H-purin-6-amine (12c)

6-Chloro-N$^4$-cyclopentyl-2-(propylthio)pyrimidine-4,5-diamine (12a)

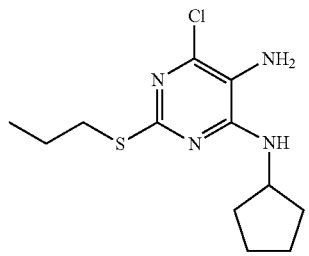 [SMILES: CCCSc1nc(Cl)c(N)c(NC2CCCC2)n1]

4,6-Dichloro-2-(propylthio)pyrimidin-5-amine (0.5 g, 2.1 mmol) was dissolved in methanol (2 mL) and supplemented with cyclopentylamine (536.0 mg, 6.3 mmol). The reaction mixture was introduced in a sealed vessel and heated at 100° C. for 2 h. After concentration of the reaction mixture to dryness under vacuum, the residue was purified by silica gel column chromatography.

Yield: 95%.

Melting point: 86-88° C.

$^1$H NMR (DMSO-d$_6$) δ 0.95 (t, J=7.4 Hz, 3H, SCH$_2$CH$_2$CH$_3$), 1.49 (m, 2H, NHCH(CH$_2$)$_4$), 1.55 (m, 2H, NHCH(CH$_2$)$_4$), 1.64 (m, 2H, SCH$_2$CH$_2$CH$_3$), 1.70 (m, 2H, NHCH(CH$_2$)$_4$), 1.96 (m, 2H, NHCH(CH$_2$)$_4$), 2.94 (t, J=7.2 Hz, 2H, SCH$_2$CH$_2$CH$_3$), 4.25 (h, J=6.7 Hz, 1H, NHCH(CH$_2$)$_4$), 4.83 (s, 2H, NH$_2$), 6.76 (d, J=6.3 Hz, 1H, NHCH(CH$_2$)$_4$).

$^{13}$C NMR (DMSO-d$_6$) δ 13.3 (SCH$_2$CH$_2$CH$_3$), 22.9 (SCH$_2$CH$_2$CH$_3$), 23.5 (NHCH(CH$_2$)$_4$), 32.1 (SCH$_2$CH$_2$CH$_3$), 32.2 (NHCH(CH$_2$)$_4$), 52.7 (NHCH(CH$_2$)$_4$), 119.9 (C-5), 137.2 (C-6), 152.0 (C-4), 155.0 (C-2).

6-Chloro-9-cyclopentyl-2-(propylthio)-9H-purine (12b)

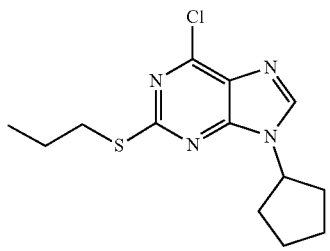 [SMILES: CCCSc1nc(Cl)c2ncn(C3CCCC3)c2n1]

A solution of (12a) (287.0 mg, 1 mmol) in acetic acid (2.5 mL) and triethyl orthoformate (2.5 mL, 15 mmol) was heated at a temperature of 130° C. under reflux for 1 h. After distillation of the acetic acid and triethyl orthoformate under vacuum, the residue was purified by silica gel column chromatography.

Yield: 37%.

Melting point: 81-83° C.

$^1$H NMR (DMSO-$d_6$) δ 1.01 (t, J=7.3 Hz, 3H, SCH$_2$CH$_2$CH$_3$), 1.74 (m, 4H, SCH$_2$CH$_2$CH$_3$/NCH(CH$_2$)$_4$), 1.90 (m, 2H, NCH(CH$_2$)$_4$), 2.06 (m, 2H, NCH(CH$_2$)$_4$), 2.19 (m, 2H, NCH(CH$_2$)$_4$), 3.16 (t, J=7.2 Hz, 2H, SCH$_2$CH$_2$CH$_3$), 4.90 (p, J=7.6 Hz, 1H, NCH(CH$_2$)$_4$), 8.59 (s, 1H, 8-H).

$^{13}$C NMR (DMSO-$d_6$) δ 13.2 (SCH$_2$CH$_2$CH$_3$), 22.1 (SCH$_2$CH$_2$CH$_3$), 23.8 (NCH(CH$_2$)$_4$), 31.5 (NCH(CH$_2$)$_4$), 32.6 (SCH$_2$CH$_2$CH$_3$), 56.4 (NCH(CH$_2$)$_4$), 128.5 (C-5), 145.2 (C-8), 148.9 (C-6), 152.5 (C-4), 163.5 (C-2).

9-Cyclopentyl-N-((1R,2S)-2-(3,4-difluorophenyl)cyclopropyl)-2-(propylthio)-9H-purin-6-amine (12c)

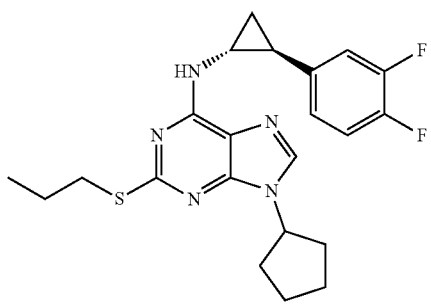 [SMILES: CCCSc1nc(N[C@@H]2C[C@H]2c2ccc(F)c(F)c2)c2ncn(C3CCCC3)c2n1]

A solution of (12b) (149.0 mg, 0.5 mmol) in acetonitrile (2.5 mL) was supplemented with (1R,2S)-2-(3,4-difluorophenyl)cyclopropanamine (93.0 mg, 0.55 mmol) and triethylamine (0.13 mL) and then heated at 90° C. under reflux for 3 h. After distillation of acetonitrile and triethylamine under vacuum, the residue was purified by silica gel column chromatography.

Yield: 35%.

Melting point: 112-114° C.

$^1$H NMR (CDCl$_3$) δ0.95 (t, J=7.4 Hz, 3H, SCH$_2$CH$_2$CH$_3$), 1.31 (m, 2H, NHCH(CH$_2$)CHPh), 1.68 (h, J=7.4 Hz, 2H, SCH$_2$CH$_2$CH$_3$), 1.79 (m, 2H, NCH(CH$_2$)$_4$), 1.94 (m, 2H, NCH(CH$_2$)$_4$), 1.99 (m, 2H, NCH(CH$_2$)$_4$), 2.09 (m, 1H, NHCH(CH$_2$)CHPh), 2.26 (m, 2H, NCH(CH$_2$)$_4$), 3.04 (m, 2H, SCH$_2$CH$_2$CH$_3$), 3.10 (bs, 1H, NHCH(CH$_2$)CHPh), 4.84 (p, J=7.4 Hz, 1H, NCH(CH$_2$)$_4$), 5.92 (bs, 1H, NH), 7.00 (m, 1H, 6'-H), 7.09 (m, 2H, 2'-H/5'-H), 7.65 (s, 1H, 8-H).

$^{13}$C NMR (CDCl$_3$) S 13.5 (SCH$_2$CH$_2$CH$_3$), 16.0 (NHCH(CH$_2$)CHPh), 22.9 (SCH$_2$CH$_2$CH$_3$), 24.1 (NCH(CH$_2$)$_4$), 25.3 (NHCH(CH$_2$)CHPh), 32.6 (NCH(CH$_2$)$_4$), 33.2 (SCH$_2$CH$_2$CH$_3$), 33.3 (NHCH(CH$_2$)CHPh), 56.0 (NCH(CH$_2$)$_4$), 115.7 (d, J=17 Hz, C-2'), 116.9 (d, J=17 Hz, C-5'), 117.9 (C-5), 122.8 (C-6'), 137.4 (C-8), 137.9 (C-1'), 147.9-149.9 (dd, 246 Hz/13 Hz, C-4'), 149.2-151.2 (dd, 247 Hz/13 Hz, C-3'), 150.0 (C-4), 154.6 (C-6), 165.0 (C-2).

Example 13: synthesis of N-((1R,2S)-2-(3,4-difluorophenyl)cyclopropyl)-9-hexyl-2-(propylthio)-9H-purin-6-amine (13c)

6-Chloro-N$^4$-hexyl-2-(propylthio)pyrimidine-4,5-diamine (13a)

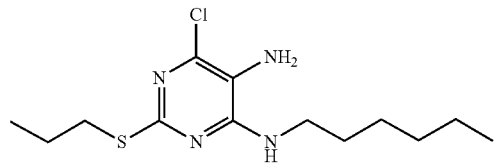 [SMILES: CCCCCCNc1nc(SCCC)nc(Cl)c1N]

4,6-Dichloro-2-(propylthio)pyrimidin-5-amine (0.5 g, 2.1 mmol) was dissolved in methanol (2 mL) and supplemented with n-hexylamine (638.0 mg, 6.3 mmol). The reaction mixture was introduced in a sealed vessel and heated at 100° C. for 1 h. After concentration of the reaction mixture to dryness under vacuum, the residue was purified by silica gel column chromatography.

Yield: 85%.

Melting point: 54-57° C.

$^1$H NMR (DMSO-$d_6$) δ 0.87 (t, J=6.4 Hz, 3H, NHCH$_2$CH$_2$CH$_2$CH$_2$CH$_2$CH$_3$), 0.95 (t, J=7.3 Hz, 3H, SCH$_2$CH$_2$CH$_3$), 1.29 (m, 6H, NHCH$_2$CH$_2$CH$_2$CH$_2$CH$_2$CH$_3$), 1.54 (p, J=6.9 Hz, 2H, NHCH$_2$CH$_2$CH$_2$CH$_2$CH$_2$CH$_3$), 1.63 (h, J=7.3 Hz, 2H, SCH$_2$CH$_2$CH$_3$), 2.94 (t, J=7.2 Hz, 2H, SCH$_2$CH$_2$CH$_3$), 3.34 (m, 2H, NHCH$_2$CH$_2$CH$_2$CH$_2$CH$_2$CH$_3$), 4.76 (s, 2H, NH$_2$), 6.95 (t, J=4.9 Hz, 1H, NHCH$_2$CH$_2$CH$_2$CH$_2$CH$_2$CH$_3$).

$^{13}$C NMR (DMSO-$d_6$) δ 13.3 (SCH$_2$CH$_2$CH$_3$), 13.9 (NHCH$_2$CH$_2$CH$_2$CH$_2$CH$_2$CH$_3$), 22.1 (NHCH$_2$CH$_2$CH$_2$CH$_2$CH$_2$CH$_3$), 22.8 (SCH$_2$CH$_2$CH$_3$), 26.1 (NHCH$_2$CH$_2$CH$_2$CH$_2$CH$_2$CH$_3$), 28.6 (NHCH$_2$CH$_2$CH$_2$CH$_2$CH$_2$CH$_3$), 31.0 (NHCH$_2$CH$_2$CH$_2$CH$_2$CH$_2$CH$_3$), 32.1 (SCH$_2$CH$_2$CH$_3$), 40.9 (NHCH$_2$CH$_2$CH$_2$CH$_2$CH$_2$CH$_3$), 119.8 (C-5), 137.3 (C-6), 152.6 (C-4), 155.2 (C-2).

6-Chloro-9-hexyl-2-(propylthio)-9H-purine (13b)

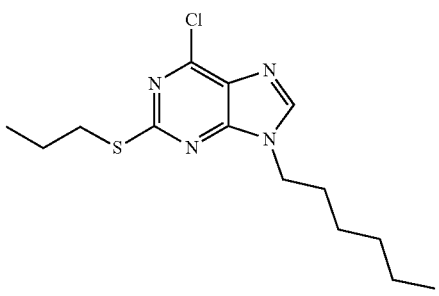 [SMILES: CCCCCCn1cnc2c(Cl)nc(SCCC)nc21]

A solution of (13a) (303.0 mg, 1 mmol) in acetic acid (2.5 mL) and triethyl orthoformate (2.5 mL, 15 mmol) was heated at a temperature of 130° C. under reflux for 1 h. After distillation of the acetic acid and triethyl orthoformate under vacuum, the residue was purified by silica gel column chromatography.

Yield: 90%.

Melting point: liquid.

$^1$H NMR (DMSO-$d_6$) δ 0.83 (t, J=6.8 Hz, 3H, NCH$_2$CH$_2$CH$_2$CH$_2$CH$_2$CH$_3$), 1.01 (t, J=7.4 Hz, 3H, SCH$_2$CH$_2$CH$_3$), 1.25 (m, 6H, NCH$_2$CH$_2$CH$_2$CH$_2$CH$_2$CH$_3$), 1.74 (h, J=7.3 Hz, 2H, SCH$_2$CH$_2$CH$_3$), 1.84 (p, J=7.2 Hz, 2H, NCH$_2$CH$_2$CH$_2$CH$_2$CH$_2$CH$_3$), 3.16 (t, J=7.2 Hz, 2H, SCH$_2$CH$_2$CH$_3$), 4.21 (t, J=7.1 Hz, 2H, NCH$_2$CH$_2$CH$_2$CH$_2$CH$_2$CH$_3$), 8.56 (s, 1H, 8-H).

$^{13}$C NMR (DMSO-$d_6$) δ 13.3 (SCH$_2$CH$_2$CH$_3$), 13.8 (NCH$_2$CH$_2$CH$_2$CH$_2$CH$_2$CH$_3$), 21.9 (NCH$_2$CH$_2$CH$_2$CH$_2$CH$_2$CH$_3$), 22.1 (SCH$_2$CH$_2$CH$_3$), 25.5 (NCH$_2$CH$_2$CH$_2$CH$_2$CH$_2$CH$_3$), 28.8 (NCH$_2$CH$_2$CH$_2$CH$_2$CH$_2$CH$_3$), 30.5 (NCH$_2$CH$_2$CH$_2$CH$_2$CH$_2$CH$_3$), 32.6 (SCH$_2$CH$_2$CH$_3$), 43.6 (NCH$_2$CH$_2$CH$_2$CH$_2$CH$_2$CH$_3$), 127.9 (C-5), 146.3 (C-8), 148.9 (C-6), 152.8 (C-4), 163.8 (C-2).

N-((1R,2S)-2-(3,4-Difluorophenyl)cyclopropyl)-9-hexyl-2-(propylthio)-9H-purin-6-amine (13c)

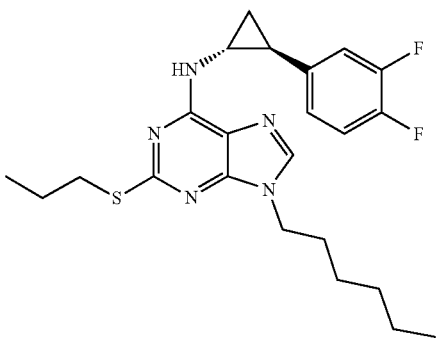 [SMILES: CCCCCCn1cnc2c(N[C@@H]3C[C@H]3c3ccc(F)c(F)c3)nc(SCCC)nc21]

A solution of (13b) (157.0 mg, 0.5 mmol) in acetonitrile (2.5 mL) was supplemented with (1R,2S)-2-(3,4-difluorophenyl)cyclopropanamine (93.0 mg, 0.55 mmol) and triethylamine (0.13 mL) and then heated at 90° C. under reflux for 1 h. After distillation of acetonitrile and triethylamine under vacuum, the residue was purified by silica gel column chromatography.

Yield: 60%.

Melting point: 84-86° C.

$^1$H NMR (CDCl$_3$) δ 0.88 (m, 3H, NCH$_2$CH$_2$CH$_2$CH$_2$CH$_2$CH$_3$), 0.95 (t, J=7.4 Hz, 3H, SCH$_2$CH$_2$CH$_3$), 1.30 (m, 8H, NCH$_2$CH$_2$CH$_2$CH$_2$CH$_2$CH$_3$/NHCH(CH$_2$)CHPh), 1.68 (h, J=7.3 Hz, 2H, SCH$_2$CH$_2$CH$_3$), 1.86 (m, 2H, NCH$_2$CH$_2$CH$_2$CH$_2$CH$_2$CH$_3$), 2.09 (m, 1H, NHCH(CH$_2$)CHPh), 3.03 (m, 2H, SCH$_2$CH$_2$CH$_3$), 3.10 (bs, 1H, NHCH(CH$_2$)CHPh), 4.12 (t, J=7.2 Hz, 2H, NCH$_2$CH$_2$CH$_2$CH$_2$CH$_2$CH$_3$), 5.96 (bs, 1H, NH), 6.99 (m, 1H, 6'-H), 7.09 (m, 2H, 2'-H/5'-H), 7.60 (s, 1H, 8-H).

$^{13}$C NMR (CDCl$_3$) δ 13.5 (SCH$_2$CH$_2$CH$_3$), 14.0 (NCH$_2$CH$_2$CH$_2$CH$_2$CH$_2$CH$_3$), 16.0 (NHCH(CH$_2$)CHPh), 22.5 (NCH$_2$CH$_2$CH$_2$CH$_2$CH$_2$CH$_3$), 22.9 (SCH$_2$CH$_2$CH$_3$), 25.2 (NHCH(CH$_2$)CHPh), 26.3 (NCH$_2$CH$_2$CH$_2$CH$_2$CH$_2$CH$_3$), 29.9 (NCH$_2$CH$_2$CH$_2$CH$_2$CH$_2$CH$_3$), 31.2 (NCH$_2$CH$_2$CH$_2$CH$_2$CH$_2$CH$_3$), 33.2 (SCH$_2$CH$_2$CH$_3$), 33.3 (NHCH(CH$_2$)CHPh), 43.7 (NCH$_2$CH$_2$CH$_2$CH$_2$CH$_2$CH$_3$), 115.7 (d, J=17 Hz, C-2'), 116.9 (d, J=17 Hz, C-5'), 117.5 (C-5), 122.7 (C-6'), 137.9 (C-1'), 139.0 (C-8), 147.9-149.9 (dd, 246 Hz/13 Hz, C-4'), 149.2-151.2 (dd, 247 Hz/13 Hz, C-3'), 150.5 (C-4), 154.6 (C-6), 165.4 (C-2).

Example 14: synthesis of 9-cyclohexyl-N-((1R,2S)-2-(3,4-difluorophenyl)cyclopropyl)-2-(propylthio)-9H-purin-6-amine (14c)

6-Chloro-N$^4$-cyclohexyl-2-(propylthio)pyrimidine-4,5-diamine (14a)

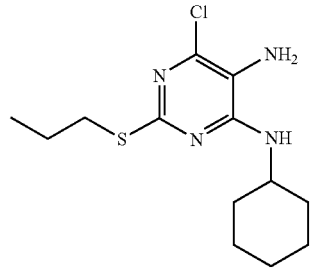 [SMILES: CCCSc1nc(Cl)c(N)c(NC2CCCCC2)n1]

4,6-Dichloro-2-(propylthio)pyrimidin-5-amine (0.5 g, 2.1 mmol) was dissolved in methanol (2 mL) and supplemented with cyclohexylamine (625.0 mg, 6.3 mmol). The reaction mixture was introduced in a sealed vessel and heated at 100° C. for 1 h. After concentration of the reaction mixture to dryness under vacuum, the residue was purified by silica gel column chromatography.

Yield: 91%.

Melting point: 90-93° C.

$^1$H NMR (DMSO-$d_6$) δ 0.96 (t, J=7.4 Hz, 3H, SCH$_2$CH$_2$CH$_3$), 1.22 (m, 5H, NHCH(CH$_2$)$_5$), 1.64 (m, 3H, SCH$_2$CH$_2$CH$_3$/NHCH(CH$_2$)$_5$), 1.75 (m, 2H, NHCH(CH$_2$)$_5$), 1.93 (m, 2H, NHCH(CH$_2$)$_5$), 2.92 (t, J=7.3 Hz, 2H, SCH$_2$CH$_2$CH$_3$), 3.84 (m, 1H, NHCH(CH$_2$)$_5$), 4.82 (s, 2H, NH$_2$), 6.68 (d, J=7.1 Hz, 1H, NHCH(CH$_2$)$_5$).

$^{13}$C NMR (DMSO-$d_6$) δ 13.4 (SCH$_2$CH$_2$CH$_3$), 23.0 (SCH$_2$CH$_2$CH$_3$), 24.8 (NHCH(CH$_2$)$_5$), 25.3 (NHCH(CH$_2$)$_5$), 32.1 (SCH$_2$CH$_2$CH$_3$), 32.3 (NHCH(CH$_2$)$_5$), 49.9 (NHCH(CH$_2$)$_5$), 119.7 (C-5), 137.4 (C-6), 151.6 (C-4), 155.0 (C-2).

6-Chloro-9-cyclohexyl-2-(propylthio)-9H-purine (14b)

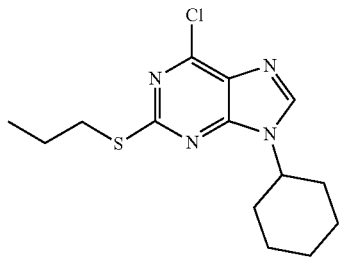 [SMILES: CCCSc1nc(Cl)c2ncn(C3CCCCC3)c2n1]

A solution of (14a) (301.0 mg, 1 mmol) in acetic acid (2.5 mL) and triethyl orthoformate (2.5 mL, 15 mmol) was heated at a temperature of 130° C. under reflux for 2 h. After distillation of the acetic acid and triethyl orthoformate under vacuum, the residue was purified by silica gel column chromatography.

Yield: 62%.
Melting point: 93-95° C.
$^1$H NMR (DMSO-$d_6$) δ 1.02 (t, J=7.3 Hz, 3H, SCH$_2$CH$_2$CH$_3$), 1.25 (m, 1H, NCH(CH$_2$)$_5$), 1.44 (m, 2H, NCH(CH$_2$)$_5$), 1.75 (m, 3H, SCH$_2$CH$_2$CH$_3$/NCH(CH$_2$)$_5$), 1.87 (m, 2H, NCH(CH$_2$)$_5$), 1.99 (m, 4H, NCH(CH$_2$)$_5$), 3.15 (t, J=7.2 Hz, 2H, SCH$_2$CH$_2$CH$_3$), 4.41 (m, 1H, NCH(CH$_2$)$_5$), 8.61 (s, 1H, 8-H).
$^{13}$C NMR (DMSO-$d_6$) δ 13.3 (SCH$_2$CH$_2$CH$_3$), 22.2 (SCH$_2$CH$_2$CH$_3$), 24.8 (NCH(CH$_2$)$_5$), 25.0 (NCH(CH$_2$)$_5$), 31.7 (NCH(CH$_2$)$_5$), 32.7 (SCH$_2$CH$_2$CH$_3$), 55.0 (NCH(CH$_2$)$_5$), 128.3 (C-5), 144.8 (C-8), 149.0 (C-6), 152.3 (C-4), 163.5 (C-2).

9-Cyclohexyl-N-((1R,2S)-2-(3,4-difluorophenyl)cyclopropyl)-2-(propylthio)-9H-purin-6-amine (14c)

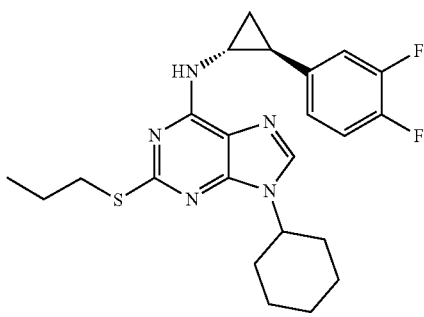 [SMILES: CCCSc1nc(N[C@@H]2C[C@H]2c2ccc(F)c(F)c2)c2ncn(C3CCCCC3)c2n1]

A solution of (14b) (156.0 mg, 0.5 mmol) in acetonitrile (2.5 mL) was supplemented with (1R,2S)-2-(3,4-difluorophenyl)cyclopropanamine (93.0 mg, 0.55 mmol) and triethylamine (0.13 mL) and then heated at 90° C. under reflux for 1 h. After distillation of acetonitrile and triethylamine under vacuum, the residue was purified by silica gel column chromatography.

Yield: 84%.
Melting point: 85-88° C.
$^1$H NMR (CDCl$_3$) δ 0.94 (t, J=7.4 Hz, 3H, SCH$_2$CH$_2$CH$_3$), 1.30 (m, 3H, NHCH(CH$_2$)CHPh/NCH(CH$_2$)$_5$), 1.49 (m, 2H, NCH(CH$_2$)$_5$), 1.68 (h, J=7.3 Hz, 2H, SCH$_2$CH$_2$CH$_3$), 1.79 (m, 3H, NCH(CH$_2$)$_5$) 1.92 (m, 2H, NCH(CH$_2$)$_5$), 2.08 (m, 1H, NHCH(CH$_2$)CHPh), 2.14 (m, 2H, NCH(CH$_2$)$_5$), 3.03 (m, 2H, SCH$_2$CH$_2$CH$_3$), 3.11 (bs, 1H, NHCH(CH$_2$)CHPh), 4.36 (m, 1H, NCH(CH$_2$)$_5$), 5.98 (bs, 1H, NH), 6.99 (m, 1H, 6'-H), 7.08 (m, 2H, 2'-H/5'-H), 7.67 (s, 1H, 8-H).
$^{13}$C NMR (CDCl$_3$) δ 13.5 (SCH$_2$CH$_2$CH$_3$), 16.1 (NHCH(CH$_2$)CHPh), 23.0 (SCH$_2$CH$_2$CH$_3$), 25.2 (NHCH(CH$_2$)CHPh), 25.3 (NCH(CH$_2$)$_5$), 25.6 (NCH(CH$_2$)$_5$), 33.2 (SCH$_2$CH$_2$CH$_3$), 33.3 (NHCH(CH$_2$)CHPh), 54.2 (NCH(CH$_2$)$_5$), 115.6 (d, J=17 Hz, C-2'), 116.9 (d, J=17 Hz, C-5'), 117.7 (C-5), 122.7 (C-6'), 137.0 (C-8), 138.0 (C-1'), 147.9-149.9 (dd, 246 Hz/13 Hz, C-4'), 149.2-151.2 (dd, 247 Hz/13 Hz, C-3'), 150.5 (C-4), 154.6 (C-6), 165.0 (C-2).

Example 15: synthesis of 9-allyl-N-((1R,2S)-2-(3,4-difluorophenyl)cyclopropyl)-2-(propylthio)-9H-purin-6-amine (15c)

N$^4$-Allyl-6-chloro-2-(propylthio)pyrimidine-4,5-diamine (15a)

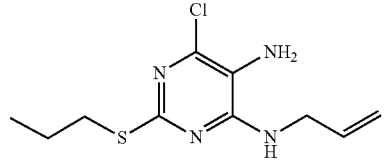 [SMILES: C=CCNc1nc(SCCC)nc(Cl)c1N]

4,6-Dichloro-2-(propylthio)pyrimidin-5-amine (0.5 g, 2.1 mmol) was dissolved in methanol (2 mL) and supplemented with allylamine (360.0 mg, 6.3 mmol). The reaction mixture was introduced in a sealed vessel and heated at 100° C. for 30 min. After concentration of the reaction mixture to dryness under vacuum, the residue was purified by silica gel column chromatography.

Yield: 92%.
Melting point: 55-57° C.
$^1$H NMR (DMSO-$d_6$) δ0.94 (t, J=7.4 Hz, 3H, SCH$_2$CH$_2$CH$_3$), 1.62 (h, J=7.3 Hz, 2H, SCH$_2$CH$_2$CH$_3$), 2.93 (t, J=7.2 Hz, 2H, SCH$_2$CH$_2$CH$_3$), 4.02 (tt, J=5.4 Hz/1.5 Hz, 2H, NHCH$_2$CHCH$_2$), 4.80 (s, 2H, NH$_2$), 5.11 (dq, J=10.3 Hz/1.4 Hz, 1H, NHCH$_2$CHCH$_2$), 5.18 (dq, J=17.2 Hz/1.5 Hz, 1H, NHCH$_2$CHCH$_2$), 5.92 (ddt, J=17.1 Hz/10.4 Hz/5.3 Hz, 1H, NHCH$_2$CHCH$_2$), 7.15 (t, J=5.4 Hz, 1H, NHCH$_2$CHCH$_2$).
$^{13}$C NMR (DMSO-$d_6$) δ 13.3 (SCH$_2$CH$_2$CH$_3$), 22.7 (SCH$_2$CH$_2$CH$_3$), 32.1 (SCH$_2$CH$_2$CH$_3$), 43.1 (NHCH$_2$CHCH$_2$), 115.6 (NHCH$_2$CHCH$_2$), 120.0 (C-5), 135.0 (NHCH$_2$CHCH$_2$), 137.5 (C-6), 152.3 (C-4), 155.2 (C-2).

9-allyl-6-chloro-2-(propylthio)-9H-purine (15b)

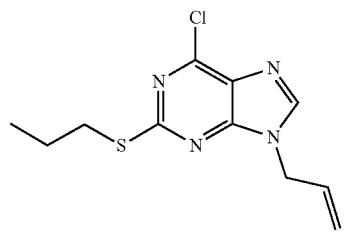 [SMILES: C=CCn1cnc2c(Cl)nc(SCCC)nc21]

A solution of (15a) (259.0 mg, 1 mmol) in acetic acid (2.5 mL) and triethyl orthoformate (2.5 mL, 15 mmol) was heated at a temperature of 130° C. under reflux for 2 h. After distillation of the acetic acid and triethyl orthoformate under vacuum, the residue was purified by silica gel column chromatography.

Yield: 89%.

Melting point: 47.5-49.5° C.

$^1$H NMR (DMSO-$d_6$) δ 1.00 (t, J=7.4 Hz, 3H, SCH$_2$CH$_2$CH$_3$), 1.73 (h, J=7.3 Hz, 2H, SCH$_2$CH$_2$CH$_3$), 3.15 (t, J=7.2 Hz, 2H, SCH$_2$CH$_2$CH$_3$), 4.87 (dt, J=5.5 Hz/1.3 Hz, 2H, NCH$_2$CHCH$_2$), 5.13 (dd, J=17.1 Hz/1.3 Hz, 1H, NCH$_2$CHCH$_2$), 5.24 (dd, J=10.3 Hz/1.3 Hz, 1H, NCH$_2$CHCH$_2$), 6.07 (m, 1H, NCH$_2$CHCH$_2$), 8.52 (s, 1H, 8-H).

$^{13}$C NMR (DMSO-$d_6$) δ 13.2 (SCH$_2$CH$_2$CH$_3$), 22.0 (SCH$_2$CH$_2$CH$_3$), 32.6 (SCH$_2$CH$_2$CH$_3$), 45.7 (NCH$_2$CHCH$_2$), 118.2 (NCH$_2$CHCH$_2$), 127.9 (C-5), 132.4 (NCH$_2$CHCH$_2$), 146.2 (C-8), 149.0 (C-6), 152.7 (C-4), 164.1 (C-2).

9-Allyl-N-((1R,2S)-2-(3,4-difluorophenyl)cyclopropyl)-2-(propylthio)-9H-purin-6-amine (15c)

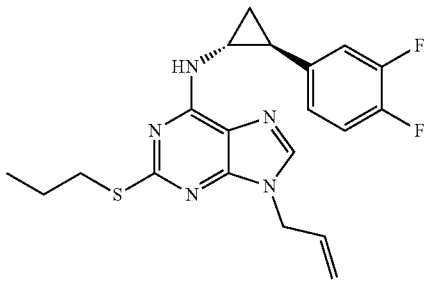 [SMILES: C=CCn1cnc2c(N[C@@H]3C[C@H]3c3ccc(F)c(F)c3)nc(SCCC)nc21]

A solution of (15b) (135.0 mg, 0.5 mmol) in acetonitrile (2.5 mL) was supplemented with (1R,2S)-2-(3,4-difluorophenyl)cyclopropanamine (93.0 mg, 0.55 mmol) and triethylamine (0.13 mL) and then heated at 90° C. under reflux for 1 h. After distillation of acetonitrile and triethylamine under vacuum, the residue was purified by silica gel column chromatography.

Yield: 89%.

Melting point: liquid.

$^1$H NMR (CDCl$_3$) δ 0.94 (t, J=7.4 Hz, 3H, SCH$_2$CH$_2$CH$_3$), 1.32 (m, 2H, NHCH(CH$_2$)CHPh), 1.66 (h, J=7.2 Hz, 2H, SCH$_2$CH$_2$CH$_3$), 2.09 (m, 1H, NHCH(CH$_2$)CHPh), 3.04 (m, 2H, SCH$_2$CH$_2$CH$_3$), 3.12 (bs, 1H, NHCH(CH$_2$)CHPh), 4.74 (d, J=5.9 Hz, 2H, NCH$_2$CHCH$_2$), 5.23 (dd, J=17.1 Hz/1.0 Hz, 1H, NCH$_2$CHCH$_2$), 5.30 (dd, J=10.2 Hz/1.0 Hz, 1H, NCH$_2$CHCH$_2$), 6.01 (m, 2H, NCH$_2$CHCH$_2$/NH), 6.99 (m, 1H, 6'-H), 7.08 (m, 2H, 2'-H/5'-H), 7.62 (s, 1H, 8-H).

$^{13}$C NMR (CDCl$_3$) δ 13.4 (SCH$_2$CH$_2$CH$_3$), 16.1 (NHCH(CH$_2$)CHPh), 22.8 (SCH$_2$CH$_2$CH$_3$), 25.2 (NHCH(CH$_2$)CHPh), 33.2 (SCH$_2$CH$_2$CH$_3$), 33.3 (NHCH(CH$_2$)CHPh), 45.6 (NCH$_2$CHCH$_2$), 115.6 (d, J=17 Hz, C-2'), 116.9 (d, J=17 Hz, C-5'), 117.3 (C-5), 119.0 (NCH$_2$CHCH$_2$), 122.7 (C-6'), 132.0 (NCH$_2$CHCH$_2$), 137.9 (C-1'), 138.7 (C-8), 147.9-149.9 (dd, 246 Hz/13 Hz, C-4'), 149.2-151.2 (dd, 247 Hz/13 Hz, C-3'), 150.3 (C-4), 154.6 (C-6), 165.7 (C-2).

Example 16: synthesis of 2-(6-(((1R,2S)-2-(3,4-difluorophenyl)cyclopropyl)amino)-2-(propylthio)-9H-purin-9-yl)ethanol (16c)

2-((5-Amino-6-chloro-2-(propylthio)pyrimidin-4-yl)amino)ethanol (16a)

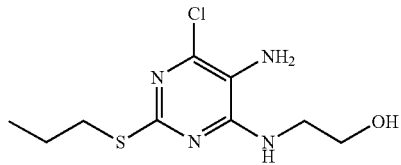 [SMILES: CCCSc1nc(Cl)c(N)c(NCCO)n1]

4,6-Dichloro-2-(propylthio)pyrimidin-5-amine (0.5 g, 2.1 mmol) was dissolved in methanol (2 mL) and supplemented with 2-aminoethanol (385.0 mg, 6.3 mmol). The reaction mixture was introduced in a sealed vessel and heated at 100° C. for 30 min. After concentration of the reaction mixture to dryness under vacuum, the residue was purified by silica gel column chromatography.

Yield: 79%.

Melting point: 99-102° C.

$^1$H NMR (DMSO-$d_6$) δ 0.95 (t, J=7.4 Hz, 3H, SCH$_2$CH$_2$CH$_3$), 1.63 (h, J=7.3 Hz, 2H, SCH$_2$CH$_2$CH$_3$), 2.93 (t, J=7.2 Hz, 2H, SCH$_2$CH$_2$CH$_3$), 3.43 (d, J=5.7 Hz, 2H, NHCH$_2$CH$_2$OH), 3.55 (d, J=5.7 Hz, 2H, NHCH$_2$CH$_2$OH), 4.78 (t, J=5.5 Hz, 1H, NHCH$_2$CH$_2$OH), 4.80 (s, 2H, NH$_2$), 7.03 (t, J=5.2 Hz, 1H, NHCH$_2$CH$_2$OH).

$^{13}$C NMR (DMSO-$d_6$) δ 13.3 (SCH$_2$CH$_2$CH$_3$), 22.7 (SCH$_2$CH$_2$CH$_3$), 32.1 (SCH$_2$CH$_2$CH$_3$), 43.7 (NHCH$_2$CH$_2$OH), 59.2 (NHCH$_2$CH$_2$OH), 120.0 (C-5), 137.4 (C-6), 152.7 (C-4), 155.1 (C-2).

2-(6-Chloro-2-(propylthio)-9H-purin-9-yl)ethanol (16b)

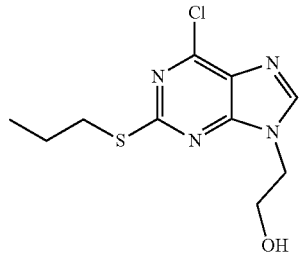 [SMILES: CCCSc1nc(Cl)c2ncn(CCO)c2n1]

A solution of (16a) (263.0 mg, 1 mmol) in acetic acid (2.5 mL) and triethyl orthoformate (2.5 mL, 15 mmol) was heated at a temperature of 130° C. under reflux for 4 h. After distillation of the acetic acid and triethyl orthoformate under vacuum, the residue was purified by silica gel column chromatography.

Yield: 57%.

Melting point: 81-83° C.

$^1$H NMR (DMSO-$d_6$) δ 1.01 (t, J=7.4 Hz, 3H, SCH$_2$CH$_2$CH$_3$), 1.73 (h, J=7.4 Hz, 2H, SCH$_2$CH$_2$CH$_3$), 3.17 (t, J=7.2 Hz, 2H, SCH$_2$CH$_2$CH$_3$), 3.78 (q, J=5.4 Hz, 2H, NCH$_2$CH$_2$OH), 4.26 (t, J=5.4 Hz, 2H, NCH$_2$CH$_2$OH), 4.99 (t, J=5.6 Hz, 1H, OH), 8.48 (s, 1H, 8-H).

$^{13}$C NMR (DMSO-d$_6$) δ 13.2 (SCH$_2$CH$_2$CH$_3$), 22.0 (SCH$_2$CH$_2$CH$_3$), 32.6 (SCH$_2$CH$_2$CH$_3$), 46.5 (NCH$_2$CH$_2$OH), 58.7 (NCH$_2$CH$_2$OH), 128.0 (C-5), 146.8 (C-8), 148.7 (C-6), 153.0 (C-4), 163.7 (C-2).

2-(6-(((1R,2S)-2-(3,4-Difluorophenyl)cyclopropyl)amino)-2-(propylthio)-9H-purin-9-yl)ethanol (16c)

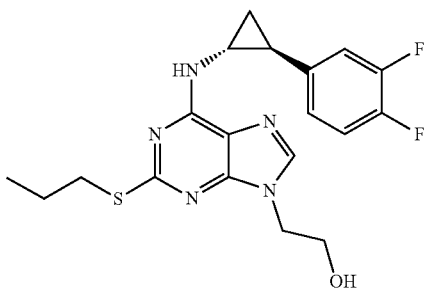 [SMILES: CCCSc1nc(N[C@@H]2C[C@H]2c2ccc(F)c(F)c2)c2ncn(CCO)c2n1]

A solution of (16b) (137.0 mg, 0.5 mmol) in acetonitrile (2.5 mL) was supplemented with (1R,2S)-2-(3,4-difluorophenyl)cyclopropanamine (93.0 mg, 0.55 mmol) and triethylamine (0.13 mL) and then heated at 90° C. under reflux for 1 h. After distillation of acetonitrile and triethylamine under vacuum, the residue was purified by silica gel column chromatography.

Yield: 42%.
Melting point: 81-83° C.
$^1$H NMR (CDCl$_3$) δ 0.95 (t, J=7.4 Hz, 3H, SCH$_2$CH$_2$CH$_3$), 1.32 (m, 2H, NHCH(CH$_2$)CHPh), 1.66 (bh, J=7.3 Hz, 3H, OH/SCH$_2$CH$_2$CH$_3$), 2.09 (m, 1H, NHCH(CH$_2$)CHPh), 3.01 (m, 2H, SCH$_2$CH$_2$CH$_3$), 3.11 (bs, 1H, NHCH(CH$_2$)CHPh), 4.02 (m, 2H, NCH$_2$CH$_2$OH), 4.29 (m, 2H, NCH$_2$CH$_2$OH), 6.05 (bs, 1H, NH), 7.00 (m, 1H, 6'-H), 7.09 (m, 2H, 2'-H/5'-H), 7.61 (s, 1H, 8-H).
$^{13}$C NMR (CDCl$_3$) S 13.4 (SCH$_2$CH$_2$CH$_3$), 15.9 (NHCH(CH$_2$)CHPh), 22.6 (SCH$_2$CH$_2$CH$_3$), 25.2 (NHCH(CH$_2$)CHPh), 33.1 (SCH$_2$CH$_2$CH$_3$), 33.2 (NHCH(CH$_2$)CHPh), 48.2 (NCH$_2$CH$_2$OH), 61.6 (NCH$_2$CH$_2$OH), 115.7 (d, J=17 Hz, C-2'), 117.0 (d, J=17 Hz, C-5'), 117.7 (C-5), 122.7 (C-6'), 137.7 (C-1'), 139.7 (C-8), 147.9-149.9 (dd, 246 Hz/13 Hz, C-4'), 149.2-151.2 (dd, 247 Hz/13 Hz, C-3'), 150.1 (C-4), 154.6 (C-6), 165.8 (C-2).

Example 17: synthesis of N-((1R,2S)-2-(3,4-difluorophenyl)cyclopropyl)-9-(prop-2-yn-1-yl)-2-(propylthio)-9H-purin-6-amine hydrochloride (17c·HCl)

6-Chloro-N$^4$-(prop-2-yn-1-yl)-2-(propylthio)pyrimidine-4,5-diamine (17a)

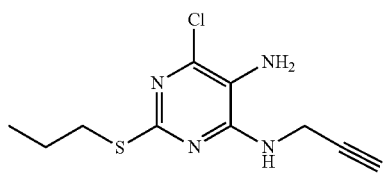 [SMILES: C#CCNc1nc(SCCC)nc(Cl)c1N]

4,6-Dichloro-2-(propylthio)pyrimidin-5-amine (0.5 g, 2.1 mmol) was dissolved in methanol (2 mL) and supplemented with propargylamine (347.0 mg, 6.3 mmol). The reaction mixture was introduced in a sealed vessel and heated at 100° C. for 3 h. After concentration of the reaction mixture to dryness under vacuum, the residue was purified by silica gel column chromatography.

Yield: 78%.
Melting point: 90-92° C.
$^1$H NMR (DMSO-d$_6$) δ0.96 (t, J=7.4 Hz, 3H, SCH$_2$CH$_2$CH$_3$), 1.66 (h, J=7.3 Hz, 2H, SCH$_2$CH$_2$CH$_3$), 2.97 (t, J=7.2 Hz, 2H, SCH$_2$CH$_2$CH$_3$), 3.15 (t, J=2.4 Hz, 1H, NHCH$_2$CCH), 4.16 (dd, J=4.8 Hz/2.3 Hz, 2H, NHCH$_2$CCH), 4.83 (s, 2H, NH$_2$), 7.41 (t, J=4.7 Hz, 1H, NHCH$_2$CCH).
$^{13}$C NMR (DMSO-d$_6$) δ 13.3 (SCH$_2$CH$_2$CH$_3$), 22.7 (SCH$_2$CH$_2$CH$_3$), 30.1 (NHCH$_2$CCH), 32.2 (SCH$_2$CH$_2$CH$_3$), 73.1 (NHCH$_2$CCH), 81.1 (NHCH$_2$CCH), 120.3 (C-5), 137.9 (C-6), 151.8 (C-4), 155.1 (C-2).

6-Chloro-9-(prop-2-yn-1-yl)-2-(propylthio)-9H-purine (17b)

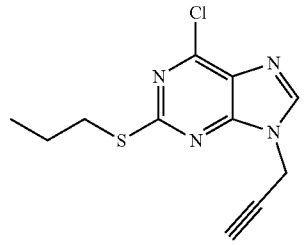 [SMILES: C#CCn1cnc2c(Cl)nc(SCCC)nc21]

A solution of (17a) (258.0 mg, 1 mmol) in acetic acid (2.5 mL) and triethyl orthoformate (2.5 mL, 15 mmol) was heated at a temperature of 130° C. under reflux for 2 h. After distillation of the acetic acid and triethyl orthoformate under vacuum, the residue was purified by silica gel column chromatography.

Yield: 62%.
Melting point: 68-70° C.
$^1$H NMR (DMSO-d$_6$) δ 1.01 (t, J=7.4 Hz, 3H, SCH$_2$CH$_2$CH$_3$), 1.75 (h, J=7.3 Hz, 2H, SCH$_2$CH$_2$CH$_3$), 3.19 (t, J=7.2 Hz, 2H, SCH$_2$CH$_2$CH$_3$), 3.57 (t, J=2.5 Hz, 1H, NCH$_2$CCH), 5.13 (d, J=2.5 Hz, 2H, NCH$_2$CCH), 8.58 (s, 1H, 8-H).
$^{13}$C NMR (DMSO-d$_6$) δ 13.2 (SCH$_2$CH$_2$CH$_3$), 22.0 (SCH$_2$CH$_2$CH$_3$), 32.7 (SCH$_2$CH$_2$CH$_3$), 33.1 (NCH$_2$CCH), 76.6 (NCH$_2$CCH), 77.2 (NCH$_2$CCH), 127.9 (C-5), 145.5 (C-8), 149.1 (C-6), 152.3 (C-4), 164.4 (C-2).

N-((1R,2S)-2-(3,4-Difluorophenyl)cyclopropyl)-9-(prop-2-yn-1-yl)-2-(propylthio)-9H-purin-6-amine (17c)

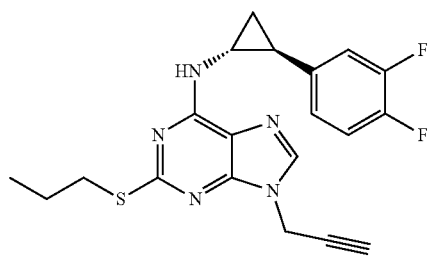 [SMILES: C#CCn1cnc2c(N[C@@H]3C[C@H]3c3ccc(F)c(F)c3)nc(SCCC)nc21]

A solution of (17b) (134.0 mg, 0.5 mmol) in acetonitrile (2.5 mL) was supplemented with (1R,2S)-2-(3,4-difluorophenyl)cyclopropanamine (93.0 mg, 0.55 mmol) and triethylamine (0.13 mL) and then heated at 90° C. under reflux for 4 h. After distillation of acetonitrile and triethylamine under vacuum, the residue was purified by silica gel column chromatography.

Yield: 86%.

Melting point: 72-74° C.

$^1$H NMR (CDCl$_3$) δ0.94 (t, J=7.4 Hz, 3H, SCH$_2$CH$_2$CH$_3$), 1.33 (m, 2H, NHCH(CH$_2$)CHPh), 1.65 (h, J=7.3 Hz, 2H, SCH$_2$CH$_2$CH$_3$), 2.09 (m, 1H, NHCH(CH$_2$)CHPh), 2.50 (t, J=2.6 Hz, 1H, NCH$_2$CCH), 3.03 (m, 2H, SCH$_2$CH$_2$CH$_3$), 3.12 (bs, 1H, NHCH(CH$_2$)CHPh), 4.90 (d, J=2.6 Hz, 2H, NCH$_2$CCH), 6.00 (bs, 1H, NH), 6.98 (m, 1H, 6'-H), 7.08 (m, 2H, 2'-H/5'-H), 7.84 (s, 1H, 8-H).

$^{13}$C NMR (CDCl$_3$) δ 13.4 (SCH$_2$CH$_2$CH$_3$), 16.1 (NHCH(CH$_2$)CHPh), 22.8 (SCH$_2$CH$_2$CH$_3$), 25.2 (NHCH(CH$_2$)CHPh), 32.8 (NCH$_2$CCH), 33.2 (SCH$_2$CH$_2$CH$_3$), 33.3 (NHCH(CH$_2$)CHPh), 74.9 (NCH$_2$CCH), 76.1 (NCH$_2$CCH), 115.6 (d, J=17 Hz, C-2'), 116.9 (d, J=17 Hz, C-5'), 117.3 (C-5), 122.6 (C-6'), 137.8 (C-1'), 138.1 (C-8), 147.9-149.9 (dd, 246 Hz/13 Hz, C-4'), 149.2-151.2 (dd, 247 Hz/13 Hz, C-3'), 149.9 (C-4), 154.6 (C-6), 166.0 (C-2).

N-((1R,2S)-2-(3,4-Difluorophenyl)cyclopropyl)-9-(prop-2-yn-1-yl)-2-(propylthio)-9H-purin-6-amine hydrochloride (17c·HCl)

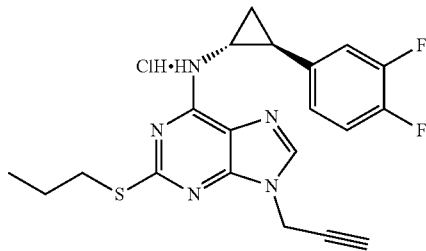

To a solution of (17c) (200.0 mg, 0.5 mmol) in diethyl ether (5 mL) was added dropwise a saturated solution of HCl in diethyl ether. The resulting precipitate of the title compound was collected by filtration, washed with diethyl ether and dried.

Yield: 99%.

Melting point: 178-180° C.

Example 18: synthesis of N-((1R,2S)-2-(3,4-difluorophenyl)cyclopropyl)-2-(propylthio)-9-(2,2,2-trifluoroethyl)-9H-purin-6-amine (18c)

6-Chloro-2-(propylthio)-N$^4$-(2,2,2-trifluoroethyl)pyrimidine-4,5-diamine (18a)

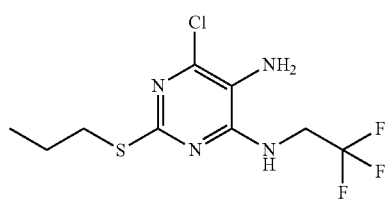 [SMILES: CCCSc1nc(Cl)c(N)c(NCC(F)(F)F)n1]

4,6-Dichloro-2-(propylthio)pyrimidin-5-amine (0.5 g, 2.1 mmol) was dissolved in methanol (2 mL) and supplemented with 2,2,2-trifluoroethanamine (625.0 mg, 6.3 mmol). The reaction mixture was introduced in a sealed vessel and heated at 100° C. for 24 h. After concentration of the reaction mixture to dryness under vacuum, the residue was purified by silica gel column chromatography.

Yield: 76%.

Melting point: 107-109° C.

$^1$H NMR (DMSO-d$_6$) δ0.95 (t, J=7.4 Hz, 3H, SCH$_2$CH$_2$CH$_3$), 1.63 (h, J=7.3 Hz, 2H, SCH$_2$CH$_2$CH$_3$), 2.95 (t, J=7.2 Hz, 2H, SCH$_2$CH$_2$CH$_3$), 4.29 (m, 2H, NHCH$_2$CF$_3$), 4.95 (s, 2H, NH$_2$), 7.53 (s, 1H, NHCH$_2$CF$_3$).

$^{13}$C NMR (DMSO-d$_6$) δ 13.2 (SCH$_2$CH$_2$CH$_3$), 22.6 (SCH$_2$CH$_2$CH$_3$), 32.1 (SCH$_2$CH$_2$CH$_3$), 41.2 (q, J=33 Hz, NHCH$_2$CF$_3$), 120.5 (C-5), 122.7-126.0 (m, NHCH$_2$CF$_3$), 138.8 (C-6), 151.9 (C-4), 154.8 (C-2).

6-Chloro-2-(propylthio)-9-(2,2,2-trifluoroethyl)-9H-purine (18b)

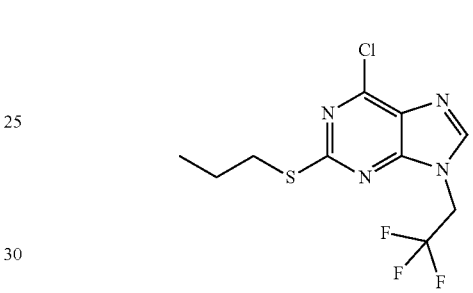

A solution of (18a) (301.0 mg, 1 mmol) in acetic acid (2.5 mL) and triethyl orthoformate (2.5 mL, 15 mmol) was heated at a temperature of 130° C. under reflux for 2 h. After distillation of the acetic acid and triethyl orthoformate under vacuum, the residue was purified by silica gel column chromatography.

Yield: 48%.

Melting point: 140-143° C.

$^1$H NMR (DMSO-d$_6$) δ 1.00 (t, J=7.4 Hz, 3H, SCH$_2$CH$_2$CH$_3$), 1.73 (h, J=7.3 Hz, 2H, SCH$_2$CH$_2$CH$_3$), 3.19 (t, J=7.2 Hz, 2H, SCH$_2$CH$_2$CH$_3$), 5.27 (q, J=9.2 Hz, 2H, NCH$_2$CF$_3$), 8.60 (s, 1H, 8-H).

$^{13}$C NMR (DMSO-d$_6$) δ 13.1 (SCH$_2$CH$_2$CH$_3$), 22.0 (SCH$_2$CH$_2$CH$_3$), 32.6 (SCH$_2$CH$_2$CH$_3$), 43.9 (q, J=35 Hz, NCH$_2$CF$_3$), 123.4 (q, J=280 Hz, NCH$_2$CF$_3$), 127.6 (C-5), 146.2 (C-8), 149.6 (C-6), 152.9 (C-4), 165.2 (C-2).

N-((1R,2S)-2-(3,4-Difluorophenyl)cyclopropyl)-2-(propylthio)-9-(2,2,2-trifluoroethyl)-9H-purin-6-amine (18c)

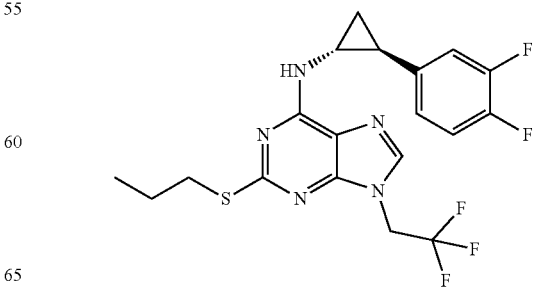

A solution of (18b) (156.0 mg, 0.5 mmol) in acetonitrile (2.5 mL) was supplemented with (1R,2S)-2-(3,4-difluorophenyl)cyclopropanamine (93.0 mg, 0.55 mmol) and triethylamine (0.13 mL) and then heated at 90° C. under reflux for 1 h. After distillation of acetonitrile and triethylamine under vacuum, the residue was purified by silica gel column chromatography.

Yield: 89%.
Melting point: 102-104° C.
$^{1}$H NMR (CDCl$_3$) δ0.95 (t, J=7.4 Hz, 3H, SCH$_2$CH$_2$CH$_3$), 1.34 (m, 2H, NHCH(CH$_2$)CHPh), 1.67 (h, J=7.3 Hz, 2H, SCH$_2$CH$_2$CH$_3$), 2.11 (m, 1H, NHCH(CH$_2$)CHPh), 3.03 (m, 2H, SCH$_2$CH$_2$CH$_3$), 3.10 (bs, 1H, NHCH(CH$_2$)CHPh), 4.73 (qd, J=8.5 Hz/3.1 Hz, 2H, NCH$_2$CF$_3$), 6.06 (bs, 1H, NH), 6.99 (m, 1H, 6'-H), 7.09 (m, 2H, 2'-H/5'-H), 7.70 (s, 1H, 8-H).
$^{13}$C NMR (CDCl$_3$) S 13.4 (SCH$_2$CH$_2$CH$_3$), 15.9 (NHCH(CH$_2$)CHPh), 22.7 (SCH$_2$CH$_2$CH$_3$), 25.2 (NHCH(CH$_2$)CHPh), 33.2 (SCH$_2$CH$_2$CH$_3$), 33.3 (NHCH(CH$_2$)CHPh), 44.0 (q, J=36 Hz, NCH$_2$CF$_3$), 115.7 (d, J=17 Hz, C-2'), 116.8 (C-5), 117.0 (d, J=17 Hz, C-5'), 122.7 (C-6'), 122.8 (q, J=279 Hz, CF$_3$), 137.7 (C-1'), 138.2 (C-8), 148.0-150.0 (dd, J=246 Hz/13 Hz, C-4'), 149.2-151.2 (dd, J=247 Hz/13 Hz, C-3'), 150.6 (C-4), 154.7 (C-6), 166.8 (C-2).

Example 19: Synthesis of (1S,2R,3S,4R)-4-(6-(((1R,2S)-2-(3,4-difluorophenyl)cyclopropyl)amino)-2-(propylthio)-9H-purin-9-yl)cyclopentane-1,2,3-triol (19d)

(3aR,4S,6R,6aS)-6-((5-Amino-6-chloro-2-(propylthio)pyrimidin-4-yl)amino)-2,2-dimethyltetrahydro-3aH-cyclopenta[d][1,3]dioxol-4-ol (19a)

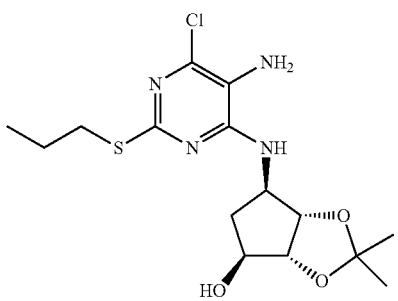 [SMILES: CCCSc1nc(Cl)c(N)c(N[C@@H]2C[C@H](O)[C@H]3OC(C)(C)O[C@H]32)n1]

4,6-Dichloro-2-(propylthio)pyrimidin-5-amine (0.5 g, 2.1 mmol) was dissolved in methanol (2 mL) and supplemented with (3aR,4S,6R,6aS)-6-amino-2,2-dimethyltetrahydro-3aH-cyclopenta[d][1,3]dioxol-4-ol (1.1 g, 6.3 mmol). The reaction mixture was introduced in a sealed vessel and heated at 100° C. for 12 h. After concentration of the reaction mixture to dryness under vacuum, the residue was purified by silica gel column chromatography.

Yield: 90%.
Melting point: ND.
$^{1}$H NMR (DMSO-d$_6$) δ0.96 (t, J=7.4 Hz, 3H, SCH$_2$CH$_2$CH$_3$), 1.21 (s, 3H, C(CH$_3$)$_2$), 1.36 (s, 3H, C(CH$_3$)$_2$), 1.64 (h, J=7.4 Hz, 2H, SCH$_2$CH$_2$CH$_3$), 1.71 (m, 1H, 5'-H), 2.22 (m, 1H, 5'-H), 2.98 (t, J=7.2 Hz, 2H, SCH$_2$CH$_2$CH$_3$), 4.06 (bs, 1H, 4'-H), 4.26 (bs, 1H, 6'-H), 4.41 (d, J=5.9 Hz, 1H, 3a'-H), 4.51 (d, J=6.0 Hz, 1H, 6a'-H), 4.70 (s, 2H, NH$_2$), 5.27 (d, J=3.1 Hz, 1H, OH), 6.63 (d, J=7.1 Hz, 1H, NH).

$^{13}$C NMR (DMSO-d$_6$) δ 13.3 (SCH$_2$CH$_2$CH$_3$), 22.9 (SCH$_2$CH$_2$CH$_3$), 24.1 (C(CH$_3$)$_2$), 26.5 (C(CH$_3$)$_2$), 32.1 (SCH$_2$CH$_2$CH$_3$), 35.9 (C-5'), 57.2 (C-6'), 75.3 (C-4'), 84.5 (C-6a'), 85.7 (3a'), 109.7 (C(CH$_3$)$_2$), 119.7 (C-5), 136.6 (C-6), 152.4 (C-4), 155.9 (C-2).

(3aR,4S,6R,6aS)-6-(6-Chloro-2-(propylthio)-9H-purin-9-yl)-2,2-dimethyltetrahydro-3aH-cyclopenta[d][1,3]dioxol-4-ol (19b)

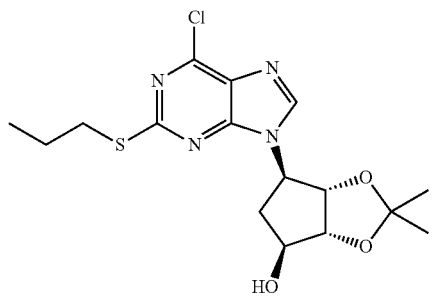 [SMILES: CCCSc1nc(Cl)c2ncn([C@@H]3C[C@H](O)[C@H]4OC(C)(C)O[C@H]43)c2n1]

A solution of (19a) (375.0 mg, 1 mmol) in acetic acid (2.5 mL) and triethyl orthoformate (2.5 mL, 15 mmol) was heated at a temperature of 130° C. under reflux for 10 h. After distillation of the acetic acid and triethyl orthoformate under vacuum, the residue was purified by silica gel column chromatography.

Yield: 23%.
Melting point: ND.
$^{1}$H NMR (DMSO-d$_6$) δ1.02 (t, J=7.4 Hz, 3H, SCH$_2$CH$_2$CH$_3$), 1.25 (s, 3H, C(CH$_3$)$_2$), 1.45 (s, 3H, C(CH$_3$)$_2$), 1.75 (h, J=7.2 Hz, 2H, SCH$_2$CH$_2$CH$_3$), 2.25 (m, 1H, 5'-H), 2.51 (m, 1H, 5'-H), 3.16 (t, J=7.2 Hz, 2H, SCH$_2$CH$_2$CH$_3$), 4.18 (bs, 1H, 4'-H), 4.56 (d, J=6.2 Hz, 1H, 3a'-H), 4.86 (m, 1H, 6'-H), 5.04 (dd, J=6.1 Hz/1.9 Hz, 1H, 6a'-H), 5.47 (bs, 1H, OH), 8.59 (s, 1H, 8-H).
$^{13}$C NMR (DMSO-d$_6$) δ 13.3 (SCH$_2$CH$_2$CH$_3$), 22.2 (SCH$_2$CH$_2$CH$_3$), 24.3 (C(CH$_3$)$_2$), 26.6 (C(CH$_3$)$_2$), 32.7 (SCH$_2$CH$_2$CH$_3$), 36.4 (C-5'), 60.4 (C-6'), 74.6 (C-4'), 83.9 (C-6a'), 86.1 (C-3a'), 110.9 (C(CH$_3$)$_2$), 128.1 (C-5), 146.0 (C-8), 148.9 (C-6), 152.7 (C-4), 163.9 (C-2).

(3aR,4S,6R,6aS)-6-(6-(((1R,2S)-2-(3,4-Difluorophenyl)cyclopropyl)amino)-2-(propylthio)-9H-purin-9-yl)-2,2-dimethyltetrahydro-3aH-cyclopenta[d][1,3]dioxol-4-ol (19c)

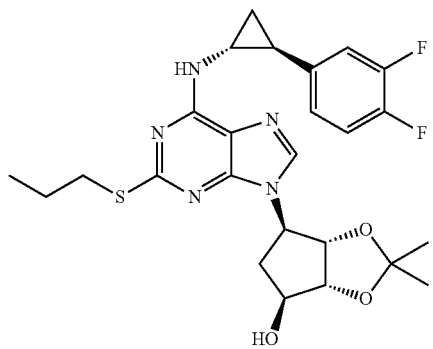 [SMILES: CCCSc1nc(N[C@@H]2C[C@H]2c2ccc(F)c(F)c2)c2ncn([C@@H]3C[C@H](O)[C@H]4OC(C)(C)O[C@H]43)c2n1]

A solution of (19b) (193.0 mg, 0.5 mmol) in acetonitrile (2.5 mL) was supplemented with (1R,2S)-2-(3,4-difluorophenyl)cyclopropanamine (93.0 mg, 0.55 mmol) and triethylamine (0.13 mL) and then heated at 90° C. under reflux for 1 h. After distillation of acetonitrile and triethylamine under vacuum, the residue was purified by silica gel column chromatography.

Yield: 91%.

Melting point: ND.

$^1$H NMR (CDCl$_3$) δ 0.90 (t, J=7.4 Hz, 3H, SCH$_2$CH$_2$CH$_3$), 1.32 (s, 3H, C(CH$_3$)$_2$), 1.34 (m, 2H, NHCH (CH$_2$)CHPh), 1.51 (s, 3H, C(CH$_3$)$_2$), 1.61 (h, J=7.3 Hz, 2H, SCH$_2$CH$_2$CH$_3$), 2.09 (m, 1H, NHCH(CH$_2$)CHPh), 2.13 (m, 1H, 5"-H), 2.96 (m, 3H, 5"-H/SCH$_2$CH$_2$CH$_3$), 3.13 (bs, 1H, NHCH(CH$_2$)CHPh), 4.42 (m, 1H, 4"-H), 4.74 (m, 1H, 6"-H), 4.79 (d, J=5.3 Hz, 1H, 3a"-H), 4.98 (d, J=5.3 Hz, 1H, 6a"-H), 5.99 (bs, 1H, OH), 6.03 (bs, 1H, NH), 6.93 (m, 1H, 6'-H), 7.05 (m, 2H, 2'-H/5'-H), 7.67 (s, 1H, 8-H).

$^{13}$C NMR (CDCl$_3$) S 13.3 (SCH$_2$CH$_2$CH$_3$), 16.2 (NHCH (CH$_2$)CHPh), 22.6 (SCH$_2$CH$_2$CH$_3$), 24.5 (C(CH$_3$)$_2$), 25.2 (NHCH(CH$_2$)CHPh), 27.1 (C(CH$_3$)$_2$), 33.2 (SCH$_2$CH$_2$CH$_3$), 33.3 (NHCH(CH$_2$)CHPh), 38.8 (C-5"), 64.0 (C-6"), 76.0 (C-4"), 86.2 (C-6a"), 88.0 (C-3a"), 111.4 (C(CH$_3$)$_2$), 115.3 (d, J=17 Hz, C-2'), 117.0 (d, J=17 Hz, C-5'), 118.3 (C-5), 122.4 (C-6'), 137.7 (C-1'), 139.8 (C-8), 148.0-150.0 (dd, 246 Hz/13 Hz, C-4'), 149.3-151.3 (dd, 247 Hz/13 Hz, C-3'), 150.5 (C-4), 154.7 (C-6), 165.7 (C-2).

(1S,2R,3S,4R)-4-(6-(((1R,2S)-2-(3,4-Difluorophenyl)cyclopropyl)amino)-2-(propylthio)-9H-purin-9-yl)cyclopentane-1,2,3-triol (19d)

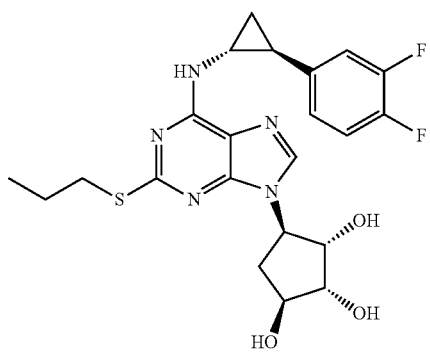 [SMILES: CCCSc1nc(N[C@@H]2C[C@H]2c2ccc(F)c(F)c2)c2ncn([C@@H]3C[C@H](O)[C@@H](O)[C@H]3O)c2n1]

A solution of (19c) (259.0 mg, 0.5 mmol) in methanol (2 mL) and 12N HCl (1 mL) was stirred at room temperature for 2 h. After distillation of the solvents under vacuum, the residue was purified by silica gel column chromatography.

Yield: 76%.

Melting point: 92-94° C.

$^1$H NMR (CDCl$_3$) δ0.87 (t, J=7.3 Hz, 3H, SCH$_2$CH$_2$CH$_3$), 1.34 (m, 2H, NHCH(CH$_2$)CHPh), 1.59 (h, J=7.3 Hz, 2H, SCH$_2$CH$_2$CH$_3$), 2.10 (m, 1H, NHCH(CH$_2$) CHPh), 2.14 (m, 1H, 5"-H), 2.71 (bs, 1H, 3"-OH), 2.83 (m, 1H, SCH$_2$CH$_2$CH$_3$), 2.98 (m, 2H, 5"-H/SCH$_2$CH$_2$CH$_3$), 3.12 (bs, 1H, NHCH(CH$_2$)CHPh), 4.14 (m, 1H, 3"-H), 4.27 (m, 1H, 1"-H), 4.47 (bs, 1H, 2"-OH), 4.56 (m, 1H, 4"-H), 4.76 (m, 1H, 2"-H), 4.98 (bs, 1H, 1"-OH), 6.16 (bs, 1H, NH), 6.93 (m, 1H, 6'-H), 7.04 (m, 2H, 2'-H/5'-H), 7.59 (s, 1H, 8-H).

$^{13}$C NMR (CDCl$_3$) S 13.2 (SCH$_2$CH$_2$CH$_3$), 16.2 (NHCH (CH$_2$)CHPh), 22.5 (SCH$_2$CH$_2$CH$_3$), 25.2 (NHCH(CH$_2$) CHPh), 33.1 (SCH$_2$CH$_2$CH$_3$), 33.3 (NHCH(CH$_2$)CHPh), 35.8 (C-5"), 61.5 (C-4"), 74.8 (C-1"), 76.9 (C-2"), 78.0 (C-3"), 115.3 (d, J=17 Hz, C-2'), 117.0 (d, J=17 Hz, C-5'), 118.3 (C-5), 122.3 (C-6'), 137.8 (C-1'), 139.0 (C-8), 148.0-150.0 (dd, 246 Hz/13 Hz, C-4'), 149.3-151.3 (dd, 247 Hz/13 Hz, C-3'), 149.3 (C-4), 154.6 (C-6), 165.8 (C-2).

Example 20: synthesis of N-((1R,2S)-2-(3,4-difluorophenyl)cyclopropyl)-2-(ethylthio)-9-methyl-9H-purin-6-amine (20c)

2-(Ethylthio)pyrimidine-4,6-diol (20e)

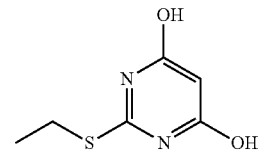

2-Thiobarbituric acid (2.5 g, 17.4 mmol) was dissolved in KOH 10% (25 mL) and supplemented with ethyl iodide (1.63 mL, 20.0 mmol). The reaction mixture was introduced in a sealed vessel and heated at 80° C. for 1 h. After cooling on an ice bath to 5° C., the mixture was acidified by addition of hydrochloric acid 6N and the resulting precipitate was filtered off and washed with diethyl ether.

Yield: 69%.

Melting point: >300° C.

$^1$H NMR (DMSO-d$_6$) δ 1.28 (t, J=7.3 Hz, 3H, CH$_3$), 3.08 (q, J=7.3 Hz, 2H, SCH$_2$), 5.12 (s, 1H, CH), 11.68 (bs, 2H, OH).

$^{13}$C NMR (DMSO-d$_6$) δ 14.6 (SCH$_3$), 24.0 (CH$_2$), 85.6 (CH), 158.1 (C-4/C-6), 162.8 (C-2).

2-(Ethylthio)-5-nitropyrimidine-4,6-diol (20f)

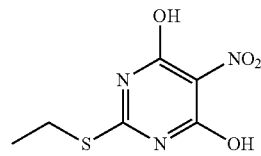

To 6 mL of acetic acid cooled at 5° C. on an ice bath were added fuming nitric acid (2.5 mL) and (20e) (1.8 g, 10.5 mmol). After 1 hour stirring at room temperature, the mixture was cooled at 5° C. on an ice bath, water (50 mL) was added and the resulting precipitate was filtered off.

Yield: 69%.

Melting point: 210-213° C. (decomposition).

$^1$H NMR (DMSO-d$_6$) δ 1.31 (t, J=7.3 Hz, 3H, CH$_3$), 3.17 (q, J=7.3 Hz, 2H, SCH$_2$).

$^{13}$C NMR (DMSO-d$_6$) δ 14.4 (CH$_3$), 24.7 (SCH$_2$), 117.4 (C-5), 158.9 (C-4/C-6), 164.0 (C-2).

4,6-Dichloro-2-(ethylthio)-5-nitropyrimidine (20g)

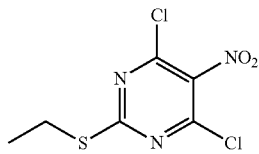

To a solution of (20f) (1.5 g, 6.9 mmol) in POCl$_3$ (10 mL) cooled at 5° C. on an ice bath was added dropwise 2,6-lutidine (2.5 mL). After 2 hours stirring at 80° C., the mixture was poured on crushed ice and extracted with ethyl acetate (3×50 mL). The organic layers were washed with water and with an aqueous saturated solution of sodium hydrogenocarbonate and ethyl acetate was evaporated to dryness under vacuum. The resulting oily residue was used without further purification in the next step (20h).

Yield: 85%.
Melting point: oil.
$^1$H NMR (DMSO-d$_6$) δ 1.35 (t, J=7.3 Hz, 3H, CH$_3$), 3.18 (q, J=7.3 Hz, 2H, SCH$_2$).
$^{13}$C NMR (DMSO-d$_6$) δ 14.0 (CH$_3$), 25.3 (SCH$_2$), 149.1 (C-4/C-6), 154.5 (C-5), 165.4 (C-2).

4,6-Dichloro-2-(ethylthio)pyrimidin-5-amine (20h)

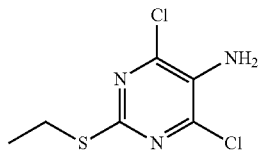

To a solution of (20g) (1.0 g, 3.9 mmol) in methanol (10 mL) and acetic acid (4 mL) was added iron powder (1.07 g, 19.5 mmol). After 1 hour stirring at room temperature, ethyl acetate (50 mL) was added and the suspension was filtered. The filtrate was washed with water and with an aqueous saturated solution of sodium hydrogenocarbonate and the organic layer was evaporated to dryness under vacuum. Water was added on the residue and the resulting precipitate was filtered off.

Yield: 86%.
Melting point: 48-50° C.
$^1$H NMR (DMSO-d$_6$) δ 1.28 (t, J=7.3 Hz, 3H, CH$_3$), 3.02 (q, J=7.3 Hz, 2H, SCH$_2$), 5.90 (s, 2H, NH$_2$).
$^{13}$C NMR (DMSO-d$_6$) δ 14.3 (CH$_3$), 24.9 (SCH$_2$), 133.5 (C-5), 143.7 (C-4/C-6), 153.8 (C-2).

6-Chloro-2-(ethylthio)-N$^4$-methylpyrimidine-4,5-diamine (20a)

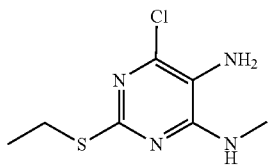

4,6-Dichloro-2-(ethylthio)pyrimidin-5-amine (20h) (0.5 g, 2.2 mmol) was dissolved in methanol (2 mL) and supplemented with a solution of methylamine 33% w/w in methanol (0.80 mL, 6.6 mmol). The reaction mixture was introduced in a sealed vessel and heated at 100° C. for 1 h. After concentration of the reaction mixture to dryness under vacuum, the residue was purified by silica gel column chromatography.

Yield: 87%.
Melting point: 112-114° C.
$^1$H NMR (DMSO-d$_6$) δ 1.27 (t, J=7.2 Hz, 3H, CH$_3$), 2.87 (d, J=3.8 Hz, 3H, NHCH$_3$), 2.97 (q, J=7.2 Hz, 2H, SCH$_2$), 4.70 (s, 2H, NH$_2$), 7.00 (s, 1H, NH).
$^{13}$C NMR (DMSO-d$_6$) δ 14.9 (CH$_3$), 24.5 (SCH$_2$), 27.8 (NHCH$_3$), 120.1 (C-5), 137.2 (C-6), 153.3 (C-4), 155.4 (C-2).

6-Chloro-2-(ethylthio)-9-methyl-9H-purine (20b)

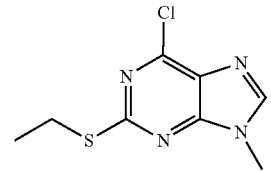

A solution of (20a) (219.0 mg, 1 mmol) in acetic acid (2.5 mL) and triethyl orthoformate (2.5 mL, 15 mmol) was heated at a temperature of 130° C. under reflux for 1 h. After distillation of the acetic acid and triethyl orthoformate under vacuum, the residue was purified by silica gel column chromatography.

Yield: 86%.
Melting point: 89-100° C.
$^1$H NMR (DMSO-d$_6$) δ 1.37 (t, J=7.3 Hz, 3H, CH$_3$), 3.20 (q, J=7.3 Hz, 2H, SCH$_2$), 3.79 (s, 3H, NCH$_3$), 8.48 (s, 1H, CH).
$^{13}$C NMR (DMSO-d$_6$) δ 14.3 (CH$_3$), 25.2 (SCH$_2$), 30.0 (NCH$_3$), 127.9 (C-5), 147.0 (C-8), 148.8 (C-6), 153.2 (C-4), 163.8 (C-2).

N-((1R,2S)-2-(3,4-Difluorophenyl)cyclopropyl)-2-(ethylthio)-9-methyl-9H-purin-6-amine (20c)

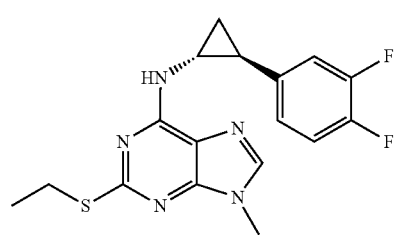 [SMILES: CCSc1nc(N[C@@H]2C[C@H]2c2ccc(F)c(F)c2)c2ncn(C)c2n1]

A solution of (20b) (114.0 mg, 0.5 mmol) in acetonitrile (2.5 mL) was supplemented with (1R,2S)-2-(3,4-difluorophenyl)cyclopropanamine (93.0 mg, 0.55 mmol) and triethylamine (0.13 mL) and then heated at 90° C. under reflux for 1 h. After distillation of acetonitrile and triethylamine under vacuum, the residue was purified by silica gel column chromatography.

Yield: 89%.

Melting point: 116-118.5° C.

$^1$H NMR (CDCl$_3$) δ 1.25 (t, J=7.3 Hz, 3H, CH$_3$), 1.32 (m, 2H, NHCH(CH$_2$)CHPh), 2.09 (ddd, J=9.5 Hz/6.3 Hz/3.2 Hz, 1H, NHCH(CH$_2$)CHPh), 3.02 (m, 2H, SCH$_2$), 3.12 (bs, 1H, NHCH(CH$_2$)CHPh), 3.76 (s, 3H, NCH$_3$), 5.96 (bs, 1H, NH), 6.97 (m, 1H, 6'-H), 7.07 (m, 2H, 2'-H/5'-H), 7.60 (s, 1H, 8-H).

$^{13}$C NMR (CDCl$_3$) δ 14.9 (CH$_3$), 16.3 (NHCH(CH$_2$)CHPh), 25.4 (NHCH(CH$_2$)CHPh), 25.7 (SCH$_2$), 29.8 (NCH$_3$), 33.5 (NHCH(CH$_2$)CHPh), 115.6 (d, J=17 Hz, C-2'), 117.1 (d, J=17 Hz, C-5'), 117.6 (C-5), 122.7 (C-6'), 138.1 (C-1'), 139.7 (C-8), 148.0-150.0 (dd, J=246 Hz/13 Hz, C-4'), 149.3-151.3 (dd, J=247 Hz/13 Hz, C-3'), 150.9 (C-4), 154.7 (C-6), 165.6 (C-2).

Example 21: synthesis of N-((1R,2S)-2-(3,4-difluorophenyl)cyclopropyl)-9-ethyl-2-(ethylthio)-9H-purin-6-amine (21c)

6-Chloro-N$^4$-ethyl-2-(ethylthio)pyrimidine-4,5-diamine (21a)

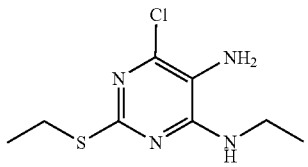

4,6-Dichloro-2-(ethylthio)pyrimidin-5-amine (20h) (0.5 g, 2.2 mmol) was dissolved in a solution of ethylamine 2.0 M in methanol (3.3 mL, 6.6 mmol). The reaction mixture was introduced in a sealed vessel and heated at 100° C. for 1 h. After concentration of the reaction mixture to dryness under vacuum, the residue was purified by silica gel column chromatography.

Yield: 91%.

Melting point: 93-95° C.

$^1$H NMR (DMSO-d$_6$) δ 1.16 (t, J=7.2 Hz, 3H, NHCH$_2$CH$_3$), 1.27 (t, J=7.2 Hz, 3H, SCH$_2$CH$_3$), 2.96 (q, J=7.2 Hz, 2H, SCH$_2$CH$_3$), 3.38 (p, J=6.1 Hz, 2H, NHCH$_2$CH$_3$), 4.74 (s, 2H, NH$_2$), 6.93 (s, 1H, NH).

$^{13}$C NMR (DMSO-d$_6$) δ 14.4 (NHCH$_2$CH$_3$), 15.0 (SCH$_2$CH$_3$), 24.5 (SCH$_2$CH$_3$), 35.8 (NHCH$_2$CH$_3$), 119.9 (C-5), 137.3 (C-6), 152.6 (C-4), 155.2 (C-2).

6-Chloro-9-ethyl-2-(ethylthio)-9H-purine (21b)

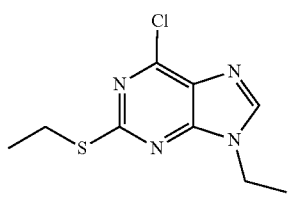

A solution of (21a) (233.0 mg, 1 mmol) in acetic acid (2.5 mL) and triethyl orthoformate (2.5 mL, 15 mmol) was heated at a temperature of 130° C. under reflux for 1 h. After distillation of the acetic acid and triethyl orthoformate under vacuum, the residue was purified by silica gel column chromatography.

Yield: 91%.

Melting point: 64-66° C.

$^1$H NMR (DMSO-d$_6$) δ 1.37 (t, J=7.3 Hz, 3H, SCH$_2$CH$_3$), 1.45 (t, J=7.3 Hz, 3H, NCH$_2$CH$_3$), 3.19 (q, J=7.3 Hz, 2H, SCH$_2$), 4.25 (q, J=7.3 Hz, 2H, NCH$_2$), 8.56 (s, 1H, CH).

$^{13}$C NMR (DMSO-d$_6$) δ 14.3 (SCH$_2$CH$_3$), 14.7 (NCH$_2$CH$_3$), 25.2 (SCH$_2$), 39.0 (NCH$_2$), 128.1 (C-5), 146.1 (C-8), 148.9 (C-6), 152.7 (C-4), 163.7 (C-2).

N-((1R,2S)-2-(3,4-Difluorophenyl)cyclopropyl)-9-ethyl-2-(ethylthio)-9H-purin-6-amine (21c)

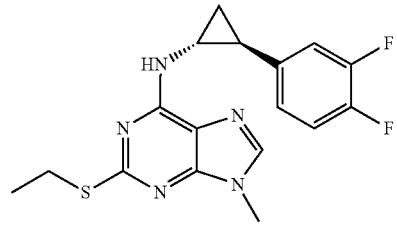 [SMILES: CCSc1nc(N[C@@H]2C[C@H]2c2ccc(F)c(F)c2)c2ncn(C)c2n1]

A solution of (21b) (121.0 mg, 0.5 mmol) in acetonitrile (2.5 mL) was supplemented with (1R,2S)-2-(3,4-difluorophenyl)cyclopropanamine (93.0 mg, 0.55 mmol) and triethylamine (0.13 mL) and then heated at 90° C. under reflux for 1 h. After distillation of acetonitrile and triethylamine under vacuum, the residue was purified by silica gel column chromatography.

Yield: 96%.

Melting point: 107.5-109.5° C.

$^1$H NMR (CDCl$_3$) δ 1.26 (t, J=7.3 Hz, 3H, SCH$_2$CH$_3$), 1.32 (m, 2H, NHCH(CH$_2$)CHPh), 1.50 (t, J=7.3 Hz, 3H, NCH$_2$CH$_3$), 2.08 (ddd, J=9.5 Hz/6.4 Hz/3.3 Hz, 1H, NHCH(CH$_2$)CHPh), 3.03 (m, 2H, SCH$_2$CH$_3$), 3.11 (bs, 1H, NHCH(CH$_2$)CHPh), 4.19 (q, J=7.3 Hz, 2H, NCH$_2$CH$_3$), 5.94 (bs, 1H, NH), 6.98 (m, 1H, 6'-H), 7.08 (m, 2H, 2'-H/5'-H), 7.63 (s, 1H, 8-H).

$^{13}$C NMR (CDCl$_3$) δ 14.9 (SCH$_2$CH$_3$), 15.7 (NCH$_2$CH$_3$), 16.3 (NHCH(CH$_2$)CHPh), 25.4 (NHCH(CH$_2$)CHPh), 25.7 (SCH$_2$CH$_3$), 33.5 (NHCH(CH$_2$)CHPh), 38.8 (NCH$_2$CH$_3$), 115.7 (d, J=17 Hz, C-2'), 117.0 (d, J=17 Hz, C-5'), 117.8 (C-5), 122.8 (C-6'), 138.1 (C-1'), 138.6 (C-8), 148.0-150.0 (dd, J=246 Hz/13 Hz, C-4'), 149.3-151.3 (dd, J=247 Hz/13 Hz, C-3'), 150.4 (C-4), 154.7 (C-6), 165.3 (C-2).

Example 22: synthesis of N-((1R,2S)-2-(3,4-difluorophenyl)cyclopropyl)-9-methyl-2-(methylthio)-9H-purin-6-amine (22c)

2-(Methylthio)pyrimidine-4,6-diol (22e)

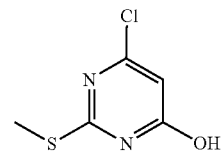

2-Thiobarbituric acid (2.5 g, 17.4 mmol) was dissolved in KOH 10% (25 mL) and supplemented with methyl iodide (1.25 mL, 20.0 mmol). The reaction mixture was introduced in a sealed vessel and heated at 80° C. for 1 h. After cooling on an ice bath to 5° C., the mixture was acidified by addition of hydrochloric acid 6N and the resulting precipitate was filtered off and washed with diethyl ether.

Yield: 77%.
Melting point: >300° C.
$^1$H NMR (DMSO-d$_6$) δ 2.46 (s, 3H, SCH$_3$), 5.13 (s, 1H, CH), 11.71 (bs, 2H, OH).
$^{13}$C NMR (DMSO-d$_6$) δ 12.7 (SCH$_3$), 85.5 (CH), 158.9 (C-4/C-6), 163.5 (C-2).

2-(Methylthio)-5-nitropyrimidine-4,6-diol (22f)

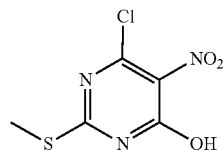

To 6 mL of acetic acid cooled at 5° C. on an ice bath were added fuming nitric acid (2.5 mL) and (22e) (2.0 g, 12.6 mmol). After 1 hour stirring at room temperature, the mixture was cooled at 5° C. on an ice bath, water (50 mL) was added and the resulting precipitate was filtered off.

Yield: 67%.
Melting point: 220-221° C. (decomposition).
$^1$H NMR (DMSO-d$_6$) δ 2.56 (s, 3H, SCH$_3$).
$^{13}$C NMR (DMSO-d$_6$) δ 13.2 (SCH$_3$), 117.4 (C-5), 158.7 (C-4/C-6), 164.6 (C-2).

4,6-Dichloro-2-(methylthio)-5-nitropyrimidine (22g)

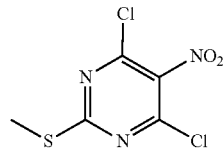

To a solution of (22f) (1.5 g, 7.4 mmol) in POCl$_3$ (10 mL) cooled at 5° C. on an ice bath was added dropwise 2,6-lutidine (2.5 mL). After 2 hours stirring at 80° C., the mixture was poured on crushed ice and the resulting precipitate was filtered off.

Yield: 92%.
Melting point: 63-64° C.
$^1$H NMR (DMSO-d$_6$) δ 2.56 (s, 3H, SCH$_3$).
$^{13}$C NMR (DMSO-d$_6$) δ 13.5 (SCH$_3$), 149.0 (C-4/C-6), 154.5 (C-5), 166.1 (C-2).

4,6-Dichloro-2-(methylthio)pyrimidin-5-amine (22h)

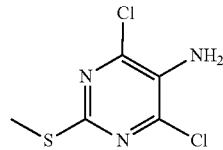

To a solution of (22g) (1.0 g, 4.2 mmol) in methanol (10 mL) and acetic acid (4 mL) was added iron powder (1.07 g, 19.5 mmol). After 1 hour stirring at room temperature, ethyl acetate (50 mL) was added and the suspension was filtered. The filtrate was washed with water and with an aqueous saturated solution of sodium hydrogenocarbonate and the organic layer was evaporated to dryness under vacuum. Water was added on the residue and the resulting precipitate was filtered off.

Yield: 95%.
Melting point: 105-108° C.
$^1$H NMR (DMSO-d$_6$) δ 2.45 (s, 3H, SCH$_3$), 5.90 (s, 2H, NH$_2$).
$^{13}$C NMR (DMSO-d$_6$) δ 13.8 (SCH$_3$), 133.4 (C-5), 143.7 (C-4/C-6), 154.4 (C-2).

6-Chloro-N$^4$-methyl-2-(methylthio)pyrimidine-4,5-diamine (22a)

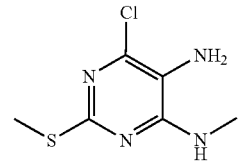

4,6-Dichloro-2-(methylthio)pyrimidin-5-amine (22h) (0.5 g, 2.4 mmol) was dissolved in methanol (2 mL) and supplemented with a solution of methylamine 33% w/w in methanol (0.87 mL, 7.2 mmol). The reaction mixture was introduced in a sealed vessel and heated at 100° C. for 1 h. After concentration of the reaction mixture to dryness under vacuum, the residue was purified by silica gel column chromatography.

Yield: 82%.
Melting point: 141-143° C.
$^1$H NMR (DMSO-d$_6$) δ 2.38 (s, 3H, SCH$_3$), 2.88 (d, J=3.0 Hz, 3H, NHCH$_3$), 4.70 (s, 2H, NH$_2$), 7.01 (s, 1H, NH).
$^{13}$C NMR (DMSO-d$_6$) δ 13.5 (SCH$_3$), 27.8 (NHCH$_3$), 120.1 (C-5), 137.2 (C-6), 153.3 (C-4), 155.9 (C-2).

6-Chloro-9-methyl-2-(methylthio)-9H-purine (22b)

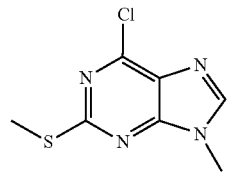

A solution of (22a) (205.0 mg, 1 mmol) in acetic acid (2.5 mL) and triethyl orthoformate (2.5 mL, 15 mmol) was heated at a temperature of 130° C. under reflux for 1 h. After distillation of the acetic acid and triethyl orthoformate under vacuum, the residue was purified by silica gel column chromatography.

Yield: 92%.
Melting point: 140-142° C.
$^1$H NMR (DMSO-d$_6$) δ 2.61 (s, 3H, SCH$_3$), 3.80 (s, 3H, NCH$_3$), 8.49 (s, 1H, CH).

$^{13}$C NMR (DMSO-d$_6$) δ 14.1 (SCH$_3$), 30.0 (NCH$_3$), 127.9 (C-5), 147.0 (C-8), 148.8 (C-6), 153.2 (C-4), 164.4 (C-2).

N-((1R,2S)-2-(3,4-Difluorophenyl)cyclopropyl)-9-methyl-2-(methylthio)-9H-purin-6-amine (22c)

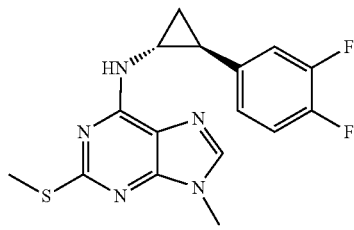 [SMILES: CSc1nc(N[C@@H]2C[C@H]2c2ccc(F)c(F)c2)c2ncn(C)c2n1]

A solution of (22b) (107.0 mg, 0.5 mmol) in acetonitrile (2.5 mL) was supplemented with (1R,2S)-2-(3,4-difluorophenyl)cyclopropanamine (93.0 mg, 0.55 mmol) and triethylamine (0.13 mL) and then heated at 90° C. under reflux for 1 h. After distillation of acetonitrile and triethylamine under vacuum, the residue was purified by silica gel column chromatography.

Yield: 80%.

Melting point: 156-159° C.

$^1$H NMR (CDCl$_3$) δ 1.33 (m, 2H, NHCH(CH$_2$)CHPh), 2.09 (m, 1H, NHCH(CH$_2$)CHPh), 2.45 (s, 3H, SCH$_3$), 3.12 (bs, 1H, NHCH(CH$_2$)CHPh), 3.77 (s, 3H, NCH$_3$), 5.95 (bs, 1H, NH), 7.00 (m, 1H, 6'-H), 7.09 (m, 2H, 2'-H/5'-H), 7.60 (s, 1H, 8-H).

$^{13}$C NMR (CDCl$_3$) δ 14.5 (SCH$_3$), 16.1 (NHCH(CH$_2$)CHPh), 25.4 (NHCH(CH$_2$)CHPh), 29.8 (NCH$_3$), 33.4 (NHCH(CH$_2$)CHPh), 115.9 (d, J=17 Hz, C-2'), 117.0 (d, J=17 Hz, C-5'), 117.5 (C-5), 122.9 (C-6'), 137.9 (C-1'), 139.7 (C-8), 148.0-150.0 (dd, J=246 Hz/13 Hz, C-4'), 149.3-151.3 (dd, J=247 Hz/13 Hz, C-3'), 151.0 (C-4), 154.7 (C-6), 166.0 (C-2).

Example 23: synthesis of N-((1R,2S)-2-(3,4-difluorophenyl)cyclopropyl)-9-methyl-2-propoxy-9H-purin-6-amine hydrochloride (23t·HCl)

N-((1R,2S)-2-(3,4-Difluorophenyl)cyclopropyl)-9-methyl-2-(methylsulfonyl)-9H-purin-6-amine (23q)

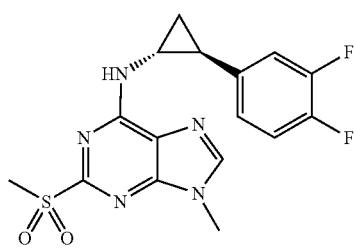 [SMILES: Cn1cnc2c(N[C@@H]3C[C@H]3c3ccc(F)c(F)c3)nc(S(C)(=O)=O)nc21]

A solution of (22c) (125.0 mg, 0.36 mmol) in methylene chloride (10 mL) was cooled to 5° C. on an ice bath and supplemented with 3-chloroperbenzoic acid (140.0 mg, 0.80 mmol). After stirring at room temperature for 4 hours, the mixture was washed with a solution of NaOH 0.1 M (2×10 mL). The organic layer was dried, filtered and methylene chloride was evaporated to dryness under vacuum. The residue was suspended in ethyl acetate and filtered off.

Yield: 88%.

Melting point: 206-208.5° C.

$^1$H NMR (CDCl$_3$) δ 1.38 (m, 2H, NHCH(CH$_2$)CHPh), 2.17 (td, J=8.0 Hz/3.3 Hz, 1H, NHCH(CH$_2$)CHPh), 3.08 (bs, 1H, NHCH(CH$_2$)CHPh), 3.19 (s, 3H, SO$_2$CH$_3$), 3.91 (s, 3H, NCH$_3$), 6.49 (bs, 1H, NH), 7.11 (m, 3H, 2'-H/5'-H/6'-H), 7.88 (s, 1H, 8-H).

$^{13}$C NMR (CDCl$_3$) δ 15.7 (NHCH(CH$_2$)CHPh), 25.4 (NHCH(CH$_2$)CHPh), 30.5 (NCH$_3$), 33.1 (NHCH(CH$_2$)CHPh), 39.4 (SO$_2$CH$_3$), 115.8 (d, J=16 Hz, C-2'), 117.3 (d, J=17 Hz, C-5'), 120.9 (C-5), 123.3 (C-6'), 137.3 (C-1'), 143.0 (C-8), 148.5-149.9 (dd, J=247 Hz/12 Hz, C-4'), 149.7-151.1 (dd, J=248 Hz/13 Hz, C-3'), 149.2 (C-4), 155.7 (C-6).

N-((1R,2S)-2-(3,4-Difluorophenyl)cyclopropyl)-9-methyl-2-propoxy-9H-purin-6-amine (23t)

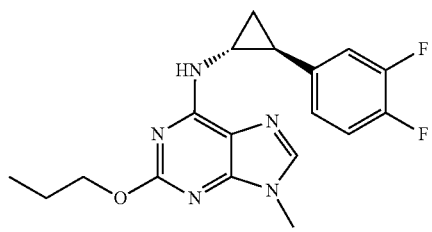 [SMILES: CCCOc1nc(N[C@@H]2C[C@H]2c2ccc(F)c(F)c2)c2ncn(C)c2n1]

Sodium was dissolved in propan-1-ol (3 mL) on an iced bath and (23q) (150.0 mg, 0.40 mmol) was added. After stirring at room temperature for 3 hours, the mixture was partitioned between water (50 mL) and dichloromethane (2×50 mL). The combined organic layers were dried and evaporated to dryness under vacuum. The residue was purified by silica gel column chromatography and the resulting oil was engaged in the next step (23t·HCl) without further purification.

Yield: 73%.

$^1$H NMR (CDCl$_3$) δ 0.94 (t, J=7.5 Hz, 3H, OCH$_2$CH$_2$CH$_3$), 1.30 (dt, J=7.5 Hz/6.2 Hz, 1H, NHCH(CH$_2$)CHPh), 1.39 (ddd, J=9.7 Hz/5.9 Hz/4.7 Hz, 1H, NHCH(CH$_2$)CHPh), 1.75 (h, J=7.3 Hz, 2H, OCH$_2$CH$_2$CH$_3$), 2.10 (m, 1H, NHCH(CH$_2$)CHPh), 3.16 (bs, 1H, NHCH(CH$_2$)CHPh), 3.74 (s, 3H, NCH$_3$), 4.18 (m, 2H, OCH$_2$CH$_2$CH$_3$), 6.86 (bs, 1H, NH), 6.94 (m, 1H, 6'-H), 7.07 (m, 2H, 2'-H/5'-H), 7.57 (s, 1H, 8-H).

$^{13}$C NMR (CDCl$_3$) δ 10.5 (OCH$_2$CH$_2$CH$_3$), 16.2 (NHCH(CH$_2$)CHPh), 22.4 (OCH$_2$CH$_2$CH$_3$), 25.1 (NHCH(CH$_2$)CHPh), 29.8 (NCH$_3$), 33.6 (NHCH(CH$_2$)CHPh), 69.3 (OCH$_2$CH$_2$CH$_3$), 115.4 (C-5), 115.7 (C-2'), 117.0 (C-5'), 122.6 (C-6'), 138.3 (C-1'), 139.1 (C-8), 148.0-149.9 (C-4'), 149.4-151.3 (C-3'), 151.7 (C-4), 156.1 (C-6), 162.6 (C-2).

N-((1R,2S)-2-(3,4-Difluorophenyl)cyclopropyl)-9-methyl-2-propoxy-9H-purin-6-amine hydrochloride (23t·HCl)

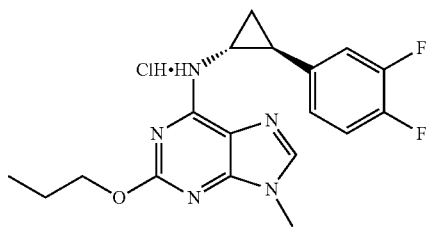

To a solution of (23t) (90.0 mg, 0.25 mmol) in diethyl ether (5 mL) was added dropwise a saturated solution of HCl in diethyl ether. The resulting precipitate of the title compound was collected by filtration, washed with diethyl ether and dried.
Yield: 95%.
Melting point: 199-202° C.

Example 24: synthesis of N-((1R,2S)-2-(3,4-difluorophenyl)cyclopropyl)-9-ethyl-2-(methylthio)-9H-purin-6-amine (24c)

6-Chloro-N[4]-ethyl-2-(methylthio)pyrimidine-4,5-diamine (24a)

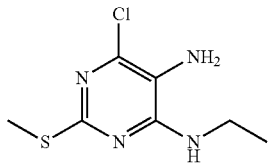

4,6-Dichloro-2-(methylthio)pyrimidin-5-amine (22h) (0.5 g, 2.4 mmol) was dissolved in a solution of ethylamine 2.0 M in methanol (3.6 mL, 7.2 mmol). The reaction mixture was introduced in a sealed vessel and heated at 100° C. for 1 h. After concentration of the reaction mixture to dryness under vacuum, the residue was purified by silica gel column chromatography.
Yield: 86%.
Melting point: 120-122° C.
$^1$H NMR (DMSO-$d_6$) δ 1.16 (t, J=7.2 Hz, 3H, CH$_3$), 2.37 (s, 3H, SCH$_3$), 3.38 (qd, J=7.2 Hz/5.3 Hz, 2H, NCH$_2$), 4.76 (s, 2H, NH$_2$), 6.94 (t, J=4.8 Hz, 1H, NH).
$^{13}$C NMR (DMSO-$d_6$) δ 13.5 (SCH$_3$), 14.3 (CH$_3$), 35.7 (NCH$_2$), 119.8 (C-5), 137.2 (C-6), 152.4 (C-4), 155.7 (C-2).

6-Chloro-9-ethyl-2-(methylthio)-9H-purine (24b)

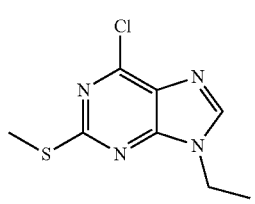

A solution of (24a) (219.0 mg, 1 mmol) in acetic acid (2.5 mL) and triethyl orthoformate (2.5 mL, 15 mmol) was heated at a temperature of 130° C. under reflux for 1 h. After distillation of the acetic acid and triethyl orthoformate under vacuum, the residue was purified by silica gel column chromatography.
Yield: 77%.
Melting point: 99.5-101.5° C.
$^1$H NMR (DMSO-$d_6$) δ 1.45 (t, J=7.3 Hz, 3H, CH$_3$), 2.60 (s, 3H, SCH$_3$), 4.25 (q, J=7.3 Hz, 2H, NCH$_2$), 8.57 (s, 1H, CH).
$^{13}$C NMR (DMSO-$d_6$) δ 14.1 (SCH$_3$), 14.7 (CH$_3$), 39.0 (NCH$_2$), 128.0 (C-5), 146.0 (C-8), 148.8 (C-6), 152.7 (C-4), 164.3 (C-2).

N-((1R,2S)-2-(3,4-Difluorophenyl)cyclopropyl)-9-ethyl-2-(methylthio)-9H-purin-6-amine (24c)

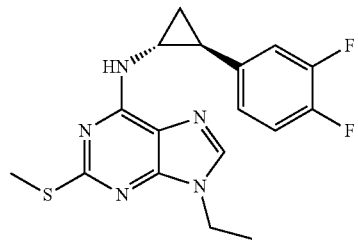 [SMILES: CCn1cnc2c(N[C@@H]3C[C@H]3c3ccc(F)c(F)c3)nc(SC)nc21]

A solution of (24b) (114.0 mg, 0.5 mmol) in acetonitrile (2.5 mL) was supplemented with (1R,2S)-2-(3,4-difluorophenyl)cyclopropanamine (93.0 mg, 0.55 mmol) and triethylamine (0.13 mL) and then heated at 90° C. under reflux for 1 h. After distillation of acetonitrile and triethylamine under vacuum, the residue was purified by silica gel column chromatography.
Yield: 38%.
Melting point: 126-127.5° C.
$^1$H NMR (CDCl$_3$) δ 1.31 (td, J=8.0 Hz/6.9 Hz/4.0 Hz, 2H, NHCH(CH$_2$)CHPh), 1.51 (t, J=7.3 Hz, 3H, CH$_3$), 2.08 (td, J=8.1 Hz/6.7 Hz/3.2 Hz, 1H, NHCH(CH$_2$)CHPh), 2.45 (s, 3H, SCH$_3$), 3.11 (bs, 1H, NHCH(CH$_2$)CHPh), 4.20 (q, J=7.3 Hz, 2H, NCH$_2$), 5.97 (bs, 1H, NH), 7.01 (m, 1H, 6'-H), 7.10 (m, 2H, 2'-H/5'-H), 7.64 (s, 1H, 8-H).
$^{13}$C NMR (CDCl$_3$) δ 14.6 (SCH$_3$), 15.6 (CH$_3$), 16.1 (NHCH(CH$_2$)CHPh), 25.4 (NHCH(CH$_2$)CHPh), 33.4 (NHCH(CH$_2$)CHPh), 38.8 (NCH$_2$), 115.9 (d, J=17 Hz, C-2'), 117.0 (d, J=17 Hz, C-5'), 117.7 (C-5), 123.0 (C-6'), 138.0 (C-1'), 138.6 (C-8), 148.0-150.0 (dd, J=246 Hz/13 Hz, C-4'), 149.3-151.3 (dd, J=247 Hz/13 Hz, C-3'), 150.4 (C-4), 154.7 (C-6), 165.8 (C-2).

Example 25: synthesis of 2-(butylthio)-N-((1R,2S)-2-(3,4-difluorophenyl)cyclopropyl)-9-methyl-9H-purin-6-amine (25c)

2-(Butylthio)pyrimidine-4,6-diol (25e)

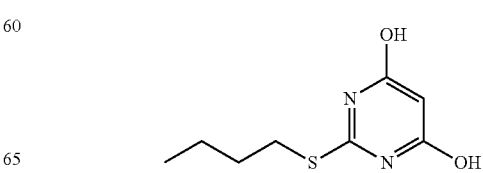

2-Thiobarbituric acid (2.5 g, 17.4 mmol) was dissolved in KOH 10% (25 mL) and supplemented with butyl iodide (2.27 mL, 20.0 mmol). The reaction mixture was introduced in a sealed vessel and heated at 80° C. for 1 h. After cooling on an ice bath to 5° C., the mixture was acidified by addition of hydrochloric acid 6N and the resulting precipitate was filtered off and washed with diethyl ether.

Yield: 72%.
Melting point: >300° C.
$^1$H NMR (DMSO-$d_6$) δ 0.90 (t, J=7.4 Hz, 3H, SCH$_2$CH$_2$CH$_2$CH$_3$), 1.38 (h, J=7.4 Hz, 2H, SCH$_2$CH$_2$CH$_2$CH$_3$), 1.60 (p, J=7.4 Hz, 2H, SCH$_2$CH$_2$CH$_2$CH$_3$), 3.09 (t, J=7.3 Hz, 2H, SCH$_2$CH$_2$CH$_2$CH$_3$), 5.12 (s, 1H, CH), 11.64 (bs, 2H, OH).
$^{13}$C NMR (DMSO-$d_6$) δ 13.5 (SCH$_2$CH$_2$CH$_2$CH$_3$), 21.3 (SCH$_2$CH$_2$CH$_2$CH$_3$), 29.2 (SCH$_2$CH$_2$CH$_2$CH$_3$), 30.8 (SCH$_2$CH$_2$CH$_2$CH$_3$), 85.6 (CH), 158.1 (C-4/C-6), 162.9 (C-2).

2-(Butylthio)-5-nitropyrimidine-4,6-diol (25f)

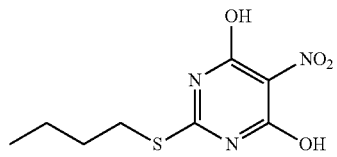

To 6 mL of acetic acid cooled at 5° C. on an ice bath were added fuming nitric acid (2.5 mL) and (25e) (2.0 g, 10.0 mmol). After 1 hour stirring at room temperature, the mixture was cooled at 5° C. on an ice bath, water (50 mL) was added and the resulting precipitate was filtered off.

Yield: 68%.
Melting point: 178-179.5° C. (decomposition).
$^1$H NMR (DMSO-$d_6$) δ 0.90 (t, J=7.4 Hz, 3H, SCH$_2$CH$_2$CH$_2$CH$_3$), 1.39 (h, J=7.4 Hz, 2H, SCH$_2$CH$_2$CH$_2$CH$_3$), 1.63 (p, J=7.4 Hz, 2H, SCH$_2$CH$_2$CH$_2$CH$_3$), 3.18 (t, J=7.3 Hz, 2H, SCH$_2$CH$_2$CH$_2$CH$_3$).
$^{13}$C NMR (DMSO-$d_6$) δ 13.5 (SCH$_2$CH$_2$CH$_2$CH$_3$), 21.2 (SCH$_2$CH$_2$CH$_2$CH$_3$), 29.9 (SCH$_2$CH$_2$CH$_2$CH$_3$), 30.5 (SCH$_2$CH$_2$CH$_2$CH$_3$), 117.5 (C-5), 158.9 (C-4/C-6), 164.2 (C-2).

2-(Butylthio)-4,6-dichloro-5-nitropyrimidine (25g)

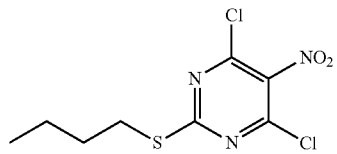

To a solution of (25f) (1.5 g, 6.1 mmol) in POCl$_3$ (10 mL) cooled at 5° C. on an ice bath was added dropwise 2,6-lutidine (2.5 mL). After 2 hours stirring at 80° C., the mixture was poured on crushed ice and extracted with ethyl acetate (3×50 mL). The organic layers were washed with water and with an aqueous saturated solution of sodium hydrogenocarbonate and ethyl acetate was evaporated to dryness under vacuum. The resulting oily residue was used without further purification in the next step (25h).

Yield: 92%.
Melting point: oil.
$^1$H NMR (DMSO-$d_6$) δ 0.90 (t, J=7.3 Hz, 3H, SCH$_2$CH$_2$CH$_2$CH$_3$), 1.39 (h, J=7.4 Hz, 2H, SCH$_2$CH$_2$CH$_2$CH$_3$), 1.65 (p, J=7.4 Hz, 2H, SCH$_2$CH$_2$CH$_2$CH$_3$), 3.17 (t, J=7.2 Hz, 2H, SCH$_2$CH$_2$CH$_2$CH$_3$).
$^{13}$C NMR (DMSO-$d_6$) δ 13.4 (SCH$_2$CH$_2$CH$_2$CH$_3$), 21.2 (SCH$_2$CH$_2$CH$_2$CH$_3$), 30.2 (SCH$_2$CH$_2$CH$_2$CH$_3$), 30.3 (SCH$_2$CH$_2$CH$_2$CH$_3$), 149.0 (C-4/C-6), 154.7 (C-5), 165.6 (C-2).

2-(Butylthio)-4,6-dichloropyrimidin-5-amine (25h)

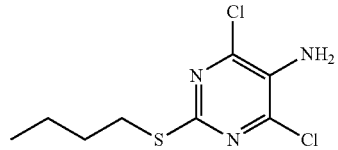 [SMILES: CCCCSc1nc(Cl)c([N+](=O)[O-])c(Cl)n1]

To a solution of (25g) (1 g, 3.5 mmol) in methanol (10 mL) and acetic acid (4 mL) was added iron powder (0.78 g, 14.0 mmol). After 1 hour stirring at room temperature, ethyl acetate (50 mL) was added and the suspension was filtered. The filtrate was washed with water and with an aqueous saturated solution of sodium hydrogenocarbonate and the organic layer was evaporated to dryness under vacuum. The resulting oily residue was used without further purification in the next step (25a).

Yield: 97%.
Melting point: oil.
$^1$H NMR (DMSO-$d_6$) δ 0.90 (t, J=7.4 Hz, 3H, SCH$_2$CH$_2$CH$_2$CH$_3$), 1.39 (h, J=7.4 Hz, 2H, SCH$_2$CH$_2$CH$_2$CH$_3$), 1.61 (p, J=7.4 Hz, 2H, SCH$_2$CH$_2$CH$_2$CH$_3$), 3.03 (t, J=7.2 Hz, 2H, SCH$_2$CH$_2$CH$_2$CH$_3$), 5.88 (s, 2H, NH$_2$).
$^{13}$C NMR (DMSO-$d_6$) δ 13.5 (SCH$_2$CH$_2$CH$_2$CH$_3$), 21.3 (SCH$_2$CH$_2$CH$_2$CH$_3$), 30.2 (SCH$_2$CH$_2$CH$_2$CH$_3$), 30.7 (SCH$_2$CH$_2$CH$_2$CH$_3$), 133.5 (C-5), 143.7 (C-4/C-6), 154.0 (C-2).

2-(Butylhtio)-6-chloro-2-$N^4$-methylpyrimidine-4,5-diamine (25a)

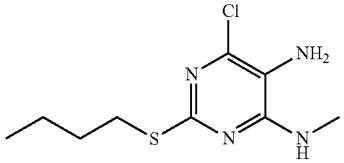

2-(Butylthio)-4,6-dichloropyrimidin-5-amine (25h) (0.5 g, 2.0 mmol) was dissolved in methanol (2 mL) and supplemented with a solution of methylamine 33% w/w in methanol (0.73 mL, 6.0 mmol). The reaction mixture was introduced in a sealed vessel and heated at 100° C. for 1 h. After concentration of the reaction mixture to dryness under vacuum, the residue was purified by silica gel column chromatography.

Yield: 87%.
Melting point: oil.

¹H NMR (DMSO-d₆) δ 0.89 (t, J=7.4 Hz, 3H, SCH₂CH₂CH₂CH₃), 1.38 (h, J=7.4 Hz, 2H, SCH₂CH₂CH₂CH₃), 1.61 (p, J=7.4 Hz, 2H, SCH₂CH₂CH₂CH₃), 2.87 (d, J=4.5 Hz, 3H, NHCH₃), 2.98 (t, J=7.3 Hz, 2H, SCH₂CH₂CH₂CH₃), 4.69 (s, 2H, NH₂), 6.99 (q, J=4.4 Hz, 1H, NHCH₃).

¹³C NMR (DMSO-d₆) δ 13.6 (SCH₂CH₂CH₂CH₃), 21.5 (SCH₂CH₂CH₂CH₃), 27.8 (NHCH₃), 29.8 (SCH₂CH₂CH₂CH₃), 31.4 (SCH₂CH₂CH₂CH₃), 120.0 (C-5), 137.2 (C-6), 153.3 (C-4), 155.5 (C-2).

2-(Butylthio)-6-chloro-9-methyl-9H-purine (25b)

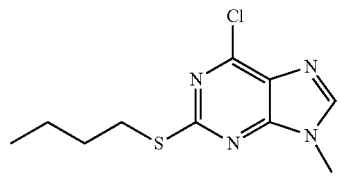 [SMILES: CCCCSc1nc(Cl)c2ncn(C)c2n1]

A solution of (25a) (247.0 mg, 1 mmol) in acetic acid (2.5 mL) and triethyl orthoformate (2.5 mL, 15 mmol) was heated at a temperature of 130° C. under reflux for 1 h. After distillation of the acetic acid and triethyl orthoformate under vacuum, the residue was purified by silica gel column chromatography.

Yield: 76%.
Melting point: 56-58° C.

¹H NMR (DMSO-d₆) δ 0.93 (t, J=7.4 Hz, 3H, SCH₂CH₂CH₂CH₃), 1.44 (h, J=7.4 Hz, 2H, SCH₂CH₂CH₂CH₃), 1.70 (p, J=7.4 Hz, 2H, SCH₂CH₂CH₂CH₃), 3.20 (t, J=7.3 Hz, 2H, SCH₂CH₂CH₂CH₃), 3.79 (s, 3H, NCH₃), 8.48 (s, 1H, CH).

¹³C NMR (DMSO-d₆) δ 13.5 (SCH₂CH₂CH₂CH₃), 21.4 (SCH₂CH₂CH₂CH₃), 30.0 (NCH₃), 30.3 (SCH₂CH₂CH₂CH₃), 30.8 (SCH₂CH₂CH₂CH₃), 127.9 (C-5), 147.0 (C-8), 148.8 (C-6), 153.2 (C-4), 163.9 (C-2).

2-(Butylthio)-N-((1R,2S)-2-(3,4-difluorophenyl)cyclopropyl)-9-methyl-9H-purin-6-amine (25c)

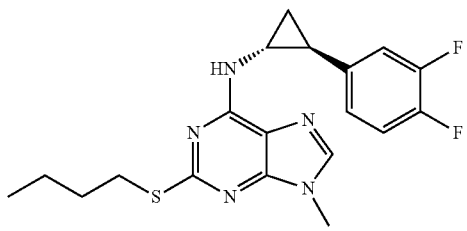 [SMILES: CCCCSc1nc(N[C@@H]2C[C@H]2c2ccc(F)c(F)c2)c2ncn(C)c2n1]

A solution of (25b) (128.0 mg, 0.5 mmol) in acetonitrile (2.5 mL) was supplemented with (1R,2S)-2-(3,4-difluorophenyl)cyclopropanamine (93.0 mg, 0.55 mmol) and triethylamine (0.13 mL) and then heated at 90° C. under reflux for 1 h. After distillation of acetonitrile and triethylamine under vacuum, the residue was purified by silica gel column chromatography.

Yield: 66%.
Melting point: 98-100° C.

¹H NMR (CDCl₃) δ 0.89 (t, J=7.4 Hz, 3H, SCH₂CH₂CH₂CH₃), 1.33 (m, 4H, NHCH(CH₂)CHPh/SCH₂CH₂CH₂CH₃), 1.62 (p, J=7.3 Hz, 2H, SCH₂CH₂CH₂CH₃), 2.09 (ddd, J=9.5 Hz/6.4 Hz/3.2 Hz, 1H, NHCH(CH₂)CHPh), 3.02 (m, 1H, SCH₂CH₂CH₂CH₃), 3.11 (m, 2H, NHCH(CH₂)CHPh/SCH₂CH₂CH₂CH₃), 3.76 (s, 3H, NCH₃), 5.92 (bs, 1H, NH), 6.98 (m, 1H, 6'-H), 7.07 (m, 2H, 2'-H/5'-H), 7.59 (s, 1H, 8-H).

¹³C NMR (CDCl₃) δ 13.9 (SCH₂CH₂CH₂CH₃), 16.3 (NHCH(CH₂)CHPh), 22.1 (SCH₂CH₂CH₂CH₃), 25.3 (NHCH(CH₂)CHPh), 29.8 (NCH₃), 31.1 (SCH₂CH₂CH₂CH₃), 31.8 (SCH₂CH₂CH₂CH₃), 33.5 (NHCH(CH₂)CHPh), 115.7 (d, J=17 Hz, C-2'), 117.1 (d, J=17 Hz, C-5'), 117.6 (C-5), 122.8 (C-6'), 138.0 (C-1'), 139.7 (C-8), 148.0-150.0 (dd, J=246 Hz/13 Hz, C-4'), 149.4-151.4 (dd, J=247 Hz/13 Hz, C-3'), 150.8 (C-4), 154.7 (C-6), 165.6 (C-2).

Example 26: synthesis of 2-(butylthio)-N-((1R,2S)-2-(3,4-difluorophenyl)cyclopropyl)-9-ethyl-9H-purin-6-amine (26c)

2-(Butylthio)-6-chloro-N⁴-ethylpyrimidine-4,5-diamine (26a)

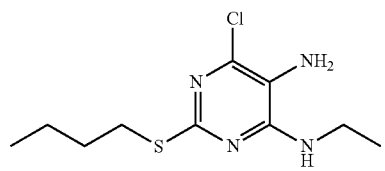 [SMILES: CCCCSc1nc(Cl)c(N)c(NCC)n1]

4,6-Dichloro-2-(ethylthio)pyrimidin-5-amine (25h) (0.5 g, 2.0 mmol) was dissolved in a solution of ethylamine 2.0 M in methanol (3.0 mL, 6.0 mmol). The reaction mixture was introduced in a sealed vessel and heated at 100° C. for 1 h. After concentration of the reaction mixture to dryness under vacuum, the residue was purified by silica gel column chromatography.

Yield: 91%.
Melting point: 80-82° C.

¹H NMR (DMSO-d₆) δ 0.89 (t, J=7.3 Hz, 3H, SCH₂CH₂CH₂CH₃), 1.16 (t, J=7.1 Hz, 3H, NHCH₂CH₃), 1.38 (h, J=7.3 Hz, 2H, SCH₂CH₂CH₂CH₃), 1.60 (p, J=7.3 Hz, 2H, SCH₂CH₂CH₂CH₃), 2.96 (t, J=7.3 Hz, 2H, SCH₂CH₂CH₂CH₃), 3.38 (p, J=7.0 Hz, 2H, NHCH₂CH₃), 4.74 (s, 2H, NH₂), 6.95 (t, J=4.7 Hz, 1H, NHCH₂CH₃).

¹³C NMR (DMSO-d₆) δ 13.5 (SCH₂CH₂CH₂CH₃), 14.4 (NHCH₂CH₃), 21.5 (SCH₂CH₂CH₂CH₃), 29.8 (SCH₂CH₂CH₂CH₃), 31.5 (SCH₂CH₂CH₂CH₃), 35.7 (NHCH₂CH₃), 119.8 (C-5), 137.3 (C-6), 152.5 (C-4), 155.4 (C-2).

2-(Butylthio)-6-chloro-9-ethyl-9H-purine (26b)

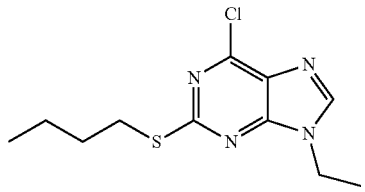 [SMILES: CCCCSc1nc(Cl)c2ncn(CC)c2n1]

A solution of (26a) (261.0 mg, 1 mmol) in acetic acid (2.5 mL) and triethyl orthoformate (2.5 mL, 15 mmol) was heated at a temperature of 130° C. under reflux for 1 h. After distillation of the acetic acid and triethyl orthoformate under vacuum, the residue was purified by silica gel column chromatography.

Yield: 70%.

Melting point: 69-71° C.

$^1$H NMR (DMSO-d$_6$) δ 0.93 (t, J=7.4 Hz, 3H, SCH$_2$CH$_2$CH$_2$CH$_3$), 1.45 (m, 5H, SCH$_2$CH$_2$CH$_2$CH$_3$/NCH$_2$CH$_3$), 1.70 (p, J=7.4 Hz, 2H, SCH$_2$CH$_2$CH$_2$CH$_3$), 3.19 (t, J=7.3 Hz, 2H, SCH$_2$CH$_2$CH$_2$CH$_3$), 4.25 (q, J=7.3 Hz, 2H, NCH$_2$CH$_3$), 8.56 (s, 1H, CH).

$^{13}$C NMR (DMSO-d$_6$) δ 13.5 (SCH$_2$CH$_2$CH$_2$CH$_3$), 14.7 (NCH$_2$CH$_3$), 21.4 (SCH$_2$CH$_2$CH$_2$CH$_3$), 30.3 (SCH$_2$CH$_2$CH$_2$CH$_3$), 30.8 (SCH$_2$CH$_2$CH$_2$CH$_3$), 39.0 (NCH$_2$CH$_3$), 128.1 (C-5), 146.0 (C-8), 148.9 (C-6), 152.7 (C-4), 163.8 (C-2).

2-(Butylthio)-N-((1R,2S)-2-(3,4-difluorophenyl)cyclopropyl)-9-ethyl-9H-purin-6-amine (26c)

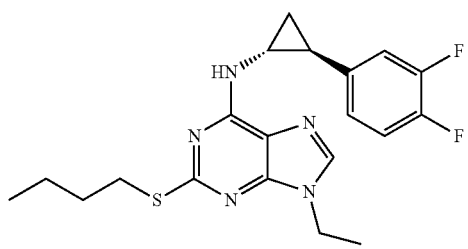 [SMILES: CCCCSc1nc(N[C@@H]2C[C@H]2c2ccc(F)c(F)c2)c2ncn(CC)c2n1]

A solution of (26b) (135.0 mg, 0.5 mmol) in acetonitrile (2.5 mL) was supplemented with (1R,2S)-2-(3,4-difluorophenyl)cyclopropanamine (93.0 mg, 0.55 mmol) and triethylamine (0.13 mL) and then heated at 90° C. under reflux for 1 h. After distillation of acetonitrile and triethylamine under vacuum, the residue was purified by silica gel column chromatography.

Yield: 56%.

Melting point: 92-94° C.

$^1$H NMR (CDCl$_3$) δ 0.89 (t, J=7.4 Hz, 3H, SCH$_2$CH$_2$CH$_2$CH$_3$), 1.31 (m, 2H, NHCH(CH$_2$)CHPh), 1.36 (m, 2H, SCH$_2$CH$_2$CH$_2$CH$_3$), 1.50 (t, J=7.3 Hz, 3H, NCH$_2$CH$_3$), 1.63 (p, J=7.3 Hz, 2H, SCH$_2$CH$_2$CH$_2$CH$_3$), 2.09 (ddd, J=9.5 Hz/6.6 Hz/3.2 Hz, 1H, NHCH(CH$_2$)CHPh), 3.02 (m, 1H, SCH$_2$CH$_2$CH$_2$CH$_3$), 3.10 (m, 2H, NHCH(CH$_2$)CHPh/SCH$_2$CH$_2$CH$_2$CH$_3$), 4.18 (q, J=7.3 Hz, 2H, NCH$_2$CH$_3$), 5.93 (bs, 1H, NH), 6.99 (m, 1H, 6'-H), 7.08 (m, 2H, 2'-H/5'-H), 7.63 (s, 1H, 8-H).

$^{13}$C NMR (CDCl$_3$) δ 13.9 (SCH$_2$CH$_2$CH$_2$CH$_3$), 15.6 (NCH$_2$CH$_3$), 16.2 (NHCH(CH$_2$)CHPh), 22.1 (SCH$_2$CH$_2$CH$_2$CH$_3$), 25.4 (NHCH(CH$_2$)CHPh), 31.1 (SCH$_2$CH$_2$CH$_2$CH$_3$), 31.8 (SCH$_2$CH$_2$CH$_2$CH$_3$), 33.5 (NHCH(CH$_2$)CHPh), 38.8 (NCH$_2$CH$_3$), 115.8 (d, J=17 Hz, C-2'), 117.1 (d, J=17 Hz, C-5'), 117.8 (C-5), 122.9 (C-6'), 138.1 (C-1'), 138.6 (C-8), 148.2-150.1 (dd, J=246 Hz/12 Hz, C-4'), 149.4-151.4 (dd, J=235 Hz/10 Hz, C-3'), 150.3 (C-4), 154.7 (C-6), 165.6 (C-2).

Example 27: synthesis of N-((1R,2S)-2-(3,4-difluorophenyl)cyclopropyl)-1-methyl-6-(methylthio)-1H-pyrazolo[3,4-d]pyrimidin-4-amine (27k)

4,6-Dichloro-2-(methylthio)pyrimidine-5-carbaldehyde (27i)

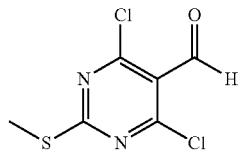

POCl$_3$ (3.2 mL) was cooled at 5° C. on an ice bath and supplemented dropwise by dimethylformamide (20 mL, 215 mmol). 2-(Methylthio)pyrimidine-4,6-diol (22e) (5 g, 31.6 mmol) was then added portion-wise and the mixture was stirred at 100° C. for 20 h. The mixture was poured on crushed ice and extracted with CH$_2$Cl$_2$ (3×50 mL). The combined organic layers were dried and evaporated to dryness under vacuum.

Yield: 52%.

Melting point: 87-89° C.

$^1$H NMR (DMSO-d$_6$) δ 2.57 (s, 3H, SCH$_3$), 10.07 (s, 1H, COH).

$^{13}$C NMR (DMSO-d$_6$) δ 13.3 (SCH$_3$), 112.9 (C-5), 159.3 (C-4/C-6), 168.2 (C-2), 186.6 (COH).

4-chloro-6-(methylthio)-1H-pyrazolo[3,4-d]pyrimidine (27i')

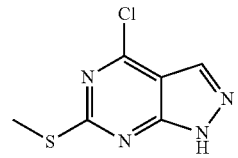

To a suspension of (27i) (2.5 g, 11.2 mmol) in THF (25 mL) cooled at 5° C. on an ice bath, were added dropwise hydrazine monohydrate (0.65 mL, 13 mmol) and triethylamine (1.8 mL, 13 mmol). After 1 hour stirring at 5° C., the mixture was evaporated to dryness under vacuum and the residue was purified by silica gel column chromatography.

Yield: 95%.

Melting point: >300° C.

$^1$H NMR (DMSO-d$_6$) δ 2.59 (s, 3H, SCH$_3$), 8.32 (s, 1H, CH), 14.25 (bs, 1H, NH).

$^{13}$C NMR (DMSO-d$_6$) δ 13.9 (SCH$_3$), 109.6 (C-3a), 133.1 (C-3), 152.9-155.4 (C-4/C-7a), 168.7 (C-6).

4-chloro-1-methyl-6-(methylthio)-1H-pyrazolo[3,4-d]pyrimidine (27j)

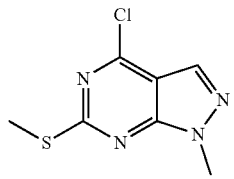

To a solution of (27') (1.0 g, 5.0 mmol) in acetonitrile (10 mL) cooled at 5° C. on an ice bath, were added NaH (144 mg, 6.0 mmol) and iodomethane (0.47 mL, 7.5 mmol). After 3 hours stirring at 50° C., acetonitrile was evaporated to dryness under vacuum and the residue was partitioned between water (50 mL) and dichloromethane (2×50 mL). The combined organic layers were dried and evaporated to dryness under vacuum. The residue was purified by silica gel column chromatography.

Yield: 82%.
Melting point: 85-87° C.
$^1$H NMR (DMSO-$d_6$) δ 2.63 (s, 3H, SCH$_3$), 4.00 (s, 3H, NCH$_3$), 8.34 (s, 1H, CH).
$^{13}$C NMR (DMSO-$d_6$) δ 13.9 (SCH$_3$), 34.0 (NCH$_3$), 110.0 (C-3a), 132.3 (C-3), 152.9 (C-4), 153.5 (C-7a), 168.8 (C-6).

N-((1R,2S)-2-(3,4-difluorophenyl)cyclopropyl)-1-methyl-6-(methylthio)-1H-pyrazolo[3,4-d]pyrimidin-4-amine (27k)

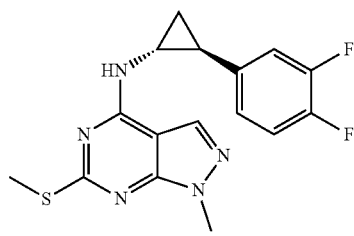 [SMILES: CSc1nc(N[C@@H]2C[C@H]2c2ccc(F)c(F)c2)c2cnn(C)c2n1]

A solution of (27j) (107.0 mg, 0.5 mmol) in acetonitrile 2.5 mL) was supplemented with (1R,2S)-2-(3,4-difluorophenyl)cyclopropanamine (93.0 mg, 0.55 mmol) and triethylamine (0.13 mL) and then heated at 90° C. under reflux for 1 h. After distillation of acetonitrile and triethylamine under vacuum, the residue was purified by silica gel column chromatography.

Yield: 84%.
Melting point: 128.5-130° C.
$^1$H NMR (CDCl$_3$) δ 1.40 (m, 2H, NHCH(CH$_2$)CHPh), 2.17 (s, 1H, NHCH(CH$_2$)CHPh), 2.55 (s, 3H, SCH$_3$), 3.10 (s, 1H, NHCH(CH$_2$)CHPh), 3.95 (s, 3H, NCH$_3$), 5.87 (bs, 1H, NH), 6.87 (m, 2H, 2'-H/6'-H), 7.12 (q, J=8.7 Hz, 1H, 5'-H), 7.59 (s, 1H, 3-H).
$^{13}$C NMR (CDCl$_3$) δ 14.2 (SCH$_3$), 18.3 (NHCH(CH$_2$) CHPh), 25.6 (NHCH(CH$_2$)CHPh), 33.8 (NCH$_3$), 34.9 (NHCH(CH$_2$)CHPh), 97.8 (C-3a), 114.6 (C-2'), 117.4 (C-5'), 121.7 (C-6'), 132.0 (C-3), 136.8 (C-1'), 149.7-150.8 (C-3'/C-4'), 154.8 (C-7a), 169.2 (C-6).

Example 28: synthesis of N-((1R,2S)-2-(3,4-difluorophenyl)cyclopropyl)-6-(ethylthio)-1-methyl-1H-pyrazolo[3,4-d]pyrimidin-4-amine hydrochloride (28x·HCl)

N-((1R,2S)-2-(3,4-difluorophenyl)cyclopropyl)-1-methyl-6-(methylsulfonyl)-1H-pyrazolo[3,4-d]pyrimidin-4-amine (28r)

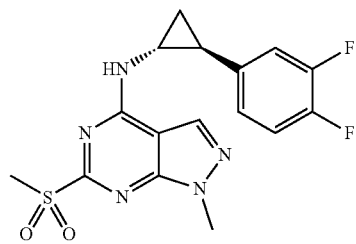 [SMILES: Cn1ncc2c(N[C@@H]3C[C@H]3c3ccc(F)c(F)c3)nc(S(C)(=O)=O)nc21]

A solution of (27j) (125.0 mg, 0.36 mmol) in methylene chloride (10 mL) was cooled to 5° C. on an ice bath and supplemented with 3-chloroperbenzoic acid (140.0 mg, 0.80 mmol). After stirring at room temperature for 4 hours, the mixture was washed with a solution of NaOH 0.1 M (2×10 mL). The organic layer was dried, filtered and methylene chloride was evaporated to dryness under vacuum. The resulting oily residue was used without further purification in the next step (28x).

Yield: 58%.
Melting point: oil.
$^1$H NMR (CDCl$_3$) δ 1.50 (m, 2H, NHCH(CH$_2$)CHPh), 2.23 (s, 1H, NHCH(CH$_2$)CHPh), 3.18 (s, 1H, NHCH(CH$_2$) CHPh), 3.34 (s, 3H, SO$_2$CH$_3$), 4.07 (s, 3H, NCH$_3$), 6.48 (s, 1H, NH), 6.86 (m, 2H, 2'-H/6'-H), 7.15 (s, 1H, 5'-H), 7.75 (s, 1H, 3-H).
$^{13}$C NMR (CDCl$_3$) δ 18.3 (NHCH(CH$_2$)CHPh), 26.1 (NHCH(CH$_2$)CHPh), 34.4 (NCH$_3$), 35.1 (NHCH(CH$_2$) CHPh), 39.1 (SO$_2$CH$_3$), 100.5 (C-3a), 114.5 (C-2'), 117.9 (C-5'), 121.8 (C-6'), 133.0 (C-3), 136.0 (C-1'), 150.1 (C-3'/C-4'), 153.4 (C-7a), 159.5 (C-4), 162.4 (C-6).

N-((1R,2S)-2-(3,4-difluorophenyl)cyclopropyl)-6-(ethylthio)-1-methyl-1H-pyrazolo[3,4-d]pyrimidin-4-amine hydrochloride (28x·HCl)

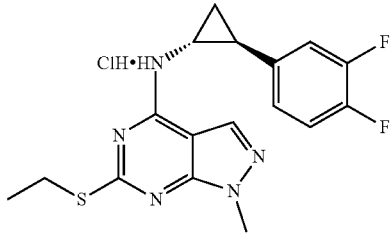

A solution of (28r) (150.0 mg, 0.40 mmol) in THF (6 mL) was supplemented with ethanethiol (0.06 mL, 0.80 mmol) and K$_2$CO$_3$ (110.0 mg, 0.80 mmol). After stirring at room temperature for 24 hours, THF was evaporated to dryness under vacuum and the residue was purified by silica gel column chromatography. The resulting oil was dissolved in diethyl ether (10 mL) and supplemented dropwise with a saturated solution of HCl in diethyl ether. The precipitate of the title compound was collected by filtration, washed with diethyl ether and dried.

Yield: 67%.

Melting point: 164-168° C.

$^1$H NMR (CDCl$_3$) δ 1.46 (t, J=7.3 Hz, 3H, SCH$_2$CH$_3$), 1.52 (d, J=6.0 Hz, 1H, NHCH(CH$_2$)CHPh), 1.69 (m, 1H, NHCH(CH$_2$)CHPh), 2.37 (s, 1H, NHCH(CH$_2$)CHPh), 3.09 (s, 1H, NHCH(CH$_2$)CHPh), 3.33 (q, J=7.2 Hz, 2H, SCH$_2$CH$_3$), 4.00 (s, 3H, NCH$_3$), 6.84 (d, J=7.0 Hz, 1H, 6'-H), 6.89 (t, J=8.5 Hz, 1H, 2'-H), 7.15 (q, J=8.4 Hz, 1H, 5'-H), 7.73 (s, 1H, 3-H), 10.48 (bs, 1H, NH).

$^{13}$C NMR (CDCl$_3$) δ 14.1 (SCH$_2$CH$_3$), 17.6 (NHCH(CH$_2$)CHPh), 25.5 (NHCH(CH$_2$)CHPh), 25.9 (SCH$_2$CH$_3$), 34.5 (NCH$_3$), 35.3 (NHCH(CH$_2$)CHPh), 96.3 (C-3a), 114.8 (C-2'), 118.1 (C-5'), 122.1 (C-6'), 135.5 (C-3), 135.3 (C-1'), 148.9-150.1 (C-4'), 150.3-151.4 (C-3'), 151.7 (C-4), 154.2 (C-7a), 160.8 (C-6).

Example 29: synthesis of N-((1R,2S)-2-(3,4-difluorophenyl)cyclopropyl)-6-(propylthio)-1-methyl-1H-pyrazolo[3,4-d]pyrimidin-4-amine hydrochloride (29x·HCl)

N-((1R,2S)-2-(3,4-difluorophenyl)cyclopropyl)-1-methyl-6-(propylthio)-1H-pyrazolo[3,4-d]pyrimidin-4-amine hydrochloride (29x·HCl)

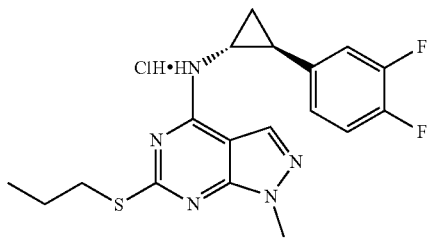

A solution of (28r) (150.0 mg, 0.40 mmol) in THF (6 mL) was supplemented with propanethiol (0.07 mL, 0.80 mmol) and K$_2$CO$_3$ (110.0 mg, 0.80 mmol). After stirring at room temperature for 24 hours, THF was evaporated to dryness under vacuum and the residue was purified by silica gel column chromatography. The resulting oil was dissolved in diethyl ether (10 mL) and supplemented dropwise with a saturated solution of HCl in diethyl ether. The precipitate of the title compound was collected by filtration, washed with diethyl ether and dried.

Yield: 66%.

Melting point: 110-115° C.

$^1$H NMR (CDCl$_3$) δ 1.08 (t, J=7.3 Hz, 3H, SCH$_2$CH$_2$CH$_3$), 1.51 (m, 1H, NHCH(CH$_2$)CHPh), 1.68 (m, 1H, NHCH(CH$_2$)CHPh), 1.82 (h, J=7.0 Hz, 2H, SCH$_2$CH$_2$CH$_3$), 2.36 (s, 1H, NHCH(CH$_2$)CHPh), 3.09 (m, 1H, NHCH(CH$_2$)CHPh/SCH$_2$CH$_2$CH$_3$), 3.29 (t, J=6.8 Hz, 1H, SCH$_2$CH$_2$CH$_3$), 4.00 (s, 3H, NCH$_3$), 6.84 (d, J=5.9 Hz, 1H, 6'-H), 6.89 (t, J=8.5 Hz, 1H, 2'-H), 7.15 (q, J=8.5 Hz, 1H, 5'-H), 7.73 (s, 1H, 3-H), 10.37 (bs, 1H, NH).

$^{13}$C NMR (CDCl$_3$) δ 13.5 (SCH$_2$CH$_2$CH$_3$), 17.6 (NHCH(CH$_2$)CHPh), 22.3 (SCH$_2$CH$_2$CH$_3$), 25.5 (NHCH(CH$_2$)CHPh), 33.3 (SCH$_2$CH$_2$CH$_3$), 34.4 (NCH$_3$), 35.3 (NHCH(CH$_2$)CHPh), 96.3 (C-3a), 114.8 (C-2'), 118.1 (C-5'), 122.1 (C-6'), 135.1 (C-3), 135.6 (C-1'), 148.9-150.1 (C-4'), 150.4-151.4 (C-3'), 151.8 (C-4), 154.3 (C-7a), 160.9 (C-6).

Example 30: synthesis of N-((1R,2S)-2-(3,4-difluorophenyl)cyclopropyl)-1-ethyl-6-(methylthio)-1H-pyrazolo[3,4-d]pyrimidin-4-amine hydrochloride (30k·HCl)

4-chloro-1-ethyl-6-(methylthio)-1H-pyrazolo[3,4-d]pyrimidine (30j)

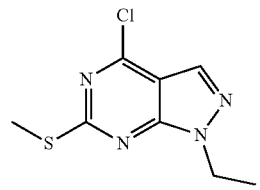

To a solution of (27i') (1.0 g, 5.0 mmol) in acetonitrile (10 mL) cooled at 5° C. on an ice bath, were added NaH (144 mg, 6.0 mmol) and iodoethane (0.60 mL, 7.5 mmol). After 3 hours stirring at 50° C., acetonitrile was evaporated to dryness under vacuum and the residue was partitioned between water (50 mL) and dichloromethane (2×50 mL). The combined organic layers were dried and evaporated to dryness under vacuum. The residue was purified by silica gel column chromatography.

Yield: 77%.

Melting point: 92-93.5° C.

$^1$H NMR (DMSO-d$_6$) δ 1.43 (t, J=7.2 Hz, 3H, NCH$_2$CH$_3$), 2.62 (s, 3H, SCH$_3$), 4.42 (q, J=7.2 Hz, 2H, NCH$_2$CH$_3$), 8.34 (s, 1H, CH).

$^{13}$C NMR (DMSO-d$_6$) δ 13.9 (SCH$_3$), 14.4 (NCH$_2$CH$_3$), 42.2 (NCH$_2$CH$_3$), 110.1 (C-3a), 132.3 (C-3), 153.0 (C-4/C-7a), 168.7 (C-6).

N-((1R,2S)-2-(3,4-difluorophenyl)cyclopropyl)-1-ethyl-6-(methylthio)-1H-pyrazolo[3,4-d]pyrimidin-4-amine hydrochloride (30k·HCl)

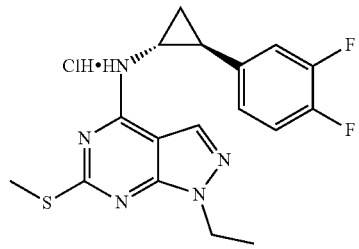

A solution of (30j) (114.0 mg, 0.5 mmol) in acetonitrile (2.5 mL) was supplemented with (1R,2S)-2-(3,4-difluorophenyl)cyclopropanamine (93.0 mg, 0.55 mmol) and triethylamine (0.13 mL) and then heated at 90° C. under reflux for 1 h. After distillation of acetonitrile and triethylamine under vacuum, the residue was purified by silica gel column chromatography. The resulting oil was dissolved in diethyl ether (10 mL) and supplemented dropwise with a saturated solution of HCl in diethyl ether. The precipitate of the title compound was collected by filtration, washed with diethyl ether and dried.

Yield: 54%.

Melting point: 176-180° C.

$^1$H NMR (CDCl$_3$) δ 1.51 (t, J=7.3 Hz, 4H, NHCH(CH$_2$)CHPh/NCH$_2$CH$_3$), 1.69 (s, 1H, NHCH(CH$_2$)CHPh), 2.37 (s, 1H, NHCH(CH$_2$)CHPh), 2.71 (s, 3H, SCH$_3$), 3.09 (s, 1H, NHCH(CH$_2$)CHPh), 4.41 (m, 2H, NCH$_2$CH$_3$), 6.85 (d, J=6.8 Hz, 1H, 6'-H), 6.89 (t, J=8.6 Hz, 1H, 2'-H), 7.16 (q, J=8.4 Hz, 1H, 5'-H), 7.75 (s, 1H, 3-H), 10.55 (s, 1H, NH).

$^{13}$C NMR (CDCl$_3$) δ 14.0 (SCH$_3$), 14.7 (NCH$_2$CH$_3$), 17.7 (NHCH(CH$_2$)CHPh), 25.4 (NHCH(CH$_2$)CHPh), 35.3 (NHCH(CH$_2$)CHPh), 43.0 (NCH$_2$CH$_3$), 96.3 (C-3a), 114.8 (C-2'), 118.1 (C-5'), 122.1 (C-6'), 135.2 (C-3), 135.5 (C-1'), 148.9-150.1 (C-4'), 150.3-151.5 (C-3'), 151.0 (C-7a), 154.2 (C-4), 160.8 (C-6).

Example 31: synthesis of N-((1R,2S)-2-(3,4-difluorophenyl)cyclopropyl)-1-ethyl-6-(ethylthio)-1H-pyrazolo[3,4-d]pyrimidin-4-amine hydrochloride (31x·HCl)

N-((1R,2S)-2-(3,4-difluorophenyl)cyclopropyl)-1-ethyl-6-(methylsulfonyl)-1H-pyrazolo[3,4-d]pyrimidin-4-amine (31r)

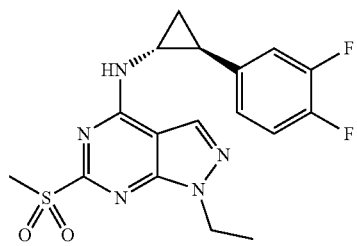 [SMILES: CCn1ncc2c(N[C@@H]3C[C@H]3c3ccc(F)c(F)c3)nc(S(C)(=O)=O)nc21]

A solution of (30k) (125.0 mg, 0.35 mmol) in methylene chloride (10 mL) was cooled to 5° C. on an ice bath and supplemented with 3-chloroperbenzoic acid (140.0 mg, 0.80 mmol). After stirring at room temperature for 4 hours, the mixture was washed with a solution of NaOH 0.1 M (2×10 mL). The organic layer was dried and filtered, methylene chloride was evaporated to dryness under vacuum and the residue was purified by silica gel column chromatography.

Yield: 87%.

Melting point: 95-100° C. (decomposition).

$^1$H NMR (CDCl$_3$) δ 1.51 (m, 5H, NHCH(CH$_2$)CHPh/NCH$_2$CH$_3$), 2.24 (s, 1H, NHCH(CH$_2$)CHPh), 3.20 (s, 1H, NHCH(CH$_2$)CHPh), 3.33 (s, 3H, SO$_2$CH$_3$), 4.53 (m, 2H, NCH$_2$CH$_3$), 6.58 (bs, 1H, NH), 6.90 (m, 2H, 2'-H/6'-H), 7.15 (m, 1H, 5'-H), 7.75 (s, 1H, 3-H).

$^{13}$C NMR (CDCl$_3$) δ 14.9 (NCH$_2$CH$_3$), 17.9 (NHCH(CH$_2$)CHPh), 25.7 (NHCH(CH$_2$)CHPh), 34.5 (NHCH(CH$_2$)CHPh), 39.2 (SO$_2$CH$_3$), 42.8 (NCH$_2$CH$_3$), 99.5 (C-3a), 114.8 (C-2'), 118.2 (C-5'), 122.1 (C-6'), 131.7 (C-3), 135.7 (C-1'), 148.9-150.1 (C-4'), 150.3-151.5 (C-3'), 152.8 (C-7a), 159.3 (C-4), 162.3 (C-6).

N-((1R,2S)-2-(3,4-difluorophenyl)cyclopropyl)-1-ethyl-6-(ethylthio)-1H-pyrazolo[3,4-d]pyrimidin-4-amine hydrochloride (31x·HCl)

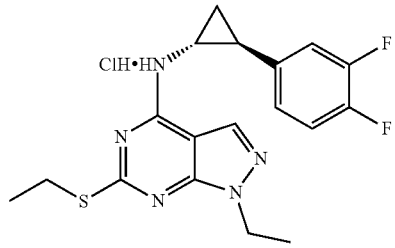

A solution of (31r) (150.0 mg, 0.38 mmol) in THF (6 mL) was supplemented with ethanethiol (0.06 mL, 0.80 mmol) and K$_2$CO$_3$ (110.0 mg, 0.80 mmol). After stirring at room temperature for 24 hours, THF was evaporated to dryness under vacuum and the residue was purified by silica gel column chromatography. The resulting oil was dissolved in diethyl ether (10 mL) and supplemented dropwise with a saturated solution of HCl in diethyl ether. The precipitate of the title compound was collected by filtration, washed with diethyl ether and dried.

Yield: 64%.

Melting point: 168-172° C.

$^1$H NMR (CDCl$_3$) δ 1.45 (t, J=7.3 Hz, 3H, SCH$_2$CH$_3$), 1.51 (t, J=7.2 Hz, 4H, NCH$_2$CH$_3$/NHCH(CH$_2$)CHPh), 1.69 (s, 1H, NHCH(CH$_2$)CHPh), 2.37 (s, 1H, NHCH(CH$_2$)CHPh), 3.09 (s, 1H, NHCH(CH$_2$)CHPh), 3.32 (q, J=7.1 Hz, 2H, SCH$_2$CH$_3$), 4.40 (hept, J=6.9 Hz, 2H, NCH$_2$CH$_3$), 6.85 (d, J=6.2 Hz, 1H, 6'-H), 6.89 (t, J=8.8 Hz, 1H, 2'-H), 7.15 (q, J=8.5 Hz, 1H, 5'-H), 7.74 (s, 1H, 3-H), 10.49 (bs, 1H, NH).

$^{13}$C NMR (CDCl$_3$) δ 14.1 (SCH$_2$CH$_3$), 14.7 (NCH$_2$CH$_3$), 17.6 (NHCH(CH$_2$)CHPh), 25.4 (NHCH(CH$_2$)CHPh), 25.9 (SCH$_2$CH$_3$), 35.3 (NHCH(CH$_2$)CHPh), 43.0 (NCH$_2$CH$_3$), 100.1 (C-3a), 114.8 (C-2'), 118.1 (C-5'), 122.1 (C-6'), 135.2 (C-3), 135.6 (C-1'), 148.9-150.1 (C-4'), 150.3-151.4 (C-3'), 151.1 (C-4), 154.2 (C-7a), 160.4 (C-6).

Example 32: synthesis of N-((1R,2S)-2-(3,4-difluorophenyl)cyclopropyl)-1-ethyl-6-(propylthio)-1H-pyrazolo[3,4-d]pyrimidin-4-amine hydrochloride (32x·HCl)

N-((1R,2S)-2-(3,4-difluorophenyl)cyclopropyl)-1-ethyl-6-(propylthio)-1H-pyrazolo[3,4-d]pyrimidin-4-amine hydrochloride (32x·HCl)

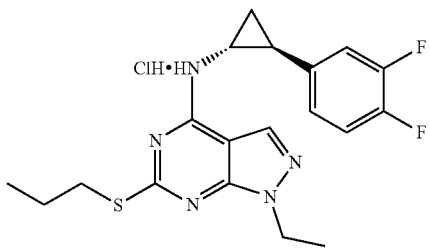

A solution of (31r) (150.0 mg, 0.38 mmol) in THF (6 mL) was supplemented with propanethiol (0.07 mL, 0.80 mmol)

and K$_2$CO$_3$ (110.0 mg, 0.80 mmol). After stirring at room temperature for 24 hours, THF was evaporated to dryness under vacuum and the residue was purified by silica gel column chromatography. The resulting oil was dissolved in diethyl ether (10 mL) and supplemented dropwise with a saturated solution of HCl in diethyl ether. The precipitate of the title compound was collected by filtration, washed with diethyl ether and dried.

Yield: 62%.

Melting point: 150-154° C.

$^1$H NMR (CDCl$_3$) δ 1.08 (t, J=7.3 Hz, 3H, SCH$_2$CH$_2$CH$_3$), 1.51 (t, J=7.3 Hz, 4H, NCH$_2$CH$_3$/NHCH(CH$_2$)CHPh), 1.69 (s, 1H, NHCH(CH$_2$)CHPh), 1.82 (h, J=7.3 Hz, 2H, SCH$_2$CH$_2$CH$_3$), 2.37 (s, 1H, NHCH(CH$_2$)CHPh), 3.08 (s, 1H, NHCH(CH$_2$)CHPh), 3.28 (t, J=7.1 Hz, 2H, SCH$_2$CH$_2$CH$_3$), 4.39 (hept, J=6.9 Hz, 2H, NCH$_2$CH$_3$), 6.85 (d, J=7.0 Hz, 1H, 6'-H), 6.89 (t, J=8.8 Hz, 1H, 2'-H), 7.15 (q, J=8.4 Hz, 1H, 5'-H), 7.73 (s, 1H, 3-H), 10.50 (bs, 1H, NH).

$^{13}$C NMR (CDCl$_3$) δ 13.5 (SCH$_2$CH$_2$CH$_3$), 14.7 (NCH$_2$CH$_3$), 17.6 (NHCH(CH$_2$)CHPh), 22.3 (SCH$_2$CH$_2$CH$_3$), 25.4 (NHCH(CH$_2$)CHPh), 33.3 (SCH$_2$CH$_2$CH$_3$), 35.3 (NHCH(CH$_2$)CHPh), 43.0 (NCH$_2$CH$_3$), 96.3 (C-3a), 114.8 (C-2'), 118.1 (C-5'), 122.1 (C-6'), 135.2 (C-3), 141.3 (C-1'), 149.2-150.4 (C-4'), 150.3-151.4 (C-3'), 151.1 (C-4), 154.2 (C-7a), 160.6 (C-6).

Example 33: synthesis of N-((1R,2S)-2-(3,4-difluorophenyl)cyclopropyl)-1-isopropyl-6-(methylthio)-1H-pyrazolo[3,4-d]pyrimidin-4-amine hydrochloride (33k·HCl)

4-chloro-1-isopropyl-6-(methylthio)-1H-pyrazolo[3,4-d]pyrimidine (33j)

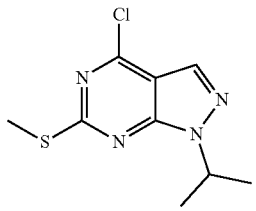

To a solution of (27i') (1.0 g, 5.0 mmol) in acetonitrile (10 mL) cooled at 5° C. on an ice bath, were added NaH (144 mg, 6.0 mmol) and 2-iodopropane (0.75 mL, 7.5 mmol). After 3 hours stirring at 50° C., acetonitrile was evaporated to dryness under vacuum and the residue was partitioned between water (50 mL) and dichloromethane (2×50 mL). The combined organic layers were dried and evaporated to dryness under vacuum. The residue was purified by silica gel column chromatography.

Yield: 73%.

Melting point: 114-115.5° C.

$^1$H NMR (DMSO-d$_6$) δ 1.50 (d, J=6.5 Hz, 6H, CH(CH$_3$)$_2$), 2.62 (s, 3H, SCH$_3$), 5.07 (hept, J=6.6 Hz, 1H, CH(CH$_3$)$_2$), 8.33 (s, 1H, CH).

$^{13}$C NMR (DMSO-d$_6$) δ 14.4 (SCH$_3$), 22.1 (CH(CH$_3$)$_2$), 49.9 (CH(CH$_3$)$_2$), 110.7 (C-3a), 132.6 (C-3), 153.0-153.4 (C-4/C-7a), 169.0 (C-6).

N-((1R,2S)-2-(3,4-difluorophenyl)cyclopropyl)-1-isopropyl-6-(methylthio)-1H-pyrazolo[3,4-d]pyrimidin-4-amine hydrochloride (33k·HCl)

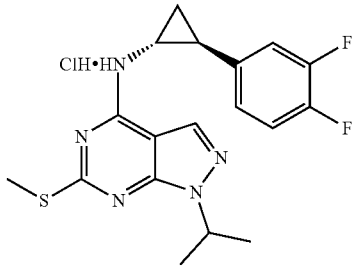

A solution of (33j) (121.0 mg, 0.5 mmol) in acetonitrile (2.5 mL) was supplemented with (1R,2S)-2-(3,4-difluorophenyl)cyclopropanamine (93.0 mg, 0.55 mmol) and triethylamine (0.13 mL) and then heated at 90° C. under reflux for 1 h. After distillation of acetonitrile and triethylamine under vacuum, the residue was purified by silica gel column chromatography. The resulting oil was dissolved in diethyl ether (10 mL) and supplemented dropwise with a saturated solution of HCl in diethyl ether. The precipitate of the title compound was collected by filtration, washed with diethyl ether and dried.

Yield: 87%.

Melting point: 159-163° C.

$^1$H NMR (CDCl$_3$) δ 1.50 (q, J=6.7 Hz, 1H, NHCH(CH$_2$)CHPh), 1.54 (d, J=6.7 Hz, 3H, NCH(CH$_3$)$_2$), 1.55 (d, J=6.7 Hz, 3H, NCH(CH$_3$)$_2$), 1.70 (ddd, J=10.4 Hz/6.6 Hz/4.5 Hz, 1H, NHCH(CH$_2$)CHPh), 2.37 (ddd, J=9.7 Hz/6.4 Hz/3.1 Hz, 1H, NHCH(CH$_2$)CHPh), 2.71 (s, 3H, SCH$_3$), 3.09 (dq, J=7.3 Hz/3.2 Hz, 1H, NHCH(CH$_2$)CHPh), 5.08 (hept, J=6.7 Hz, 1H, NCH(CH$_3$)$_2$), 6.84 (d, J=8.4 Hz, 1H, 6'-H), 6.89 (m, 1H, 2'-H), 7.16 (dt, J=9.6 Hz/8.4 Hz, 1H, 5'-H), 7.75 (s, 1H, 3-H), 10.57 (s, 1H, NH).

$^{13}$C NMR (CDCl$_3$) δ 14.0 (SCH$_3$), 17.7 (NHCH(CH$_2$)CHPh), 21.9 (CH(CH$_3$)$_2$), 25.4 (NHCH(CH$_2$)CHPh), 35.2 (NHCH(CH$_2$)CHPh), 50.1 (CH(CH$_3$)$_2$), 96.3 (C-3a), 114.7 (C-2'), 118.1 (C-5'), 122.0 (C-6'), 135.0 (C-3), 135.6 (C-1'), 148.9-150.1 (C-4'), 150.3-151.5 (C-3'), 150.4 (C-7a), 154.1 (C-4), 160.4 (C-6).

Example 34: synthesis of N-((1R,2S)-2-(3,4-difluorophenyl)cyclopropyl)-6-(methylthio)-1-propyl-1H-pyrazolo[3,4-d]pyrimidin-4-amine hydrochloride (34k·HCl)

4-Chloro-1-propyl-6-(methylthio)-1-propyl-1H-pyrazolo[3,4-d]pyrimidine (34j)

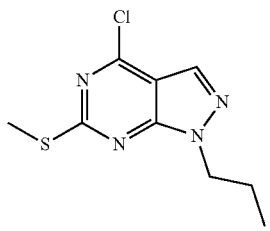

To a solution of (27i') (1.0 g, 5.0 mmol) in acetonitrile (10 mL) cooled at 5° C. on an ice bath, were added NaH (144 mg, 6.0 mmol) and 1-iodopropane (0.73 mL, 7.5 mmol). After 3 hours stirring at 50° C., acetonitrile was evaporated to dryness under vacuum and the residue was partitioned between water (50 mL) and dichloromethane (2×50 mL). The combined organic layers were dried and evaporated to dryness under vacuum. The residue was purified by silica gel column chromatography.

Yield: 78%.

Melting point: 41-43° C.

$^1$H NMR (DMSO-d$_6$) δ 0.83 (t, J=6.0 Hz, 3H, NCH$_2$CH$_2$CH$_3$), 1.88 (h, J=6.1 Hz, 2H, NCH$_2$CH$_2$CH$_3$), 2.62 (s, 3H, SCH$_3$), 4.35 (t, J=6.2 Hz, 2H, NCH$_2$CH$_2$CH$_3$), 8.35 (s, 1H, CH).

$^{13}$C NMR (DMSO-d$_6$) δ 11.0 (NCH$_2$CH$_2$CH$_3$), 13.9 (SCH$_3$), 22.2 (NCH$_2$CH$_2$CH$_3$), 48.6 (NCH$_2$CH$_2$CH$_3$), 110.0 (C-3a), 132.4 (C-3), 153.0 (C-4), 153.5 (C-7a), 168.7 (C-6).

N-((1R,2S)-2-(3,4-difluorophenyl)cyclopropyl)-6-(methylthio)-1-propyl-1H-pyrazolo[3,4-d]pyrimidin-4-amine hydrochloride (34k·HCl)

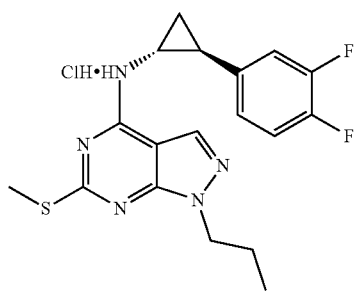

A solution of (34j) (121.0 mg, 0.5 mmol) in acetonitrile (2.5 mL) was supplemented with (1R,2S)-2-(3,4-difluorophenyl)cyclopropanamine (93.0 mg, 0.55 mmol) and triethylamine (0.13 mL) and then heated at 90° C. under reflux for 1 h. After distillation of acetonitrile and triethylamine under vacuum, the residue was purified by silica gel column chromatography. The resulting oil was dissolved in diethyl ether (10 mL) and supplemented dropwise with a saturated solution of HCl in diethyl ether. The precipitate of the title compound was collected by filtration, washed with diethyl ether and dried.

Yield: 76%.

Melting point: 155-159° C.

$^1$H NMR (CDCl$_3$) δ 0.93 (t, J=7.4 Hz, 3H, NCH$_2$CH$_2$CH$_3$), 1.51 (q, J=6.7 Hz, 1H, NHCH(CH$_2$)CHPh), 1.69 (m, 1H, NHCH(CH$_2$)CHPh), 1.94 (h, J=7.3 Hz, 2H, NCH$_2$CH$_2$CH$_3$), 2.38 (ddd, J=9.6 Hz/6.4 Hz/3.0 Hz, 1H, NHCH(CH$_2$)CHPh), 2.71 (s, 3H, SCH$_3$), 3.09 (dd, J=6.7 Hz/3.5 Hz, 1H, NHCH(CH$_2$)CHPh), 4.32 (m, 2H, NCH$_2$CH$_2$CH$_3$), 6.85 (d, J=8.3 Hz, 1H, 6'-H), 6.89 (m, 1H, 2'-H), 7.16 (m, 1H, 5'-H), 7.75 (s, 1H, 3-H), 10.57 (s, 1H, NH).

$^{13}$C NMR (CDCl$_3$) δ 11.3 (NCH$_2$CH$_2$CH$_3$), 14.0 (SCH$_3$), 17.6 (NHCH(CH$_2$)CHPh), 22.8 (NCH$_2$CH$_2$CH$_3$), 25.4 (NHCH(CH$_2$)CHPh), 35.3 (NHCH(CH$_2$)CHPh), 49.5 (NCH$_2$CH$_2$CH$_3$), 96.1 (C-3a), 114.8 (C-2'), 118.1 (C-5'), 122.0 (C-6'), 135.2 (C-3), 135.5 (C-1'), 148.9-150.1 (C-4'), 150.3-151.5 (C-3'), 151.5 (C-7a), 154.2 (C-4), 160.8 (C-6).

Example 35: synthesis of N-((1R,2S)-2-(3,4-difluorophenyl)cyclopropyl)-7-ethyl-2-(methylthio)-7H-pyrrolo[2,3-d]pyrimidin-4-amine hydrochloride (35p·HCl)

6-Amino-2-(methylthio)pyrimidin-4-ol (35l)

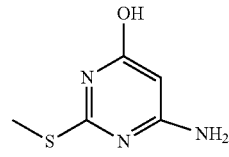

6-Amino-2-mercaptopyrimidin-4-ol (2.5 g, 17.5 mmol) was dissolved in KOH 10% (25 mL) and supplemented with methyl iodide (1.25 mL, 20.0 mmol). The reaction mixture was introduced in a sealed vessel and heated at 80° C. for 1 h. After cooling on an ice bath to 5° C., the mixture was acidified by addition of hydrochloric acid 6N and the resulting precipitate was filtered off and dried.

Yield: 95%.

Melting point: 261-264° C.

$^1$H NMR (DMSO-d$_6$) δ 2.42 (s, 3H, SCH$_3$), 4.90 (s, 1H, CH), 6.44 (s, 2H, NH$_2$), 11.47 (s, 1H, OH).

$^{13}$C NMR (DMSO-d$_6$) δ 12.6 (SCH$_3$), 81.2 (C-5), 163.6 (C-2), 164.3 (C-6).

2-(Methylthio)-7H-pyrrolo[2,3-d]pyrimidin-4-ol (35m)

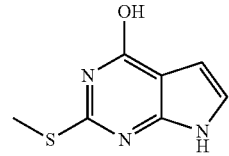

To a suspension of 35l (1.57 g, 10.0 mmol) in water (40 mL) were added sodium acetate (2.0 g, 24.5 mmol) and a 50% chloroacetaldehyde aqueous solution (2 mL, 14.2 mmol). After 1 hour at 80° C., the reaction mixture was cooled on an ice bath to 5° C. and the resulting precipitate was filtered off and purified by silica gel column chromatography.

Yield: 45%.

Melting point: >300° C.

$^1$H NMR (DMSO-d$_6$) δ 2.52 (s, 3H, SCH$_3$), 6.36 (m, 1H, 5-H), 6.91 (m, 1H, 6-H), 11.75 (s, 1H, NH), 12.03 (s, 1H, OH).

$^{13}$C NMR (DMSO-d$_6$) δ 12.8 (SCH$_3$), 102.0 (C-5), 104.2 (C-4a), 119.3 (C-6), 148.3 (C-7a), 154.2 (C-2), 158.8 (C-4).

4-Chloro-2-(methylthio)-7H-pyrrolo[2,3-d]pyrimidine (35n)

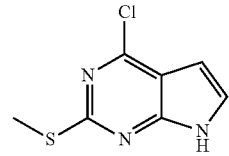

To a solution of (35m) (1.0 g, 5.5 mmol) in POCl₃ (10 mL) cooled at 5° C. on an ice bath was added dropwise diethylaniline (1.0 mL, 6.2 mmol). After 2 hours stirring at 80° C., the mixture was poured on crushed ice and the resulting precipitate was filtered off and purified by silica gel column chromatography.

Yield: 33%.

Melting point: 206-208° C.

¹H NMR (DMSO-d₆) δ 2.56 (s, 3H, SCH₃), 6.52 (s, 1H, 5-H), 7.52 (s, 1H, 6-H), 12.39 (s, 1H, NH).

¹³C NMR (DMSO-d₆) δ 13.8 (SCH₃), 99.0 (C-5), 113.2 (C-4a), 126.9 (C-6), 150.4-152.7 (C-4/C-7a), 162.7 (C-2).

N-((1R,2S)-2-(3,4-difluorophenyl)cyclopropyl)-2-(methylthio)-7H-pyrrolo[2,3-d]pyrimidin-4-amine (35o')

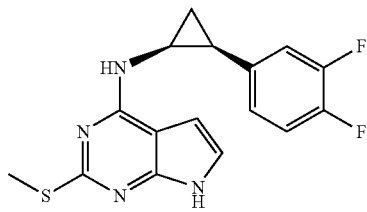 [SMILES: CSc1nc(N[C@H]2C[C@H]2c2ccc(F)c(F)c2)c2cc[nH]c2n1]

A solution of (35n) (200.0 mg, 1.0 mmol) in acetonitrile (5 mL) was supplemented with (1R,2S)-2-(3,4-difluorophenyl)cyclopropanamine (340.0 mg, 2.0 mmol) and triethylamine (0.30 mL) and then heated at 90° C. under reflux for 1 h. After distillation of acetonitrile and triethylamine under vacuum, the residue was purified by silica gel column chromatography.

Yield: 15%.

Melting point: 208-211° C.

¹H NMR (DMSO-d₆) δ 1.34 (m, 2H, NHCH(CH₂)CHPh), 2.03 (s, 1H, NHCH(CH₂)CHPh), 2.30 (s, 3H, SCH₃), 3.03 (s, 1H, NHCH(CH₂)CHPh), 6.40 (s, 1H, 5-H), 6.93 (s, 1H, 2'-H), 7.08 (s, 1H, 6'-H), 7.33 (m, 2H, 6-H/5'-H), 7.84 (s, 1H, NHCH(CH₂)CHPh), 11.40 (s, 1H, NH).

¹³C NMR (CDCl₃) δ 13.3 (SCH₃), 99.5 (C-5), 112.1 (C-4a), 117.0 (C-5'), 119.9 (C-2'), 122.9 (C-6'), 139.6 (C-1'), 147.0-148.3 (C-4'), 148.6-150.0 (C-3'), 162.3 (C-2).

N-((1R,2S)-2-(3,4-difluorophenyl)cyclopropyl)-7-ethyl-2-(methylthio)-7H-pyrrolo[2,3-d]pyrimidin-4-amine hydrochloride (35p·HCl)

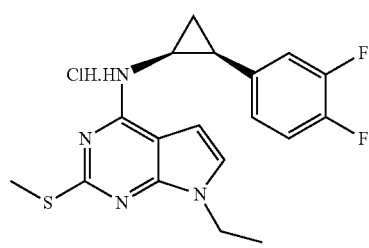

To a solution of (35o') (166.0 mg, 0.5 mmol) in acetonitrile (10 mL) cooled at 5° C. on an ice bath, were added NaH (15 mg, 0.6 mmol) and iodoethane (0.060 mL, 0.75 mmol). After 1 hour stirring at 50° C., acetonitrile was evaporated to dryness under vacuum and the residue was partitioned between water (50 mL) and dichloromethane (2×50 mL). The combined organic layers were dried and evaporated to dryness under vacuum. The residue was purified by silica gel column chromatography. The resulting oil was dissolved in diethyl ether (10 mL) and supplemented dropwise with a saturated solution of HCl in diethyl ether. The precipitate of the title compound was collected by filtration, washed with diethyl ether and dried.

Yield: 74%.

Melting point: 189-194° C.

¹H NMR (CDCl₃) δ 1.46 (t, J=7.3 Hz, 4H, NHCH(CH₂)CHPh/NCH₂CH₃), 1.66 (m, 1H, NHCH(CH₂)CHPh), 2.30 (m, 1H, NHCH(CH₂)CHPh), 2.70 (s, 3H, SCH₃), 3.09 (m, 1H, NHCH(CH₂)CHPh), 4.22 (q, J=7.3 Hz, 2H, NCH₂CH₃), 6.35 (d, J=3.4 Hz, 1H, 5-H), 6.81 (d, J=8.3 Hz, 1H, 6'-H), 6.87 (m, 1H, 2'-H), 6.90 (d, J=3.6 Hz, 1H, 6-H), 7.13 (q, J=8.5 Hz, 1H, 5'-H), 9.99 (s, 1H, NH).

¹³C NMR (CDCl₃) δ 14.0 (SCH₃), 15.5 (NCH₂CH₃), 17.9 (NHCH(CH₂)CHPh), 25.7 (NHCH(CH₂)CHPh), 35.2 (NHCH(CH₂)CHPh), 40.3 (NCH₂CH₃), 98.1 (C-4a), 103.4 (C-5), 114.8 (C-2'), 117.8 (C-5'), 122.0 (C-6'), 125.4 (C-6), 136.4 (C-1'), 148.3 (7a), 149.1-151.1 (C-3'/C-4'), 153.4 (C-4), 155.9 (C-2).

2. Examples of Pyrimidines Derivatives for Use in Prevention and Treatment of Gram-Negative Bacterial Infection The following biological examples are provided for the purpose of illustrating the present invention and by no means should be interpreted to limit the scope of the present invention.

Example 1: Antibacterial Effects of Molecules 2329, 2412, 2452, and 2461 Together with Polymyxin B Nonapeptide on *Escherichia coli* (ATCC8739): Determination of Minimal Inhibitory Concentration (MIC)

Molecules 2329, 2412, 2452, and 2461 correspond respectively to the following formulae:

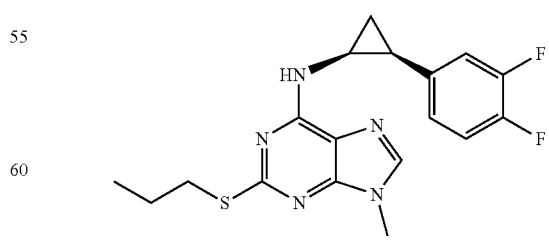

2329 (1c)

2329 is N-((1R,2S)-2-(3,4-difluorophenyl)cyclopropyl)-9-methyl-2-(propylthio)-9H-purin-6-amine (Also Called 1c Above)

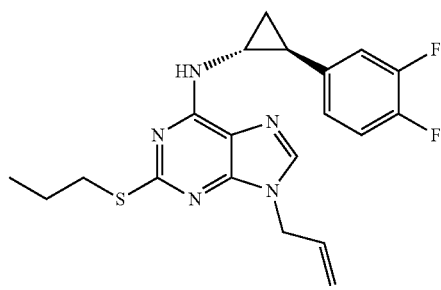

2412 (15c)

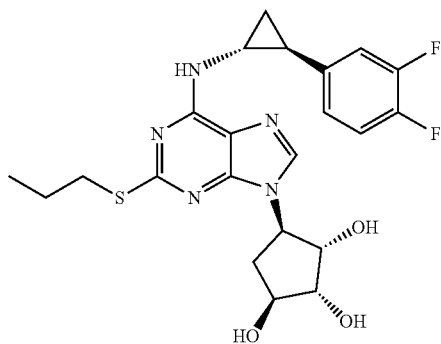

2461 (19d)

2412 is 9-allyl-N-((1R,2S)-2-(3,4-difluorophenyl)cyclopropyl)-2-(propylthio)-9H-purin-6-amine (Also Called 15c)

2461 is (1S,2R,3S,4R)-4-(6-(((1R,2S)-2-(3,4-difluorophenyl)cyclopropyl)amino)-2-(propylthio)-9H-purin-9-yl)cyclopentane-1,2,3-triol (Also Called 19d).

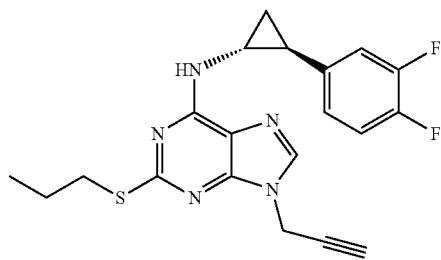

2452 (17c)

2452 is N-((1R,2S)-2-(3,4-difluorophenyl)cyclopropyl)-9-(prop-2-yn-1-yl)-2-(propylthio)-9H-purin-6-amine (Also Called 17c).

Polymyxin B nonapeptide (PMBN) is represented by the following formula (VII) and is produced by Sigma-Aldrich (product P2076).

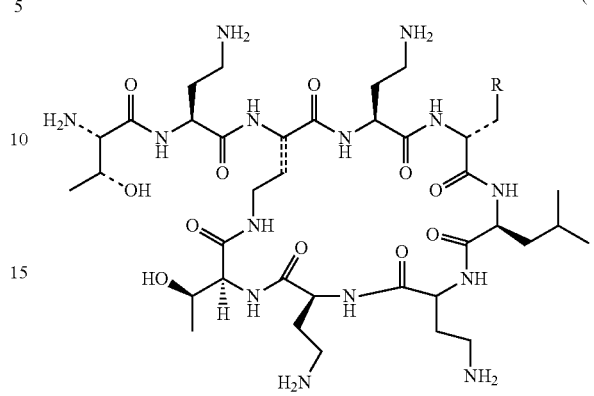

(VII)

wherein R is Ph.

The Minimal Inhibitory Concentration (MIC) of molecules 2329, 2412, 2452 and 2461 together with polymyxin B nonapeptide (PMBN) was determined on *Escherichia coli* (ATCC 8739) according to EUCAST (European Committee on Antimicrobial Susceptibility Testing) recommendations.

Briefly, a single colony grown on a Luria-Bertani Agar (LB) plate was resuspended and cultured in the LB medium overnight (O/N) in aerobic conditions (37° C. with 220 rpm shaking), next day a 1:50 inoculum in Mueller-Hinton broth (MHB) was incubated in aerobic conditions for 1h30 (OD=0.08-0.1) and an inoculum of 1:300 dilution, corresponding to $3 \times 10^6$ CFU/ml, was incubated in presence or absence of different concentrations of the molecules in 1% DMSO (vehicle) with or without Polymyxin B nonapeptide (PMBN) at 40 µg/ml. After O/N growth the OD of each culture was measured at 600 nm in a spectrophotometer ($OD_{600}$). The MIC represents the concentration at which there is no visible growth of bacteria, i.e. ΔOD at 600 nm equal to zero wherein ΔOD is the difference between the resulting optical density (OD) with the molecule together with PMBN, and the optical density (OD) of the blank (blank is the medium) alone.

As shown in Table 1, the MIC for molecules 2329, 2452 and 2461 together with PMBN against *Escherichia coli* (ATCC 8739) is equal to 10 µM, while it is 50 µM for molecules 2412. The molecules 2329, 2452, 2461 and 2412 taken alone in concentrations up to 100 µM or 40 µg/ml PMBN alone was unable to inhibit *E. coli* growth.

Example 2: Antibacterial Effects of Pyrazolopyrimidine Molecule 2666 Together with Polymyxin B Nonapeptide on *Escherichia coli* (ATCC 8739): Determination of Minimal Inhibitory Concentration (MIC)

Pyrazolopyrimidine molecule 2666 corresponds to 2666 (28x.HCl)

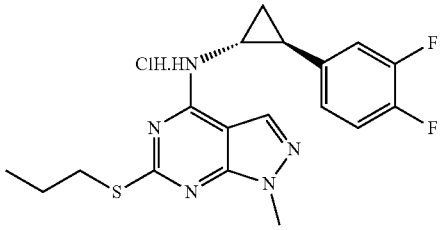

2666 is N-((1R,2S)-2-(3,4-difluorophenyl)cyclopropyl)-6-(ethylthio)-1-methyl-1H-pyrazolo[3,4-d]pyrimidin-4-amine hydrochloride (Also Called 28x·HCl Above);

Further experiments were conducted in order to determine the Minimal Inhibitory Concentration (MIC) which is the minimal-concentration required to prevent bacterial growth A single colony grown on an Lurian-Bertani (LB) agar plate is resuspended and cultured in LB medium overnight (O/N) in aerobic conditions (37° C. with 220 rpm shaking), next day a 1:50 inoculum in Mueller-Hinton broth (MHB) is incubated in aerobic conditions for 1h30 (OD=0.08-0.1) and an inoculum of 1:300 dilution, corresponding to $3 \times 10^6$ CFU/ml, is incubated in presence or absence of different concentrations of the tested molecules in 1% DMSO (vehicle) with or without PMBN at 40 µg/ml. After O/N growth the OD of each culture was measured at 600 nm ($OD_{600}$) in a spectrophotometer (Victor 3-Perkin Elmer). The MIC represents the concentration at which there is no visible growth of bacteria, i.e. ΔOD at 600 nm equal to zero wherein ΔOD is the difference between the resulting optical density (OD) with the molecule together with PMBN, and the optical density (OD) of the blank (blank is the medium) alone.

As shown in Table 1, the MIC for 2666 together with PMBN against *Escherichia coli* (ATCC 8739) is equal to 10 µM. The molecule 2666 alone in concentrations up to 100 µM or 40 µg/ml PMBN alone did not inhibit *E. coli* growth.

Example 3: Antibacterial Effects of Molecules 2329, 2412, 2452, and 2461 Together with Polymyxin B Nonapeptide on *Pseudomonas aeruginosa*: Determination of Minimal Inhibitory Concentration (MIC)

Further experiments were conducted using the clinically relevant Gram-negative bacterial strain of *Pseudomonas aeruginosa* (ATCC27853).

A single colony grown on an tryptic soy agar plate is resuspended and cultured in tryptic soy broth medium overnight (O/N) in aerobic conditions (37° C. with 220 rpm shaking), next day a 1:100 inoculum in Mueller-Hinton broth (MHB) is incubated in aerobic conditions for 3h (OD=0.5-0.6) and an inoculum of 1:1000 dilution, corresponding to $1-3 \times 10^5$ CFU/ml, is incubated in presence or absence of different concentrations of the tested molecules in 1% DMSO (vehicle) with or without PMBN at 0.5 µg/ml. After 28-30h growth the OD of each culture was measured at 600 nm ($OD_{600}$) in a spectrophotometer (Victor 3-Perkin Elmer). The MIC represents the concentration at which there is no visible growth of bacteria, i.e. ΔOD at 600 nm equal to zero (blank is the medium alone) wherein ΔOD is the difference between the resulting optical density (OD) with the molecule together with PMBN, and the optical density (OD) of the blank (blank is the medium) alone.

As shown in Table 1, the MIC for molecules 2329, 2412, 2452 and 2461 together with PMBN against *Pseudomonas aeruginosa* (ATCC27853) is equal to 50 µM.

Molecules 2329, 2412, 2452, and 2461 alone in concentrations up to 100 µM or 0.5 µg/ml PMBN alone did not inhibit *Pseudomonas aeruginosa* growth.

Example 4: Antibacterial Effects of Pyrazolopyrimidine Molecule 2666 Together with Polymyxin B Nonapeptide on *Pseudomonas aeruginosa* (ATCC27853): Determination of Minimal Inhibitory Concentration (MIC)

Further experiments were conducted using the clinically relevant Gram-negative bacterial strain of *Pseudomonas aeruginosa* (ATCC27853).

A single colony grown on an tryptic soy agar plate is resuspended and cultured in tryptic soy broth medium overnight (O/N) in aerobic conditions (37° C. with 220 rpm shaking), next day a 1:100 inoculum in Mueller-Hinton broth (MHB) is incubated in aerobic conditions for 3h (OD=0.5-0.6) and an inoculum of 1:1000 dilution, corresponding to $1-3 \times 10^5$ CFU/ml, is incubated in presence or absence of different concentrations of the tested molecules in 1% DMSO (vehicle) with or without PMBN at 0.5 µg/ml. After 28-30h growth the OD of each culture was measured at 600 nm ($OD_{600}$) in a spectrophotometer (Victor 3-Perkin Elmer). The MIC represents the concentration at which there is no visible growth of bacteria, i.e. ΔOD at 600 nm equal to zero (blank is the medium alone) wherein ΔOD is the difference between the resulting optical density (OD) with the molecule together with PMBN, and the optical density (OD) of the blank (blank is the medium) alone.

As shown in Table 1, the MIC for molecules 2666 together with PMBN against *Pseudomonas aeruginosa* is equal to 50 µM. Molecule 2666 alone in concentration up to 100 µM or 0.5 µg/ml PMBN alone, did not inhibit *P. aeruginosa* growth.

Example 5: Antibacterial Effects of Purine Molecules 2511, 2525 and 2833 Together with Polymyxin B Nonapeptide on *Escherichia coli* (ATCC8739): Determination of Minimal Inhibitory Concentration (MIC)

Molecules 2511, 2525 and 2833 correspond respectively to the following formulae:

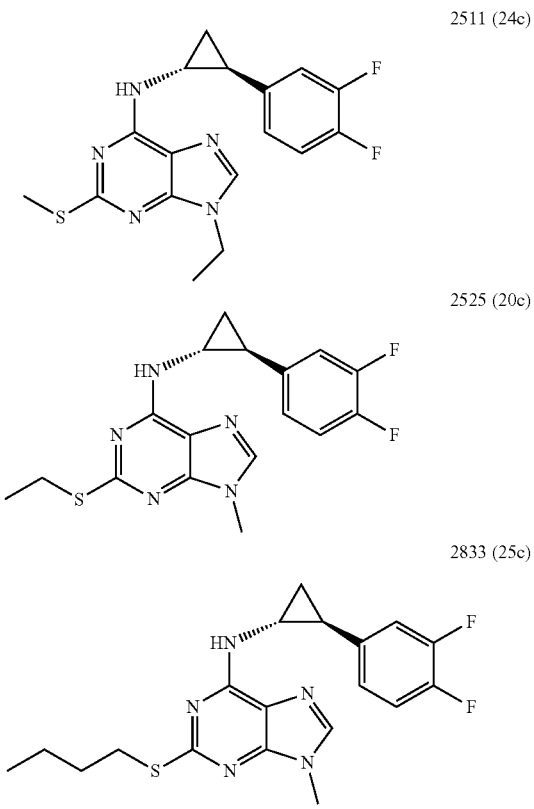

2511 is N-((1R,2S)-2-(3,4-difluorophenyl)cyclopropyl)-9-ethyl-2-(methylthio)-9H-purin-6-amine (Also Called 24c Above).

2525 is N-((1R,2S)-2-(3,4-difluorophenyl)cyclopropyl)-2-(ethylthio)-9-methyl-9H-purin-6-amine (Also Called 20c Above);

2833 is 2-(butylthio)-N-((1R,2S)-2-(3,4-difluorophenyl)cyclopropyl)-9-methyl-9H-purin-6-amine (Also Called 25c Above);

Further experiments were conducted in order to determine the Minimal Inhibitory Concentration (MIC) of molecules 2511, 2525 and 2833 together with polymyxin B nonapeptide (PMBN) provided by MedChemExpress #HY-106783. MIC was determined on *Escherichia coli* (ATCC 8739) according to EUCAST (European Committee on Antimicrobial Susceptibility Testing) recommendations.

Briefly, a single colony grown on a Luria-Bertani Agar (LB) plate was resuspended and cultured in LB medium overnight (O/N) in aerobic conditions (37° C. with 220 rpm shaking), next day a 1:50 inoculum in Mueller-Hinton broth (MHB) was incubated in aerobic conditions for 1h30 (OD=0.08-0.1) and an inoculum of 1:300 dilution, corresponding to $3\times10^6$ CFU/ml, was incubated in presence or absence of different concentrations of the above-mentioned molecules in 1% DMSO (vehicle) with or without Polymyxin B nonapeptide (PMBN) at 40 µg/ml. After O/N growth the OD of each culture was measured at 600 nm in a spectrophotometer ($OD_{600}$). The MIC represents the concentration at which there is no visible growth of bacteria, i.e. $\Delta OD$ at 600 nm equal to zero wherein $\Delta OD$ is the difference between the resulting optical density (OD) with the molecule together with PMBN, and the optical density (OD) of the blank (blank is the medium) alone.

As shown in Table 1, the MIC for molecules 2511 and 2525 together with PMBN against *Escherichia coli* (ATCC 8739) is equal to 50 µM, while it is 90 µM for molecule 2833. The molecules 2511, 2525 and 2833 taken alone in concentrations up to 100 µM or 40 µg/ml PMBN alone was unable to inhibit *E. coli* growth.

Example 6: Antibacterial Effects of Pyrazolopyrimidine Molecule 2539 Together with Polymyxin B Nonapeptide (Provided by MedChemExpress #HY-106783) on *Escherichia coli* (ATCC 8739): Determination of Minimal Inhibitory Concentration (MIC)

Pyrazolopyrimidine molecule 2539 corresponds to

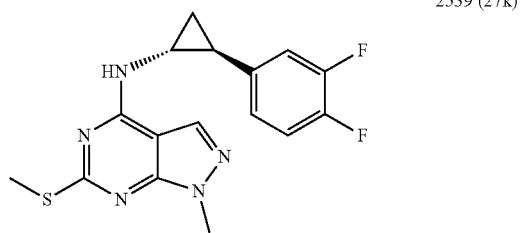

2539 (27k)

2539 is N-((1R,2S)-2-(3,4-difluorophenyl)cyclopropyl)-1-methyl-6-(methylthio)-1H-pyrazolo[3,4-d]pyrimidin-4-amine (Also Called 27k Above);

Further experiments were conducted in order to determine the Minimal Inhibitory Concentration (MIC) which is the minimal concentration required to prevent bacterial growth.

A single colony grown on a Luria-Bertani (LB) agar plate is resuspended and cultured in LB medium overnight (O/N) in aerobic conditions (37° C. with 220 rpm shaking), next day a 1:50 inoculum in Mueller-Hinton broth (MHB) is incubated in aerobic conditions for 1h30 (OD=0.08-0.1) and an inoculum of 1:300 dilution, corresponding to $3\times10^6$ CFU/ml, is incubated in presence or absence of different concentrations of the above-mentioned pyrazolopyrimidine molecule in 1% DMSO (vehicle) with or without PMBN at 40 µg/ml. After O/N growth the OD of each culture was measured at 600 nm ($OD_{600}$) in a spectrophotometer (Victor 3-Perkin Elmer). The MIC represents the concentration at which there is no visible growth of bacteria, i.e. $\Delta OD$ at 600 nm equal to zero wherein $\Delta OD$ is the difference between the resulting optical density (OD) with the molecule together with PMBN, and the optical density (OD) of the blank (blank is the medium alone).

As shown in Table 1, the MIC for 2539 together with PMBN against *Escherichia coli* (ATCC 8739) is equal to 25 µM. The molecule 2539 alone in concentrations up to 100 µM or 40 µg/ml PMBN alone did not inhibit *E. coli* growth.

TABLE 1

Minimal Inhibitory Concentrations of purines and pyrazolopyrimidine molecules together with PMBN against *E. coli* and *P. aeruginosa*. PMBN (polymyxin B nonapeptide) was used at 40 µg/ml for *E. coli* and 0.5 µg/ml for *P. aeruginosa*.

| Strains | Group | molecules | Minimal inhibitory concentration (in µM) without PMBN | With PMBN |
|---|---|---|---|---|
| *E. coli* (ATCC 8739) | Purin | 2329 | >100 | 10 |
| | | 2412 | >100 | 50 |
| | | 2452 | >100 | 10 |
| | | 2461 | >100 | 10 |
| | | 2511 | >100 | 50 |
| | | 2525 | >100 | 50 |
| | | 2833 | >100 | 90 |
| | Pyrazolo | 2539 | >100 | 25 |
| | | 2666 | >100 | 10 |
| *Pseudomonas aeruginosa* (ATCC 27853) | Purin | 2329 | >100 | 50 |
| | | 2412 | >100 | 50 |
| | | 2452 | >100 | 50 |
| | | 2461 | >100 | 50 |
| | Pyrazolo | 2666 | >100 | 50 |

3. Examples of Pyrimidine Derivatives for Use in Inhibition of Biofilm Formation of Gram-Negative Bacteria with and without Polymixyn B Nonapeptide $1.5\times10^4$ CFU of *E. coli* (ATCC 8739) in early logarithmic phase were added in a well of a 48-well polystyrene plate containing Luria Bertani (LB) medium supplemented with 5% mannose (purchased from Sigma-aldrich #M6020-25G) and incubated for 48h at 37° C. The incubation was carried in static conditions in presence or absence of different concentrations of the molecules 2329 or 2666 in combination or not with the penetrating agent polymyxin B nonapeptide (PMBN) (35 µg/ml) (provided by Sigma-aldrich #P2076-5MG). After incubation, planktonic bacteria, which are bacteria floating in the liquid medium, were removed and adherent bacteria were washed 2 times in PBS. Crystal Violet (Sigma-aldrich #C0775-25G) (1% solution in $dH_2O$) was then added to the wells for 15 min at RT to stain the biofilm. Wells were washed 3 times with PBS (phosphate buffered saline provided by Lonza #17-516F) to eliminate unbound crystal violet and 2501 Acetic Acid 20% was added and incubated at RT for 10 min. The absorbance of the solution was measured at 570 nm with an Infinite 200 PRO (Tecan) reflecting the total biomass of the biofilm, which corresponds to the sum of live and dead bacteria. The Biofilm Mass, expressed in percentage, is calculated by the following formula: Abs(sample)/Abs(DMSO 1%)*100, wherein the Abs(sample) or Abs(DMSO) represents the difference between the absorbance of the sample or DMSO and the blank (blank is the medium alone without bacteria).

Figure 2:
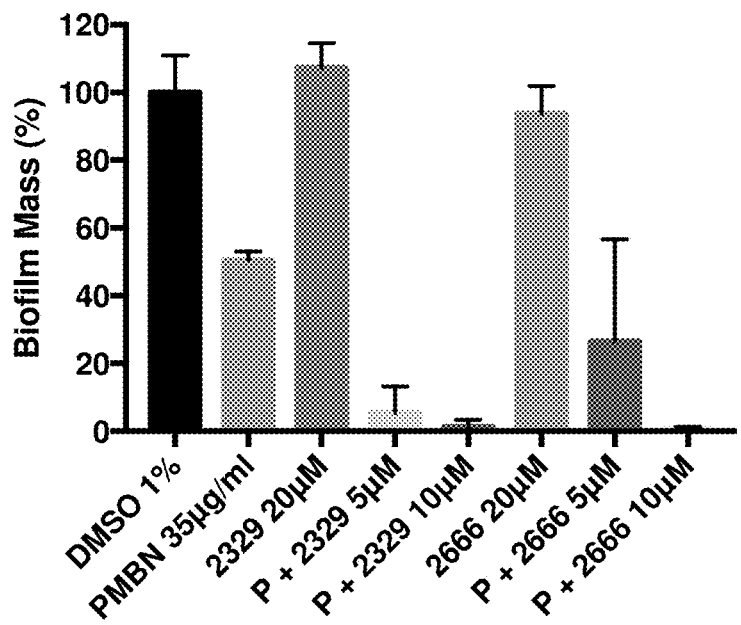
FIG. 2 illustrates the effect of molecules 2329 (purine) and 2666 (pyrazolopyimidine) at different concentrations combined with 35 µg/ml PMBN (represented by P) on E. coli biofilm formation.

As shown in FIG. 2, the purine 2329 molecule (5 µM) combined with 35 µg/ml PMBN fully inhibited *E. coli* biofilm formation in a synergistic manner. The molecule 2329 alone had no effect, while PMBN (35 µg/ml) alone only reduced by half biofilm growth. Similarly, the pyrazolopyrimidine 2666 molecule (10 µM) combined with 35 µg/ml PMBN fully inhibited *E. coli* biofilm formation in a synergistic manner. The molecule 2666 alone had no effect on biofilm growth.

TABLE 2

Reduction *E. coli* biofilm mass expressed in percentage, in presence of different concentration of pyrimidine derivatives (2329 and 2666) with and without polymixyn B nonapeptide (called P in the table)

| DMSO 1% | PMBN 35 µg/ml | 2329 20 µM | P + 2329 5 µM | P + 2329 10 µM | 2666 20 µM | P + 2666 5 µM | P + 2666 10 µM |
|---|---|---|---|---|---|---|---|
| 90.97 | 53.90 | 97.41 | −1.25 | 2.96 | 100.43 | 0.40 | 1.07 |
| 90.05 | 50.87 | 107.12 | −1.59 | 3.11 | 100.95 | 0.49 | 0.92 |
| 109.44 | 47.94 | 110.45 | 12.79 | 0.12 | 85.72 | 53.62 | 0.95 |
| 109.53 | 48.98 | 124.24 | 11.45 | −1.01 | 87.82 | 51.67 | −0.122 |

4. Comparison of Pyrimidine Derivatives According to the Present Invention with Purines Disclosed in WO2009/034386

We have synthesized 4 molecules (84, 127, 128 and 129) from WO2009/034386. In this patent application, the ability of 2 molecules (25 and 81) to inhibit the MurI enzyme from *E. faecalis*, *E. faecium* and *S. aureus* is described. The 2 molecules were able to inhibit the enzymatic activity of MurI isozymes from *E. faecalis* and *E. faecium* with half maximal inhibitory concentrations (IC$_{50}$) equal to 2 and 5 µM, respectively (Table 9 of WO2009/034386). In contrast, IC$_{50}$>400 µM is reported against *S. aureus* MurI isozyme for the 2 molecules, indicating a failure to inhibit the MurI enzyme from this bacterial strain. WO2009/034386 does not report any other testing demonstrating the antibacterial efficacy of these purine molecules.

We found no antibacterial activity of molecules 84, 127, 128 and 129 against *E. coli* (ATCC8739)

The molecules 84, 127, 128 and 129 were synthesized according to a similar chemical pathway as described in the present invention, with the exception that the nucleophilic substitution of the chlorine atom on Xb is carried out by another amine.

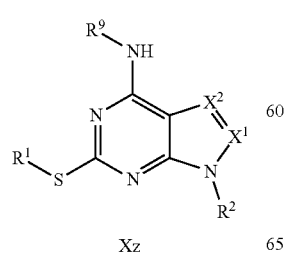

Xb

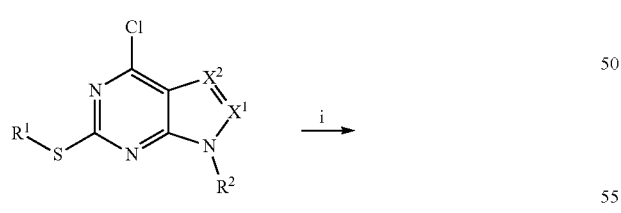

Xz

When R$^1$=CH$_3$, the corresponding alkoxy-substituted compounds Xz″ wherein Y=O was provided starting from Xz according to scheme 6 below:

Scheme 6

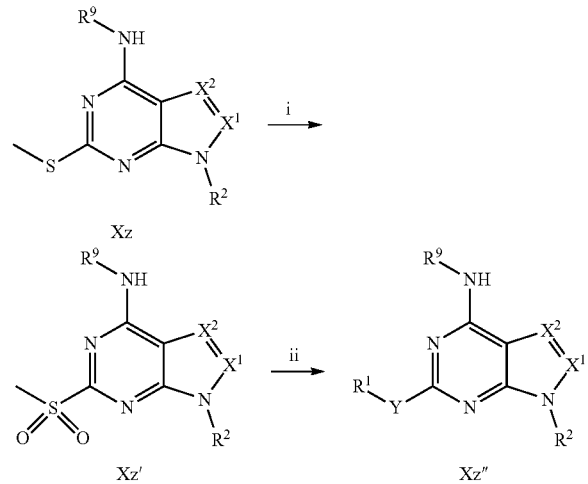

Xz'

Xz″

Example 1

2-butoxy-N-cyclopropyl-9-(2,6-difluoro-3-methyl-benzyl)-9H-purin-6-amine (38z″)

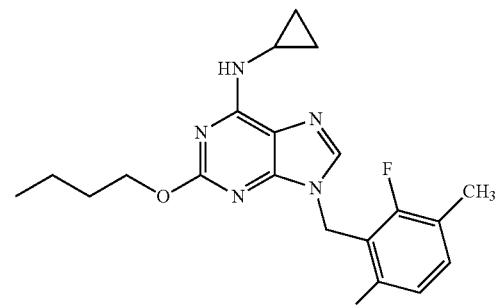

We have synthesized 38z" (molecule 129 in WO2009/034386) that is bearing a cyclopropyl ring attached to the nitrogen atom linked at position-6 of the heterocycle ring. The chemical structure of this compound is the most tightly related to that of the compounds described in the present application.

6-Chloro-N⁴-(2,6-difluoro-3-methylbenzyl)-2-(methylthio)pyrimidine-4,5-diamine (38a)

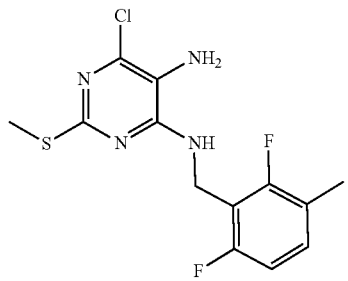

4,6-Dichloro-2-(methylthio)pyrimidin-5-amine (22h) (0.5 g, 2.4 mmol) was dissolved in methanol (10 mL) and supplemented with 2,6-difluoro-3-methylbenzylamine (0.80 mL, 6.0 mmol). The reaction mixture was introduced in a sealed vessel and heated at 130° C. for 2 h. After concentration of the reaction mixture to dryness under vacuum, the residue was purified by silica gel column chromatography.

Yield: 95%.
Melting point: 190-192° C.
$^1$H NMR (DMSO-d$_6$) δ 2.21 (s, 3H, CH$_3$), 2.38 (s, 3H, SCH$_3$), 4.61 (d, J=4.8 Hz, 2H, NHCH$_2$), 4.85 (s, 2H, NH$_2$), 7.01 (t, J=8.8 Hz, 1H, 5'-H), 7.27 (m, 2H, NHCH$_2$/4'-H).
$^{13}$C NMR (DMSO-d$_6$) δ 13.4 (SCH$_3$), 13.8 (CH$_3$), 33.1 (NHCH$_2$), 110.8 (C-5'), 113.4 (C-1'), 120.1 (C-5), 120.2 (C-3'), 130.8 (C-4'), 137.5 (C-6), 151.8 (C-4), 155.5 (C-2), 158.5-159.9 (C-2'/C-6').

6-Chloro-9-(2,6-difluoro-3-methylbenzyl)-2-(methylthio)-9H-purine (38b)

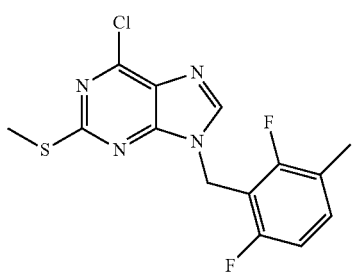

A solution of (38a) (331.0 mg, 1 mmol) in acetic acid (3.0 mL) and triethyl orthoformate (3.0 mL, 18 mmol) was heated at a temperature of 130° C. under reflux for 3 hours. After distillation of acetic acid and triethyl orthoformate under vacuum, the residue was purified by silica gel column chromatography.

Yield: 66%.
Melting point: 124-126° C.
$^1$H NMR (DMSO-d$_6$) δ 2.19 (s, 3H, CH$_3$), 2.52 (s, 3H, SCH$_3$), 5.52 (s, 2H, NCH$_2$), 7.05 (t, J=8.9 Hz, 1H, 5'-H), 7.34 (q, J=8.4 Hz, 1H, 4'-H), 8.63 (s, 1H, 8-H).

$^{13}$C NMR (DMSO-d$_6$) δ 13.6 (CH$_3$), 13.8 (SCH$_3$), 35.9 (NCH$_2$), 110.6 (C-1'), 111.1 (m, C-5'), 120.6 (C-3'), 127.6 (C-5), 132.2 (C-4'), 149.0 (C-4), 152.5 (C-6), 158.3-159.7 (C-2'/C-6'), 164.7 (C-2).

N-Cyclopropyl-9-(2,6-difluoro-3-methylbenzyl)-2-(methylthio)-9H-purin-6-amine (38z)

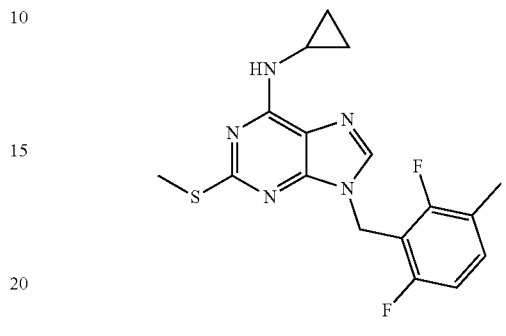

A solution of (38b) (170.0 mg, 0.5 mmol) in acetonitrile (3 mL) was supplemented with cyclopropylamine (0.07 mL, 1.0 mmol) and triethylamine (0.10 mL) and then heated at 90° C. under reflux for 5 hours. After distillation of acetonitrile and triethylamine under vacuum, the residue was purified by silica gel column chromatography.

Yield: 86%.
Melting point: 150-152° C.
$^1$H NMR (CDCl$_3$) δ 0.60 (m, 2H, CH(CH$_2$)$_2$), 0.86 (m, 2H, CH(CH$_2$)$_2$), 2.23 (s, 3H, CH$_3$), 2.60 (s, 3H, SCH$_3$), 3.06 (bs, 1H, CH(CH$_2$)$_2$), 5.36 (s, 2H, NCH$_2$), 5.77 (bs, 1H, NH), 6.83 (t, J=8.3 Hz, 1H, 5'-H), 7.14 (q, J=8.3 Hz, 1H, 4'-H), 7.66 (s, 1H, 8-H).
$^{13}$C NMR (CDCl$_3$) δ 7.6 (CH(CH$_2$)$_2$), 14.3 (CH$_3$), 14.6 (SCH$_3$), 24.4 (CH(CH$_2$)$_2$), 35.1 (NCH$_2$), 111.1 (C-5'), 111.2 (C-1'), 117.1 (C-5), 121.1 (C-3'), 132.0 (C-4'), 138.8 (C-8), 155.2 (C-4), 159.0-160.4 (C-2'/C-6'), 166.0 (C-2).

N-Cyclopropyl-9-(2,6-difluoro-3-methylbenzyl)-2-(methylsulfonyl)-9H-purin-6-amine (38z')

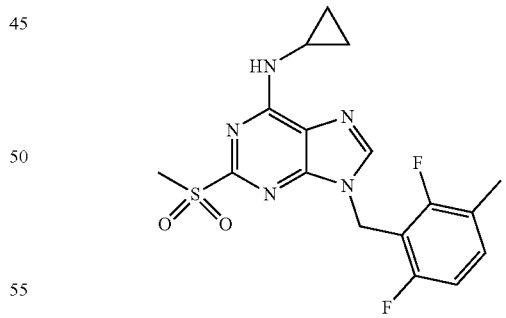

A solution of (38z) (195.0 mg, 0.54 mmol) in methylene chloride (10 mL) was cooled to 5° C. on an ice bath and supplemented with 3-chloroperbenzoic acid (208.0 mg, 1.20 mmol). After stirring at room temperature for 2 hours, the mixture was washed with a solution of NaOH 0.1 M (2×10 mL). The organic layer was dried, filtered and methylene chloride was evaporated to dryness under vacuum. The residue was engaged in the next step (38z") without further purification.

Yield: 69%.

2-Butoxy-N-cyclopropyl-9-(2,6-difluoro-3-methyl-benzyl)-9H-purin-6-amine (38z")

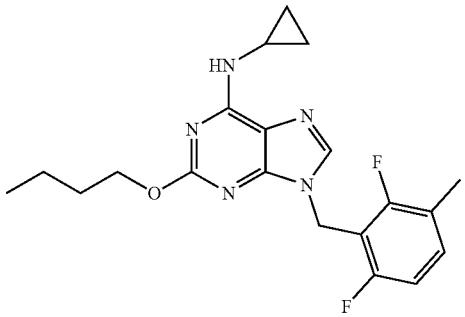 [SMILES: CCCCOc1nc(NC2CC2)c2ncn(Cc3c(F)ccc(C)c3F)c2n1]

Sodium metal (46.0 mg, 2 mmol) was dissolved in butan-1-ol (3 mL) on an iced bath and (37z') (150.0 mg, 0.38 mmol) was added. After stirring at room temperature for 3 hours, the mixture was partitioned between water (50 mL) and dichloromethane (2×50 mL). The combined organic layers were dried and evaporated to dryness under vacuum. The residue was purified by silica gel column chromatography.

Yield: 75%.

Melting point: 123-125° C.

The conformity and the purity of compound 38z" was attested by NMR spectroscopy and elemental analysis and is reported hereafter:

$^1$H NMR (CDCl$_3$) δ 0.60 (m, 2H, CH(CH$_2$)$_2$), 0.86 (m, 2H, CH(CH$_2$)$_2$), 0.98 (t, J=7.4 Hz, 3H, OCH$_2$CH$_2$CH$_2$CH$_3$), 1.50 (h, J=7.4 Hz, 2H, OCH$_2$CH$_2$CH$_2$CH$_3$), 1.81 (p, J=7.0 Hz, 2H, OCH$_2$CH$_2$CH$_2$CH$_3$), 2.23 (s, 3H, CH$_3$), 3.06 (bs, 1H, CH(CH$_2$)$_2$), 4.38 (t, J=6.9 Hz, 2H, OCH$_2$CH$_2$CH$_2$CH$_3$), 5.32 (s, 2H, NCH$_2$), 5.75 (bs, 1H, NH), 6.83 (td, J=8.7 Hz/1.1 Hz, 1H, 5'-H), 7.14 (q, J=8.3 Hz, 1H, 4'-H), 7.59 (s, 1H, 8-H).

$^{13}$C NMR (CDCl$_3$) δ 7.6 (CH(CH$_2$)$_2$), 14.1 (OCH$_2$CH$_2$CH$_2$CH$_3$), 14.3 (CH$_3$), 19.4 (OCH$_2$CH$_2$CH$_2$CH$_3$), 24.2 (CH(CH$_2$)$_2$), 31.2 (OCH$_2$CH$_2$CH$_2$CH$_3$), 34.8 (NCH$_2$), 67.2 (OCH$_2$CH$_2$CH$_2$CH$_3$), 111.0 (C-5'), 111.3 (C-1'), 115.8 (C-5), 121.2 (C-3'), 132.0 (C-4'), 138.4 (C-8), 156.8 (C-4), 158.7-160.6 (C-2'/C-6'), 160.7 (C-2).

Anal. (C$_{20}$H$_{23}$F$_2$N$_5$O) theoretical: C, 62.00; H, 5.98; N, 18.08. Found: C, 61.97; H, 6.07; N, 18.03.

The molecule 38z" (molecule 129 in WO2009/034386) was tested for its potential antibacterial activity by determining an eventual minimal inhibitory concentration according to protocols recommended by EUCAST to assess the efficacy of antibiotics against bacterial strains. MIC for 38z" (molecule 129 in WO2009/034386) together with polymyxin B nonapeptide (PMBN) provided by Sigma-aldrich #P2076-5MG was determined on *Escherichia coli* (ATCC 8739). Briefly, a single colony grown on a Luria-Bertani Agar (LB) plate was resuspended and cultured in the LB medium overnight (O/N) in aerobic conditions (37° C. with 220 rpm shaking), next day a 1:50 inoculum in Mueller-Hinton broth (MHB) was incubated in aerobic conditions for 1h30 (OD=0.08-0.1) and an inoculum of 1:300 dilution, corresponding to 3×10$^6$ CFU/ml, was incubated in presence or absence of different concentrations of the molecules in 1% DMSO (vehicle) with or without Polymyxin B nonapeptide (PMBN) at 40 μg/ml. After O/N growth the OD of each culture was measured at 600 nm in a spectrophotometer (OD$_{600}$). The MIC represents the concentration at which there is no visible growth of bacteria, i.e. ΔOD at 600 nm equal to zero wherein ΔOD is the difference between the resulting optical density (OD) with the molecule together with PMBN, and the optical density (OD) of the blank (blank is the medium) alone. NO antibacterial activity was found against the *Escherichia coli* (ATCC 8739) strain when the molecule 38z" was used at concentrations up to 100 μM together with 40 μg/ml PMBN.

Example 2: N-benzyl-2-butoxy-9-(2,6-difluoro-3-methylbenzyl)-9H-purin-6-amine (39z")

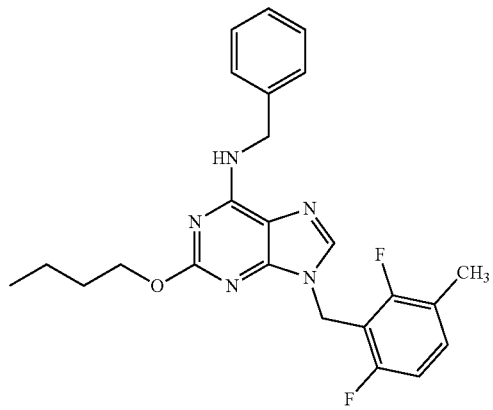 [SMILES: CCCCOc1nc(NCc2ccccc2)c2ncn(Cc3c(F)ccc(C)c3F)c2n1]

We have synthesized compound 127 (39z") reported in WO2009/034386.

N-Benzyl-9-(2,6-difluoro-3-methylbenzyl)-2-(methylthio)-9H-purin-6-amine (39z)

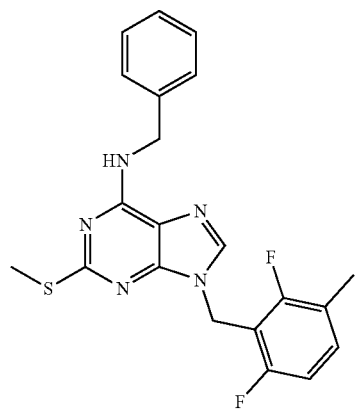

A solution of (38b) (170.0 mg, 0.5 mmol) in acetonitrile (3 mL) was supplemented with benzylamine (0.09 mL, 1.0 mmol) and triethylamine (0.10 mL) and then heated at 90° C. under reflux for 5 hours. After distillation of acetonitrile and triethylamine under vacuum, the residue was purified by silica gel column chromatography.

Yield: 78%.

Melting point: 164-165.5° C.

$^1$H NMR (DMSO-d$_6$) δ 2.18 (s, 3H, CH$_3$), 2.38 (s, 3H, SCH$_3$), 4.61 (s, 2H, NHCH$_2$), 5.37 (s, 2H, NCH$_2$), 6.17 (bs, 1H, NHCH$_2$), 7.02 (t, J=8.8 Hz, 1H, 5"-H), 7.20 (t, J=7.5 Hz, 1H, 4'-H), 7.27-7.33 (m, 5H, 2'-H/3'-H/5'-H/6'-H/4"-H), 8.06 (s, 1H, 8-H), 8.42 (s, 1H, NH).

$^{13}$C NMR (DMSO-d$_6$) δ 13.5 (SCH$_3$), 13.7 (CH$_3$), 35.0 (NCH$_2$), 42.9 (NHCH$_2$), 111.0 (d, J=21 Hz, C-5"), 111.4 (t, J=19 Hz, C-1"), 116.4 (C-5), 120.5 (C-3"), 126.6 (C-4'), 127.3 (C-2'/C-6'), 128.2 (C-3'/C-5'), 131.8 (C-4"), 139.8 (C-8), 139.9 (C-1'), 149.5 (C-4), 153.6 (C-6), 158.2-159.6 (dd, J=248 Hz/7 Hz, C-2'), 158.3-159.7 (dd, J=247 Hz/7 Hz, C-6'), 164.0 (C-2).

N-Benzyl-9-(2,6-difluoro-3-methylbenzyl)-2-(methylsulfonyl)-9H-purin-6-amine (39z')

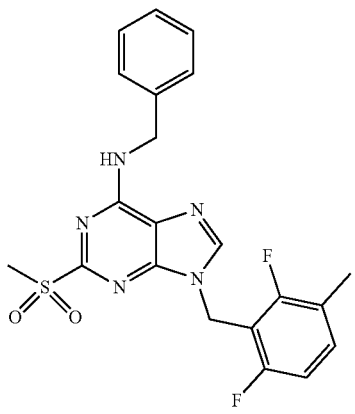

A solution of (39z) (180.0 mg, 0.41 mmol) in methylene chloride (10 mL) was cooled to 5° C. on an ice bath and supplemented with 3-chloroperbenzoic acid (155.0 mg, 0.90 mmol). After stirring at room temperature for 2 hours, the mixture was washed with a solution of NaOH 0.1 M (2×10 mL). The organic layer was dried, filtered and the solvent was evaporated to dryness under vacuum. The residue was recrystallized in a mixture of ethyl acetate and hexane.

Yield: 65%.

Melting point: 143-144° C.

$^1$H NMR (DMSO-d$_6$) δ 2.18 (s, 3H, CH$_3$), 3.24 (s, 3H, SO$_2$CH$_3$), 4.69 (d, J=6.1 Hz, 2H, NHCH$_2$), 5.48 (s, 2H, NCH$_2$), 6.17 (bs, 1H, NHCH$_2$), 7.04 (t, J=8.9 Hz, 1H, 5"-H), 7.22 (t, J=7.3 Hz, 1H, 4'-H), 7.28-7.38 (m, 5H, 2'-H/3'-H/5'-H/6'-H/4"-H), 8.39 (s, 1H, 8-H), 9.10 (t, J=6.1 Hz, 1H, NH).

$^{13}$C NMR (DMSO-d$_6$) δ 13.7 (CH$_3$), 35.5 (NCH$_2$), 38.9 (SO$_2$CH$_3$), 43.4 (NHCH$_2$), 111.0 (C-1"), 111.1 (d, J=21 Hz, C-5"), 119.7 (C-5), 120.7 (d, J=17 Hz, C-3"), 126.9 (C-4'), 127.6 (C-2'/C-6'), 128.3 (C-3'/C-5'), 132.1 (C-4"), 139.2 (C-1'), 143.2 (C-8), 147.8 (C-4), 154.3 (C-6), 158.2-159.6 (C-2'/C-6'), 159.4 (C-2).

N-Benzyl-2-butoxy-9-(2,6-difluoro-3-methylbenzyl)-9H-purin-6-amine (39z")

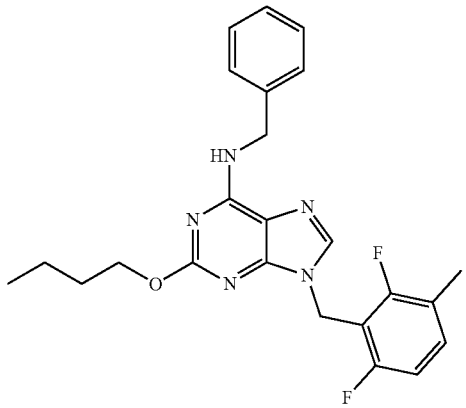 [SMILES: CCCCOc1nc(NCc2ccccc2)c2ncn(Cc3c(F)ccc(C)c3F)c2n1]

Sodium metal was dissolved in 1-butanol (3 mL) on an ice bath and (39z') (150.0 mg, 0.34 mmol) was added. After stirring at room temperature for 3 hours, the mixture was partitioned between water (50 mL) and dichloromethane (2×50 mL). The combined organic layers were dried and evaporated to dryness under vacuum. The residue was purified by silica gel column chromatography.

Yield: 72%.

Melting point: 124-127.5° C.

The conformity and the purity of compound 127 was attested by NMR spectroscopy and elemental analysis (see below):

$^1$H NMR (DMSO-d$_6$) δ 0.89 (t, J=7.4 Hz, 3H, OCH$_2$CH$_2$CH$_2$CH$_3$), 1.34 (h, J=7.0 Hz, 2H, OCH$_2$CH$_2$CH$_2$CH$_3$), 1.60 (p, J=6.9 Hz, 2H, OCH$_2$CH$_2$CH$_2$CH$_3$), 2.18 (s, 3H, CH$_3$), 4.14 (t, J=6.7 Hz, 2H, OCH$_2$CH$_2$CH$_2$CH$_3$), 4.60 (d, J=4.5 Hz, 2H, NHCH$_2$), 5.32 (s, 2H, NCH$_2$), 7.01 (t, J=8.9 Hz, 1H, 5"-H), 7.19 (t, J=7.1 Hz, 1H, 4'-H), 7.26-7.33 (m, 5H, 2'-H/3'-H/5'-H/6'-H/4"-H), 7.96 (s, 1H, 8-H), 8.33 (t, J=5.0 Hz, 1H, NH).

$^{13}$C NMR (DMSO-d$_6$) δ 13.7 (CH$_3$/OCH$_2$CH$_2$CH$_2$CH$_3$), 18.7 (OCH$_2$CH$_2$CH$_2$CH$_3$), 30.5 (OCH$_2$CH$_2$CH$_2$CH$_3$), 34.8 (NCH$_2$), 42.9 (NHCH$_2$), 67.8 (OCH$_2$CH$_2$CH$_2$CH$_3$), 111.0 (d, J=21 Hz, C-5"), 111.5 (t, J=19 Hz, C-1"), 115.1 (C-5), 120.5 (d, J=18 Hz, C-3"), 126.6 (C-4'), 127.1 (C-2'/C-6'), 128.2 (C-3'/C-5'), 131.8 (C-4"), 139.3 (C-1'), 140.1 (C-8), 150.3 (C-4), 155.1 (C-6), 158.3-159.7 (C-2'/C-6'), 161.4 (C-2).

Anal. (C$_{24}$H$_{25}$F$_2$N$_5$O) theoretical: C, 65.89; H, 5.76; N, 16.01. Found: C, 65.98; H, 6.03; N, 16.24.

The molecule 39z" (molecule 127 in WO2009/034386) was tested for its potential antibacterial activity by determining an eventual minimal inhibitory concentration according to protocols recommended by EUCAST to assess the efficacy of antibiotics against bacterial strains. MIC for 39z" (molecule 127 in WO2009/034386) together with polymyxin B nonapeptide (PMBN) provided by Sigma-aldrich #P2076-5MG was determined on *Escherichia coli* (ATCC 8739). Briefly, a single colony grown on a Luria-Bertani Agar (LB) plate was resuspended and cultured in the LB medium overnight (O/N) in aerobic conditions (37° C. with 220 rpm shaking), next day a 1:50 inoculum in Mueller-Hinton broth (MHB) was incubated in aerobic conditions for 1h30 (OD=0.08-0.1) and an inoculum of 1:300 dilution, corresponding to 3×10$^6$ CFU/ml, was incubated in presence or absence of different concentrations of the molecules in 1% DMSO (vehicle) with or without Polymyxin B nonapeptide (PMBN) at 40 μg/ml. After O/N growth the OD of each culture was measured at 600 nm in a spectrophotometer ($OD_{600}$). The MIC represents the concentration at which there is no visible growth of bacteria, i.e. ΔOD at 600 nm equal to zero wherein ΔOD is the difference between the resulting optical density (OD) with the molecule together with PMBN, and the optical density (OD) of the blank (blank is the medium) alone. NO antibacterial activity was found against the *Escherichia coli* (ATCC 8739) strain when the molecule 39z" was used at concentrations up to 100 μM together with 40 μg/ml PMBN.

Example 3: N-benzyl-9-(2,6-difluoro-3-methylbenzyl)-2(pentyloxy)-9H-purin-6-amine (40z")

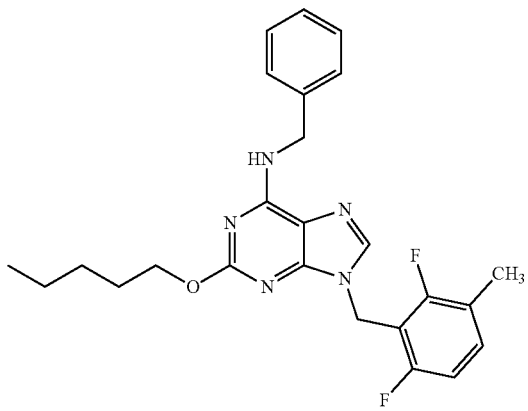 [SMILES: CCCCCOc1nc(NCc2ccccc2)c2ncn(Cc3c(F)ccc(C)c3F)c2n1]

We have synthesized compound 128 (40z") reported in WO2009/034386.

Sodium metal was dissolved in 1-pentanol (3 mL) on an ice bath and (39z') (150.0 mg, 0.34 mmol) was added. After stirring at room temperature for 3 hours, the mixture was partitioned between water (50 mL) and dichloromethane (2×50 mL). The combined organic layers were dried and evaporated to dryness under vacuum. The residue was purified by silica gel column chromatography.

Yield: 68%.

Melting point: 112-114° C.

The conformity and the purity of compound 128 was attested by NMR spectroscopy and elemental analysis (see below):

$^1$H NMR (DMSO-$d_6$) δ 0.87 (t, J=6.6 Hz, 3H, $OCH_2CH_2CH_2CH_2CH_3$), 1.30 (m, 4H, $OCH_2CH_2CH_2CH_2CH_3/OCH_2CH_2CH_2CH_2CH_3$), 1.62 (m, 2H, $OCH_2CH_2CH_2CH_2CH_3$), 2.18 (s, 3H, $CH_3$), 4.14 (t, J=6.7 Hz, 2H, $OCH_2CH_2CH_2CH_2CH_3$), 4.60 (d, J=4.4 Hz, 2H, $NHCH_2$), 5.32 (s, 2H, $NCH_2$), 7.01 (t, J=8.8 Hz, 1H, 5"-H), 7.19 (t, J=7.1 Hz, 1H, 4'-H), 7.26-7.33 (m, 5H, 2'-H/3'-H/5'-H/6'-H/4"-H), 7.96 (s, 1H, 8-H), 8.33 (t, J=5.0 Hz, 1H, NH).

$^{13}$C NMR (DMSO-$d_6$) δ 13.7 ($CH_3$), 13.9 ($OCH_2CH_2CH_2CH_2CH_3$), 21.9 ($OCH_2CH_2CH_2CH_2CH_3$), 27.7 ($OCH_2CH_2CH_2CH_2CH_3$), 28.2 ($OCH_2CH_2CH_2CH_2CH_3$), 34.8 ($NCH_2$), 42.9 ($NHCH_2$), 66.1 ($OCH_2CH_2CH_2CH_2CH_3$), 111.0 (dd, J=21 Hz/3 Hz, C-5"), 111.5 (t, J=19 Hz, C-1"), 115.1 (C-5), 120.5 (dd, J=18 Hz/3 Hz, C-3"), 126.6 (C-4'), 127.1 (C-2'/C-6'), 128.1 (C-3'/C-5'), 131.8 (C-4"), 139.3 (C-1'), 140.1 (C-8), 150.4 (C-4), 155.1 (C-6), 158.3-159.7 (C-2'/C-6'), 161.3 (C-2).

Anal. ($C_{25}H_{27}F_2N_5O$) theoretical: C, 66.50; H, 6.03; N, 15.51. Found: C, 66.60; H, 6.36; N, 15.88.

The molecule 40z" (molecule 128 in WO2009/034386) was tested for its potential antibacterial activity by determining an eventual minimal inhibitory concentration according to protocols recommended by EUCAST to assess the efficacy of antibiotics against bacterial strains. 40z" (molecule 127 in WO2009/034386) together with polymyxin B nonapeptide (PMBN) provided by Sigma-aldrich #P2076-5MG was determined on *Escherichia coli* (ATCC 8739). Briefly, a single colony grown on a Luria-Bertani Agar (LB) plate was resuspended and cultured in the LB medium overnight (O/N) in aerobic conditions (37° C. with 220 rpm shaking), next day a 1:50 inoculum in Mueller-Hinton broth (MHB) was incubated in aerobic conditions for 1h30 (OD=0.08-0.1) and an inoculum of 1:300 dilution, corresponding to 3×10⁶ CFU/ml, was incubated in presence or absence of different concentrations of the molecules in 1% DMSO (vehicle) with or without Polymyxin B nonapeptide (PMBN) at 40 μg/ml. After O/N growth the OD of each culture was measured at 600 nm in a spectrophotometer ($OD_{600}$). The MIC represents the concentration at which there is no visible growth of bacteria, i.e. ΔOD at 600 nm equal to zero wherein ΔOD is the difference between the resulting optical density (OD) with the molecule together with PMBN, and the optical density (OD) of the blank (blank is the medium) alone. NO antibacterial activity was found against the *Escherichia coli* (ATCC 8739) strain when the molecule 40z" was used at concentrations up to 100 μM together with 40 μg/ml PMBN.

Example 4: 2-(butylthio)-N,9-bis(2,6-difluoro-3-methylbenzyl)-9H-purin-6-amine (41z")

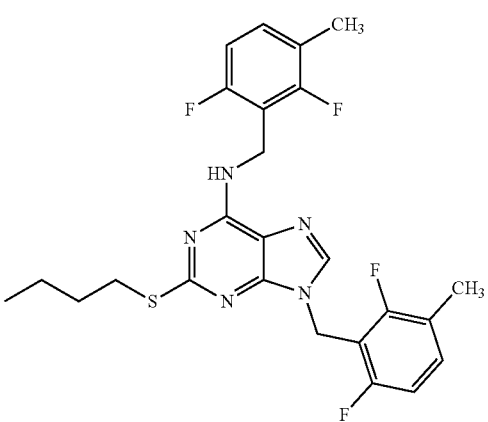 [SMILES: CCCCSc1nc(NCc2c(F)ccc(C)c2F)c2ncn(Cc3c(F)ccc(C)c3F)c2n1]

We have synthesized compound 84 (41z") reported in WO2009/034386.

N,9-bis(2,6-difluoro-3-methylbenzyl)-2-(methylthio)-9H-purin-6-amine (41z)

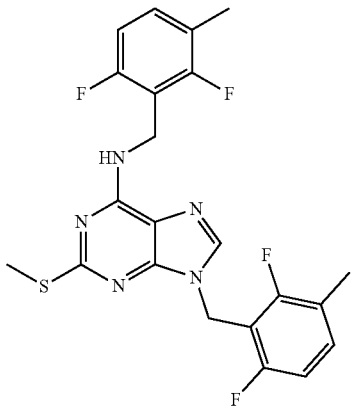

A solution of (38b) (170.0 mg, 0.5 mmol) in acetonitrile (3 mL) was supplemented with 2,6-difluoro-3-methylbenzylamine (0.135 mL, 1.0 mmol) and triethylamine (0.10 mL) and then heated at 90° C. under reflux for 5 hours. After distillation of acetonitrile and triethylamine under vacuum, the residue was purified by silica gel column chromatography.

Yield: 75%.
Melting point: 151-153° C.
$^1$H NMR (DMSO-$d_6$) δ 2.17 (s, 3H, CH$_3$), 2.18 (s, 3H, CH$_3$), 2.40 (s, 3H, SCH$_3$), 4.65 (bs, 2H, NHCH$_2$), 5.37 (s, 2H, NCH$_2$), 6.93 (t, J=8.8 Hz, 1H, 5'-H), 7.01 (t, J=8.8 Hz, 1H, 5"-H), 7.21 (m, 1H, 4'-H), 7.31 (m, 1H, 4"-H), 8.04 (s, 1H, 8-H), 8.22 (bs, 1H, NH).
$^{13}$C NMR (DMSO-$d_6$) δ 13.3 (SCH$_3$), 13.7 (CH$_3$), 13.8 (CH$_3$), 32.2 (NHCH$_2$), 35.1 (NCH$_2$), 110.6 (d, J=21 Hz, C-5'), 111.0 (dd, J=21 Hz/3 Hz, C-5"), 111.4 (t, J=19 Hz, C-1"), 113.9 (t, J=17 Hz, C-1'), 116.4 (C-5), 120.0 (dd, J=18 Hz/4 Hz, C-3'), 120.5 (dd, J=17 Hz/3 Hz, C-3"), 130.4 (C-4'), 131.8 (C-4"), 139.8 (C-8), 149.5 (C-4), 153.2 (C-6), 158.3-159.7 (C-6'/C-6"), 158.6-160.0 (C-2'/C-2"), 164.0 (C-2).

N,9-bis(2,6-difluoro-3-methylbenzyl)-2-(methylsulfonyl)-9H-purin-6-amine (41z')

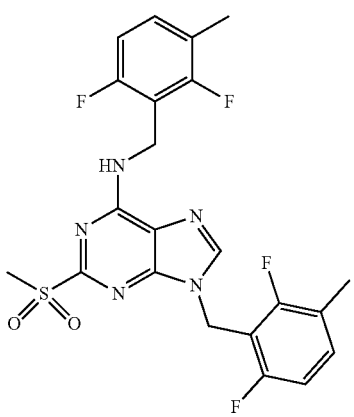

A solution of (39z) (180.0 mg, 0.39 mmol) in methylene chloride (10 mL) was cooled to 5° C. on an ice bath and supplemented with 3-chloroperbenzoic acid (155.0 mg, 0.90 mmol). After stirring at room temperature for 2 hours, the mixture was washed with a solution of NaOH 0.1 M (2×10 mL). The organic layer was dried, filtered and the solvent was evaporated to dryness under vacuum. The residue was recrystallized in a mixture of ethyl acetate and hexane.

Yield: 72%.
Melting point: 183-185° C.
$^1$H NMR (DMSO-$d_6$) δ 2.17 (s, 3H, CH$_3$), 2.18 (s, 3H, CH$_3$), 3.28 (s, 3H, SO$_2$CH$_3$), 4.74 (d, J=4.9 Hz, 2H, NHCH$_2$), 5.48 (s, 2H, NCH$_2$), 6.95 (t, J=8.8 Hz, 1H, 5'-H), 7.04 (t, J=8.8 Hz, 1H, 5"-H), 7.23 (m, 1H, 4'-H), 7.33 (m, 1H, 4"-H), 8.37 (s, 1H, 8-H), 8.97 (t, J=4.3 Hz, 1H, NH).
$^{13}$C NMR (DMSO-$d_6$) δ 13.7 (CH$_3$), 13.8 (CH$_3$), 32.5 (NHCH$_2$), 35.5 (NCH$_2$), 38.8 (SO$_2$CH$_3$), 110.7 (dd, J=22 Hz/3 Hz, C-5'), 110.9 (t, J=19 Hz, C-1"), 111.1 (dd, J=21 Hz/4 Hz, C-5"), 113.3 (t, J=20 Hz, C-1'), 119.7 (C-5), 120.1 (dd, J=19 Hz/5 Hz, C-3'), 120.7 (dd, J=17 Hz/3 Hz, C-3"), 130.6 (t, J=8 Hz, C-4'), 132.2 (t, J=8 Hz, C-4"), 143.2 (C-8), 147.9 (C-4), 154.0 (C-6), 158.2-159.6 (dd, J=249 Hz/7 Hz, C-6'/C-6"), 158.5-159.9 (dd, J=247 Hz/9 Hz, C-2'/C-2"), 159.3 (C-2).

2-(Butylthio)-N,9-bis(2,6-difluoro-3-methylbenzyl)-9H-purin-6-amine (41z")

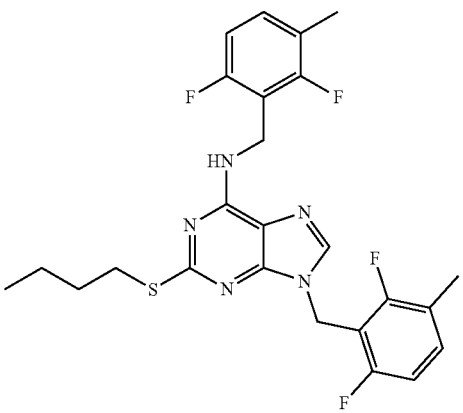 [SMILES: CCCCSc1nc(NCc2c(F)ccc(C)c2F)c2ncn(Cc3c(F)ccc(C)c3F)c2n1]

A solution of (41z') (150.0 mg, 0.30 mmol) in acetonitrile (3 mL) was supplemented with K$_2$CO$_3$ (100 mg, 0.72 mmol) and butanethiol (0.08 mL, 0.75 mmol). After stirring at 100° C. for 4 hours in a sealed vessel, the mixture was evaporated and partitioned between water (50 mL) and dichloromethane (2×50 mL). The combined organic layers were dried and evaporated to dryness under vacuum. The residue was purified by silica gel column chromatography.

Yield: 65%.
Melting point: 127.5-129.5° C.
The conformity and the purity of compound 84 was attested by NMR spectroscopy and elemental analysis (see below):
$^1$H NMR (DMSO-$d_6$) δ 0.89 (t, J=7.4 Hz, 3H, SCH$_2$CH$_2$CH$_2$CH$_3$), 1.39 (h, J=7.4 Hz, 2H, OCH$_2$CH$_2$CH$_2$CH$_3$), 1.59 (p, J=7.4 Hz, 2H, OCH$_2$CH$_2$CH$_2$CH$_3$), 2.17 (s, 3H, CH$_3$), 2.18 (s, 3H, CH$_3$), 3.03 (t, J=7.2 Hz, 2H, SCH$_2$CH$_2$CH$_2$CH$_3$), 4.65 (s, 2H, NHCH$_2$), 5.37 (s, 2H, NCH$_2$), 6.93 (t, J=8.8 Hz, 1H, 5'-H), 7.01 (t, J=8.8 Hz, 1H, 5"-H), 7.21 (m, 1H, 4'-H), 7.31 (m, 1H, 4"-H), 8.03 (s, 1H, 8-H), 8.19 (bs, J=4.3 Hz, 1H, NH).

$^{13}$C NMR (DMSO-d$_6$) δ 13.6 (SCH$_2$CH$_2$CH$_2$CH$_3$), 13.7 (CH$_3$), 13.8 (CH$_3$), 21.4 (SCH$_2$CH$_2$CH$_2$CH$_3$), 29.7 (SCH$_2$CH$_2$CH$_2$CH$_3$), 31.3 (SCH$_2$CH$_2$CH$_2$CH$_3$), 32.2 (NHCH$_2$), 35.0 (NCH$_2$), 110.6 (dd, J=23 Hz/3 Hz, C-5'), 111.0 (dd, J=21 Hz/3 Hz, C-5"), 111.5 (t, J=19 Hz, C-1"), 113.8 (C-1'), 120.0 (C-5/C-3'), 120.5 (dd, J=18 Hz/3 Hz, C-3"), 130.4 (C-4'), 131.8 (C-4"), 139.8 (C-8), 149.5 (C-4), 153.3 (C-6), 158.2-159.6 (C-6'/C-6"), 158.6-160.0 (C-2'/C-2"), 163.6 (C-2).

Anal. (C$_{25}$H$_{25}$F$_4$N$_5$S) theoretical: C, 59.63; H, 5.00; N, 13.91; S, 6.37. Found: C, 59.46; H, 5.12; N, 13.92; S, 6.11.

The molecule 41z" (molecule 84 in WO2009/034386) was tested for its potential antibacterial activity by determining an eventual minimal inhibitory concentration according to protocols recommended by EUCAST to assess the efficacy of antibiotics against bacterial strains. 41z" (molecule 84 in WO2009/034386) together with polymyxin B nonapeptide (PMBN) provided by Sigma-aldrich #P2076-5MG, was determined on *Escherichia coli* (ATCC 8739). Briefly, a single colony grown on a Luria-Bertani Agar (LB) plate was resuspended and cultured in the LB medium overnight (O/N) in aerobic conditions (37° C. with 220 rpm shaking), next day a 1:50 inoculum in Mueller-Hinton broth (MHB) was incubated in aerobic conditions for 1h30 (OD=0.08-0.1) and an inoculum of 1:300 dilution, corresponding to 3×10$^6$ CFU/ml, was incubated in presence or absence of different concentrations of the molecules in 1% DMSO (vehicle) with or without Polymyxin B nonapeptide (PMBN) at 40 µg/ml. After O/N growth the OD of each culture was measured at 600 nm in a spectrophotometer (OD$_{600}$). The MIC represents the concentration at which there is no visible growth of bacteria, i.e. ΔOD at 600 nm equal to zero wherein ΔOD is the difference between the resulting optical density (OD) with the molecule together with PMBN, and the optical density (OD) of the blank (blank is the medium) alone. NO antibacterial activity was found against the *Escherichia coli* (ATCC 8739) strain when the molecule 41z" was used at concentrations up to 100 µM together with 40 µg/ml PMBN.

Example 5. Time-Kill Experiments: Comparison of Pyrimidine Derivatives According to the Present Invention with Ampicillin as Bactericidal Antibiotic Against *E. coli*

To evaluate the bactericidal effect of the molecules 2329 and 2666 on Gram-negative bacteria, we exposed an inoculum of 1×10$^8$ CFU/ml *E. coli* (ATCC 8739) to 5 times the MIC of one or the other molecule in combination with 50 µg/ml PMBN in Luria-Bertani (LB) medium. *E. coli* were grown for 240 min at 37° C. with 220 rpm shaking.

An aliquot of the culture was taken before the addition of the tested molecules and after 30, 90, 150 and 240 min of incubation.

Figure 3:
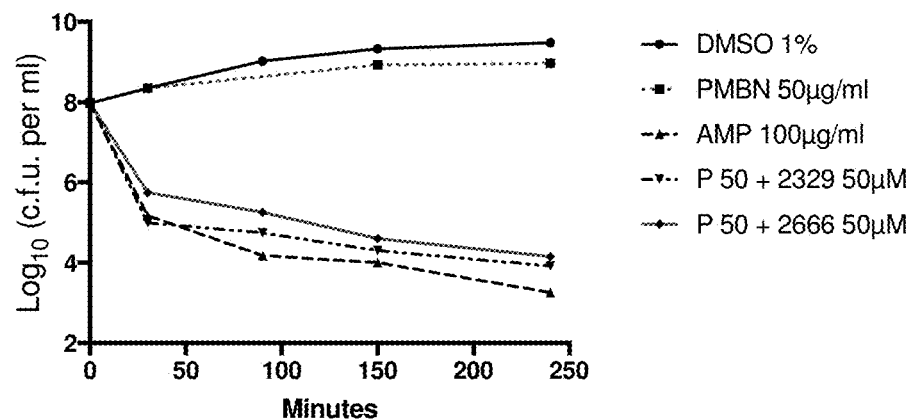
FIG. 3 illustrates the kinetic of inhibition of E. coli of a pyrazolo molecule (2666) and a purine (2329) in combination with 50 µg/ml PMBN (represented by P50) compared to Ampicillin.

The diluted culture aliquot was spread on a LB agar plate to evaluate the number of CFU at each time point. These numbers are represented as Log (c.f.u. *E. coli* per ml) in FIG. 3 which illustrates the antibacterial effect of the tested molecules.

The antibacterial effect of the molecules was also compared to 100 µg/ml Ampicillin (AMP) provided by Sigma-aldrich #A0166-5G. The antibacterial effect of the pyrimidine derivatives 2329 and 2666 combined with Polymyxin B nonapeptide (called P in FIG. 3) on *Escherichia coli* (ATCC8739) is surprisingly similar to Ampicillin.

Example 6: Optimization of PMBN Concentration to be Used in Combination with Pyrimidine Derivatives Against *Escherichia coli*

Each of the following molecules synthetized as described in the specification (2329, 2666, 2461, 2511, 2525, 2539) was tested in combination with 5, 10, 20, 30, 35, 40, 50 g/ml PMBN provided by Sigma-Aldrich #P2076-5MG and according to the following protocol. 1% DMSO is used as vehicle.

A single colony of *Escherichia coli* (ATCC 8739) grown on a Luria-Bertani Agar (LB) plate was resuspended and cultured in the LB medium overnight (O/N) in aerobic conditions (37° C. with 220 rpm shaking), next day a 1:50 inoculum in Mueller-Hinton broth (MHB) was incubated in aerobic conditions for 1.5 hours (OD=0.08-0.1) and an inoculum of 1:300 dilution, corresponding to 3×10$^6$ CFU/ml, was incubated in presence or absence of different concentrations of the molecules in 1% DMSO (vehicle) with 40 µg/ml PMBN. After O/N growth the OD of each culture was measured at 600 nm (OD$_{600\ nm}$) in a spectrophotometer (Victor 3-Perkin Elmer). The MIC represents the concentration at which there is no visible growth of bacteria, i.e. ΔOD at 600 nm equal to zero wherein ΔOD is the difference between the resulting optical density (OD) with the molecule together with PMBN, and the optical density (OD) of the blank (blank is the medium) alone.

The best minimum range of PMBN concentration to get an effect against *Escherichia coli* is 35 to 40 µg/ml. The latter 40 g/ml will be further used in example 7.

Example 7: Comparison of Pyrimidine Derivatives According to the Present Invention with Purines Disclosed in WO2009/034386

Each of the following molecules (38z", 39z", 40z", 41z") synthetized as described in examples 1 to 4 was tested again for its potential antibacterial activity against *Escherichia coli* (ATCC 8739) in presence of polymyxin B nonapeptide (PMBN), provided by Sigma-aldrich #P2076-5MG, by determining an eventual minimal inhibitory concentration (MIC) according to protocols recommended by EUCAST to assess the efficacy of antibiotics against bacterial strains. In these experiments, the antibacterial activity of these molecules combined with PMBN was compared to the antibacterial activity of our molecules 2329, 2666, 2461, 2511, 2525, 2539 combined with PMBN according to the following protocol.

A single colony of *Escherichia coli* (ATCC 8739) grown on a Luria-Bertani Agar (LB) plate was resuspended and cultured in the LB medium overnight (O/N) in aerobic conditions (37° C. with 220 rpm shaking), next day a 1:50 inoculum in Mueller-Hinton broth (MHB) was incubated in aerobic conditions for 1.5 hours (OD=0.08-0.1) and an inoculum of 1:300 dilution, corresponding to 3×10$^6$ CFU/ml, was incubated in presence or absence of different concentrations of the molecules in 1% DMSO (vehicle) with PMBN at 40 µg/ml in DMSO. After O/N growth the OD of each culture was measured at 600 nm (OD$_{600\ nm}$) in a spectrophotometer (Victor 3-Perkin Elmer). The MIC represents the concentration at which there is no visible growth of bacteria, i.e. ΔOD at 600 nm equal to zero wherein ΔOD is the difference between the resulting optical density (OD) with the molecule together with PMBN, and the optical density (OD) of the blank (blank is the medium) alone. In sharp contrast with our molecules 2329, 2666, 2461, 2511, 2525, 2539 (FIG. 4), no antibacterial activity was found against *Escherichia coli* (ATCC 8739) when any of the molecules 38z", 39z", 40z" or 41z" were used at concentrations up to 100 μM in presence of PMBN at 40 μg/ml.

Figure 4:
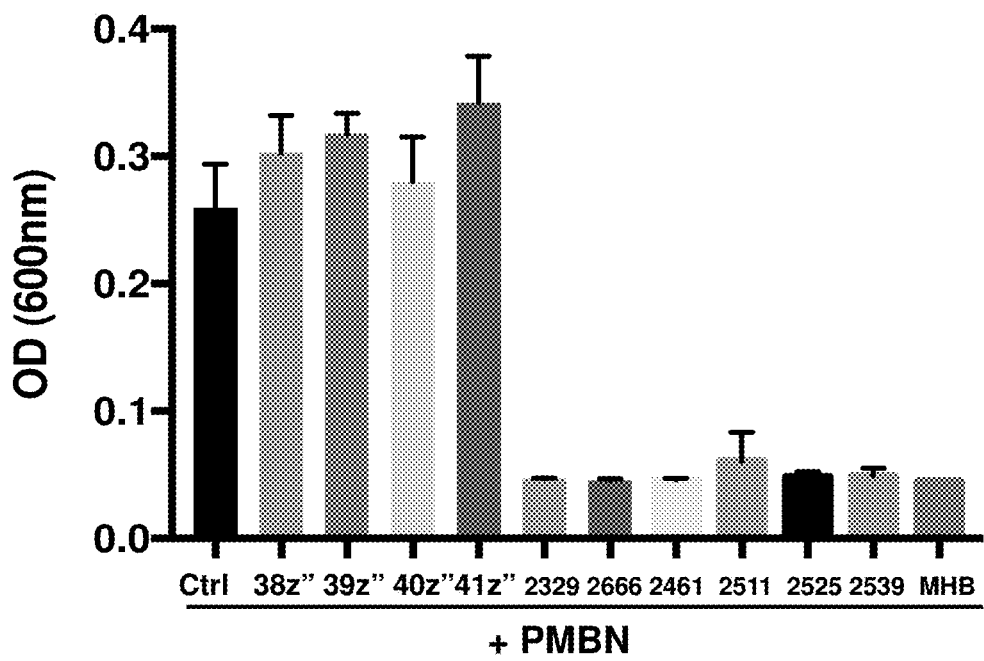
FIG. 4 illustrates a comparison of the pyrimidine derivatives according to the invention with purines (127=39z"; 128=40z"; 129=38z" and 84=41z") disclosed in WO 2009/034386.

The results are displayed in FIG. 4, which represents the $OD_{600\ nm}$ values obtained after O/N growth of *Escherichia coli* (ATCC 8739) in presence of 1% DMSO vehicle (Ctrl) or the indicated concentrations of tested molecules combined with 40 g/ml PMBN. The $OD_{600\ nm}$ value obtained in presence of molecules 38z", 39z", 40z" or 41z" did not differ from vehicle control (DMSO), indicating that none of the four molecules reported in WO2009/034386 shows antibacterial activity against *Escherichia coli* (ATCC 8739) when used at 100 μM together with 40 μg/ml PMBN. In contrast, the $OD_{600\ nm}$ values obtained in presence of molecules 2329 (10 μM), 2666 (20 μM), 2461 (20 μM), 2511 (50 μM), 2525 (50 μM) or 2539 (50 μM) with 40 μg/ml PMBN were much lower than that of vehicle control (Ctrl), and reached levels corresponding to MHB growth medium without bacteria (Medium), indicating that molecules 2329, 2666, 2461, 2511, 2525 or 2539 with 40 μg/ml PMBN killed all bacteria.

We therefore demonstrate that molecules 2329, 2666, 2461, 2511, 2525 or 2539 with 40 g/ml PMBN have bactericidal activity against *Escherichia coli* (ATCC 8739), while molecules 38z", 39z", 40z" and 41z" with 10 to 50 g/ml PMBN, particularly 40 μg/ml have no antibacterial activity.

We conclude that a phenyl unit on a cyclopropyl group in the pyrimidine derivative according to the invention, which is lacking in the purine 38z", 39z", 40z" and 41z" disclosed in WO2009/034386 play an essential role in antibacterial activity.

What is claimed is:

1. A method of treating or reducing the risk of a Gram-negative bacterial infection in a host mammal in need of such treatment or reduction of the risk of a Gram-negative bacterial infection, comprising administering to the host mammal:

(a) a pharmaceutical composition comprising a pyrimidine derivative represented by formula (I):

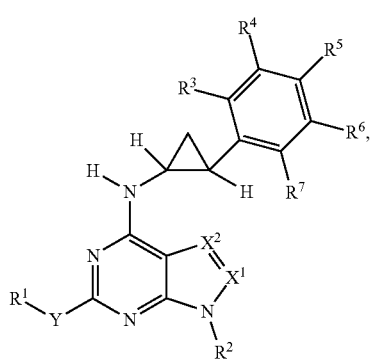

(I)

or an optical isomer, a racemic mixture of optical isomers, a pharmaceutically acceptable acid addition salt, a pharmaceutically acceptable metal salt, or an alkylated ammonium salt thereof; and (b) a membrane penetrating agent;

wherein:
$X^1$ and $X^2$ are independently N, CH, or $CR^8$, wherein $R^8$ is $C_{1-6}$ alkyl, $C_{2-6}$ alkenyl or $C_{2-6}$ alkynyl; with the exception that if one of $X^1$ or $X^2$ is equal to N, then the remaining of $X^1$ or $X^2$ is selected from CH and $CR^8$, —Y— is —O— or —S—;

$R^1$ and $R^2$ are independently $C_{1-6}$-alkyl, $C_{2-6}$-alkenyl, $C_{2-6}$-alkynyl, $C_{3-6}$-cycloalkyl, aryl, or aryl-$C_{1-6}$-alkyl wherein the alkyl or cycloalkyl moiety is optionally mono or polysubstituted with OH or an halogen and the aryl moiety is optionally mono or polysubstituted with an halogen, —$C_{1-6}$ alkyl, —$C_{1-6}$ alkoxy, —OH, —$NO_2$, —CN, —$NH_2$, —$NHR^8$, —$N(R^8)_2$—COOH, —$COOR^8$, —$CONH_2$, —$CONHR^8$, —$CON(R^8)_2$, —$SO_2NH_2$, —$SO_2NHR^8$, or —$SO_2N(R^8)_2$; and $R^3$, $R^4$, $R^5$, $R^6$ and $R^7$ are independently H, an halogen, a $C_{1-6}$ alkyl, $C_{1-6}$ alkoxy, —OH, —$NO_2$, —CN, —$NH_2$, —$NHR^8$, —$N(R^8)_2$—COOH, —$COOR^8$, —$CONH_2$, —$CONHR^8$, —$CON(R^8)_2$, —$SO_2NH_2$, —$SO_2NHR^8$, or —$SO_2N(R^8)_2$.

2. The method according to claim 1, wherein $R^3$ and $R^7$ are hydrogen and $R^4$ and $R^5$ are independently a halogen.

3. The method according to claim 1, wherein $X^1$ is CH or $CR^8$ and $X^2$ is N.

4. The method according to claim 3, wherein the pyrimidine derivative is selected from the group consisting of:
    N-((1R,2S)-2-(3,4-difluorophenyl)cyclopropyl)-9-methyl-2-(propylthio)-9H-purin-6-amine (1c);
    9-methyl-N-((1R,2S)-2-phenylcyclopropyl)-2-(propylthio)-9H-purin-6-amine (2c);
    N-((1R,2S)-2-(3,4-difluorophenyl)cyclopropyl)-9-ethyl-2-(propylthio)-9H-purin-6-amine (3c);
    N-((1R,2S)-2-(3,4-difluorophenyl)cyclopropyl)-9-propyl-2-(propylthio)-9H-purin-6-amine (4c);
    N-((1R,2S)-2-(3,4-difluorophenyl)cyclopropyl)-9-isopropyl-2-(propylthio)-9H-purin-6-amine (5c);
    9-cyclopropyl-N-((1R,2S)-2-(3,4-difluorophenyl)cyclopropyl)-2-(propylthio)-9H-purin-6-amine (6c);
    9-butyl-N-((1R,2S)-2-(3,4-difluorophenyl)cyclopropyl)-2-(propylthio)-9H-purin-6-amine (7c);
    9-(sec-butyl)-N-((1R,2S)-2-(3,4-difluorophenyl)cyclopropyl)-2-(propylthio)-9H-purin-6-amine (8c);
    9-(tert-butyl)-N-((1R,2S)-2-(3,4-difluorophenyl)cyclopropyl)-2-(propylthio)-9H-purin-6-amine (9c);
    9-cyclobutyl-N-((1R,2S)-2-(3,4-difluorophenyl)cyclopropyl)-2-(propylthio)-9H-purin-6-amine (10c);
    N-((1R,2S)-2-(3,4-difluorophenyl)cyclopropyl)-9-pentyl-2-(propylthio)-9H-purin-6-amine (11c);
    9-cyclopentyl-N-((1R,2S)-2-(3,4-difluorophenyl)cyclopropyl)-2-(propylthio)-9H-purin-6-amine (12c);
    N-((1R,2S)-2-(3,4-difluorophenyl)cyclopropyl)-9-hexyl-2-(propylthio)-9H-purin-6-amine (13c);
    9-cyclohexyl-N-((1R,2S)-2-(3,4-difluorophenyl)cyclopropyl)-2-(propylthio)-9H-purin-6-amine (14c);
    9-allyl-N-((1R,2S)-2-(3,4-difluorophenyl)cyclopropyl)-2-(propylthio)-9H-purin-6-amine (15c);
    2-(6-(((1R,2S)-2-(3,4-difluorophenyl)cyclopropyl) amino)-2-(propylthio)-9H-purin-9-yl) ethanol (16c);
    N-((1R,2S)-2-(3,4-difluorophenyl)cyclopropyl)-9-(prop-2-yn-1-yl)-2-(propylthio)-9H-purin-6-amine (17c);
    N-((1R,2S)-2-(3,4-difluorophenyl)cyclopropyl)-2-(propylthio)-9-(2,2,2-trifluoroethyl)-9H-purin-6-amine (18c);

(1S,2R,3S,4R)-4-(6-(((1R,2S)-2-(3,4-difluorophenyl)cyclopropyl) amino)-2-(propylthio)-9H-purin-9-yl) cyclopentane-1,2,3-triol (19d);

N-((1R,2S)-2-(3,4-difluorophenyl)cyclopropyl)-2-(ethylthio)-9-methyl-9H-purin-6-amine (20c);

N-((1R,2S)-2-(3,4-difluorophenyl)cyclopropyl)-9-ethyl-2-(ethylthio)-9//-purin-6-amine (21c);

N-((1R,2S)-2-(3,4-difluorophenyl)cyclopropyl)-9-methyl-2-(methylthio)-9H-purin-6-amine (22c);

N-((1R,2S)-2-(3,4-difluorophenyl)cyclopropyl)-9-methyl-2-propoxy-9H-purin-6-amine hydrochloride (23t·HCl);

N-((1R,2S)-2-(3,4-difluorophenyl)cyclopropyl)-9-ethyl-2-(methylthio)-9H-purin-6-amine (24c);

2-(butylthio)-N-((1R,2S)-2-(3,4-difluorophenyl)cyclopropyl)-9-methyl-9H-purin-6-amine (25c); and 2-(butylthio)-N-((1R,2S)-2-(3,4-difluorophenyl)cyclopropyl)-9-ethyl-9H-purin-6-amine (26c);

or an optical isomer, a racemic mixture of optical isomers, pharmaceutically acceptable acid addition salts, pharmaceutically acceptable metal salts, or alkylated ammonium salts thereof.

5. The method according to claim 3, wherein the pyrimidine derivative is selected from the group consisting of:

N-((1R,2S)-2-(3,4-difluorophenyl)cyclopropyl)-9-methyl-2-(propylthio)-9H-purin-6-amine (1c);

N-((1R,2S)-2-(3,4-difluorophenyl)cyclopropyl)-9-ethyl-2-(propylthio)-9H-purin-6-amine (3c);

9-allyl-N-((1R,2S)-2-(3,4-difluorophenyl)cyclopropyl)-2-(propylthio)-9H-purin-6-amine (15c);

N-((1R,2S)-2-(3,4-difluorophenyl)cyclopropyl)-9-(prop-2-yn-1-yl)-2-(propylthio)-9H-purin-6-amine (17c);

(1S,2R,3S,4R)-4-(6-(((1R,2S)-2-(3,4-difluorophenyl)cyclopropyl) amino)-2-(propylthio)-9H-purin-9-yl) cyclopentane-1,2,3-triol (19d);

N-((1R,2S)-2-(3,4-difluorophenyl)cyclopropyl)-9-methyl-2-(methylthio)-9H-purin-6-amine (22c);

N-((1R,2S)-2-(3,4-difluorophenyl)cyclopropyl)-9-ethyl-2-(methylthio)-9H-purin-6-amine (24c);

N-((1R,2S)-2-(3,4-difluorophenyl)cyclopropyl)-2-(ethylthio)-9-methyl-9H-purin-6-amine (20c);

N-((1R,2S)-2-(3,4-difluorophenyl)cyclopropyl)-9-ethyl-2-(ethylthio)-9H-purin-6-amine (21c); and 2-(butylthio)-N-((1R,2S)-2-(3,4-difluorophenyl)cyclopropyl)-9-methyl-9H-purin-6-amine (25c);

or an optical isomer, a racemic mixture of optical isomers, pharmaceutically acceptable acid addition salts, pharmaceutically acceptable metal salts, or alkylated ammonium salts thereof.

6. The method according to claim 3, wherein the pyrimidine derivative is selected from the group consisting of:

N-((1R,2S)-2-(3,4-difluorophenyl)cyclopropyl)-9-methyl-2-(propylthio)-9H-purin-6-amine (1c);

9-allyl-N-((1R,2S)-2-(3,4-difluorophenyl)cyclopropyl)-2-(propylthio)-9H-purin-6-amine (15c); and N-((1R,2S)-2-(3,4-difluorophenyl)cyclopropyl)-9-(prop-2-yn-1-yl)-2-(propylthio)-9H-purin-6-amine (17c)

(1S,2R,3S,4R)-4-(6-(((1R,2S)-2-(3,4-difluorophenyl)cyclopropyl) amino)-2-(propylthio)-9H-purin-9-yl) cyclopentane-1,2,3-triol (19d).

7. The method according to claim 1, wherein $X^1$ is N and $X^2$ is CH or $CR^8$.

8. The method according to claim 7, wherein the pyrimidine derivative is selected from the group consisting of:

N-((1R,2S)-2-(3,4-difluorophenyl)cyclopropyl)-1-methyl-6-(methylthio)-1H-pyrazolo[3,4-d]pyrimidin-4-amine (27k);

N-((1R,2S)-2-(3,4-difluorophenyl)cyclopropyl)-6-(ethylthio)-1-methyl-1H-pyrazolo[3,4-d]pyrimidin-4-amine hydrochloride (28x·HCl);

N-((1R,2S)-2-(3,4-difluorophenyl)cyclopropyl)-6-(propylthio)-1-methyl-1H-pyrazolo[3,4-d]pyrimidin-4-amine hydrochloride (29x·HCl);

N-((1R,2S)-2-(3,4-difluorophenyl)cyclopropyl)-1-ethyl-6-(methylthio)-1H-pyrazolo[3,4-d]pyrimidin-4-amine (30k);

N-((1R,2S)-2-(3,4-difluorophenyl)cyclopropyl)-1-ethyl-6-(ethylthio)-1H-pyrazolo[3,4-d]pyrimidin-4-amine hydrochloride (31x·HCl);

N-((1R,2S)-2-(3,4-difluorophenyl)cyclopropyl)-1-ethyl-6-(propylthio)-1H-pyrazolo[3,4-d]pyrimidin-4-amine hydrochloride (32x·HCl);

N-((1R,2S)-2-(3,4-difluorophenyl)cyclopropyl)-1-isopropyl-6-(methylthio)-1H-pyrazolo[3,4-d]pyrimidin-4-amine hydrochloride (33k·HCl); and N-((1R,2S)-2-(3,4-difluorophenyl)cyclopropyl)-6-(methylthio)-1-propyl-1H-pyrazolo[3,4-d]pyrimidin-4-amine hydrochloride (34k·HCl);

or an optical isomer, a racemic mixture of optical isomers, pharmaceutically acceptable acid addition salts, pharmaceutically acceptable metal salts, or alkylated ammonium salts thereof.

9. The method according to claim 7, wherein the pyrimidine derivative is selected from the group consisting of:

N-((1R,2S)-2-(3,4-difluorophenyl)cyclopropyl)-1-methyl-6-(methylthio)-1H-pyrazolo[3,4-d]pyrimidin-4-amine (27k);

N-((1R,2S)-2-(3,4-difluorophenyl)cyclopropyl)-1-ethyl-6-(methylthio)-1H-pyrazolo[3,4-d]pyrimidin-4-amine (30k);

N-((1R,2S)-2-(3,4-difluorophenyl)cyclopropyl)-6-(ethylthio)-1-methyl-1H-pyrazolo[3,4-d]pyrimidin-4-amine hydrochloride (28x·HCl); and N-((1R,2S)-2-(3,4-difluorophenyl)cyclopropyl)-1-isopropyl-6-(methylthio)-1H-pyrazolo[3,4-d]pyrimidin-4-amine hydrochloride (33k·HCl);

or an optical isomer, a racemic mixture of optical isomers, pharmaceutically acceptable acid addition salts, pharmaceutically acceptable metal salts, or alkylated ammonium salts thereof.

10. The method according to claim 1, wherein $X^1$ and $X^2$ are CH or $CR^8$.

11. The method according to claim 10, wherein the pyrimidine derivative is N-((1R,2S)-2-(3,4-difluorophenyl)cyclopropyl)-7-ethyl-2-(methylthio)-7H-pyrrolo[2,3-d]pyrimidin-4-amine hydrochloride (35p·HCl); or an optical isomer, a racemic mixture of optical isomers, pharmaceutically acceptable acid addition salts, pharmaceutically acceptable metal salts, or alkylated ammonium salts thereof.

12. The method according to claim 1, wherein $R^3$ and $R^7$ are H and $R^4$, $R^5$ is a fluorine.

13. A method for killing or reducing the risk of Gram-negative bacterial growth in biofilm formation comprising applying on a surface of a medical device, an effective amount of pyrimidine derivatives represented by formula (I) together with a membrane penetrating agent:

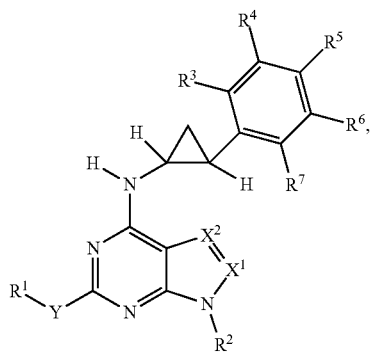

(I)

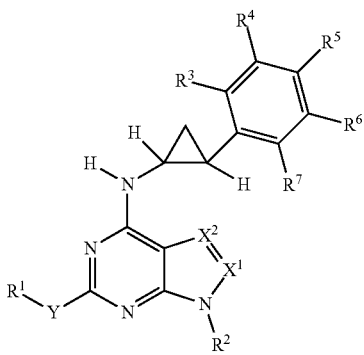

(I)

wherein:

X$^1$ and X$^2$ are independently N, CH, or CR$^8$ wherein R$^8$ is C$_{1-6}$ alkyl, C$_{2-6}$ alkenyl or C$_{2-6}$ alkynyl; with the exception that if one of X$^1$ or X$^2$ is equal to N, then the remaining of X$^1$ or X$^2$ are selected from CH, CR$^8$, —Y— is —O— or —S—;

R$^1$ and R$^2$ are independently C$_{1-6}$-alkyl, C$_{2-6}$-alkenyl, C$_{2-6}$-alkynyl, C$_{3-6}$-cycloalkyl, aryl, or aryl-C$_{1-6}$-alkyl wherein the alkyl or cycloalkyl moiety is optionally mono or polysubstituted with OH or an halogen and the aryl moiety is optionally mono or polysubstituted with an halogen, —C$_{1-6}$ alkyl, —C$_{1-6}$ alkoxy, —OH, —NO$_2$, —CN, —NH$_2$, —NHR$^8$, —N(R$^8$)$_2$—COOH, —COOR$^8$, —CONH$^2$, —CONHR$^8$, —CON(R$^8$)$_2$, —SO$_2$NH$_2$, —SO$_2$NHR$^8$, or —SO$_2$N (R$^8$)$_2$;

R$^3$, R$^4$, R$^5$, R$^6$ and R$^7$ are independently H, an halogen, a C$_{1-6}$ alkyl, C$_{1-6}$ alkoxy, —OH, —NO$_2$, —CN, —NH$_2$, —NHR$^8$, —N(R$^8$)$_2$—COOH, —COOR$^8$, —CONH$^2$, —CONHR$^8$, —CON(R$^8$)$_2$, —SO$_2$NH$_2$, —SO$_2$NHR$^8$, or —SO$_2$N (R$^8$)$_2$, wherein said method is not a method of treatment of the human or animal body.

14. The method according to claim 13, wherein the medical device is a cardiovascular device.

15. A method of diagnosing or prognosing a Gram-negative bacterial infection comprising using the pyrimidine derivative represented by formula (I) together with a membrane penetrating agent:

wherein:

X$^1$ and X$^2$ are independently N, CH, or CR$^8$ wherein R$^8$ is C$_{1-6}$ alkyl, C$_{2-6}$ alkenyl or C$_{2-6}$ alkynyl; with the exception that if one of X$^1$ or X$^2$ is equal to N, then the remaining of X$^1$ or X$^2$ are selected from CH or CR$^8$, —Y— is —O— or —S—;

R$^1$ and R$^2$ are independently C$_{1-6}$-alkyl, C$_{2-6}$-alkenyl, C$_{2-6}$-alkynyl, C$_{3-6}$-cycloalkyl, aryl, aryl-C$_{1-6}$-alkyl wherein the alkyl or cycloalkyl moiety is optionally mono or polysubstituted with OH or an halogen and the aryl moiety is optionally mono or polysubstituted with an halogen, —C$_{1-6}$ alkyl, —C$_{1-6}$ alkoxy, —OH, —NO$_2$, —CN, —NH$_2$, —NHR$^8$, —N(R$^8$)$_2$—COOH, —COOR$^8$, —CONH$^2$, —CONHR$^8$, —CON(R$^8$)$_2$, —SO$_2$NH$_2$, —SO$_2$NHR$^8$, or —SO$_2$N (R$^8$)$_2$;

R$^3$, R$^4$, R$^5$, R$^6$ and R$^7$ are independently H, an halogen, a C$_{1-6}$ alkyl, C$_{1-6}$ alkoxy, —OH, —NO$_2$, —CN, —NH$_2$, —NHR$^8$, —N(R$^8$)$_2$—COOH, —COOR$^8$, —CONH$^2$, —CONHR$^8$, —CON(R$^8$)$_2$, —SO$_2$NH$_2$, —SO$_2$NHR$^8$, or —SO$_2$N (R$^8$)$_2$; and wherein the pyrimidine derivative comprises a detectable marker.

16. The method according to claim 1, wherein the membrane penetrating agent is polymyxin B nonapeptide.

17. The method according to claim 13, wherein the membrane penetrating agent is polymyxin B nonapeptide.

18. The method according to claim 15, wherein the membrane penetrating agent is polymyxin B nonapeptide.

* * * * *